US009624553B2

(12) United States Patent
Laskar et al.

(10) Patent No.: US 9,624,553 B2
(45) Date of Patent: Apr. 18, 2017

(54) MOLECULAR MARKERS FOR VARIOUS TRAITS IN WHEAT AND METHODS OF USE

(71) Applicants: Pioneer Hi-Bred International, Inc., Johnston, IA (US); E.I. du Pont de Nemours and Company, Wilmington, DE (US)

(72) Inventors: Bill Laskar, Windfall, IN (US); Stanley Luck, Wilmington, DE (US); Ajay Sandhu, Wilmington, DE (US); Petra Wolters, Kennett Square, PA (US)

(73) Assignees: E I DU PONT DE NEMOURS AND COMPANY, Wilmington, DE (US); PIONEER HI-BRED INTERNATIONAL, INC., Johnston, IA (US)

( * ) Notice: Subject to any disclaimer, the term of this patent is extended or adjusted under 35 U.S.C. 154(b) by 774 days.

(21) Appl. No.: 13/940,326

(22) Filed: Jul. 12, 2013

(65) Prior Publication Data
US 2014/0020128 A1  Jan. 16, 2014

Related U.S. Application Data

(60) Provisional application No. 61/671,423, filed on Jul. 13, 2012.

(51) Int. Cl.
*C12Q 1/68* (2006.01)
*A01H 1/04* (2006.01)
*A01H 5/10* (2006.01)

(52) U.S. Cl.
CPC ............ *C12Q 1/6895* (2013.01); *A01H 1/04* (2013.01); *A01H 5/10* (2013.01); *C12Q 2600/156* (2013.01)

(58) Field of Classification Search
None
See application file for complete search history.

(56) References Cited

FOREIGN PATENT DOCUMENTS

FR          2834720 A1      7/2003

OTHER PUBLICATIONS

Akhunova et al. (BMC Genomics 2010, 11:702).*
Monica Baga et al., Identification of genomic regions determining the phenological development leading to floral transition in wheat (*Triticum aestivum* L.), Journal of Experimental Botany, 2009, pp. 3575-3585, vol. 60, No. 12.
Matthieu Bogard et al., Anthesis date mainly explained correlations between post-anthesis leaf senescene, grain yield, and grain protein concentration in a winter wheat population segregating for flowering time QTLs., Journal of Experimental Botany, 2011, pp. 3621-3636, vol. 62, No. 10.
H. Buerstmayr et al., Molecular mapping of QTLs for Fusarium head blight resistance in spring wheat. I. Resistance to fungal spread (Type II resistance), Theor Appl Genet, 2002, pp. 84-91, vol. 104.
H. Buerstmayr et al., Molecular mapping of QTLs for Fusarium head blight resistance in spring wheat. II. Resistance to fungal penetration and spread, Theor Appl Genet, 2003, pp. 503-508, vol. 107.
A. H. Carter et al., Genetic Mapping of Quantitative Trait Loci Associated with Important Agronomic Traits in the Spring Wheat (*Triticum aestivum* L.) Cross 'Louise' x 'Penawawa', Crop Science, Jan.-Feb. 2011, pp. 84-85, vol. 51.
J. Chrpova et al., Effectiveness of Marker-based Selection for Fusarium Head Blight Resistance in Spring Wheat, Czech J. Genet. Plant Breed., 2011, (Special Issue) S123-S129, vol. 47.
Gaofeng Jia et al., QTLs for Fusarium head blight response in a wheat DH population of Wangshuibai/Alondra's', Euphytica, 2005, pp. 183-191, vol. 146(3).
L. Gervais et al., Mapping of quantitative trait loci for field resistance to Fusarium head blight in an European winter wheat, Theor Appl Genet, 2003, pp. 961-970, vol. 106.
Kai-Ming Zhang et al., Resistance to Fusarium Head Blight and Deoxynivalenol Accumulation and Allele Variation of Related SSR Markers in Wheat, Acta Agronomica Sinica, 2006, pp. 1788-1795, vol. 32, No. 12 (English Abstract Only).
Jing Kang et al., Exotic Scab Resistance Quantitative Trait Loci Effects on Soft Red Winter Wheat, Crop Science, May-Jun. 2011, pp. 924-933, vol. 51(3).
J. Le Gouis et al., Genome-wide association analysis to identify chromosomal regions determining components of earliness in wheat, Theor Appl Genet, 2012, pp. 597-611, vol. 124.
F. Lin et al., Mapping QTL associated with resistance to Fusarium head blight in the Nanda2419 x Wangshuibai population. II: Type I resistance, Theor Appl Genet, 2006, pp. 528-535, vol. 112.
Shuyu Liu et al., Meta-Analysis of QTL Associated with Fusarium Head Blight Resistance in Wheat, Crop Science, Nov.-Dec. 2009, pp. 1955-1968, vol. 49.
H. X. Ma et al., Quantitative trait loci for resistance to fusarium head blight and deoxynivalenol accumulation in Wangshuibai wheat under field conditions, Plant Pathology, 2006, pp. 739-735, vol. 55.
Thomas Miedaner et al., Marker-Assisted Selection for Disease Resistance in Wheat and Barley Breeding, Phytopathology, 2012, pp. 560-566, vol. 102(6).
Qiongxian Lu et al., Two Major Resistance Quantitative Trait Loci are Required to Counteract the Increased Susceptibility to Fusarium Head Blight of the Rht-D1b Dwarfing Gene in Wheat, Crop Science, Nov.-Dec. 2011, pp. 2430-2438, vol. 51.
S. A. Quarrie et al., A high-density genetic map of hexaploid wheat (*Triticum aestivum* L.) from the cross Chinese Spring x SQ1 and its use to compare QTLs for grain yield across a range of environments, Theor Appl Genet, 2005, pp. 865-880, vol. 110.
A. Salameh et al., Effects of introgression of two QTL for fusarium head blight resistance from Asian spring wheat by marker-assisted backcrossing into European winter wheat on fusarium head blight resistance, yield and quality traits, Mol. Breeding, 2011, pp. 485-494, vol. 28.

(Continued)

*Primary Examiner* — Brent Page
*Assistant Examiner* — Jared Shapiro

(57) ABSTRACT

This disclosure relates to methods of identifying and/or selecting wheat plants or germplasm by detecting markers associated with flowering date, anther-extrusion, heading date and/or *fusarium* head blight resistance.

2 Claims, No Drawings

(56) References Cited

OTHER PUBLICATIONS

Wolfgang Schweiger et al., Transcriptomic characterization of two major Fusarium resistance quantitative trait loci (QTLs), Fhb1 and Qfhs.ifa-5A, identifies novel candidate genes, Molecular Plant Pathology, 2013, pp. 772-785, vol. 14(8).

Xiaorong Shen et al., Quantitative Trait Loci Conditioning Resistance to Fusarium Head Blight in Wheat Line F201R, Crop Sci, 2003, pp. 850-857, vol. 43.

A. Szabo-Hever et al., Mapping of FHB Resistance QTLS in the Mini Mano/Frontana and Frontana/Remus DH Populations, Cereal Research Communication, 2008, pp. 271-275 vol. 36.

A Szabo-Hever et al., Identification and validation of fusarium head blight and Fusarium-damaged kernel QTL in a Frontana/Remus DH mapping population, Can. J. Plant Pathol., 2012, pp. 224-238, vol. 34, No. 2.

Ljiljana Tamburic-Ilincic, Effect of 3B, 5A and 3A QTL for Fusarium head blight resistance on agronomic and quality performance of Canadian winter wheat, Plant Breeding 2012, pp. 722-727, vol. 131.

C. Von Der Ohe et al., Agronomic and Quality Performance of Winter Wheat Backcross Populations Carrying Non-Adapted Fusarium Head Blight Resistance QTL, Crop Science, Nov.-Dec. 2010, pp. 2283-2290, vol. 50(6).

Shulin Xue et al., Fine mapping TaFLW1, a major QT: controlling flag leaf width in bread wheat (*Triticum aestivum* L.), Theor Appl Genet, 2013, pp. 1941-1949, vol. 126.

Yuefeng Ruan et al., Identification of novel QTL for resistance to Fusarium head blight in a tetraploid wheat population, Genome, 2012, pp. 853-864, vol. 55(12).

Eduard D. Akhunov et al., Nucleotide diversity maps reveal variation in diversity among wheat genomes and chromosomes, BMC Genomics, 2010, vol. 11:702.

International Search Report—PCT/US2013/050053—mailed Feb. 11, 2014.

\* cited by examiner

fbreak

```
                        SEQUENCE LISTING

<160> NUMBER OF SEQ ID NOS: 450

<210> SEQ ID NO 1
<211> LENGTH: 201
<212> TYPE: DNA
<213> ORGANISM: Triticum aestivum

<400> SEQUENCE: 1
tgccctattt ggtacattaa aactgctcag gtttcagttt gggaacacaa aacctggccc       60
ctcaacgaga gaatctgcag ctacatcttc tctgaatgaa rcatctccgt cagaaggttc      120
ttttatcagt agcagagtaa gggaacagtt tgagaagctg tcaaaaatgc tttggttgaa      180
caatagggtc catttgagaa g                                                 201

<210> SEQ ID NO 2
<211> LENGTH: 201
<212> TYPE: DNA
<213> ORGANISM: Triticum aestivum

<400> SEQUENCE: 2
ctccaggcat ctcacctcgg acatgcacgc gaacgactgg gactttccgt cgtagtattt       60
cgacaaccct ttcttggcgg agagttcggc cttcatggac racagatcgt agacgctgtc      120
agagttgagt ctccgcaccg gcggggaagc cggcacaaac tggtcctcgc cgtctgagaa      180
ctgggcctcg tcgtcggagt c                                                 201

<210> SEQ ID NO 3
<211> LENGTH: 201
<212> TYPE: DNA
<213> ORGANISM: Triticum aestivum

<400> SEQUENCE: 3 aactttttwww ttgttggaag gccaataatt gtggaaatga tttcaagagg cttcacaaca      60
tagtcatggg tacagatata gaacctactg agaaaacttg kgccagtatg cagagcacac      120
cattcatcat attcaacctc catactctta gaacaaatct aaaaagctgg aaacataaac      180
caacggatcc acaaaacaag c                                                 201

<210> SEQ ID NO 4
```

```
<211> LENGTH: 201
<212> TYPE: DNA
<213> ORGANISM: Triticum aestivum

<400> SEQUENCE: 4
ctgggcctcg tcgtcggagt cgcaggagaa ggaggaggag gtctcgaaca ggtcctcgtc      60
ttcctggtgc accggaaggg cctgagaaac agcagatctg yccatggctg cgagtttctt     120
gtttctgcga tgaacctcaa ggagaaaggc gaggaaggta tgcttgctgc tgtatatgga     180
tggatatatt cctgctcttg t                                               201

<210> SEQ ID NO 5
<211> LENGTH: 121
<212> TYPE: DNA
<213> ORGANISM: Triticum aestivum

<400> SEQUENCE: 5
actccaaatg actgagtcaa aatccgtgcc ataggtgtgg caatagtatg ggtacccttg      60
rtaacgaaat ttcaacataa ttttgaaaca gacaccaaga accatcttgg gtttcaactg     120
t                                                                     121

<210> SEQ ID NO 6
<211> LENGTH: 201
<212> TYPE: DNA
<213> ORGANISM: Triticum aestivum

<400> SEQUENCE: 6
gctcaccaag gcagttcagt agtttaagta acatgcagaa ctttcacaat ataaggatgg      60
ccatagctgt tgtcatttgt aagtgctatt ggcaccaacc ratacccaa gacagggaac     120 aaaactgtgg aacaaaattt cctgccatta attgacacta cggcactgcc tgttaaatta     180
atctgatatt aaggacaaag a                                               201

<210> SEQ ID NO 7
<211> LENGTH: 107
<212> TYPE: DNA
<213> ORGANISM: Triticum aestivum

<400> SEQUENCE: 7
tgaatggtgc aggattggca atggctacga tggacatcat taagctrcat ggtggtacac      60
ctgccaattt tcttgatgtt ggtgggagtg catccgaggg acaggta                   107

<210> SEQ ID NO 8
<211> LENGTH: 201
<212> TYPE: DNA
<213> ORGANISM: Triticum aestivum

<400> SEQUENCE: 8
gcgctggtaa ccacatgctt tttggatatc taaaagaagc tcctttgcat aagagtttgt      60
aaggctttcc tgcatcccaa tttctctaag aatggcaaca ratggaagat acagacttgg     120
aagttcaaaa gcaaaaggtg acatgttgat agtcagacga gcaaaaagtg atttcgcttc     180
tattaagcga gtaccatttg c                                               201

<210> SEQ ID NO 9
<211> LENGTH: 201
<212> TYPE: DNA
<213> ORGANISM: Triticum aestivum

<400> SEQUENCE: 9
```

```
tgggatagaa cgtcactgga aactagcaag gatcttcgga tattttcgct ggaaactcga      60
gagctcgcgg gcggtcgtag tcggtcgctg ttcttcctcc yccgtgatgc tgccgctcgt     120
cctcctcgtt ggtctcgtgc tccggatatt attctttctg ccgttgtttt ctcctttta     180 ttccacacca gttcttattt c                                               201

<210> SEQ ID NO 10
<211> LENGTH: 201
<212> TYPE: DNA
<213> ORGANISM: Triticum aestivum

<400> SEQUENCE: 10
gctttgtggg aacttagcgg ggatcrtctt gagcacacta aatttgttga gataaatatc      60
gacaagatga ggcatgtttg caaatatgtt aatcacttct racgggatat ggctaatcgc     120
ccaagagaag gttgttactt gattcatctg gcccaaaaaa ataaccatgt tatgacgtcg     180
gtatttagtt tcggcacgcg t                                               201

<210> SEQ ID NO 11
<211> LENGTH: 201
<212> TYPE: DNA
<213> ORGANISM: Triticum aestivum

<400> SEQUENCE: 11
ccaagccttg ggacaagccc gccagaccga gtcgctagac tttgctgaaa gagatggcgc      60
cccgaggctc cgtagaaaga gaagagaagt gttgttgtat ygccaatttt tcgaaatata     120
ccgtctgctg ttcctttttt cccgccttgt tgctccttt tttcaccttg ttgtttgact     180
agacggctcg aaatagacag a                                               201

<210> SEQ ID NO 12
<211> LENGTH: 201
<212> TYPE: DNA
<213> ORGANISM: Triticum aestivum

<400> SEQUENCE: 12
gatgccactt actactgctg aaaagattat ggattctcat ggaatggacc aggttcctgt      60
agtttcagaa catgttaatc atcaggatgg aggaatcttg rttggttttg tagatagaga     120
atgcatcacc attgctcgaa gagctttggc agcaaaagaa ttttttcagtt tcacatcgga    180 gatcagaggg gaagagagtt g                                               201

<210> SEQ ID NO 13
<211> LENGTH: 201
<212> TYPE: DNA
<213> ORGANISM: Triticum aestivum

<400> SEQUENCE: 13
agctgacgga cgagtggccc ggttgtccaa cgtctgccac tctaccaaca tccggttggg      60
aaggtgcaga agagaggtca gccgttgaaa cactcttaaa ygagtaaacc tgactggaga    120
gtagcatgcg agtctcgccg ggggctgtct ccacgggaaa cctgtaaagt gcttggccag    180
ctgatggcct tacgtcttca g                                               201

<210> SEQ ID NO 14
<211> LENGTH: 201
<212> TYPE: DNA
<213> ORGANISM: Triticum aestivum
```

<400> SEQUENCE: 14

```
ccaagataca tgtacttggg aacaagtgtc aaagtaagct acttgaaata attgatgcta     60
gtgaattgcc agaatttctt ggtggcactt gtacctgtcc ygaatatgga gggtgcctca    120
aagctgaaaa agggccatgg aaggatgcaa acatactgaa gaaagtcctt aatggcgagg    180
ctcagtgtgc tcggcagatt g                                              201
```

<210> SEQ ID NO 15
<211> LENGTH: 201
<212> TYPE: DNA
<213> ORGANISM: Triticum aestivum

<400> SEQUENCE: 15

```
gtgctgctac ccccaaagag caagtggtag atgccagtgt cgaagaagcc aagcctccac     60
aagatgcagg cgttgcggcg gcaaacggtg tcgggccttc ractgtaaag ccggaggaca    120
aaatggaaat cgatggttga tatttaggga taactgtatc ggacccctc ttcagtttag    180
ttgctaaact ggttctagtg t                                              201
```

<210> SEQ ID NO 16
<211> LENGTH: 201
<212> TYPE: DNA
<213> ORGANISM: Triticum aestivum

<400> SEQUENCE: 16

```
gtaacaacaa taggttgttg attctttgag ggggagctgt gtgcgtcctc cgcatgggtt     60
ttctgtaaat ttggcgcgct acctgagttt gagcaaggtt ktaacggcat ttcttttttc    120
ctcaatgcca cgcttgccag atcatgcaat gttcatgaag acttgttgtt ttgaagaaag    180
tgggatgagc aattttattt t                                              201
```

<210> SEQ ID NO 17
<211> LENGTH: 201
<212> TYPE: DNA
<213> ORGANISM: Triticum aestivum

<400> SEQUENCE: 17

```
gcttcatctg cgagggagat gaagctctag ggtccatgaa ggaagttgaa gctcaaacta     60
ttggagatct tctaccaacc gatgatgatt tgatatcggg ygttatcgat ggctttgaac    120
tctctggcct gtctatcaac caggatgacg ccgatgaaga tatatttggc actgrcggag    180
ggttggagct tgagaatgat g                                              201
```

<210> SEQ ID NO 18
<211> LENGTH: 201
<212> TYPE: DNA
<213> ORGANISM: Triticum aestivum

<400> SEQUENCE: 18

```
ggcagcctaa tcaggtggtt tgagatctat ctctctgttt taatcgtgaa atggttagtt     60
tttcatggca gggtattatc tatcaataaa cttgtatgtg ycatgcaag tgctacctta    120
gactggtcag tagaatttga gaattgtatg gaaggaactg gtttgttgct ttgatatcta    180
tcaaaatgag atgatgtcct g                                              201
```

<210> SEQ ID NO 19
<211> LENGTH: 201
<212> TYPE: DNA
<213> ORGANISM: Triticum aestivum

<400> SEQUENCE: 19

```
catctgtttc tgagcatcag ccaacagcct ggtcttcttt tatgtttgat ttccacatcc      60
ttctttcct attcccagcg ggcctctatt tctgcttcaa rcgcctgtca gatgccacaa      120
tatttatagt tatgtatggc ctcacaagta tgtactttgc tggtgtgatg gtgaggttga    180
ttcttgttgc agcacctgct g                                               201
```

<210> SEQ ID NO 20
<211> LENGTH: 192
<212> TYPE: DNA
<213> ORGANISM: Triticum aestivum

<400> SEQUENCE: 20

```
gtgttcaagt cacaacggtt cacatagcgc gggcaagacc actggagatc acatcgtttg      60
tttgtttaca gcaggtgaaa tagagcgagc grgcaaacaa caggccaaat gaattgggat    120
tcgctgattc tccattccag gtacaaaatg gaactagtct actattgtac tgttagcctc    180
tcatacgtaa ta                                                         192
```

<210> SEQ ID NO 21
<211> LENGTH: 201
<212> TYPE: DNA
<213> ORGANISM: Triticum aestivum

<400> SEQUENCE: 21

```
aaaccaagtc ccctcagtag gtaaaaatca cggcctatgg catcctcgat gccaggtctt      60
tgcaccttga cagctaccaa ctgctcagag tatttcaacc rtgccttgta aacttgacct    120
aaacttgctg cagctatcgg tgaaggtgac attgctgagt acattgaatc aagaggaaag    180
ccaagctccc tctcgacaca g                                               201
```

<210> SEQ ID NO 22
<211> LENGTH: 201
<212> TYPE: DNA
<213> ORGANISM: Triticum aestivum

<400> SEQUENCE: 22

```
aagcgcctca ctccagatgt agtagggcct aagaaggaga cataaattca atggcatgta      60
caatgaaccc rtggcactgg caactgttaa ttcacagtat ygccgacagg gcgaaatgac    120
aatcgtatgc ttttttgttc ccatacatcc aaaattatta caaaattttg gaacttcctg    180
agacaagtga taacagaaaa a                                               201
```

<210> SEQ ID NO 23
<211> LENGTH: 201
<212> TYPE: DNA
<213> ORGANISM: Triticum aestivum

<400> SEQUENCE: 23

```
aagcccgacc accgggcttg ctgtcctatg gaagaaggcg gtgactatta tgttgtcaag      60
aaagggggaca tggttgctgt ttacaaaact ttaaatgatt kccaggcgca aatttgctct   120
tcggtatctg gtcctgctgc aagtgcctac aagggttact gctggagcaa agaaaaggca   180
gaatacctct cttcacgtgg a                                               201
```

<210> SEQ ID NO 24
<211> LENGTH: 201
<212> TYPE: DNA

<213> ORGANISM: Triticum aestivum

<400> SEQUENCE: 24

```
tgaggatgtt ttatcgtgtc attgaagtaa tatcttgccc tagctctgtc acagcaaata    60
tatactttaa tgaggtttgg aaagtgagga cggtgttgca mgaagaagca tcaaatggta   120
atggagaatt ttccagaatg gttatggaga tgcaggaagc gttccatggg tattggcaaa   180
atacgtactt gtggttgtca a                                             201
```

<210> SEQ ID NO 25
<211> LENGTH: 201
<212> TYPE: DNA
<213> ORGANISM: Triticum aestivum

<400> SEQUENCE: 25

```
ggaggtgaag aggcagttgc agccatggga cgcttgcgat tgtggtgct tgccaatggt     60
gaggctttat ttgtgcacgg tgcttcttcc cattcatcaa ytcctccagc tgagcgtagc   120
aaagtagatg atgagtggat accgacaagc gaactggttc ttggtgctct ggttgcttta   180
cccttggtca caggacttaa g                                             201
```

<210> SEQ ID NO 26
<211> LENGTH: 201
<212> TYPE: DNA
<213> ORGANISM: Triticum aestivum

<400> SEQUENCE: 26

```
attatggtaa tttctatgcc tcaaagtcat ttttcgactc gaagaagrgc aggaggatca    60
tatggggttg gactaacgag acagacagtt cttcggacga ygttgcaaaa ggttgggcag   120
gaatccatgc aattcccagg acaatttggt tagacagcca tggcaagcag ttgctgcaat   180
ggccagttga agaggtcgag t                                             201
```

<210> SEQ ID NO 27
<211> LENGTH: 201
<212> TYPE: DNA
<213> ORGANISM: Triticum aestivum

<400> SEQUENCE: 27

```
gtgatggcgt tcatgccgga gctggggcca ttcgatgtct ctggtagcta gctagtgttc    60
tgctcattgt ggctgctgtt gctgtgcacc ggtggcacta rattcctggc agcagtattt   120
caagcttact cttttgttct tgtaataaaa cgtttgttga atgtacctcg ctcaaataag   180
tgctcttagt tagaactatc g                                             201
```

<210> SEQ ID NO 28
<211> LENGTH: 201
<212> TYPE: DNA
<213> ORGANISM: Triticum aestivum

<400> SEQUENCE: 28

```
casctttatt ccagatactg tcctagatga ccgccggcta tggttgagga tcgattatgg    60
taatttctat gcctcaaagt catttttcga ctcgaagaag rgcaggagga tcatatgggg   120
ttggactaac gagacagaca gttcttcgga cgaygttgca aaaggttggg caggaatcca   180
tgcaattccc aggacaattt g                                             201
```

<210> SEQ ID NO 29
<211> LENGTH: 201

<212> TYPE: DNA
<213> ORGANISM: Triticum aestivum

<400> SEQUENCE: 29

```
attttctatt tgacgctgct cttctaaata ctgcactcaa cttgaatatc cgcaaatagt    60
agataccatc agaaaacatg gaagaagata atagtgtgtc mtgaactgta caatagccac   120
tgaaaccatg gtggcagctg ctctggaggt acagttgta tcggtacaga tatgggttcc   180
tcgtaccctg tttgtgtaaa t                                             201
```

<210> SEQ ID NO 30
<211> LENGTH: 201
<212> TYPE: DNA
<213> ORGANISM: Triticum aestivum

<400> SEQUENCE: 30

```
cgggtagtgg caacttggaa agaagaatg cttcagcctc acacatgaaa aatggttttt    60
caagaccact cttgaaatgc tcagaagagg ctaggcgaaa yggtaatgtt gcaagtacat   120
ccgggaaagt tcctgcaact ttacaggctg aagcatctga tttggcgaac ttccttacca   180
tggataggaa tgggggttat c                                             201
```

<210> SEQ ID NO 31
<211> LENGTH: 99
<212> TYPE: DNA
<213> ORGANISM: Triticum aestivum

<400> SEQUENCE: 31

```
ttctgatcat atttgtaggt tgtattggtg cgacttgccc ctgctttctc tttggaaaaa    60
rtgcacagtt cttgggatct ggaactctcg ctggatcat                           99
```

<210> SEQ ID NO 32
<211> LENGTH: 121
<212> TYPE: DNA
<213> ORGANISM: Triticum aestivum

<400> SEQUENCE: 32

```
tgttatcggg acatgcataa aaataccctt taatcgcagg aaaggaaaac tgttcttatg    60
ycctggattg ttctgatcat atttgtaggt tgtattggtg cgacttgccc ctgctttctc   120
t                                                                   121
```

<210> SEQ ID NO 33
<211> LENGTH: 201
<212> TYPE: DNA
<213> ORGANISM: Triticum aestivum

<400> SEQUENCE: 33

```
gtcatcatca aactgagcag aaaccggtat tgatcatca ggactctttt tccaatgacc    60
ttgagggtta tgcgccatct catgtgcctc agagatcaac rtcgttggag gacgatccgt   120
tctcctaccc caacctcttc tcatcgaagc cttgagttct agttatctgc aaattagtcg   180
ttgagcctgg tttgaagtca t                                             201
```

<210> SEQ ID NO 34
<211> LENGTH: 201
<212> TYPE: DNA
<213> ORGANISM: Triticum aestivum

<400> SEQUENCE: 34

```
aggggttaag tccaagaata agaactaaaa cggtcgctgc ccacggtttg aagacgaggt    60
cgcacatgcc gtctgtacta ctgcatggtt ttcctatccc rcaagtaaaa tcacccgtta   120
ctctaccgtt taagatttgc gacatctcct agagacttat gctctatatt ttgttgtgcc   180
cacgttgttg tacgcgtgtt a                                             201

<210> SEQ ID NO 35
<211> LENGTH: 201
<212> TYPE: DNA
<213> ORGANISM: Triticum aestivum

<400> SEQUENCE: 35
caatcattgt tgtagaaaca tcaatattaa gagaaagccc actctgtgtg gctcgaaagc    60
ttgagtggaa acctctgcag cccatcacac ccccacccaa rtccacaaag tttgaaggat   120
tgttgtgaaa aaatgactgg cggactaaca ggcagccctg tttggcagag tgttgtctta   180
atatgatatc aataacccga a                                             201

<210> SEQ ID NO 36
<211> LENGTH: 201
<212> TYPE: DNA
<213> ORGANISM: Triticum aestivum

<400> SEQUENCE: 36
cacatctgtg ctctcaggtg ccgttgcaaa cttgagaggg tgcgggaaag aatcggccgc    60
gatcttgttc tgggtgcaca ttttgcagt gttctccatg rcggatgga ttattttcta    120 tttgacgctg ctcttctaaa tactgcactc aacttgaata ccgcaaata gtagatacca   180 tcagaaaaca tggaagaaga t                                             201

<210> SEQ ID NO 37
<211> LENGTH: 101
<212> TYPE: DNA
<213> ORGANISM: Triticum aestivum

<400> SEQUENCE: 37
gcattgcaaa attcagttgt gatgtcaaca ttcttactgc gatttctatt ttctaaagat    60
rrwttaacca tttttcatat gcagaaactc ttgtccattc a                       101

<210> SEQ ID NO 38
<211> LENGTH: 201
<212> TYPE: DNA
<213> ORGANISM: Triticum aestivum

<400> SEQUENCE: 38
tcttccaagt caggtgggtt tgagaaatca tgagcagccg actgtgagct ttgcacatgt    60
ggaccaatat ctggggttga ttgagtacca gaagctggac raattgctgc ttttgggact   120
tcaggcaaat ccaatgagtc aaagccgcca tcagattgat aatcttcacc aggttcgtca   180
gcggcagttg cagctactgg t                                             201

<210> SEQ ID NO 39
<211> LENGTH: 201
<212> TYPE: DNA
<213> ORGANISM: Triticum aestivum

<400> SEQUENCE: 39
atgcaactgt gacagctaca catagcacca taaggatcca atttatttca ggaatgtata    60
tctgcccatg gatccacctc gatgtgtgaa caatcttcac ycgtgggaaa catcccaaag   120
```

```
catggcactg ctttacaata gagaatgttg ctgaaatcac agcctggctt ccaacaactg    180
cagcaagagt ggccaccaca a                                              201

<210> SEQ ID NO 40
<211> LENGTH: 201
<212> TYPE: DNA
<213> ORGANISM: Triticum aestivum

<400> SEQUENCE: 40
ctaatgagat atttatgtgt tcataggggga gtgcatcggg gcatcgggcg gtcgtatgag    60
aagaagtgcg ttcagctgag gacccatgat gccaacggtg yagagccgtt caccatcgag   120
aggatcaggg ctgccattag gaccttcgag acgaagctca acatctccgc cgcctttctc   180
gacgaaatct cccaaaggct c                                              201

<210> SEQ ID NO 41
<211> LENGTH: 201
<212> TYPE: DNA
<213> ORGANISM: Triticum aestivum

<400> SEQUENCE: 41
gttgtaagtt ttttgtattc taatttggtt gagatactta aacagtgatt tgttacttca    60
cctgtcgata aatgtagggc taaagcaata actgggaaat yatgaattcc atgtacttgt   120
catagccgat tctttgttgt tcagtagttt gtttcaagag tgcaggtcgt ttttctataa   180
gctggatgaa tagctccctt g                                              201

<210> SEQ ID NO 42
<211> LENGTH: 121
<212> TYPE: DNA
<213> ORGANISM: Triticum aestivum

<400> SEQUENCE: 42
ggttgttctc acatagttta ttctgtatct agtacttta ctaacgacat cttttactat     60
ygcagccact ttatcgtccc tgaattggct cctagcacca agttctccta ctcttctcac   120
a                                                                    121

<210> SEQ ID NO 43
<211> LENGTH: 201
<212> TYPE: DNA
<213> ORGANISM: Triticum aestivum

<400> SEQUENCE: 43
atatttgcga acaagagcat ggagtggtca gagtttcagc aggctgtaca ggcaggccac    60
aaaggtagat acgggcagat ccggctgagg aagccgaagc rgtctatcta tacttatcct   120
gccccggatt gtatgtgcca agggtagatc gccgagtttt ctgcagtgca ccgacaaaag   180
aaatgtgccg agttacttgc a                                              201

<210> SEQ ID NO 44
<211> LENGTH: 201
<212> TYPE: DNA
<213> ORGANISM: Triticum aestivum

<400> SEQUENCE: 44
cgaattaatt ctccaccaaa ctcaagctca gagagcgttg tcagatgagc gattgagctg    60
attggaaggc tgtaacattc cattatccgc agcttctcta yaactgggct gctcggaaca   120
```

```
cttgcaacct tcggacaggc atacatactt agctcttcaa gcagaggaaa catcaccaag    180
ctatgaggag gttccctgc a                                               201

<210> SEQ ID NO 45
<211> LENGTH: 201
<212> TYPE: DNA
<213> ORGANISM: Triticum aestivum

<400> SEQUENCE: 45
tttattctct tgaggaggca acatttggag aaattctcac gtccagagca ataagagcgg     60
ctcattgttt aacttccatt cagttttcgc ctacttcaga rcacatactg ttggcatatg    120
gacgtcgtca tagctcgttg ctcaggagca ttgttatgga tgcggagacg actggaattc    180
ctgtatatac tatcttagag g                                              201

<210> SEQ ID NO 46
<211> LENGTH: 201
<212> TYPE: DNA
<213> ORGANISM: Triticum aestivum

<400> SEQUENCE: 46
gaaacttgag gattaggatt gcgagctttc taaaatacaa cagcggttgt tttaagctga     60
ttggagatta catgtacagt tttataatta cagggtcgtg kgaacttgac agcaacgatg    120
accatgacca tgccaaattt acatcttcac acygcctgtg cacagacctg agttaaaagt    180
tgcaaaacga tgcacgatta g                                              201

<210> SEQ ID NO 47
<211> LENGTH: 201
<212> TYPE: DNA
<213> ORGANISM: Triticum aestivum

<400> SEQUENCE: 47
gaatgggcga gtggccattg aaggtgaagg ggttcacaaa gatgtggtaa ctgatgaagc     60
tgagggaagc ttgattgtga atgggcgatc gtccatggaa kgtgatgtgg atcatccaga    120
tcttcccatt tccaaggaga tagcagaaga cacagttaat gagagggagg atgagggtaa    180
tgctttcagc agtgaaaata a                                              201

<210> SEQ ID NO 48
<211> LENGTH: 201
<212> TYPE: DNA
<213> ORGANISM: Triticum aestivum

<400> SEQUENCE: 48
gaatctttct cgtcaaatag aggatgagaa tgctgattgt taccctcaca aacaaactca     60
ggacttgtaa ttgttctttc agcattttca acagtgattt ycgatgaggc caggcgatca    120 tgttttttgac acacgactgt ctcggcttgg tctagcacca cattgcactt agcattcagc    180
tcttttaatt acagattggt a                                              201

<210> SEQ ID NO 49
<211> LENGTH: 201
<212> TYPE: DNA
<213> ORGANISM: Triticum aestivum

<400> SEQUENCE: 49 aatcattat ctgcgatgag tactgcttgt tgctatcttc agtggttaat agttcattag      60
tactccttgt gacttcttgg cgcagaaacg agatctctga rtctctctct tgcaattgtg    120
```
actgaaggct ttccacttct gcaagaagac tttcagacaa gctatgcaac tcgtcaaact    180
tctcgacagt ggttgcaagt t                                              201

<210> SEQ ID NO 50
<211> LENGTH: 201
<212> TYPE: DNA
<213> ORGANISM: Triticum aestivum

<400> SEQUENCE: 50
catgagttac agtggatatg atattgaaga tgcaattgta atgaataaat catcccttga    60
tcgaggtttt ggtcgctgca tagcaatcaa aaagtacaag rtcactatgc agaagtatgg    120
aaataatata tcagaaaaga atgttaaacc ggagagggat aaagatggtg ttttgatgaa    180
aaagaatatg caggcattgg a                                              201

<210> SEQ ID NO 51
<211> LENGTH: 201
<212> TYPE: DNA
<213> ORGANISM: Triticum aestivum

<400> SEQUENCE: 51
caaagtattc agtacactct ctttgtcatc tctaccagtc tctgatgtag aagcgtcgtt    60
agacagcttg gtttcatcta atgaatttc cttctcggca rcattgctta gagtcgactc    120
tgacaaaaga gtttcataat ggtctaaaac tttcctcaaa agttcaccca agcacagtac    180
agcaccacca ccagatggaa t                                              201

<210> SEQ ID NO 52
<211> LENGTH: 201
<212> TYPE: DNA
<213> ORGANISM: Triticum aestivum

<400> SEQUENCE: 52
aagctcggac taacagccac agcagtatat gtgcatttga tgactgtccc ttcagatgtg    60
gcagcgggtg actcatcatc atcctcgcat acacggagcg ycgtatctat gagcccttgg    120
tttatctcct cratctcctc caagagagca tgatttacct caattttcg ccgcttggca    180 cgcgaggttg cggttgactg t                                              201

<210> SEQ ID NO 53
<211> LENGTH: 201
<212> TYPE: DNA
<213> ORGANISM: Triticum aestivum

<400> SEQUENCE: 53
tcccagctgc aatagcatca gtcaggtcct ttgtggcatg ggtgtggcag gtgcctccta    60
cagtaacggc ttcatcatct aagaggcact tcacaccaca ygtaggcttc caatggaact    120
taacaaggtg cgccttttcca tccctgctga ttaaggtgta ggtgttgaca ccaaaaccgt    180
ccatgtgcct gtagttgagt g                                              201

<210> SEQ ID NO 54
<211> LENGTH: 166
<212> TYPE: DNA
<213> ORGANISM: Triticum aestivum

<400> SEQUENCE: 54
tgcgcccggc cagcaagatg caaataygta aatgaattag ttacccatat actgtaaatt    60

```
aacggccaag gaatataccg cagtaaatat gcaagtaata rtactagctc ttttttctta    120
acctatatat agtagctctc tttgattcgt tttcaaaaaa aaaga                    166

<210> SEQ ID NO 55
<211> LENGTH: 201
<212> TYPE: DNA
<213> ORGANISM: Triticum aestivum

<400> SEQUENCE: 55
cttgatcttc actgttgttt tgtatatgtt taataccatc ttgcttttca taccatctcc     60
aagaagggta aacctccccg aagaactcaa taacaaagtc rtccatgcca aatccaccct    120
ttttgttgca aacaactcca agacccttc tataagcaac atagttatgt tcagggcggc    180
tcctcatggc cttcagcatt c                                              201

<210> SEQ ID NO 56
<211> LENGTH: 201
<212> TYPE: DNA
<213> ORGANISM: Triticum aestivum

<400> SEQUENCE: 56
catccgtctt ggacaagttc gtcttygcat attgcgtatt ttaagaaaat ccggtgctga     60
tatatataaa tattatatat atggttggtt tcgttctttc rtagcgtcgg tcggtcggtc    120
cctagggtct atctatctgt tcatacccct tcattgtttc ataccttgta atcataaaat    180
catcagccct ccctcccaac c                                              201

<210> SEQ ID NO 57
<211> LENGTH: 201
<212> TYPE: DNA
<213> ORGANISM: Triticum aestivum

<400> SEQUENCE: 57
attatgttac tgtactttct cttctcttcg agcggcaggc ggaaaaaatc ccttgatgcg     60
ttcatcacag aatccatgag agaggtctcc attccatggt yagaaaccttt gaagaatccc   120 caggtctgca gcgctgaccg cagcttggcg gcctcctccg catcgttgga tgcggacagc   180
argccgagat cgattgttgg a                                              201

<210> SEQ ID NO 58
<211> LENGTH: 201
<212> TYPE: DNA
<213> ORGANISM: Triticum aestivum

<400> SEQUENCE: 58
gcagtgattt tggaagtgca attcatggtg ttgacgcaga ttttctaccc tatgatgatg     60
atggggactt tgatgaggca attgatctcg atgatgatga ygatgagcca aatcctgacg    120
aattccagtc tcatgatgca cttagtggct ggtcttctcg taccaagggt gctgcaagat    180
atctcaagac tctgttcgat g                                              201

<210> SEQ ID NO 59
<211> LENGTH: 201
<212> TYPE: DNA
<213> ORGANISM: Triticum aestivum

<400> SEQUENCE: 59 tttttttttct tctccgtttg aggttttgac cgtttgtatt caatttgatt ctattttttgc   60 ccttgcattc tctccctccg ctgtctgtaa tttgttagct mgggcagtgt ggtgtggtga   120
```

```
cagggagaga gaacagtgga ttctatcatg taatgtagat tatctttcgc tacttgatgg      180
aggtgagatg gtttgatgta a                                                201

<210> SEQ ID NO 60
<211> LENGTH: 201
<212> TYPE: DNA
<213> ORGANISM: Triticum aestivum

<400> SEQUENCE: 60
ataatggcga tgcctgatag gatatacagg aagtttgtca agcaatgcga gcgccaacgc      60
gtcgagctta taaggcaagt tcagcagatg caaaaggcat ygagagagaa gcagctgaaa     120
tccattttcc aatggcgcaa gaagcttttg gaagcacatt gggctattcg tgatgcacga     180
ataactcgta acagaggggt g                                               201

<210> SEQ ID NO 61
<211> LENGTH: 201
<212> TYPE: DNA
<213> ORGANISM: Triticum aestivum

<400> SEQUENCE: 61
acgcgagaga agagggagtc aagggcacag atctggtcga cagagtggtg ggcacgacaa      60
ggctgacccg aggaccttac aaggcgctgg atctcggcgg ygacaaatct cctggtgctg     120
cgactggtga tgatggagga ggggtggcaa atcccttgtt gcggtggcta gtgatgaggg     180
aggagagagg agggagatgg t                                               201

<210> SEQ ID NO 62
<211> LENGTH: 201
<212> TYPE: DNA
<213> ORGANISM: Triticum aestivum

<400> SEQUENCE: 62
ctaatgtggc tcacgacttg gacaaattgc aaaacaacac ctactcgctg tgcattgaag      60
gaaactgcta tgttctgcta tcccccaggg atgatggtac ygggtctcaa tccagcaagg     120
aaaaacttct cgtgttccat gtgcagacg agttggtgac cagcattgac acgccagagg     180
atggcaccct gttttcaggc a                                               201

<210> SEQ ID NO 63
<211> LENGTH: 201
<212> TYPE: DNA
<213> ORGANISM: Triticum aestivum

<400> SEQUENCE: 63
ggtagtggta gtactagctg cagcagctga aacttcggtt gcacgggaac tcagattgtt      60
ggtactttct agtgaagatt ttggctgctg ggagaagata rgttgcttct taacagggct     120
cacagaagga atgaagact ccgtcattct taacttggag gggctcgtaa catcaacatg     180
ccgctgtgca ttttgcttct t                                               201

<210> SEQ ID NO 64
<211> LENGTH: 201
<212> TYPE: DNA
<213> ORGANISM: Triticum aestivum

<400> SEQUENCE: 64
agggacatgc tgcataccag ctacaccaga ggactgtaat ccagtgctca tacttgacaa      60
```

```
acttgcttga ggattagtat gactatcatg ctgctgcaaa ytctgggaag tctgttgctg    120
ctgtaaaatg ctggaattag gagcttgtcc tgcaggtggc tggaactgtt gctgtatttg    180
tggctgcact ggcttccttc t                                              201

<210> SEQ ID NO 65
<211> LENGTH: 201
<212> TYPE: DNA
<213> ORGANISM: Triticum aestivum

<400> SEQUENCE: 65
ggatatgttg agggtggaga ttactaagga gttggtcatg gcttcgcctg ctgtgattca    60
cttcaggtcc taattaataa ttgaaaaata agatgcatgg mgtcatcagt aaaatctaga    120
gtccatctgt ccatgtaaat cattcatggc atatgtactc ttatttatcg tctatgtagt    180
ttcaaggagc ttcggtgctc t                                              201

<210> SEQ ID NO 66
<211> LENGTH: 121
<212> TYPE: DNA
<213> ORGANISM: Triticum aestivum

<400> SEQUENCE: 66
gcacaagaaa atattaggat ctttttttat aatacttcac attctattga caggaagaat    60
rcaggacgga gatgggttct cttttccag gacacaaatg gattgctctt taatgtttgt     120
a                                                                    121

<210> SEQ ID NO 67
<211> LENGTH: 121
<212> TYPE: DNA
<213> ORGANISM: Triticum aestivum

<400> SEQUENCE: 67
tttgtttttg ctggtgatac aaactgtttt ccagtcactc ttttttttcaa ataagaaaga   60 ygtggcaagt gatgtttgta tggagcacca cttaatttta tttacctttg cactagacta    120
g                                                                    121

<210> SEQ ID NO 68
<211> LENGTH: 201
<212> TYPE: DNA
<213> ORGANISM: Triticum aestivum

<400> SEQUENCE: 68
cactaatttt ccctggcacc attacatcaa gaatcgatat acaaacaaca atcatatatg    60
ctatatagaa aacatgcact cttttttatt caatgggact yatgtttcca tgacgtttac    120
ttggtctccg aagcagcggc ggcggcatca gcctgtgcct gtctcttctt ggcaaattcg    180 accacccctat caacttctgg c                                             201

<210> SEQ ID NO 69
<211> LENGTH: 121
<212> TYPE: DNA
<213> ORGANISM: Triticum aestivum

<400> SEQUENCE: 69
gtttctattt acttctgaat gctaatttac cgttcttgat ttttgttctc agggttgata   60
kagcatgcta atcttgtct aatttccatg tgtatatttc tttgtgtttg caggggctgc    120
c                                                                    121
```

<210> SEQ ID NO 70
<211> LENGTH: 201
<212> TYPE: DNA
<213> ORGANISM: Triticum aestivum

<400> SEQUENCE: 70
gtctgcacac cgaaatagga tttgcctcat gctctgatgc ttgatggctt ctcgacaaca    60
agggtaagta acaggaacaa gccaaaggag atgacgagtg mtgtggccat caagataagc   120
attgcttgta gtgtgatgct tgggctcaag aagaagatga ctgcgatggc acctgattgc   180
caaaccttca actgtgcaaa a                                             201

<210> SEQ ID NO 71
<211> LENGTH: 201
<212> TYPE: DNA
<213> ORGANISM: Triticum aestivum

<400> SEQUENCE: 71
ctgatgagaa agccaggcta gaggagctta agaaacagcg ggagctgkct gccgccacca    60
aagaggaaga gaagaagaag agggaggagg caaaggccgc rgcagcggct cgtgtgcaag   120
ccaaacttga cgccaagaag ggcaagggaa aaggaaaggg caaatagatt actcccaact   180
gatgtattag tcgttgcatt t                                             201

<210> SEQ ID NO 72
<211> LENGTH: 201
<212> TYPE: DNA
<213> ORGANISM: Triticum aestivum

<400> SEQUENCE: 72
ctcaacgtgg gccactttcc tcatcttgcg gatttggtca cgaggatcaa ctacaaccac    60
tattacatgt ctgacaccgg aagtttcact gcgatccctg rgtcccgccc tcggcagcag   120
ccttgatagg gttgtaggtg cttttcacct ccatttgtgg gggagtgtat ataaacccga   180
ggtggccagg cccaggtggc a                                             201

<210> SEQ ID NO 73
<211> LENGTH: 201
<212> TYPE: DNA
<213> ORGANISM: Triticum aestivum

<400> SEQUENCE: 73
acatacgtga cagggaatca aacacatttt aatgaggggt cagtaaacat gcaagggtat    60
aattttcttg cttctaatgt atctgtagag ccatacccctg rtggttctac cgagccatgg  120
gtgacagggc aacaacaaca aagcttcttg tcccaagcaa gttggggtag gcctagtggt   180
tctaccgagc cacgcgtgac a                                             201

<210> SEQ ID NO 74
<211> LENGTH: 201
<212> TYPE: DNA
<213> ORGANISM: Triticum aestivum

<400> SEQUENCE: 74
gcccaagttc tttggttgct tccttgtgtc ctcctggtgt gagtggttcc atccaatctc    60
catcgattga acctaaagat gtctcaaacc catttttttc kgtggcttct gaacctgaca   120
gggtggatat gattgatatg aatgaagaaa tgacttctga ttatctactt gattctgatg   180
atgatgatgc taatagaatc t                                                201

<210> SEQ ID NO 75
<211> LENGTH: 201
<212> TYPE: DNA
<213> ORGANISM: Triticum aestivum

<400> SEQUENCE: 75 aagggagcg gccgttgctt tcaatctgaa gcaaagtggt ggtgctttca ttaatgctgt         60
aatttgtcca gaagatagct gagaaaaatg gcatatctct yggcatcggt tttcttagtc      120
atataaagat agacccaaac cagaaacagt caaatggagc actagatata cccgaggctt      180
ccttttataa gaatggtcgc a                                                201

<210> SEQ ID NO 76
<211> LENGTH: 201
<212> TYPE: DNA
<213> ORGANISM: Triticum aestivum

<400> SEQUENCE: 76
tctctcaagg acttgaaggt gaagggctgt gggaaactta agggaatccc tatcggtgtc        60
actgaaaata acccgttctt cgcaacaata ataggagaaa ygcaatggtg gaacgattta      120
gtctggggtg atgaaagtgt caagcgctgg atattgttta ggaactgggg ccccttgcta      180
ccgcattttg caactgaagg a                                                201

<210> SEQ ID NO 77
<211> LENGTH: 201
<212> TYPE: DNA
<213> ORGANISM: Triticum aestivum

<400> SEQUENCE: 77
cacacactgc ggtgttgaaa gcacacttac tcaaggctca ggctaagatg aagcactatg        60
ctgacaagaa caggacacct agggtcttct ctgtgggtga kgcagtctac ttgaaattac      120
aaccttatgc acaacactct gtggtgaata gaccctgtgc aaaactggcc tacaagtact      180
atggaccatt tgaaatattg g                                                201

<210> SEQ ID NO 78
<211> LENGTH: 92
<212> TYPE: DNA
<213> ORGANISM: Triticum aestivum

<400> SEQUENCE: 78
tcgccgtact cgcgggtatt cccctccct cgagggctca gccctagctt atccctctgt         60
yccattcggt tcaccttctt tttggaagga at                                     92

<210> SEQ ID NO 79
<211> LENGTH: 201
<212> TYPE: DNA
<213> ORGANISM: Triticum aestivum

<400> SEQUENCE: 79
acagttttgc ctccgaagca tgagaagctc cctgtgagcg tgtgaactgg atccgtagcc        60
acttcgccgt cagtctggtg aattgatgtt tttgatgtta rtaatggtac catgagccgc      120
cgtgacgacg accggcattg taaatttata agcagcagtt tatattacac ttgttagcag      180
aagtcttcag tcattggtcc a                                                201

<210> SEQ ID NO 80
<211> LENGTH: 201
<212> TYPE: DNA
<213> ORGANISM: Triticum aestivum

<400> SEQUENCE: 80

| | | |
|---|---|---|
| gaacgagaac cacgacaagg tctacgagcg gtacggcgtg aggagctccg agcgggtgtc | 60 |
| gtcggccgcg tcracccggt cagctcggtg acttgaggac ygacctgctc tgccccggca | 120 |
| atcatcggat atcgcatgag cttccgggaa ggcctcagtt ttgctcctgt aactccgatg | 180 |
| aatcgttttc ttgtttcgcg a | 201 |

<210> SEQ ID NO 81
<211> LENGTH: 201
<212> TYPE: DNA
<213> ORGANISM: Triticum aestivum

<400> SEQUENCE: 81

| | | |
|---|---|---|
| aaaggcctta agcatgtctt ctgcaagttt ttgttagtta tcacttcata gcttggtcaa | 60 |
| acttttggc cggtgacaag ttataggtaa ggtctccatc mtctccttta tttctttgga | 120 |
| tcactacagt tcttatagct ttccgaatca tgcatgccat ggtgcaaact caaatatgta | 180 |
| aataatgcgt ttccttttttt t | 201 |

<210> SEQ ID NO 82
<211> LENGTH: 201
<212> TYPE: DNA
<213> ORGANISM: Triticum aestivum

<400> SEQUENCE: 82

| | | |
|---|---|---|
| tcttagagag gatgcaggtt ctcaaggcat ctatcgtgcg aaccctctcc aggatgttga | 60 |
| gtagaacgtg atctggcagc ttgctaagcc tatcaacttc rgcttcatcc gaagctgctt | 120 |
| cgtggcagcg agctttggct ttattattgt tttccatctc ccgcaaagtc cctcattggc | 180 |
| cagggatagc ctcattagat g | 201 |

<210> SEQ ID NO 83
<211> LENGTH: 201
<212> TYPE: DNA
<213> ORGANISM: Triticum aestivum

<400> SEQUENCE: 83

| | | |
|---|---|---|
| gcctccaaca agttaaaaca tgcattgata tcgggtcaaa ctgtgttgag attgatagga | 60 |
| caaaagacc tcgcatagaa gaaattgttg actcgctcaa yggactacgt tcaagccaaa | 120 |
| aagttaccga ggtctcccgt ccgcctacaa ctggcaagaa gctaatgggc tccattttg | 180 |
| gtctgaagaa atgaaacatg c | 201 |

<210> SEQ ID NO 84
<211> LENGTH: 201
<212> TYPE: DNA
<213> ORGANISM: Triticum aestivum

<400> SEQUENCE: 84

| | | |
|---|---|---|
| ccaaagttca agtggcatat gtaggcattc tgcataggct tggactaatt cacacctctc | 60 |
| aagagatttt caaagatgca tctcagctcg ccgcaaaatt kgatcagtgt ccaacacatt | 120 |
| agaagcaaca ccaagttgag aagacactca cctgtgttca atcataccct gcccacgaaa | 180 |
| aaataatcat ccccagtcgg c | 201 |

<210> SEQ ID NO 85
<211> LENGTH: 201
<212> TYPE: DNA
<213> ORGANISM: Triticum aestivum

<400> SEQUENCE: 85

| ttcctgcaac | acctccttca | ttaatttgac | attgtcagtc | aagtctttac | aaggacgagg | 60 |
| ggcacatcga | tatgaaggat | tccatggatc | gttttcttcc | rtgcttgata | catccttacc | 120 |
| tttaccatta | tcttcatcat | aagcagattc | agttgccttg | tgcattatct | ccattggtga | 180 |
| agaacaagcg | tgggattcca | g | | | | 201 |

<210> SEQ ID NO 86
<211> LENGTH: 201
<212> TYPE: DNA
<213> ORGANISM: Triticum aestivum

<400> SEQUENCE: 86

| atagcagcgt | tatattgagg | aacaccaggc | ctaccaatgc | aagaagtaat | atacacgaac | 60 |
| atgacttcaa | atatcctagg | gagggaaaag | tttccagtag | ygaggtcaat | gctgacagta | 120 |
| aatttcaaag | ataccagcaa | agaacagaga | attcaggaag | aaatcttgta | ggtagtttta | 180 |
| gagataataa | tgtggactat | a | | | | 201 |

<210> SEQ ID NO 87
<211> LENGTH: 201
<212> TYPE: DNA
<213> ORGANISM: Triticum aestivum

<400> SEQUENCE: 87

| tgccaaatga | cccaaccgct | ggccagcatt | caggcagaga | tgacgaccag | gaggtggtta | 60 |
| gacaaaagct | gatcaagggg | ttctctgaaa | ttgatggtgg | rcagtttatt | gggataaaga | 120 |
| aaatggggaa | actaagtgag | aagccattcc | gggatgcttg | tgctgtcaag | ctggccccta | 180 |
| aatatgctgg | cgcgaaatct | t | | | | 201 |

<210> SEQ ID NO 88
<211> LENGTH: 201
<212> TYPE: DNA
<213> ORGANISM: Triticum aestivum

<400> SEQUENCE: 88

| caatgatctg | ctgcagcttt | cttagagart | ggtctaccttt | cttgatcttt | cgtgatggcc | 60 |
| agcgatttat | accatgctgc | ctgcatattc | ttttcagggt | rgtagggcac | actccaaggc | 120 |
| tccttgctgc | atctttcagg | ctaccagcaa | agtactgccg | aagaaccggc | aagctcacag | 180 |
| tcttctccgt | ctttgtgcgc | c | | | | 201 |

<210> SEQ ID NO 89
<211> LENGTH: 201
<212> TYPE: DNA
<213> ORGANISM: Triticum aestivum

<400> SEQUENCE: 89

| gcaagagtgg | catgatatac | atacatctta | caatatctgt | cacagcacca | tcaacaacat | 60 |
| acagatcgtc | ttcttcatcy | ttgtcatcgt | cgtcgtgact | yggcccccgt | ttttcgttgt | 120 |
| ttgttgttaa | atttatcccc | ctccgtagta | gtatcgtgcc | cccgcacta | atctgtgcct | 180 |
| agcagagctg | agccgagctg | a | | | | 201 |

<210> SEQ ID NO 90
<211> LENGTH: 201
<212> TYPE: DNA
<213> ORGANISM: Triticum aestivum

<400> SEQUENCE: 90
ttaaccaata ctacccggcg kcatagagtt gtactccttc agacggcttg ctcctggtgt     60
tacgttgtca acatgtcctg gagatttagt aatagctctg ygatgttcta caaaatgaga    120
tacctgtgca cttacatttg tgaaatggtg gtgtacttct tagttctcaa gtcggcctac    180
atggaggtac aaccagtcaa g                                              201

<210> SEQ ID NO 91
<211> LENGTH: 201
<212> TYPE: DNA
<213> ORGANISM: Triticum aestivum

<400> SEQUENCE: 91
gccaagtgaa acgcttcaga ccaatgcgac cgagtatcga ctacccaagc atagcgaaat     60
caagctgatc acttatgtac gtatatatgt atttgggagt ktagtttcca tcaagtctcc    120
gcacgcactg aacacttgct ctaaacaaca atgctttgtg agggtataag agtgtatcat    180
atgttaaata acttatgttg g                                              201

<210> SEQ ID NO 92
<211> LENGTH: 201
<212> TYPE: DNA
<213> ORGANISM: Triticum aestivum

<400> SEQUENCE: 92
cccaatatca atttcccatg ctggttgtga agacagagca gcggatcatc cagctccgac     60
gctatgcatg cgtgcagcct gctgtatttg tttcgcatag ytgcaatact tatctgttta    120
ataatactag ggagtagtag gttattgagg ctgtagcgga agttggaacc tgcctgaatg    180
taagtgaaag gggacagttg c                                              201

<210> SEQ ID NO 93
<211> LENGTH: 201
<212> TYPE: DNA
<213> ORGANISM: Triticum aestivum

<400> SEQUENCE: 93
actagacgta gtagatcatg ccgacctcga tgaggctgat gtggggtatg tgcagcgtca     60
ccgacgggcc cctgcagttc ttgcggagga acgagtaggc rtagtcgatg gcgaacgact    120
tcaagaagtt ggagttcttc ctcgcccttga cgtaggagtg gccgatgatg tacgccacgc    180
cggcctcctt agcctccagg a                                              201

<210> SEQ ID NO 94
<211> LENGTH: 201
<212> TYPE: DNA
<213> ORGANISM: Triticum aestivum

<400> SEQUENCE: 94
actggattct gcgcaaattg acatcgtcga caaagctgac aaaggtgaaa ctgtaaggaa     60
tccatcagtt gaacacactg agatggtcaa gcttgcagga maagatgaag gcaataccga    120
gcgtgcttta catgccggag gcagaaatga agagtcacct gatgttctct cagataccat    180
gcaaactgga attgtagatg a                                                    201

<210> SEQ ID NO 95
<211> LENGTH: 201
<212> TYPE: DNA
<213> ORGANISM: Triticum aestivum

<400> SEQUENCE: 95
agcctgaaga atcttcacca atcgtggata tgatactgta ggaactgccc actccaaatc          60
agaattgtta ggaataattt cttccaacag cttcctgtaa rgtatagacg ggacaaactg         120
ttcttggttg tacagaatcc tgtgcagagt cctgactgct atttctctta tcttatctat         180
tttctcaact gcctgctttg c                                                   201

<210> SEQ ID NO 96
<211> LENGTH: 201
<212> TYPE: DNA
<213> ORGANISM: Triticum aestivum

<400> SEQUENCE: 96
agtgcagaca ttctcgtact cgttcaacag ttcctcaacc attgccttag tctttgagta          60
gaatgaacca gtgaagtttg gtttatcctc ttctttgaag ycgatgcctg acccttcagg         120
atgatttgca tcatattcaa atatgcaccc agtggcatag tttatcacca ataacccatg         180
ctcccgacaa acatcagcta g                                                   201

<210> SEQ ID NO 97
<211> LENGTH: 201
<212> TYPE: DNA
<213> ORGANISM: Triticum aestivum

<400> SEQUENCE: 97
acacgtagga gccaaccttt tgtacctggg agtcgaaacs aatttctgcc ttctgcatta          60
tttcagtgtt aaagatgatg attgcatgcc gcatttgctt ygattgctta ctttctctgt         120
caagtatgat aagaatggag acatctggac ctgccgaatt ctagagtcta gcgtgaatgg         180
ygcaaggtgg accaaatcac g                                                   201

<210> SEQ ID NO 98
<211> LENGTH: 201
<212> TYPE: DNA
<213> ORGANISM: Triticum aestivum

<400> SEQUENCE: 98
aggcactcgt cagacttgag cagcgcrtag tagatccaca acatcgcgct gaagagcgcc          60
accacgtaag ggaccgattg gaacccctgc gtcgacttgc yccggtagat tcggtagaat         120
gtcggcagtg gggccaggta ggtcatgaac gagatgacat tgcctaggag gccaaaggca         180
aaggcccacg ggtgctgaag a                                                   201

<210> SEQ ID NO 99
<211> LENGTH: 201
<212> TYPE: DNA
<213> ORGANISM: Triticum aestivum

<400> SEQUENCE: 99
ccaccggtgc tagcagcgag tgatatgata gaaagtgtgt aacggtcgaa gacatgaacc          60
tgtgcgggtt tcctctagaa cttttatgag gatcgaccy ycagacaagc actttaacgt         120
gcatatgtgt cgcagaagaa gggacggcgg gtgtcgataa gttagtcagt gtttgctcag         180

```
gattcgtgcc attttccrta g                                              201
```

<210> SEQ ID NO 100
<211> LENGTH: 201
<212> TYPE: DNA
<213> ORGANISM: Triticum aestivum

<400> SEQUENCE: 100

```
acggcttcca acctgaggac aactttgtgc gatacgttag gcgtgtcatg gagattgcag     60
tgaacctgaa ggagatatct ctgtatgact ggcaggtctg kaagcgctgc agggacttgg    120
atcccagtat caaggtctgt ccttctcggt atccacggac cagtgagcar aaggatatgt    180
tgagggtgga gattactaag g                                              201
```

<210> SEQ ID NO 101
<211> LENGTH: 201
<212> TYPE: DNA
<213> ORGANISM: Triticum aestivum

<400> SEQUENCE: 101

```
cgtggagcat gccttggcca atggtgaggc tgagcgcgat gtggagacat cggtgtttgc     60
taaacttgcc atatttgaac aggagctccg tgcagtgctt ycaaaggagg tcgaggctgc    120
ccgaggtgcc gtagagaatg gtactgctac acaacaaaac cgtatcgctg agtgtcgatc    180
ataccctctc taccggtttg t                                              201
```

<210> SEQ ID NO 102
<211> LENGTH: 201
<212> TYPE: DNA
<213> ORGANISM: Triticum aestivum

<400> SEQUENCE: 102

```
acttagttag tgacttgagc tactgcagtt gaaagattgt gttggtctga cttgggagat     60
tttgattcga catcatttgt cctgtctttt cgtatcgaga rtggaaatta gacctagaag    120
tcatttgttc tgttgtcgaa tgactgacga tatgagtatc ttcagctctg taaacctgag    180
gatgaaatta gcagtgtctt t                                              201
```

<210> SEQ ID NO 103
<211> LENGTH: 201
<212> TYPE: DNA
<213> ORGANISM: Triticum aestivum

<400> SEQUENCE: 103

```
acgcccagtc ccctcgccac tacgggcgat gttctatagt taggcctcca tgcaatgaac     60
cctgtaaaca aactgcgtgg agctgaaaat aatgtaacat ygtatcagaa ttaaactagt    120
tcgccaacat ggagttgggc tgaactttgt taccaatttt ctccttgtgt ttcaccctgg    180
tgctcatcgg tcttaagggc g                                              201
```

<210> SEQ ID NO 104
<211> LENGTH: 121
<212> TYPE: DNA
<213> ORGANISM: Triticum aestivum

<400> SEQUENCE: 104

```
tactaacatg ttaattttgt tttccaggag gcaatgagga aagacaccct agaacgtgcg     60
mgagagccag ggtttgacct gaaaacgtac ctggcaagtg cgtacatcca cccggttttc    120
``` a                                                                        121

<210> SEQ ID NO 105
<211> LENGTH: 201
<212> TYPE: DNA
<213> ORGANISM: Triticum aestivum

<400> SEQUENCE: 105
tacatcagaa gctttcaatt tgactcctgg aaaagtacca gtatttccat ccctcaattc    60
ttctttcatt tcatacaagt accatataat aaggaaatgc rcccattatt aactggagaa   120
caaacatata tgatttcctt cattaaggta gatgtatgta atccactaca taaaatgtat   180
gtagaaaatg aaatttttca g                                             201

<210> SEQ ID NO 106
<211> LENGTH: 201
<212> TYPE: DNA
<213> ORGANISM: Triticum aestivum

<400> SEQUENCE: 106
gggatgagaa tggctactat gctggatcga atggactgga gatgcaaccg acagtcgttc    60
aagctgagaa tgggtcttat tgtgttatg ttccgggtta ygaaaatggt tatactgctt    120
atagtccagt cgttcctgga actggcgtgg atagtcagta tgtcaacaaa gagccatatt   180
actccgctgt gattcccgtg c                                             201

<210> SEQ ID NO 107
<211> LENGTH: 201
<212> TYPE: DNA
<213> ORGANISM: Triticum aestivum

<400> SEQUENCE: 107
tccatgtccg aacttcgaaa tccttttta ttgtatgatc taatgtactt tgaaaactat    60
gtcggaggta atcgtcaaca tatttgtcaa cttctgcgac raggtcttct cccattggag   120
gtgcccgtat gtcgtgtttg agaaacgaca accaagaaga gagtctaaaa tatctctcct   180
ggatctctgt tagagcttcg c                                             201

<210> SEQ ID NO 108
<211> LENGTH: 201
<212> TYPE: DNA
<213> ORGANISM: Triticum aestivum

<400> SEQUENCE: 108
ttcgccctaa ggacgttgtt cctatcaaaa ctgatggtca ggttcctccc atgattctgc    60
gtgggcccat attggatgaa gtgcatcagc agattaatcc rtggatatat cagataacta   120
gagtttacaa gggaaaggac tatatggaaa ccgagttcat agttggacca ataccaatcg   180
acgatgaaaa tggaaaagaa c                                             201

<210> SEQ ID NO 109
<211> LENGTH: 201
<212> TYPE: DNA
<213> ORGANISM: Triticum aestivum

<400> SEQUENCE: 109
tctattcaga aagcaggtgc ttgatggtaa ttgggacaat gcagtagcta ccttgaataa    60
acttggcctt ctggatgaaa acattgtgaa gtctgctgca yttttgttat ggagcagaa    120 attctttgac cttttgagaa atgacaactt aatgggtgcc ataagacgt tgcaaaatga   180 aatctccccc cttggtgtta a                                                 201

<210> SEQ ID NO 110
<211> LENGTH: 201
<212> TYPE: DNA
<213> ORGANISM: Triticum aestivum

<400> SEQUENCE: 110
gcacgtttag ctgcagcgtt gcacaactcg gacatgatga tcaaccggac gtgatgttag        60
ccattggcag ctacgcgtag ctgcatccag cagaagcata ycgttgtaca gacctgagct       120
ctcgttgcag gaagcaaagc atgcggcaca ggtttcagac ctatcgagtg aaggctgcgg       180
agtccctctc ctgttctaca g                                                 201

<210> SEQ ID NO 111
<211> LENGTH: 201
<212> TYPE: DNA
<213> ORGANISM: Triticum aestivum

<400> SEQUENCE: 111
cttcagtgct aggccaccgt tgcgctgcgg agaggtagat caacactcat gtcctagagg        60
gatcaagaca caattaggag aagacaagcc tgaaaatgtt yagacttgac cctccactta       120
tgtaggcatg agttaaatac atggtcaaac catcgccttg agttttgcta catgggtggt       180
caaatcatcg cctcagattt g                                                 201

<210> SEQ ID NO 112
<211> LENGTH: 201
<212> TYPE: DNA
<213> ORGANISM: Triticum aestivum

<400> SEQUENCE: 112
tctgaacaat tagatgccag agcgccggta cacgttacgt taaaatttgg aatgaaacta        60
tttgcttgtt tctaaataaa gataaaacat atgcgattgc rttcaatata catcggaaac       120
taaaatcccg tatgatactc cgttggtgga gcgcgaggct cgcaccccccc gcccgaaatg      180 gatggcagtg ttcttcttcc t                                                 201

<210> SEQ ID NO 113
<211> LENGTH: 201
<212> TYPE: DNA
<213> ORGANISM: Triticum aestivum

<400> SEQUENCE: 113
atgacatgaa tgcagtgttc aagaagctgt ctgatggcca tgaggaaagt actgtaaagg        60
caatggagtc cgagaatgat catgacggaa gagacgcaac ygaacaacac tgaattacta       120
tcgcatgatt ggtaaaaggg aatgcaagtt gaagaagctt attcttggtt accttatgaa       180
gcactccacg gtacttgggt t                                                 201

<210> SEQ ID NO 114
<211> LENGTH: 201
<212> TYPE: DNA
<213> ORGANISM: Triticum aestivum

<400> SEQUENCE: 114
tgtcggggtt gtttgctttg atccttcgta tctcttcctt gatgaatctg ttgtacgccg        60
aaggaacacg ctgcctcttc tccggaggac gtgcgtgcag ygtttgttcc tgcagcagat      120

```
cgttttgcga cgagaacatc atcgtcggca tccsgaattt ggacgacgat gaagaagaag    180
acgaaccaaa ctccgggtta t                                              201

<210> SEQ ID NO 115
<211> LENGTH: 201
<212> TYPE: DNA
<213> ORGANISM: Triticum aestivum

<400> SEQUENCE: 115
agaaggcact tctggaccat gggcagcaaa tagaccctgc aaaattacag ttggaaaagg    60
agaggctgga aaaaggcag caagaagaga agaaaggat ygaagcccag gtgaaggccg     120
ctgaagctgc tgcacagttc aagttagatg aagaattaag gaagaagagg gagcgagaaa   180
gagaggcagc acgcctggca c                                              201

<210> SEQ ID NO 116
<211> LENGTH: 201
<212> TYPE: DNA
<213> ORGANISM: Triticum aestivum

<400> SEQUENCE: 116
tccccagttt tgctatttat ttttctcccc ggcaaggctg gggtatgtag cgagttcgaa    60
cggtctgctg gcgattcgcc gtaagtaagt tgcgcaaggg ygccctcgtg tttgccccgc   120
cgacgaacta gagttcggac gggtgcaagg agggatggcg aaatgcgcaa gaggtgatgt   180
gtgttttggg tgtgtgttct g                                              201

<210> SEQ ID NO 117
<211> LENGTH: 201
<212> TYPE: DNA
<213> ORGANISM: Triticum aestivum

<400> SEQUENCE: 117
tctgattttg gggcactcta taaggcctaa cttgtggtgg agctgcacct tctaccaaag    60
gtattttgtg gtccaatgct ctatgaggtg gcagtgtttt rggttcctca aacagatcag   120
catattgcag caataactgc tgtatttatg gtggagtttt aaaatcctct ggtgcatcca   180
agagtatgtt gtggatttga c                                              201

<210> SEQ ID NO 118
<211> LENGTH: 201
<212> TYPE: DNA
<213> ORGANISM: Triticum aestivum

<400> SEQUENCE: 118
ctgatggatg ttcagaatca aacttaacct tttcctgtga tatgtataaa ccatccaaaa    60
tgccagattc ccacacctcg ccaccgcggc tgagatcgcc rctcgagctc tccccaggcc   120
ccaaatggaa ctgggggtca cttagttgca catcctccat attctcctca gttgaagaaa   180
tgggagcagt tagaacacac c                                              201

<210> SEQ ID NO 119
<211> LENGTH: 201
<212> TYPE: DNA
<213> ORGANISM: Triticum aestivum

<400> SEQUENCE: 119
tatcacgtag aagaaggacg caatgctgtt ttacctggtg gtgtcttcca cctataaaat    60
caatatatag tcggcggccc agtgtagcga cagtttgttg yttagacggc ggctttagcc   120
```

```
ttactgttgt atgactttgt aaggtcttgt gagaataatt aataaagtgg ccgtatgcat    180
cgcccagatg cagaggccgg g                                              201

<210> SEQ ID NO 120
<211> LENGTH: 201
<212> TYPE: DNA
<213> ORGANISM: Triticum aestivum

<400> SEQUENCE: 120
ccaaaagatg cagttaaaat tccttgtgat gtgaagctgg aggatgaagc attgactgaa    60
gaatctgtag atcaagttgt aactgagcaa gtcaaagttc yatcagatgc tgtacccgac   120
acttcaaaag ttcaaccaga aacaccagtc gaacacgtgg gtacagcagc agaaggggac   180
actgctcaag acctaactga a                                              201

<210> SEQ ID NO 121
<211> LENGTH: 101
<212> TYPE: DNA
<213> ORGANISM: Triticum aestivum

<400> SEQUENCE: 121
cccgctattg gctaagagtc tatgttaatc agatgtcccg agaagacttc raatccctct    60
ccagaggcat gaagcataag atgcaaaagt tctttgggga g                        101

<210> SEQ ID NO 122
<211> LENGTH: 121
<212> TYPE: DNA
<213> ORGANISM: Triticum aestivum

<400> SEQUENCE: 122
cctaaatatt ttagttgcct cttcaatgga gtataaaagg aacattaaga gaatgataca    60
kaacaagaaa gaactaacct tatttttaga attttttgtcc atctttgtta ctgttgcttt   120
c                                                                    121

<210> SEQ ID NO 123
<211> LENGTH: 201
<212> TYPE: DNA
<213> ORGANISM: Triticum aestivum

<400> SEQUENCE: 123
gcccaagttc tttggttgct tccttgtgtc ctcctggtgt gagtggttcc atccaatctc    60
catcgattga acctaaagat gtctcaaacc catttttttc kgtggcttct gaacctgaca   120
gggtggatat gattgatatg aatgaagaaa tgacttctga ttatctactt gattctgatg   180
atgatgatgc taatagaatc t                                              201

<210> SEQ ID NO 124
<211> LENGTH: 121
<212> TYPE: DNA
<213> ORGANISM: Triticum aestivum

<400> SEQUENCE: 124 catctttttaa tggagttgtg atatggaaga ttaatagttt ttttatgggg aaatccggca    60
rgtggaagat taaaaattaa tctgtagaga tgttgctttt attcgcataa tctgtaagat   120
g                                                                    121

<210> SEQ ID NO 125
```

```
<211> LENGTH: 201
<212> TYPE: DNA
<213> ORGANISM: Triticum aestivum

<400> SEQUENCE: 125
aaacgattgg attcactgag ctacacatct gccctatcag ttgctctcgc tgtggttttt      60
gttgttatta ctgctgggat tgccataatc aaagtcatca rtggaactgt agcaatgccc     120
aagcttttc  cagaaataga tgatcttagt tctgtctgga agcttttac  agctgtccct     180
gtccttgtca ctgcatatat c                                               201

<210> SEQ ID NO 126
<211> LENGTH: 201
<212> TYPE: DNA
<213> ORGANISM: Triticum aestivum

<400> SEQUENCE: 126
gacagccatt tcagcgagcc ctcatcctcc tctcctcctt gataaggtag ctccccaaag      60
aacttttgca tcttatgctt catgcctctg gagagggatt ygaagtcttc tcggacatc     120
tgattaacat agactcttag ccaatagcgg gcttctgggg ataaaaacaa tgaattgtag    180
agaagacgcc aaagcttagg t                                               201

<210> SEQ ID NO 127
<211> LENGTH: 201
<212> TYPE: DNA
<213> ORGANISM: Triticum aestivum

<400> SEQUENCE: 127
ccttctcctg ttcatacaaa atcgataagt agcaaaacgg attgtaatga agacggcgcc      60
ttcagagtcc aaggagactc tgatttgagg ttacaatcag rtcaacagac agatagattc    120
caatcctcag ggacattgga tgctctcagg gaaaggatga agagcatcca agccgcagct    180
gtgggggca  atttcgatgt a                                               201

<210> SEQ ID NO 128
<211> LENGTH: 201
<212> TYPE: DNA
<213> ORGANISM: Triticum aestivum

<400> SEQUENCE: 128
atattcacgg aaaagatcaa gaaatatact ccattaaact gcctgggaac cccaagcttg      60
gtgaggggaa acctgaaaay caaaatcatg ctataatttt yactcgtgga gatgcaatac    120
agactatcga tatgaatcag gataactact tggaggaggc aatgaaagta aggaatttac    180
ttgaagaatt tcgtggtaac c                                               201

<210> SEQ ID NO 129
<211> LENGTH: 201
<212> TYPE: DNA
<213> ORGANISM: Triticum aestivum

<400> SEQUENCE: 129
tggcggagca gcttgaaatg gtaaagaagg agcttaaaga aataaaatat gagcatgtgg      60
gagcaaagga ggagcttgct gtggcaaaag agcaacttgc ycagaagaac aaagacctga    120
aggttctaag gaagaagctt caggagagtg aagccatgca cactcaacat gagcagcaaa    180
ttggaagtgc ttctgagcct g                                               201
```

```
<210> SEQ ID NO 130
<211> LENGTH: 201
<212> TYPE: DNA
<213> ORGANISM: Triticum aestivum

<400> SEQUENCE: 130
gtattgagaa gagtttggta accctctctt ccaccccaga atacatagtt ctcaccgcct    60
aggtagtgag taacctccaa agctttcttc acttgagcag yagcataagc atacaccttg   120
acctctgggc tagtagcagc tccgtgcatg taacgtggat gcatgaaaag ctgtgcagtc   180
ccccacaatg gctttatatt g                                             201

<210> SEQ ID NO 131
<211> LENGTH: 201
<212> TYPE: DNA
<213> ORGANISM: Triticum aestivum

<400> SEQUENCE: 131
tacttcggag gaatggaact gtttgtttgt ctttccgtgt gttggtcttt tttccacatc    60 agtgggtct tagatagctt ttttagaatg ctaaacttag raacggaagt actgaacaaa    120
tcaatagagg ttggtaacaa gtgtttgaga ggaaattttt gtctgcagtc tgcactaaca   180
aaatcttgtg gcccttttgtt t                                            201

<210> SEQ ID NO 132
<211> LENGTH: 121
<212> TYPE: DNA
<213> ORGANISM: Triticum aestivum

<400> SEQUENCE: 132
aaaggtactg tctgccctaa gtgaagctgg gcttttacc agtggcggtt tggtgagaga    60
kaaggtaaac ttcataataa gaccttggag acagacattt atcactgctt tagttttgga   120
t                                                                  121

<210> SEQ ID NO 133
<211> LENGTH: 201
<212> TYPE: DNA
<213> ORGANISM: Triticum aestivum

<400> SEQUENCE: 133
gcctgatgga gtcaaacact cagttgaggg atatgttcca aaacccagaa tttcttcgcc    60
agatggcatc cccagaggct ttgcagcaat tactctcatt mcagcagaca atgtcatcac   120
agcttggcca aaatcaacct agccaggctg gtaacctagg aggcaatggc acaggcacgc   180
ggggaaatgt tggtctggac a                                            201

<210> SEQ ID NO 134
<211> LENGTH: 201
<212> TYPE: DNA
<213> ORGANISM: Triticum aestivum

<400> SEQUENCE: 134
acagatcttg atgcagccaa gagaagcgag gagaccaaca tggtgacagc agatgttgat    60
acatccaaga gaagcgagga acagagcaac atggtcgccg ygaagcttga tacagccaag   120
aaaagcgagg agcagaccag cagtgttgct gcggcaggct gattacagga tgggcgcatc   180
tgaacggaag ctacatccaa a                                            201

<210> SEQ ID NO 135
```

```
<211> LENGTH: 201
<212> TYPE: DNA
<213> ORGANISM: Triticum aestivum

<400> SEQUENCE: 135
gctgccttgt cctgctccag gacatactta acactagtcc cattcagtga agctatacga      60
tcagatatcc aagtccgaga tagtacaagt actgcaactg maagcaattg tgccccttgc     120
ttatcaacga ttttaggaac cagtatttta gacattgcag caactctaac aggcaaaggt     180
ctcggcgagc actgcaattg t                                                201

<210> SEQ ID NO 136
<211> LENGTH: 201
<212> TYPE: DNA
<213> ORGANISM: Triticum aestivum

<400> SEQUENCE: 136
gaccatgcac atatgggaag gtgcgaacca tggcagactg tttctggtaa tccgcattga      60
aacaaatgaa gaatgatcgt ggagcaattc accacgctac rtctgtaact cagtggcttt     120
gccattggat atgcactgga cggtgtgtgc gcgcatgatg tatctcaaga tatcagttct     180
cacagtgacc agttgacttg t                                                201

<210> SEQ ID NO 137
<211> LENGTH: 201
<212> TYPE: DNA
<213> ORGANISM: Triticum aestivum

<400> SEQUENCE: 137
agcccatgca ccctagtgcc aacagaggat acaaaactca ggggaatatc aatctcgtaa      60
aggtcctctt ccttcatgct agtgaaatca agtgtatgat rcgtagattg agaaatcaac     120
aatcttggat caaatgcatc caccacgggc tgtgaaaagt atccgtcaaa cgctgagcca     180
tgcaagggtg taagatcaac a                                                201

<210> SEQ ID NO 138
<211> LENGTH: 176
<212> TYPE: DNA
<213> ORGANISM: Triticum aestivum

<400> SEQUENCE: 138
taggcaccgg taaagaagga ggaaattttt tgcacagaag caaagcaaac tgacctctct      60
ctcttcctga tctggaactg tacatagtat aaagaagaac rgcctgttag gggagggtag     120
ttagtgccat ttataatata tattattaac aaaaaagaag taaggaggc tgatgg          176

<210> SEQ ID NO 139
<211> LENGTH: 201
<212> TYPE: DNA
<213> ORGANISM: Triticum aestivum

<400> SEQUENCE: 139
aggtttcatt accataaaga ggaaatttat cagaagtatt tgttgtatat acrtgcaaaa      60
ttaatgaatg atacagagaa tgatgaagtg catacatgcg ygacagaaat agaacgaatg     120
ttgcctcacc accattgtta cctcccatca gtatggcgac taggaataca aaagacataa     180
ttcagtcatt tcagcctgga a                                                201

<210> SEQ ID NO 140
<211> LENGTH: 201
```

```
<212> TYPE: DNA
<213> ORGANISM: Triticum aestivum

<400> SEQUENCE: 140
aagccaacca cctgggtgat ccatgagctt ccccagaata tttctacaga cccttgtctt      60
gctagcattc atgcttccag ccttgttgtt agaagatggt ygatgctcag atgaagaaat     120
tgacgtcgtt ccagattttt gagaccgttt acttccctcc acctctgaat ctgtaccaga    180
atcttccgat ccactgctta t                                              201

<210> SEQ ID NO 141
<211> LENGTH: 201
<212> TYPE: DNA
<213> ORGANISM: Triticum aestivum

<400> SEQUENCE: 141
tcaagtagta tattgtcagg tttcatatcc atatgatata tttgcttttc cttgtgcaga     60
tgatacaaac cttcacaaat gcctctaata atttcataac rtgtcttcca ttcaagtccc    120
cgtaattcat ctggaagatc tgtttgggga tccagctagc tactcgagga acatccaagt    180
agacgagagg cgcaggaaga t                                              201

<210> SEQ ID NO 142
<211> LENGTH: 201
<212> TYPE: DNA
<213> ORGANISM: Triticum aestivum

<400> SEQUENCE: 142
ccagaacttt tccaggtcat cctgctttag atgatgttgg aagaaatgcc ttgagacgct     60
tgcttctggc ttatgctaga cacaatccaa cagttggtta ytgtcaggca atgaacttct    120
ttgctggtct cttacttcta ttgatgccag aagagaacgc attttggaca ttggcaggaa    180
ttattgatga ctactttgat g                                              201

<210> SEQ ID NO 143
<211> LENGTH: 201
<212> TYPE: DNA
<213> ORGANISM: Triticum aestivum

<400> SEQUENCE: 143
ataactcaac cccaagcgac cttctaacaa attcacagca tacagcagca aacgctgtca     60
gagctgatgc aacagtaaca gctgaccaga ctgatacatt ygatgaagag cttaagaagc    120
tggttgcgat gggctttgaa aggactcagg ctgaagttgc tcttgccgcc gcggacggag    180
atccaaacgt tgccattgag a                                              201

<210> SEQ ID NO 144
<211> LENGTH: 201
<212> TYPE: DNA
<213> ORGANISM: Triticum aestivum

<400> SEQUENCE: 144
gaacactgga ttccagacac cacagacaat ttycctgacc atattctcac ttgagaggaa     60
tgaacctcga cgagtgggta gcaccgatac caggcctccc rtgcttcacc ggcttgtacg    120
acagggagaa ctctgccagg tagtgcccga tcatctccgg cttgatctcc acctggttga    180
agcacttgcc attgtagatg c                                              201

<210> SEQ ID NO 145
```

```
<211> LENGTH: 201
<212> TYPE: DNA
<213> ORGANISM: Triticum aestivum

<400> SEQUENCE: 145
gccggcagcg ccccttcgt ccctccgtc ggcttcccg gcgagctacc aagdaaggag    60
gaatggttcg tcccttggaa gtgcggttcg ttcccttgtc yggctttgca cctggagggg  120
atccaccaca aggtcctaga gcaaagaaag tatccaaggc tgcacctgtg tttgaagtcc  180
ctgggttatg gacacccgat g                                            201

<210> SEQ ID NO 146
<211> LENGTH: 201
<212> TYPE: DNA
<213> ORGANISM: Triticum aestivum

<400> SEQUENCE: 146
ttccagcttc tgtgcttcag ggagctcaag acaaatgtta gaatatttac ccaatggatg   60
atgtaatctc taggtatctt ttgtgcgcta gctgtgccaa rcagccgtta tgtatgttca  120
tctaattgtc acttctcatt tctcctgtta acactggtct tacttatgct agtataattt  180
aggaaacctg catagtaaca t                                            201

<210> SEQ ID NO 147
<211> LENGTH: 201
<212> TYPE: DNA
<213> ORGANISM: Triticum aestivum

<400> SEQUENCE: 147
aygagttcaa tgataattta ctaactagag catccatcga cttctatagc ttgtgcactg   60
gtgttatgcc cagcaggtgg aagcattgcc gcatgacgac ygccgacgct tggcacagca  120
acaggcggct cgtttcctcc ggtgacccga caacctggca gttggtgtaa aattgtgaga  180
atctttcaga tagggtgtac a                                            201

<210> SEQ ID NO 148
<211> LENGTH: 121
<212> TYPE: DNA
<213> ORGANISM: Triticum aestivum

<400> SEQUENCE: 148
atcgatgttg tttgtctatg ggagatgtac tacaatagct actgaatctt gcttctttgc   60
maacacatcc atgcttctat cacttgttgt tgcatgacac cctctccatt tttcagtagt  120
t                                                                  121

<210> SEQ ID NO 149
<211> LENGTH: 93
<212> TYPE: DNA
<213> ORGANISM: Triticum aestivum

<400> SEQUENCE: 149
ctcctattct ctctgtctct ctcatgccaa tgycgctgtc ttggtctcat tctcttctct   60
cctgatgtga ctggaagcag ccatgcagtg acc                                93

<210> SEQ ID NO 150
<211> LENGTH: 201
<212> TYPE: DNA
<213> ORGANISM: Triticum aestivum

<400> SEQUENCE: 150
```

```
gaaggaggat gccaaggtcg ataactcact gtaactcact tcttttaagt tcgccttaag    60
ttatctgtac actgatcttc agttatttat ctatcccttt rcagacatca atgagtgcag   120
ttttcgtaga tcagyatcct tgccatggaa cctgcagcaa cacaattggg gacgtacagt   180
tgctcatgcg actctgggac t                                             201
```

<210> SEQ ID NO 151
<211> LENGTH: 201
<212> TYPE: DNA
<213> ORGANISM: Triticum aestivum

<400> SEQUENCE: 151

```
gacgacagtc ttccagaagg aacacatctt gaaagtctac agaaacacct accacgtgac    60
gagccagaag tcacagaaac accttcagtc aatactccgt yggaagcata cttagcagtt   120
ggagcaactg aactggaagt tactaaaaat gagcctagga cagctaaaac tgatgctgag   180
atgatggctg ttgatgccaa g                                             201
```

<210> SEQ ID NO 152
<211> LENGTH: 201
<212> TYPE: DNA
<213> ORGANISM: Triticum aestivum

<400> SEQUENCE: 152

```
gatacaccat gttttctctc gcggcaatcc gacaagaggc gagcatgtca cattcttgct    60
gcagaggaga cgaagcgtga aggcgccgtg gttgtgaata ygcattcttt cctccaaccc   120
ccggatctcc cctctccaaa ggagcttggc gaagctggag gacacgggct ggacacggaa   180
cagttttcct tcatgctcat a                                             201
```

<210> SEQ ID NO 153
<211> LENGTH: 201
<212> TYPE: DNA
<213> ORGANISM: Triticum aestivum

<400> SEQUENCE: 153

```
ttctttgcat gtactgctcc attggtttgc agattttttgg gggcattgtg tatgctggwa   60
acccaacact agaagaaacg gacctcttca ataatgacta ycttctttt aacttcaatg   120 actatccaag tggtatggtt actctgttca atttgttagt gatgggcaat tggcaagtat   180
ggatggagag ttattggcaa c                                             201
```

<210> SEQ ID NO 154
<211> LENGTH: 201
<212> TYPE: DNA
<213> ORGANISM: Triticum aestivum

<400> SEQUENCE: 154

```
tggttcttgc tgctccaatt caacaatgct ttcaggatag ctcaacaaga tttgarcrgg    60 ttctttcct tgctctgctt cctctaacat atctggccgc rggctatctc tgcatagttc   120
ttctgggatg cagacgattt cagaacagtc tattttgcca attccttcaa tagatatggc   180
gtctgctaca tcagtaacat c                                             201
```

<210> SEQ ID NO 155
<211> LENGTH: 121
<212> TYPE: DNA
<213> ORGANISM: Triticum aestivum

```
<400> SEQUENCE: 155
tacataatat agcatatagc ctagctaata ttcttgttta cgcgatttct tgagaacact      60
ygagagttac gtgtcatgtc tattatccat tttgtaatac ccttgtgatt gttagaaagt    120
a                                                                    121

<210> SEQ ID NO 156
<211> LENGTH: 201
<212> TYPE: DNA
<213> ORGANISM: Triticum aestivum

<400> SEQUENCE: 156
gcccaagttc tttggttgct tccttgtgtc ctcctggtgt gagtggttcc atccaatctc     60
catcgattga acctaaagat gtctcaaacc catttttttc kgtggcttct gaacctgaca    120
gggtggatat gattgatatg aatgaagaaa tgacttctga ttatctactt gattctgatg    180
atgatgatgc taatagaatc t                                              201

<210> SEQ ID NO 157
<211> LENGTH: 121
<212> TYPE: DNA
<213> ORGANISM: Triticum aestivum

<400> SEQUENCE: 157
atacaatagt atgtttatgc ttattgtggc aatgaaacat gtgattagcc tatatgcacg     60
yatataacag taaagctaaa cttcaagctt gtcttgtgtg gcgatgagac aattatgcca    120
t                                                                    121

<210> SEQ ID NO 158
<211> LENGTH: 201
<212> TYPE: DNA
<213> ORGANISM: Triticum aestivum

<400> SEQUENCE: 158
tctttcaaga gaggagcttg gctgggcaag tttaccgcta aataaagctt gtctactaaa     60
tcatgcgact taagaaaacc ctggagtttg tatttcgct ytggtttggg tgaatgtaat    120
tattagcttc tgtgaacaac tctgtatctg ggtttcgttt cgtcagtgtg tcgtcgtgaa    180
tgtgaactct tctgaatgcc t                                              201

<210> SEQ ID NO 159
<211> LENGTH: 201
<212> TYPE: DNA
<213> ORGANISM: Triticum aestivum

<400> SEQUENCE: 159
ttctcgcaac aatgccagaa tcattaacag aatgtacaat aggcaaggct tcaacaaaat     60
ctgcctcatc atccaacatt gcaggaactg ggggactctc mtcggcctgt ggctcattaa    120
ccgcttcaga ttcagcctcc gctacaaatg gctccagctt ggtgccttga tgttctgcca    180
tttgtcgtct atcaatcgca t                                              201

<210> SEQ ID NO 160
<211> LENGTH: 138
<212> TYPE: DNA
<213> ORGANISM: Triticum aestivum

<400> SEQUENCE: 160
atacaagcga gagtggtacc ttacggccgg gatattttrtt atattaatta aaagaaaagg     60
```

```
gcaaagttag ttaggttgtg ccgccataga atgcaatgca cgctcccttc atcatcttca    120
tcatcatcat aatgtgat                                                   138

<210> SEQ ID NO 161
<211> LENGTH: 201
<212> TYPE: DNA
<213> ORGANISM: Triticum aestivum

<400> SEQUENCE: 161
tgagctctgg gcggtgaccg atggcaaggt cgccccgttc ccrggcacgt tcaaggagta     60
caagaagatg ctcacgacat aaaccttgaa aaaggacggg rcataggga aggtgctcac    120 acagacatac agagactata tgtatgatat gtactccctg gcattggaaa ctgatgtaat   180
attatgcttg tggcctacct g                                              201

<210> SEQ ID NO 162
<211> LENGTH: 201
<212> TYPE: DNA
<213> ORGANISM: Triticum aestivum

<400> SEQUENCE: 162
tactgatggg aggtaacaat ggtggtgagg caacattcgt tctatttctg tcgcgcatgt     60
atgcacttca tcattctctg tatcattcat taattttgca ygtatataca acaaatactt   120
ctgataaatt tcctctttat ggtaatgaaa cctttgtgca tacgacactc acgtgtctga   180
tttctgtcca acaattgatc c                                              201

<210> SEQ ID NO 163
<211> LENGTH: 201
<212> TYPE: DNA
<213> ORGANISM: Triticum aestivum

<400> SEQUENCE: 163
cgatggtgat ttcttgccaa ggcccttcag ggacaggaag tggttgaagt aaacctgggg     60
atttaacatg ttcatgtttt gcttgctgac agacatcaca ytgatggaca taatcaacta   120
tgtcttgctt caacccagtc cacacaaaca gtttccgaat tttgtaatat gtagcttgaa   180
tgctagaatg ccctccccaca g                                             201

<210> SEQ ID NO 164
<211> LENGTH: 201
<212> TYPE: DNA
<213> ORGANISM: Triticum aestivum

<400> SEQUENCE: 164
cacatatgtg ttcaagatgc tttctccacc accaggagag acctttgatg gtgaagagga     60
gaagcttccg gttctggcat ctgaagaaaa cgcgatgcct raactaggta aatatccaac   120
aggcactcac actagtactg tacccgagga tgagcctttg ttagctctcg aggggaatca   180
aaaaggcgct acttctctag g                                              201

<210> SEQ ID NO 165
<211> LENGTH: 201
<212> TYPE: DNA
<213> ORGANISM: Triticum aestivum

<400> SEQUENCE: 165
ccgtacactt aaatgaatca ccccttgca atattgcaca tgttgcaagt cttacacttc      60
```

```
tatgtataca tatttactat ttacattcct ccaatgaggc ycatatatat gatgatgcta      120
tatcctaaca aattgcaatt tacacwgctt cagaacttgt tgaattcttc agacctcatg      180
tcctgccttg ccatgcagga t                                                201
```

<210> SEQ ID NO 166
<211> LENGTH: 201
<212> TYPE: DNA
<213> ORGANISM: Triticum aestivum

<400> SEQUENCE: 166

```
ctccctccgt cccacaatat aagatccttt ttcaagttat actgtgggac gaagggagta      60
atatttacaa gatcgcgtcc actaaaccta tcatgttaga ygagttcaat gataatttac      120
taactagagc atccatcgac ttctatagct tgtgcactgg tgttatgccc agcaggtgga      180
agcattgccg catgacgacy g                                                201
```

<210> SEQ ID NO 167
<211> LENGTH: 201
<212> TYPE: DNA
<213> ORGANISM: Triticum aestivum

<400> SEQUENCE: 167

```
cagcatgaac tgcaagggca tgcttgacag ctccatcttg tttggcttct tttgacaagc      60
ttgccattga tgacaacagg tcacgtttgt tattagagtg yagcatgacg cagagcaaat      120
tgtaggctga gaattcaaaa taacaaccat tgtttccctc tctatatagc ctcttcagtt      180
gtgactggca ctggttaaat t                                                201
```

<210> SEQ ID NO 168
<211> LENGTH: 201
<212> TYPE: DNA
<213> ORGANISM: Triticum aestivum

<400> SEQUENCE: 168

```
gactttcggt ccataggttg agtggtaaat agtccagtac catcttttaa ggctatcaaa      60
cctgtgtacg gacttcggca tcagtatcgg ggcagcttct rtatcagaca taagcatgga      120
attttggags aacatatgct acaagtattt tgttttactg ttgttatcag ccctgatat       180 tagccgacga gagacgactg a                                                201
```

<210> SEQ ID NO 169
<211> LENGTH: 201
<212> TYPE: DNA
<213> ORGANISM: Triticum aestivum

<400> SEQUENCE: 169

```
tcttcctagc gcccatcctt ctactttga accaggattc agacatcgtt gcaggattcg       60
gtgacagaca gcgttacttc cctgtgacaa tttctatttc ygggtatttg ctattggcat      120
cattgtataa gatatgggag gaggcttggc ctggcgctgg cagtggagga tgggctcttg      180
atatcggggg ctcagtttgg c                                                201
```

<210> SEQ ID NO 170
<211> LENGTH: 201
<212> TYPE: DNA
<213> ORGANISM: Triticum aestivum

<400> SEQUENCE: 170

```
tggctgggtt gcggatgacg tagccatcga ccaaggtata gagatcagac tgcacaagca      60
```

```
acaaatcaga tgtagccttc acgggcagaa accttgagcg rggaacgttg atgccgattg    120
ccttctcaaa gaacctgatc gctgctccag ctgcggtttc tagctgcagg actttcacgc    180
catcaacttc cttagggttg g                                              201

<210> SEQ ID NO 171
<211> LENGTH: 201
<212> TYPE: DNA
<213> ORGANISM: Triticum aestivum

<400> SEQUENCE: 171
cattgttcct tagtgttgaa gtatagctgt cttgtggtgg tagcacacga acagttgcac    60
gcagttcttg gatggcagac ggtggaggtg atgatgtagg rgagcagtaa ccagtatgca    120
ttaacacagc cacaaggtct gaatcatttg tataaacatc tgttccccaa agctgagcgc    180
cttttacttg ccgattcgtg g                                              201

<210> SEQ ID NO 172
<211> LENGTH: 201
<212> TYPE: DNA
<213> ORGANISM: Triticum aestivum

<400> SEQUENCE: 172
agtttggagc atgggggttt gctgctgcac taatggaggc attggggta ctctctatac     60 atgtatgtat attgttagtc taggatccta ggatgtagaa rtgagtctcc ctccctcccc    120
catctgtgtg gagagatcga tcttgtaact tcaccataca tgtaaatttt gcttagcaga    180
tgccagcagg gacggaaaag a                                              201

<210> SEQ ID NO 173
<211> LENGTH: 201
<212> TYPE: DNA
<213> ORGANISM: Triticum aestivum

<400> SEQUENCE: 173
cgaaggaggt gtggcgaaaa gacmgattcc atagtgtgtg gacctgaatc ctccatgcag    60
ggtcttttgg gatgcatgga gagcaagcct gagaagagct rcactagaca agttttaaag    120
cctacgagtg tgcagatttg catcatattg ttgtgtaaga agcatttgta tctggtgctg    180
tgctggggct tagggcctgc t                                              201

<210> SEQ ID NO 174
<211> LENGTH: 201
<212> TYPE: DNA
<213> ORGANISM: Triticum aestivum

<400> SEQUENCE: 174
acccaatgga gaacacgccc gatgtagtga ttccggaata tcaaagctag tgtttgggca    60
ctaaccggag cattatggtt aacttttcg gagatgtctt ytctgtcttg ccattttcca    120
ggttttcgca tacatgagaa agtagtgcat atgttagcag tcacttgagt gtgtaaactc    180
aagctccttt ttgctgctgg c                                              201

<210> SEQ ID NO 175
<211> LENGTH: 201
<212> TYPE: DNA
<213> ORGANISM: Triticum aestivum

<400> SEQUENCE: 175
```

```
tactttgcga ttttttggaag gtggtatgct tgcggggttg cattagactg acaagcgggt    60
tcgttttgcg gggttgatgt ggctttctgg ttattggtga raatcggcct actagctgaa   120
acgataggcg gccaaacaaa aaggtttatc gtgtaggggg gcatcaaatg cgatgagggg   180
gagaagctga agaagaggat g                                             201

<210> SEQ ID NO 176
<211> LENGTH: 201
<212> TYPE: DNA
<213> ORGANISM: Triticum aestivum

<400> SEQUENCE: 176
tatgttgtct ctgttgctac tgaagcaagc attatcgaaa aaagtacatc aaagaggagg    60
agaaagaaga gggttttgcc ttctcctgag ctagagacta ytgatcatat gcaggactcc   120
tactggtctg gtttgagttt gcttaatcac ccgattcata gcctcaaaag agcttctacc   180
aacacgaggc caaggcgtag g                                             201

<210> SEQ ID NO 177
<211> LENGTH: 201
<212> TYPE: DNA
<213> ORGANISM: Triticum aestivum

<400> SEQUENCE: 177
ttgttatcct tgctgctgct ccatttcagt tttcattgag gctgtgtgct ggcgggttga    60
acaagaactg tcattggttt cggggtggtt ttattttggg rcagctgtgg agttggattt   120
gtatatttac ggggactgta taatttggcg gaactctgcc gactcctatc tcatgtgtca   180
gtatcattcg ctgtgtatac a                                             201

<210> SEQ ID NO 178
<211> LENGTH: 201
<212> TYPE: DNA
<213> ORGANISM: Triticum aestivum

<400> SEQUENCE: 178
tgatctgttc catggccttc atgcttatcg gcggctcctt gcagcagctg gaactgcgtt    60
tgatctgttc catggccttc agtacaggta cggggggcat rgcttcttcc acggcggcac   120
tagccagtgg ctgccacggc gataacttgt gatattcagg aacactagtg tcagttctgc   180
tggtaatgct gctgccatat g                                             201

<210> SEQ ID NO 179
<211> LENGTH: 201
<212> TYPE: DNA
<213> ORGANISM: Triticum aestivum

<400> SEQUENCE: 179
atgacactgc agctcttgat ctgggacgta ccagatggag ctcacaacgc tggcatctct    60
ggtgcaaatg acagtgcagc tcttgatcac caacttcata ygggactacc agatggtgct   120
caattagatg ctacaccaca agaagcaact gatgcagttg acgctacagc tgcatttggt   180
ttgcaaatgc catctgatga a                                             201

<210> SEQ ID NO 180
<211> LENGTH: 201
<212> TYPE: DNA
<213> ORGANISM: Triticum aestivum

<400> SEQUENCE: 180
```

```
gcggcagctc aagctacagc tcctcagact cggaggacaa gaagaagcgc cgacgcaaga      60
cgacgcagaa gaagagaagg caccgtaggg atagcacgtc rtcctcctcc tctggatctg     120
aatctgagtc cgagtctgat tccgattctg acggcaaagg cagccggaag aagagcaaga    180
agcacggcga caagcgccga t                                                201

<210> SEQ ID NO 181
<211> LENGTH: 201
<212> TYPE: DNA
<213> ORGANISM: Triticum aestivum

<400> SEQUENCE: 181
tgcgacaatt aaatatgtcc ccagatgaag atctgtcatt ctgtgatgat aaaggagaaa      60
ctgccaaggc taaaagaccc tgggatttta tatcagcagg mcacaaaata ggaaagccag    120
ttcctctatt taaggaactg aaagatgaag aagttgaggc gtttaggatc aaattcgctg    180
gcagccaagc tgaaaggatc t                                                201

<210> SEQ ID NO 182
<211> LENGTH: 201
<212> TYPE: DNA
<213> ORGANISM: Triticum aestivum

<400> SEQUENCE: 182
ggctacctgc tgacagccac atttatctgt caggccgctc tctgagtgga atgtttacag      60
aaacctcata tttgtttgta aaagttttag aacaactata rttttgtgtt tgtatcaggc    120
aatttataca ctaggtgtag ggcaaaagrt agggacaaga aaggttcgga aatttatttg    180
taaaacagac acagccaatc c                                                201

<210> SEQ ID NO 183
<211> LENGTH: 201
<212> TYPE: DNA
<213> ORGANISM: Triticum aestivum

<400> SEQUENCE: 183
aagcaaatcc agaaaaacca attggaaatc gacgcggtat actgctcctc tggtttgtat      60
gccatccagt gacctgatca cccttacaaa gggggccttc yaaaaccaat ttatacttgg    120
tcccaacatg cgttgctact ggccatgtac caaagcgcct gatttcctc atttcttcaa    180 atagatcaac tgagtatgct c                                                201

<210> SEQ ID NO 184
<211> LENGTH: 201
<212> TYPE: DNA
<213> ORGANISM: Triticum aestivum

<400> SEQUENCE: 184
gcaccagttc catcaacgcg agattcgatc aagcggtgcg aaagagaaga ctgatatgtg      60
gcaagctttg aaactctgag cagcaagctc tgttattagg mggctgcctc aagcgatccc    120
cattaggaag ctgtaggatc gtttgactcg gagattgtgg ggagtggtgg tagagcaatg    180
ggttctcttc ctatctcgtt c                                                201

<210> SEQ ID NO 185
<211> LENGTH: 201
<212> TYPE: DNA
<213> ORGANISM: Triticum aestivum
```

```
<400> SEQUENCE: 185
gcccaaccgg ttctccccat caggatgcca tgttttgtat aggaaaaggc gggagtctgt    60
ctgaccctag catcgcaccg ctgttaggtt agctaaggct rtagcatata tttgggccct   120
ttcacataag cttcatcaat catctagggt attggtgtaa ccataaagcg gagctgttgc   180
ggaacttcgg ttggtgcggc t                                             201

<210> SEQ ID NO 186
<211> LENGTH: 201
<212> TYPE: DNA
<213> ORGANISM: Triticum aestivum

<400> SEQUENCE: 186
ctcatccttc cgcggcccgg aaggataccc ctgtacattg cgtggaacgc ggtcctccta    60
caatagtggc aatgcgcctg cttgcttggt tcgccggttc kwgagtaaat gatggctgtg   120
ctgctgcggc ggtgacagct tcgggtggat gacagttaca gttttgggga ataaggaagg   180
gggtgctgca ggaatggtta a                                             201

<210> SEQ ID NO 187
<211> LENGTH: 166
<212> TYPE: DNA
<213> ORGANISM: Triticum aestivum

<400> SEQUENCE: 187
gtcttaacag ataacagtag catggtcaca ttttattgtg tcaaataagc aagtatgatt    60 caaatycat tgtgacctca gagctcatga aactgaaaac aaagctctaa ttgtcccaat    120
ttaatgggat tctgttccga tttctcaacc aatatcaaat gaacag                  166

<210> SEQ ID NO 188
<211> LENGTH: 201
<212> TYPE: DNA
<213> ORGANISM: Triticum aestivum

<400> SEQUENCE: 188
gcaagatacg ctcctgaagg ttttcagcga ggacaaggag gagtttgcca gaacgacagc    60
cctttcatct tcctcatcgt cgacgtccct cagcaaggaa yttgacaggt cggcctagga   120
gcaccctggc tcattcttgc catattggta gctgattttt attttccgt ctgaaactgc    180 tcgccagatc tttcttttct g                                             201

<210> SEQ ID NO 189
<211> LENGTH: 201
<212> TYPE: DNA
<213> ORGANISM: Triticum aestivum

<400> SEQUENCE: 189
tcagacttct cctcctctgt cttggccctc aacgactgta cccatggggt sacgagctta    60
tcgtcaatgt aggcggccca aaaacgggca attgcacgtt ygtagggtc agagggaaga   120 agagaggggc cgacaaggaa cgcctcatcg atgtactgaa cgatgatcat tgactcgcaa   180 atgggttttcc cgttgtggac g                                            201

<210> SEQ ID NO 190
<211> LENGTH: 101
<212> TYPE: DNA
<213> ORGANISM: Triticum aestivum

<400> SEQUENCE: 190
```

```
atgaatgaat ctgggaagca caatgcccat ccacaggcaa gatgcttcgg rtgtgtagac      60
aagtagtgtg tgtgccgttc gtcagcctgc gatgctgttt a                         101
```

<210> SEQ ID NO 191
<211> LENGTH: 121
<212> TYPE: DNA
<213> ORGANISM: Triticum aestivum

<400> SEQUENCE: 191

```
caccacaagg tccacaacta cagctaactc ggtcgagatg gctcgcactg cagctactaa      60
rctcgtgctg gtcgccctgg tggcggcaat gatcctcgca gcctccgacg cggccatcag     120
c                                                                    121
```

<210> SEQ ID NO 192
<211> LENGTH: 201
<212> TYPE: DNA
<213> ORGANISM: Triticum aestivum

<400> SEQUENCE: 192

```
cgaaccgcgc aaggcttaaa gaggcagtgg aagaacgggc gctgatggat gagaattatc      60
aggaagcaac cgccatgctg aaggcaaagc tgagagagac rtgccgtgag gtcctgaagc     120
tgagagaaga gcttaaacga ccagaagccg catcaaactg acgcagtaac ctttcttctt     180
cgcagctacg tgctcctaac c                                              201
```

<210> SEQ ID NO 193
<211> LENGTH: 201
<212> TYPE: DNA
<213> ORGANISM: Triticum aestivum

<400> SEQUENCE: 193

```
tgtttatagg ctgcggcatt tcggtgcctc caagccgctg atagggtcga tcgagcattt      60
tacaggcacc tctcgagcgt ttgcagtgcg ttaagcaata ygcaacttgt gacgatgtct     120
gagaactgct gctctttatg cttttgttac aagcaaatat atagcgcgta cattagggaa     180
aatacatccc actgtcgggt g                                              201
```

<210> SEQ ID NO 194
<211> LENGTH: 201
<212> TYPE: DNA
<213> ORGANISM: Triticum aestivum

<400> SEQUENCE: 194

```
atgatcagtg ccttcgagag cggctcttcg caggctccgc cttcagtgcc aaggatcaag      60
tcggaagggt cgttggaagg gatgctatcg gcttccacca rtcctccaga caagtcatct     120
ggcaaagtga ccgttacttc tggtgatata ggttccgagt cgcggttagg aaggcacatc     180
atcaacaaga aaccaagcgc g                                              201
```

<210> SEQ ID NO 195
<211> LENGTH: 201
<212> TYPE: DNA
<213> ORGANISM: Triticum aestivum

<400> SEQUENCE: 195

```
ccgtaatcgc gtctagacca tggcagagtg caataacacc gcgacccggg cgacctttca      60
gtcggtgtcg cccttgccct tgtctcgttc tgatgcaata rggcccgaag aaatttaaag     120
```

```
agcttgtacc tttgaatatt atagagcgtg caccgagcaa tcgtgatgtt caaatcaaac    180
cgtcgccttc aggcacttga t                                              201

<210> SEQ ID NO 196
<211> LENGTH: 201
<212> TYPE: DNA
<213> ORGANISM: Triticum aestivum

<400> SEQUENCE: 196
gtgaactatc tcaggggtgg ttgtaagtat agaaaggctg gtaatgtaca ttatgtttgt    60
actagagcat tgtggtatcc tgtttgccgt ggttaattaa kggcttggta attaatagat   120
ggaagatgat gtcgttttgt cttgtggcaa gtgtgatgac acatattgta gggttggttg   180
aaaagtatat tatgttacta g                                              201

<210> SEQ ID NO 197
<211> LENGTH: 201
<212> TYPE: DNA
<213> ORGANISM: Triticum aestivum

<400> SEQUENCE: 197
acatttgatc ttgtctccaa atcatcattg atagaatcat tgaacccttg taagatarct    60
ccgcgctttg ctgaagaata cctatctgtc tcaggtccct yattaagttt accgtagcag   120
ctatcacaga cacggtaagg cttgtttggg tttggtgcta atgaagcctt cagagatttc   180
ttactgctgc aggaatgaca a                                              201

<210> SEQ ID NO 198
<211> LENGTH: 201
<212> TYPE: DNA
<213> ORGANISM: Triticum aestivum

<400> SEQUENCE: 198
gtttcaccat cagccctctc gacaccgatg ggactgaacc tcccaccaga caatcaccgc    60
catgggggca ctggcatagg cagtgcccct ttctactggg rtggtgttaa tcctagcagc   120
agcggtagta ccgggagcag cggragcaac agcatggggt tcgagccaca gagcacgaac   180
tcaattctgg agaacagtgt a                                              201

<210> SEQ ID NO 199
<211> LENGTH: 201
<212> TYPE: DNA
<213> ORGANISM: Triticum aestivum

<400> SEQUENCE: 199
atgcatgtct gctttcttgt gaggaraagt gctccggtag agaaactaat acagtttctt    60
cagaagtgca tctaagctca tcaactttag gactggtgca rtattttatg aattagttgg   120
tattaaactg tatctccacc agaactcaga atgtttcctg atatgtttga tgcttaaata   180
gaaacaatgt tcctcatgtc a                                              201

<210> SEQ ID NO 200
<211> LENGTH: 201
<212> TYPE: DNA
<213> ORGANISM: Triticum aestivum

<400> SEQUENCE: 200
cagaaatctg cagcccttca aagatcggcc ctcccagggt atcttgggaa tggaatgaca    60
tctctgatgt tctccaggcc cgtggcgaaa aggatcatcc kctcgaaccc caggccgaac   120
```
ccgctgtgct tcactgagcc aaagcgtcgg aggtccaggt accactcgta cggctccaga    180
ggaagatcgg cgtccagtat c                                              201

<210> SEQ ID NO 201
<211> LENGTH: 201
<212> TYPE: DNA
<213> ORGANISM: Triticum aestivum

<400> SEQUENCE: 201
tgaatgcata ttgctgcagt gaagttaatt ccacaaacaa cactcctgac ttgcttatct    60
ttcagagctt caactagtgt aggagaattc ctatcatcg yatcaccatg tcctaaccgg    120
ccattagcac cyttacccca tgtatacacc tctgtcctgg aagtcaaaac agcaacatga    180
taagcgccac atgaaatctc c                                              201

<210> SEQ ID NO 202
<211> LENGTH: 201
<212> TYPE: DNA
<213> ORGANISM: Triticum aestivum

<400> SEQUENCE: 202
tttgatccag ctggatagag cccgcagaat gttgcgggtg cgattcgatc ttcactagcc    60
tggtctggac aactcaggat gctcctgtat gttatagcag rtttgcatgg cggtcatccc    120
attataaacg atgaacttcc atgcgaattt gagaatgttg tacggtggtg tgaagcctgt    180
tgatatattg gttatatggc t                                              201

<210> SEQ ID NO 203
<211> LENGTH: 201
<212> TYPE: DNA
<213> ORGANISM: Triticum aestivum

<400> SEQUENCE: 203
acattgattt gtagctgtcc ccgtacaccc agatatcttc aataattgga gggaagacat    60
atactttctc cagatactca actgcgacat actcccttg ygatagctta aatatgttct    120
tctttcggtc aataaccttc aggattccat ctgggctcat ctctccaata tctcctgtat    180
gaaaccatcc atcaaccatg a                                              201

<210> SEQ ID NO 204
<211> LENGTH: 201
<212> TYPE: DNA
<213> ORGANISM: Triticum aestivum

<400> SEQUENCE: 204
attatatacc atgttctgaa cagaggagcg gagttattgt aaaaactatc taatgtttag    60
ttgcttgtat aaaacacaag ttttgaagaa ataggatat mtgtgttgtg aatatacatg    120
gcctgcaaat tccagtgcta acagcataat atttcaaatg tggatgtaag gccgatcaga    180
tttcaccaaa gtagccatgg g                                              201

<210> SEQ ID NO 205
<211> LENGTH: 201
<212> TYPE: DNA
<213> ORGANISM: Triticum aestivum

<400> SEQUENCE: 205
ctgctttcca ctgaaatctc ctatctgcaa ccatacacac tgttgctctt cttgctcaat    60

```
tctgctctca gcaaccattt cyccatatat aagtcactat mccctctgca tttcccaccc    120
cttcttcagc catggattcc tgaagaagct ccgtgctacc agaggaggct tctgctgtga    180
gcaattgcaa gctgtgtgag t                                              201
```

<210> SEQ ID NO 206
<211> LENGTH: 201
<212> TYPE: DNA
<213> ORGANISM: Triticum aestivum

<400> SEQUENCE: 206

```
cccattagac ccgttcaaat atggctctcc tgaatttctt gggctaccta aattctcagt    60
tgccattgat atgtcattaa caggcactcc agaaagtggt rgcagtctac tgtgcttaac    120
tgcccctgcc cctgctcctg ctcctgctcc tgctccttca ggtagcttct ctgccatacc    180
cttcaattgt gcagtgagcg a                                              201
```

<210> SEQ ID NO 207
<211> LENGTH: 201
<212> TYPE: DNA
<213> ORGANISM: Triticum aestivum

<400> SEQUENCE: 207

```
gtgggttgac tatgccaagt ttataggcat acaataagtt gaagacagac ctagaattgc    60
acaaatcatt cgcaatgttg attcgtcgct acgccatatc ycatatcctt accgtgcttc    120
ctatcctgac tcatctgcct tcataggaga cactaacgac agaggtcgat tgcttttgct    180
ggaaaagaaa gatgcgtgca g                                              201
```

<210> SEQ ID NO 208
<211> LENGTH: 201
<212> TYPE: DNA
<213> ORGANISM: Triticum aestivum

<400> SEQUENCE: 208

```
gtcgcccct aacctttccc tgctttccac tgaaatctcc tatctgcaac catacacact     60
gttgctcttc ttgctcaatt ctgctctcag caaccatttc yccatatata agtcactatm    120
ccctctgcat ttcccacccc ttcttcagcc atggattcct gaagaagctc cgtgctacca    180
gaggaggctt ctgctgtgag c                                              201
```

<210> SEQ ID NO 209
<211> LENGTH: 201
<212> TYPE: DNA
<213> ORGANISM: Triticum aestivum

<400> SEQUENCE: 209

```
tatgactcaa aactgtcrga acagacatgg taacatgagc gctgaaaggc gagcttaaca    60
agttttacag cttagttggc tgcctgttct tcttcttgat yccagactttt gaaacctgga   120 ggctgcggta cacggcgctc agccttgcaa gggccggctt ggtcagatca ggcctgtagt    180
agttgtcgca gacctggttc t                                              201
```

<210> SEQ ID NO 210
<211> LENGTH: 201
<212> TYPE: DNA
<213> ORGANISM: Triticum aestivum

<400> SEQUENCE: 210

```
tgaacgatgg cgttagtgag aagtcagtgt catctacagc tcaggagtcg tcacaagccg    60
```

```
gaggacatgg tgcgtcaaca ccctcggatg cagaaaggga ygaagtctcc atttcaagcc    120
gattgttgga aaataaaaat gcaggtacta tgaaccaggg cctgtctgct tctgatatct    180
cccacacggc ggagagctac a                                              201

<210> SEQ ID NO 211
<211> LENGTH: 121
<212> TYPE: DNA
<213> ORGANISM: Triticum aestivum

<400> SEQUENCE: 211
tttacggatt gtttaattag tagttggcat agttgtagtt ttcatagttt gctgatgcat     60
yctatttatt cagttttttgg acgctgattt aagtactatt actatttctg gttatgtagc   120
t                                                                    121

<210> SEQ ID NO 212
<211> LENGTH: 201
<212> TYPE: DNA
<213> ORGANISM: Triticum aestivum

<400> SEQUENCE: 212
atttatcatt gccaaatggt tcaatcccgg tgatgtcatt gctggatatg caaggtctca     60
ttgggcaagg tattcgaagt tcttaagtgc ctaggaacct mgctgtgctt ttgtattgac    120
gtgattagca agtgtattta ccgaagcata gatgtaatgt gggttatgtg tagcaccgaa    180
tctgagatgg ctgcaatcca g                                              201

<210> SEQ ID NO 213
<211> LENGTH: 201
<212> TYPE: DNA
<213> ORGANISM: Triticum aestivum

<400> SEQUENCE: 213
actcctacat gtcccctggc aagaaagagg gcagcacatc cattgatttg agcactggca     60
gtgcaagcag tagaggaaaa catgaacata tttcttctga rccaaagaca tccttgcaga    120
aaaatcccaa tggtcctaat gctttaggtg acttctctga gcaaaatagt ccctccttag    180
tttatacata tcctgattct g                                              201

<210> SEQ ID NO 214
<211> LENGTH: 189
<212> TYPE: DNA
<213> ORGANISM: Triticum aestivum

<400> SEQUENCE: 214
gtggtttgca atttgcctgg ttttagctat atggcattgt gcttgtaggt gcatgtagat     60
gctggtacgg atcatgttgt aaaggctaac aataagtgct rcctgggcca aagaccaaat    120
aggaatttta ccttacgttt catggattct ttcatgttta tggttaattt ggtggttcca    180
caggaaact                                                            189

<210> SEQ ID NO 215
<211> LENGTH: 201
<212> TYPE: DNA
<213> ORGANISM: Triticum aestivum

<400> SEQUENCE: 215
cttgagttgt aaaacaactg tacatactag gtcaggatgg tgtatatact ccctttttc     60
```

```
ctccaagtgt tcagtcaggg agtattgtca actgggaaat ratccagatc atcctatttc    120
tagttgagat tacgtatatg cagaaccaaa actataaaca gacatgaccc ccagtagcat    180
aagtctaytg catgccttac a                                              201

<210> SEQ ID NO 216
<211> LENGTH: 121
<212> TYPE: DNA
<213> ORGANISM: Triticum aestivum

<400> SEQUENCE: 216
aagaacgtac taaacataaa tcaagaacca caccctaaat ctaccgctat tacggccaac     60
raaggcgccc agaccaacac atacttgcag gcatataaag ggttacagat cagacgaaat    120
a                                                                    121

<210> SEQ ID NO 217
<211> LENGTH: 201
<212> TYPE: DNA
<213> ORGANISM: Triticum aestivum

<400> SEQUENCE: 217
tagaatttgg acgctagtgt cagagtttga gcagtatggc accatcaaga tcccttgtga     60
tcttccctac aaaaaaaaga tcccttgtga tccattctgc ratggggcct gaacagcctt    120
ttacgtttgt gagagtcgaa tcttgtgttg ccatgtggaa tgtttgtctt tgtttcagag    180
caactcgtgg tgcagtatct g                                              201

<210> SEQ ID NO 218
<211> LENGTH: 201
<212> TYPE: DNA
<213> ORGANISM: Triticum aestivum

<400> SEQUENCE: 218
aaaggatact gctaagccag tagaaagtaa ggcccagtct acatcgggaa tcgaagactt     60
atttaaagac tcgccagctg tggcagcgtc ttcagctcca rttgcttcca aatcaaaccc    120
acagacagat atcatgagtc tgtttgagaa gtcgaatatg gtatcaccat ttgctatcca    180
tcagcagcag cttgctttta t                                              201

<210> SEQ ID NO 219
<211> LENGTH: 201
<212> TYPE: DNA
<213> ORGANISM: Triticum aestivum

<400> SEQUENCE: 219
gggggccatg gtgggatttg gaccaggttt caccatggag acggtggtgc tgcgcgcaac     60
tggcttttta aagaaaagtt agaacttcat taagcacaaa ygggagaaca agaacaaagt    120
ccatgctctc aactgaaata acttcgatac tctactatta tgtgtgcaca ctctaagtga    180
ctcataacaa taagtggtta c                                              201

<210> SEQ ID NO 220
<211> LENGTH: 201
<212> TYPE: DNA
<213> ORGANISM: Triticum aestivum

<400> SEQUENCE: 220 gaccttttt ccaaccgcca gaagcagtca gagctcatca aatgaaaaaa agcgactcgt      60
ctcaaagtgc tcagagcacg aaaggtcctg gtgttcatga yatgctttcc ccaaacaatg    120
```

```
gtattgggca tcctaaaccc ttcttccaat ctcaggaacc agttgcacca cagccaaaaa    180
atgaagctac atgggtgtac c                                              201

<210> SEQ ID NO 221
<211> LENGTH: 201
<212> TYPE: DNA
<213> ORGANISM: Triticum aestivum

<400> SEQUENCE: 221
tcaactggga aatratccag atcatcctat ttctagttga gattacgtat atgcagaacc    60
aaaactataa acagacatga cccccagtag cataagtcta ytgcatgcct tacataacac   120
ccactgtaat gatctgtaga tctcaccagg acgttgccta ttttcatagc tcagaggaag   180
caacattcca gtcacagaaa g                                              201

<210> SEQ ID NO 222
<211> LENGTH: 121
<212> TYPE: DNA
<213> ORGANISM: Triticum aestivum

<400> SEQUENCE: 222
atcagatgac caggcaatac gaaataatgt ttcttggaga aatgcggaag attacaagat    60
mtctacggta acttataaca tattacctcc atcccaaatt acttgtctta gatttgtcta   120
a                                                                    121

<210> SEQ ID NO 223
<211> LENGTH: 201
<212> TYPE: DNA
<213> ORGANISM: Triticum aestivum

<400> SEQUENCE: 223
gcttgagaac tgatccttga tcctcttcac tcagctacca agctatgtgt atctagcgct    60
catcttaatc cttgatcctt gatcttgtca gttctttcaa rgtttgcagc tgggctcccg   120
gtggcctaag agtggttttt atctgtgttg ctttaatggt tcatgtggtt tgtacgggca   180
gtgtgttctg ctcatgtatc t                                              201

<210> SEQ ID NO 224
<211> LENGTH: 201
<212> TYPE: DNA
<213> ORGANISM: Triticum aestivum

<400> SEQUENCE: 224
gatggtgaca tgctggtgca attcttagag ctcaccagtg agcaacagca aaactgttct    60
tgatgatggg tcttcagtaa aggcaccaca caggtctatc yccgtttttcc aggtcatgcg   120 aatgttggag cgggtccact atgcgctgaa cygaggtttt ctgcaaccaa cttggttcac   180
tcataccact ggacataccg t                                              201

<210> SEQ ID NO 225
<211> LENGTH: 201
<212> TYPE: DNA
<213> ORGANISM: Triticum aestivum

<400> SEQUENCE: 225
ggagcctgag ccatggctga cccattcact gctgtgccta cctccttgcc ggatttggtg    60
atgatgccaa aggaaacaat gggttgttgg gatacccgga rttatcttct atcagcactt   120
```

```
gcattcaaaa cccaaactga cctttaattt aatggaacrt acgtacattc actgatttgt    180
atacttatta ggttgcccag a                                              201
```

<210> SEQ ID NO 226
<211> LENGTH: 201
<212> TYPE: DNA
<213> ORGANISM: Triticum aestivum

<400> SEQUENCE: 226

```
tcaccttctg cttcttcatt ggcttaacgt cttcatcaga cttttcatcc tcaaagaaat     60
catcatcttc atcagcacca tcttcgttgc tatcgtcgtc rtcatcatca tcatccttcg    120
acgacctctt cctagctttc cgcttttcct tcatttttc ttgatgcatc tcccagacag     180
tcttcttctc gctgctcttc c                                              201
```

<210> SEQ ID NO 227
<211> LENGTH: 201
<212> TYPE: DNA
<213> ORGANISM: Triticum aestivum

<400> SEQUENCE: 227

```
gatgatctag gcgactcctg caacgaagag attgctaagc cattttgttt gaatggccaa     60
gacgcattgg gttcaaatgt ctctcctgcc accattgttt mtgcaggaga tggctctgat    120
ggcttaagcg tgtcacaggc taacggtgct gagcccctg aatctactgc agccgatggg    180
tgttccaaca aagacatcag t                                              201
```

<210> SEQ ID NO 228
<211> LENGTH: 201
<212> TYPE: DNA
<213> ORGANISM: Triticum aestivum

<400> SEQUENCE: 228

```
tgcttttaag atttgtcatt atgctggaga ggtttcatat gatacaactg ggttcttgga     60
gaagaataga gatccactgc acaccgagtc aattcaatta ytctcttcgt gcaaaagtga    120
tcttccaaaa gattttgcgt ctgtcatgat tgctgattct cagaataaat caagtttgtc    180
acgtcactta ttagttgata c                                              201
```

<210> SEQ ID NO 229
<211> LENGTH: 201
<212> TYPE: DNA
<213> ORGANISM: Triticum aestivum

<400> SEQUENCE: 229

```
tttactctga aacggatgac atctgtacga agacccaatg cccggcaact tctgattttg     60
agctatctca ctcgcaaacc ttaccatcaa tcactccacc rggttcttac accattcaga    120
tgaagatgct cggaaagcac gatgaggaat tgagctgcat ctccttcggg ttcaacattg    180
gcttccttgc gccggttgcc t                                              201
```

<210> SEQ ID NO 230
<211> LENGTH: 201
<212> TYPE: DNA
<213> ORGANISM: Triticum aestivum

<400> SEQUENCE: 230

```
aatcaagatg cccatcgagg agtcatgatg cattcgattg gatgacatca cttctactct     60
tgtacagtac aagttgtacc tgctgtacgt cgaacgtcga yatgatccat agccaccca    120
```

```
ttagtaaaga agtacttcct ccgttcccaa ttacttgtcr cagatatgca tgtatctaga    180
tgtattttag ttttakatac a                                              201

<210> SEQ ID NO 231
<211> LENGTH: 201
<212> TYPE: DNA
<213> ORGANISM: Triticum aestivum

<400> SEQUENCE: 231
cttgtccact tgcacatgct agctcttgtt ccgtctgyga aacttgcata agcttccttt    60
cctccaccat tctgctcatc tcgctcacca aagcaacatg ytttgtcaca tttccatgtg    120
tctttcgata ttcaggatag ttgctcacaa attttgccat atcatctata ctctgaaaat    180
tctggctgct ttttgaaaga t                                              201

<210> SEQ ID NO 232
<211> LENGTH: 201
<212> TYPE: DNA
<213> ORGANISM: Triticum aestivum

<400> SEQUENCE: 232
actgcctgac caccatggtt ggccactgag gatcactgca ccgtgcctgg gatgttaacc    60
cactccaggt gcaggatgat ctcgctggtg tcggtgttcc ycagcttgag gacaatgttc    120
tgagagacct tgccgtcttt ccatgtgatg tggctctcgg tggagaagca gttgcccttg    180
tcagggtgga tcgtcttcat c                                              201

<210> SEQ ID NO 233
<211> LENGTH: 201
<212> TYPE: DNA
<213> ORGANISM: Triticum aestivum

<400> SEQUENCE: 233
tctgatttat gccaatgaag ttgaccaaat gagaaacctc aatgataagt aattctttaa    60
taaaacatct aactataatt atgcttaaga tattctagct ytctacatgg ttaaattatt    120
attctattac atcattatac actatcctat aattttaaat ggctagaaat ttcagtcttc    180
ttctggctaa ttgtttttta a                                              201

<210> SEQ ID NO 234
<211> LENGTH: 201
<212> TYPE: DNA
<213> ORGANISM: Triticum aestivum

<400> SEQUENCE: 234
aactctgccc tggctcggag gctcttgtgt agatcgggca acaatttgtg ctgtatgttg    60
tgaaaacagt ttaactaggt gtgactcatg ccatcttatc rcgctctttt ttacacttca    120
attcatgttc atatgttgtt aatagctatt tgattgtttg atacttggaa mmwwwrccta    180
cttgctgtgc taattgataa t                                              201

<210> SEQ ID NO 235
<211> LENGTH: 201
<212> TYPE: DNA
<213> ORGANISM: Triticum aestivum

<400> SEQUENCE: 235
cctctacctt cctgtggtag cagtatttct cagggaggat ctggcgagga ataaagcagc    60
```

```
gagaaccaag atagtgctgg agcagcagca cagctgcttg katgctcatg aatgttgtca    120
cagctatgca ccatttcttg tcaggctcaa tgcgcatgaa gttgctagga caaccaaata    180
tatatagcgc gatggcgacc c                                              201

<210> SEQ ID NO 236
<211> LENGTH: 201
<212> TYPE: DNA
<213> ORGANISM: Triticum aestivum

<400> SEQUENCE: 236
aggtgggtga gatatgtgac gcaggccaac tcgtatgtag ctcgtctatg aggacattgt    60
acaattccaa aggcatttcc cacctgttcc ttgtgcaatt rtcttggacc gacttgaagc    120
ttggacagag tgacatgtat tgtaactcta tagtgggatc ccaacatcac tctgctcctc    180
tagcttaact ttcttttagt g                                              201

<210> SEQ ID NO 237
<211> LENGTH: 201
<212> TYPE: DNA
<213> ORGANISM: Triticum aestivum

<400> SEQUENCE: 237
ctttgaggga tattcatgat atatcactta acttgaagat ctccttggac agtgaaaaat    60
caggcagcat gtcaaaatat ggaaggagtt caaccagtga yaggagaaac cttgaggatg    120
ctgtacaaaa attttcagaa gctgttagtg ctggcacaaa ggatgagtct ggtgagaaag    180
ctggggccac cacaggctcc a                                              201

<210> SEQ ID NO 238
<211> LENGTH: 201
<212> TYPE: DNA
<213> ORGANISM: Triticum aestivum

<400> SEQUENCE: 238
tgtacagcca tgatggcagc aagttgaact tcatacctgt tctagcatca cgatcccaag    60
cactaaggta cttgtatata aggtggggcg tagagctgtc raacatgacg gtggttgttg    120
gtgaaagcgg cgatacagat tatgaagggc tactcggagg cgtgcagaag accatcatac    180
tcaaaggctc atttaattcc g                                              201

<210> SEQ ID NO 239
<211> LENGTH: 142
<212> TYPE: DNA
<213> ORGANISM: Triticum aestivum

<400> SEQUENCE: 239
gtacatccat caagttgcac ttcttcttag cagggggtcga tcgatgtaca tcatgtgaat    60
aataagcaag aacatgctgc tacgctgtct gtactgtttt kcacataaac gaaatgcagt    120
gatcaattcg ttcgtcttag gg                                             142

<210> SEQ ID NO 240
<211> LENGTH: 201
<212> TYPE: DNA
<213> ORGANISM: Triticum aestivum

<400> SEQUENCE: 240
gtgatggcgt tcatgccgga gctggggcca ttcgatgtct ctggtagcta gctagtgttc    60
tgctcattgt ggctgctgtt gctgtgcacc ggtggcacta rattcctggc agcagtattt    120
```

```
caagcttact cttttgttct tgtaataaaa cgtttgttga atgtacctcg ctcaaataag    180
tgctcttagt tagaactatc g                                              201

<210> SEQ ID NO 241
<211> LENGTH: 121
<212> TYPE: DNA
<213> ORGANISM: Triticum aestivum

<400> SEQUENCE: 241
cccatcttct tcyccgcttc ttcttccagc aatggtggtg gacggttttc tgaatcctgg    60
yagtgtctct gtttcttctt cttcttcttc aggaaggaca ggccgccgct caccttctcg   120
c                                                                    121

<210> SEQ ID NO 242
<211> LENGTH: 121
<212> TYPE: DNA
<213> ORGANISM: Triticum aestivum

<400> SEQUENCE: 242
ggttttcatc tttgttttta tatatatccg ctcttcttca ggaaagcaag cctaagccac    60
mtccgaagag gagccagcct gagttcctga gaaatattac agtttccgtg aagccacgag   120
c                                                                    121

<210> SEQ ID NO 243
<211> LENGTH: 201
<212> TYPE: DNA
<213> ORGANISM: Triticum aestivum

<400> SEQUENCE: 243
aggcgacaga tgattttga accacaatcc agtgaagccg tccatgcatg caacaaacg     60 tgtttgcaaa ccgctagatg ggtcatcgtg caatggtcgt ycaccctata tgtcatgtgc   120
acagtagttt cctagaccga cagagtgcag caaggcagtt taagaaggaa gtgattggga   180
ttttggacga gatgaatcga t                                              201

<210> SEQ ID NO 244
<211> LENGTH: 201
<212> TYPE: DNA
<213> ORGANISM: Triticum aestivum

<400> SEQUENCE: 244
agacgcggct gctgcgattc acaggataag ggatgctcat gcacattaag gtatactaga    60
tgacataacg aggaagccaa taaatataag atataactgc rcataaacgc aggtcctttt   120
ttgctgaaac aagtgtgtca ctcacgcgct taattggctt tgtagtgttt attatgtatt   180
ccagtctagg tgtggtttag c                                              201

<210> SEQ ID NO 245
<211> LENGTH: 201
<212> TYPE: DNA
<213> ORGANISM: Triticum aestivum

<400> SEQUENCE: 245
aatgtttctg gtctggaatc gctggacgga agcattgtta gcgagatgga aggtgagagc    60
accatcgacc ggctgagacg acagattgat ctagaccgga rgtcgataca cctcctctgc   120
agggagctgg aagaagagag gaacgccgcg gcgatcgctg caaaccaagc actggccatg   180
```
atcaccaggc tgcaggatga g                                                 201

<210> SEQ ID NO 246
<211> LENGTH: 201
<212> TYPE: DNA
<213> ORGANISM: Triticum aestivum

<400> SEQUENCE: 246
tgacatcacc tgtagtctct ttctctcgtg ccatttcttt gcctggcaat ggcagccaga        60
tgacccgtat gcacagatta tttggtcgtg cgtcgcagcg yggttgttca tctggccaaa       120
tattrctaca gatagaagga ttctgggaag gaagccctgt gaaaaggatg atgggcacca       180
tcattgcaat tgtgtattgt t                                                 201

<210> SEQ ID NO 247
<211> LENGTH: 201
<212> TYPE: DNA
<213> ORGANISM: Triticum aestivum

<400> SEQUENCE: 247
ataagcaatt gtgggcaaaa tgccgtcaga atggtctgga taatatccat cgattttctt        60
ggcctgaaca ttgcaaaaac tatttgtcac gggttggtac rctcaagtct agacatccac       120
gatggcaaaa gagcgatgat gctactgaag tttctgaaac agattcacct ggtgactctt       180
tgagggatat tcatgatata t                                                 201

<210> SEQ ID NO 248
<211> LENGTH: 121
<212> TYPE: DNA
<213> ORGANISM: Triticum aestivum

<400> SEQUENCE: 248
tggaattaaa ctgcaagaaa attgatgatc aactattaaa taataacctg tggggatttg        60
rttatgctct cctaagatta ggattgttta atcaatccc tgcaagcccc atcaatatgt       120
t                                                                       121

<210> SEQ ID NO 249
<211> LENGTH: 201
<212> TYPE: DNA
<213> ORGANISM: Triticum aestivum

<400> SEQUENCE: 249
gcctggaact tgccaacttg aatttgaaga acagtcgtgg gtacacagca ctccacctag        60
ctgctatgag gagagaacca gctattatta tgtgtctctt ragcaaagga gcagtggcgt       120
cgcaattgac agatgatggc cgccttgcaa gtaatatttg tcgaagatta acaagactaa       180
aagattataa tgcaaagatg g                                                 201

<210> SEQ ID NO 250
<211> LENGTH: 201
<212> TYPE: DNA
<213> ORGANISM: Triticum aestivum

<400> SEQUENCE: 250
tctcgtgcca tttctttgcc tggcaatggc agcagatgac ccgtatgcac agattatttg        60
gtcgtgcgtc gcagcgyggt tgttcatctg gccaaatatt rctacagata gaaggattct       120
gggaaggaag ccctgtgaaa aggatgatgg gcaccatcat tgcaattgtg tattgttaat       180
tgtacactag cggcggcatc a                                                 201

<210> SEQ ID NO 251
<211> LENGTH: 201
<212> TYPE: DNA
<213> ORGANISM: Triticum aestivum

<400> SEQUENCE: 251
cccagctaag cagcccagca tcgatggtgg atctcttgag gtcgccatcg ccattgatga    60
caagcagggt gagaaggttg cgaagagtct cactccgctg yggaggtgga agagctaccc   120
caacacccag aactccaaca cggggagcag aggggggaaa tggtccaaag accagtcgga   180
cgtcctccaa gtgcacgaag a                                             201

<210> SEQ ID NO 252
<211> LENGTH: 121
<212> TYPE: DNA
<213> ORGANISM: Triticum aestivum

<400> SEQUENCE: 252
gaagatggaa gcaaatctgg aagaaggaag tttgtccccg acccagcacg ccgcgcaaaa    60
yaaaatgatg actctaggga tgagaggagc agggccgtgc gttctctgaa ttctrtgctg   120
a                                                                   121

<210> SEQ ID NO 253
<211> LENGTH: 201
<212> TYPE: DNA
<213> ORGANISM: Triticum aestivum

<400> SEQUENCE: 253
gaatatatgt cgccaccatc tgataagtct accacaatgc actcacaaca cgatctatga    60
ggtaaatagg tacagtaaaa cagcatccac ggttcaaaca kaaaaaataa gccatgtcta   120
gccagagcac caaagtttcc cgcaaaacaa ctatgccggc ctgtatcaga agacacctcc   180
acctccctac ggctgtggat g                                             201

<210> SEQ ID NO 254
<211> LENGTH: 201
<212> TYPE: DNA
<213> ORGANISM: Triticum aestivum

<400> SEQUENCE: 254
aaaaaggcat gtactcagac gatgatgtgg cagatccagt ctacagtggc gtttctggtg    60
atgaaactga tgaatactat catcatgatg actatggtca ytatgtgcga tccccatgag   120
catgttgtcc agcctgctga gctatctggt caacatgtga agctctatat gcatagcttc   180
accacgaagg cttgctkctt c                                             201

<210> SEQ ID NO 255
<211> LENGTH: 201
<212> TYPE: DNA
<213> ORGANISM: Triticum aestivum

<400> SEQUENCE: 255
atcgtgtgcg attgagattg cccattgaac cacaaagtgc gctagttaaa ataatatacg    60
ctggtgtaaa tgctagtgat gtaaacttca gctccggacg rtatttcagt ggtagtgcta   120
aagaaactgc tgcacgcctt ccgttcgatg ctggttttga ggctgtggga attgttgctt   180
ctgttggaga tgcagtgagc c                                             201

<210> SEQ ID NO 256
<211> LENGTH: 201
<212> TYPE: DNA
<213> ORGANISM: Triticum aestivum

<400> SEQUENCE: 256

| | | |
|---|---|---|
| gtcaytatgt gcgatcccca tgagcatgtt gtccagcctg ctgagctatc tggtcaacat | 60 |
| gtgaagctct atatgcatag cttcaccacg aaggcttgct kcttcttagc aagaaccagt | 120 |
| ctggttacta tgtttagtct actggtttat ctaaataaaa tgtgaagctc tatgcttaca | 180 |
| gcttcacttt aggaactgtc t | 201 |

<210> SEQ ID NO 257
<211> LENGTH: 140
<212> TYPE: DNA
<213> ORGANISM: Triticum aestivum

<400> SEQUENCE: 257

| | | |
|---|---|---|
| atatcataca acactatcat cgcggcgtac gcgcagagcr ggaatttccg cagcatgaat | 60 |
| tacttcgtcc aaaagatgca ggacgcgggg tttccggttt ctctcgaggc gtacaactgc | 120 |
| atgctgaatg cttatgggaa | 140 |

<210> SEQ ID NO 258
<211> LENGTH: 201
<212> TYPE: DNA
<213> ORGANISM: Triticum aestivum

<400> SEQUENCE: 258

| | | |
|---|---|---|
| aggcttacgg gatagcggga atgcccgaag atgctgtcaa gctgatgcag gagatgagga | 60 |
| tcaaaggtat caatgctgac cgagtaacgt atactaacct yatagcagct ctacaggaga | 120 |
| atgagaattt cctggaggca gtcaagtggt ccctctggat gaagcaaacc ggagttgtag | 180 |
| gcgtcggagc tcgcccataa t | 201 |

<210> SEQ ID NO 259
<211> LENGTH: 201
<212> TYPE: DNA
<213> ORGANISM: Triticum aestivum

<400> SEQUENCE: 259

| | | |
|---|---|---|
| ggctcacgga tcagcagtga aaggtatctg gacggacggt gcctgggctt tctccaccgg | 60 |
| gcttgatcag agaatcagat gttggaagat gggcccgtcc rgcaaattca tggagcattc | 120 |
| ccatgttatc atcagcgtgc ccgagccgga aactctggat gttttccatg accgtgggag | 180 |
| cgggatatac cacatcgccg t | 201 |

<210> SEQ ID NO 260
<211> LENGTH: 201
<212> TYPE: DNA
<213> ORGANISM: Triticum aestivum

<400> SEQUENCE: 260

| | | |
|---|---|---|
| cttcgaccac tacacttaca acattatgat gaacatatat gggagaaagg gctggatcga | 60 |
| aggcgtcgcc tacgttcttt cagaactaaa gagccgcggc rttgagccag acctgtacag | 120 |
| ttacaacaca ttgataaagg cttacgggat agcgggaatg cccgaagatg ctgtcaagct | 180 |
| gatgcaggag atgaggatca a | 201 |

<210> SEQ ID NO 261
<211> LENGTH: 201
<212> TYPE: DNA
<213> ORGANISM: Triticum aestivum

<400> SEQUENCE: 261

| | | | | | |
|---|---|---|---|---|---|
| tgccaatcta | ataatgacca | gccagacatt | cttgacgcat | caactacgcg | tgaagagcta | 60
| gtttctctga | ctgagtatcc | ttgcctgcca | gttgttacat | yggaatctgg | agttaaggct | 120
| cctcacaccg | acaaggcgac | aggcacgtca | gatgagacat | ccaaagatac | tgaaaatata | 180
| aatgcatgca | atatatcttc | t | | | | 201

<210> SEQ ID NO 262
<211> LENGTH: 201
<212> TYPE: DNA
<213> ORGANISM: Triticum aestivum

<400> SEQUENCE: 262
cttcggtgaa gtgtgaagtc cagctgactg gaattgagga atgcctgttc atacattgga      60
acattttgtc aatctktgta gcgtgtatct aatgttttca ytcaagaact ccagctccct    120
gcttagttgt agcttcttac tcggtacttc agttttcgtc tcgaaaagat gtctcgttga    180
tcactgacaa aattacagtg c                                              201

<210> SEQ ID NO 263
<211> LENGTH: 201
<212> TYPE: DNA
<213> ORGANISM: Triticum aestivum

<400> SEQUENCE: 263
gcgagagatt aggcacaagt tctacaatcg tatcttgcag tcggctcaca ccaatccagc      60
gtctcaagtt gaaggtggaa gatggaccat tcctttgat ycagtaataa ggtctccctc     120
attatagtga aaagttttc cctgtcgaaa tcaagtgttt aygcgccaaa cgctatctac     180
caaacgacat ccatatccat a                                              201

<210> SEQ ID NO 264
<211> LENGTH: 201
<212> TYPE: DNA
<213> ORGANISM: Triticum aestivum

<400> SEQUENCE: 264
tgtccaagat tctcgctcca acaagcttcg gtgaagtgtg aagtccagct gactggaatt      60
gaggaatgcc tgttcataca ttggaacatt ttgtcaatct ktgtagcgtg tatctaatgt    120
tttcaytcaa gaactccagc tccctgctta gttgtagctt cttactcggt acttcagttt    180
tcgtctcgaa aagatgtctc g                                              201

<210> SEQ ID NO 265
<211> LENGTH: 201
<212> TYPE: DNA
<213> ORGANISM: Triticum aestivum

<400> SEQUENCE: 265
cttgatgtgg ctgaggaaga acaaacctag gactttaatt ccaattattt atgcatgtgc      60
tctgcttctg gcaacaatgc catctatcac cagttacttg mggagatcat tggagtggca    120
gactcccaag gtagtcggct tcgagctctt ctcctccctg gttatggctt tcatcagctg    180
gcagctgttc tcggcttgtc a                                              201

<210> SEQ ID NO 266
<211> LENGTH: 201
<212> TYPE: DNA
<213> ORGANISM: Triticum aestivum

<400> SEQUENCE: 266

| | |
|---|---|
| cgcgaggagg ggcatctctg gctgttcaac accaattaat ttctagtcct gcaattgata | 60 |
| attctattaa tcaggagtct tcaagtggtg accatagaag ractgagcat gttgagcgac | 120 |
| agagtggtgt gggttcgcaa ccattaccgg gagagactga ccttgcagaa atggaagtta | 180 |
| acatcgacaa tggaggcggt a | 201 |

<210> SEQ ID NO 267
<211> LENGTH: 201
<212> TYPE: DNA
<213> ORGANISM: Triticum aestivum

<400> SEQUENCE: 267

| | |
|---|---|
| atttcactgt taaaacagaa gcttaaagat atgaggatct tagacaacgt tgatcttcca | 60 |
| gcctctgttg ctaaactgtt tattaaacct aaagagaaaa mggggaagtt gcttgttsaa | 120 |
| tctttggagt ctattgctga aggtgacgag aaaactgagt cacaagagga ggaaaacatt | 180 |
| ctatccgaga cagcagagaa a | 201 |

<210> SEQ ID NO 268
<211> LENGTH: 201
<212> TYPE: DNA
<213> ORGANISM: Triticum aestivum

<400> SEQUENCE: 268

| | |
|---|---|
| gaaaactgag tcacaagagg aggaaaacat tctatccgag acagcagaga aaaagggcgg | 60 |
| atctgactct gaagaagctc ctgatgcaga aaaggaggat mctgtgtatg agttagatcc | 120 |
| atttgcaaaa tacgatcctc agttacctag agttgttcga atggcaaatc tctgtgttgt | 180 |
| tggtggacat tcagttaatg g | 201 |

<210> SEQ ID NO 269
<211> LENGTH: 161
<212> TYPE: DNA
<213> ORGANISM: Triticum aestivum

<400> SEQUENCE: 269

| | |
|---|---|
| gacccacctg catctcgaaa gcatcgcgca gcatcaggcg attcgacctc gccgttgctc | 60 |
| kggcgccgga gacgccgacg ccgacgagat gacggtgttc cacttcctca actgcgcggt | 120 |
| cctcaccttc ggcccccacg tcgtctacta ctccgccacc c | 161 |

<210> SEQ ID NO 270
<211> LENGTH: 201
<212> TYPE: DNA
<213> ORGANISM: Triticum aestivum

<400> SEQUENCE: 270

| | |
|---|---|
| gaatgggcga gtggccattg aaggtgaagg ggttcacaaa gatgtggtaa ctgatgaagc | 60 |
| tgagggaagc ttgattgtga atgggcgatc gtccatggaa kgtgatgtgg atcatccaga | 120 |
| tcttcccatt tccaaggaga tagcagaaga cacagttaat gagagggagg atgagggtaa | 180 |
| tgctttcagc agtgaaaata a | 201 |

<210> SEQ ID NO 271
<211> LENGTH: 201
<212> TYPE: DNA
<213> ORGANISM: Triticum aestivum

<400> SEQUENCE: 271

```
cggtcaccaa gatccattgc gacatgtctg atgcggtcaa tatcctaaca catactgatg    60
aagtaaagct caargcagaa aggattacag cgattgagaa maagaaagag agtttggcca   120
gagaagaaga caacagaaat cttcaagctt cacaaataga ccctgattgt gacatgtcaa   180
tagctctcag tgaaggaact g                                             201
```

<210> SEQ ID NO 272
<211> LENGTH: 201
<212> TYPE: DNA
<213> ORGANISM: Triticum aestivum

<400> SEQUENCE: 272

```
caagagattg gaaaaatatt ctgtccaaag tgtggcaatg gtggcacctt gcgaaaggtt    60
tcagtaacag ttggtgaaaa tgggatcact atggcttcac rgcgcccgcg tgttactctc   120
cgaggcacaa aattttccct tccaatgccc caaggtggaa gagatgccgt cattaagaat   180
cccattttac gtgaagacca a                                             201
```

<210> SEQ ID NO 273
<211> LENGTH: 201
<212> TYPE: DNA
<213> ORGANISM: Triticum aestivum

<400> SEQUENCE: 273

```
agccacattc tcctgacaac cgtgctctag caagagagtg caaagatgtc aagattgacc    60
gagtctatat tggttcttgc actggtggta agaccgagga ytttattgct gctgcaaagg   120
tgttcttagc ttcgggcaag aaggttaagg ttcccacttt tctcgttcct gcgactcaaa   180
aggtgtggat ggacgtgtat a                                             201
```

<210> SEQ ID NO 274
<211> LENGTH: 201
<212> TYPE: DNA
<213> ORGANISM: Triticum aestivum

<400> SEQUENCE: 274

```
aggatgaatt gaggaacgga ggaagtggag atctggagga tgaccttgct ggaaaggaca    60
gatacatggg ttcaatcgaa agtctcatcc gcaataatat mcaacaatac aaaattgata   120
tggcagatga agtcattaat gctggtcgtt ttgatcaaag aacgacccat gaggaaaggc   180
gcatgactct ggagacwctg c                                             201
```

<210> SEQ ID NO 275
<211> LENGTH: 201
<212> TYPE: DNA
<213> ORGANISM: Triticum aestivum

<400> SEQUENCE: 275

```
aggccattct gtccatcagg aatcttttga ctcacggcat tatcatgact acttgtctgt    60
tgcaaattty ccttgccttc tacctcaggt tgtgtaagga ycgtgatact tgcagcagca   120
gcaccaggac aacgcccaag acgaagctcc cggcagcaaa ttaggcagag atcataggaa   180
cacttattgc agcttctgtg g                                             201
```

```
<210> SEQ ID NO 276
<211> LENGTH: 201
<212> TYPE: DNA
<213> ORGANISM: Triticum aestivum

<400> SEQUENCE: 276
tgactacttg tctgttgcaa atcttgcttg ccttctacct caggttgtgc aaggaccatg      60
ctacttgcag cagcagcact atcctcaaca ggaactgcac ygtccctcaa caggccattc     120
tgtccatcag gaatcttttg actcacggca ttatcatgac tacttgtctg ttgcaaattt    180
yccttgcctt ctacctcagg t                                              201

<210> SEQ ID NO 277
<211> LENGTH: 201
<212> TYPE: DNA
<213> ORGANISM: Triticum aestivum

<400> SEQUENCE: 277
ttgctcagga attaggaatt ggtgattcgg tcaccaagat ccattgcgac atgtctgatg     60
cggtcaatat cctaacacat actgatgaag taaagctcaa rgcagaaagg attacagcga   120
ttgagaamaa gaaagagagt ttggccagag aagaagacaa cagaaatctt caagcttcac   180
aaatagaccc tgattgtgac a                                              201

<210> SEQ ID NO 278
<211> LENGTH: 201
<212> TYPE: DNA
<213> ORGANISM: Triticum aestivum

<400> SEQUENCE: 278 tttttcttc tctgtgcttg ctttcttttt tcttctcttt gcttgctttc atttctctct      60
ctgataaatt agaataacga gcgccacttc gtctgggtcg kgtctgatga ccagtaggtt   120
caaaaatagc ayctgtatta tctggagatt cactttttatt ttcactgctg aaagcattac  180
cctcatcctc cctctcatta a                                              201

<210> SEQ ID NO 279
<211> LENGTH: 201
<212> TYPE: DNA
<213> ORGANISM: Triticum aestivum

<400> SEQUENCE: 279
acgacatggc caattctttc atctccttct gatgaaacat gttctctagc atgcagctgc     60
ctaagctata taccaccgcg tggacgcatc aatctgtgga ygtacccaat gtttatacgt   120
gtctgtccat cgtatttgtt cattagaaga accgtacgtg cgtgcatgca tgattgcatg   180
aattatacag taggttgtac t                                              201

<210> SEQ ID NO 280
<211> LENGTH: 201
<212> TYPE: DNA
<213> ORGANISM: Triticum aestivum

<400> SEQUENCE: 280
gtcatgtgtg tgtcgtgctg agaaataagc tactcaacga gtagcagttg taactgagaa     60
aggttctgtt gtatgctttt tcattggcat taccagtgtg mtgtcaggaa caaacataac   120
tgttacatta ttccagaatg atactgtatc ttagtacatg atctggtagc tgttgatgtg   180
gaacggcgaa gtacaccaga g                                              201
```

<210> SEQ ID NO 281
<211> LENGTH: 201
<212> TYPE: DNA
<213> ORGANISM: Triticum aestivum

<400> SEQUENCE: 281
gagagtttgg ccagagaaga agacaacaga aatcttcaag cttcacaaat agaccctgat    60
tgtgacatgt caatagctct cagtgaagga actgaacatg rctcagtcat tgagcaggca   120
ttatctgatg ctcttttaga tgagcggcat ggggctcatc aagatgtggt agcagatgaa   180
gctgagggaa acttgactgt g                                             201

<210> SEQ ID NO 282
<211> LENGTH: 201
<212> TYPE: DNA
<213> ORGANISM: Triticum aestivum

<400> SEQUENCE: 282
cttctctttg cttgctttca tttctctctc tgataaatta gaataacgag cgccacttcg    60
tctgggtcgk gtctgatgac cagtaggttc aaaaatagca yctgtattat ctggagattc   120
acttttattt tcactgctga aagcattacc ctcatcctcc ctctcattaa ctgtgtcttc   180
tgctatctcc ttggaaatgg g                                             201

<210> SEQ ID NO 283
<211> LENGTH: 201
<212> TYPE: DNA
<213> ORGANISM: Triticum aestivum

<400> SEQUENCE: 283
cacgagaata cccatcaaaa aagaagtgag tgtttacttc aacctccatc cacgacaggc    60
actcaagagc tgtaacacat agccgctcac gttcatcctt ytctttcttt tctcgtacag   120
cccgccacat aaccattggt tcccagctca acccagaagt taattcaagc acgttacgaa   180
caataacagg ctcacccttc a                                             201

<210> SEQ ID NO 284
<211> LENGTH: 121
<212> TYPE: DNA
<213> ORGANISM: Triticum aestivum

<400> SEQUENCE: 284
tgagcattgg tcatgtagcc tttatctctg cgcgatatag ctgtctcgtt tgggaacaca    60
rcatcttatt ggtggaaatg ttgtgaccaa gaacatgagg ctctcttgcc atttgggctc   120
c                                                                   121

<210> SEQ ID NO 285
<211> LENGTH: 201
<212> TYPE: DNA
<213> ORGANISM: Triticum aestivum

<400> SEQUENCE: 285
caacgatcgc accgacaaat acggtgggag cttagagaac cgttgccgct ttgcgctaga    60
agtagtccag gccgtagctg atgagattgg agctgataag rtcggcataa ggctttcacc   120
ctttgcaagt tactcggatg catcagactc aaacccagaa gctctgggcc tatacatggc   180
acaggcgctg aacaagcttg g                                             201

<210> SEQ ID NO 286
<211> LENGTH: 201
<212> TYPE: DNA
<213> ORGANISM: Triticum aestivum

<400> SEQUENCE: 286

```
cccettgatc aagaagcrgg atacgtgagg tgtatgagcc gatttaatgc agcgggccca    60
aactcgcgag gcaggctgtg aagattgctg ttatgttgct ygtttgtttg acggctggcg   120
ctactccgaa ttcacacggg ccatcggtcc aggatgtgca acccttatgt tccatggttt   180
ccagcctgta accgaggact c                                             201
```

<210> SEQ ID NO 287
<211> LENGTH: 201
<212> TYPE: DNA
<213> ORGANISM: Triticum aestivum

<400> SEQUENCE: 287

```
ttctcctcac tggcactctc caggacaact tctttgccag ctttgctctt ggttggttga    60
tcaccaatgg tgcaggtctt gcatcttacc ccattgacac ygtccgcaga aggatgatga   120
tgacctccgg agaggcygtc aagtacaaga gctccttgga tgctttccag cagatcctga   180
agaaggaggg tgccaagtcc c                                             201
```

<210> SEQ ID NO 288
<211> LENGTH: 201
<212> TYPE: DNA
<213> ORGANISM: Triticum aestivum

<400> SEQUENCE: 288

```
cggsgttcct gctgaagcag caaaagtttg atcagcccca aattcaagtc cacgaatcgt    60
ttcatcacca actctatgag aatgagcatc ctcgcatttc ytgtacctag tttgaatata   120
ttacagctag aagacggtag aaagttcact gcagaagtca tgaaaacctg cattttgaac   180
ttctcgaaaa tcctctccat g                                             201
```

<210> SEQ ID NO 289
<211> LENGTH: 201
<212> TYPE: DNA
<213> ORGANISM: Triticum aestivum

<400> SEQUENCE: 289

```
aygtgcagaa ctgcctgttg cttgtggaca ttttaagcat ggaacatcag acacagctaa    60
agaagctaat atgttctccc aaactatttc ctgtgcgaaa rgcaagacaa aaaactcgta   120
tgagatatat cctaggaaag atgaagtttg ggccctgcac aagggatggg acatcagctg   180
gagttcggat gctgacagcc a                                             201
```

<210> SEQ ID NO 290
<211> LENGTH: 201
<212> TYPE: DNA
<213> ORGANISM: Triticum aestivum

<400> SEQUENCE: 290

```
ccaattacta tgccatcata aagaaagtcg atctcaagaa taataaagta caagtgaaat    60
ggcttgatct ctgtcctcgg ggagaggagg agaaaagatt ractggtaaa gaggatcgga   120
ctcttgcgtg tggaatcttt aaggtttcct ctggcaatga tggtactacg acttacactg   180
gtacagagtc attttctcat c                                             201
```

<210> SEQ ID NO 291
<211> LENGTH: 201
<212> TYPE: DNA
<213> ORGANISM: Triticum aestivum

<400> SEQUENCE: 291

| | |
|---|---|
| ttttcgagat ctcatagagg catcgaagag actttataac atcctcatgt ttaaacatgc | 60 |
| catgcacttg aagagatgca gctgcagatc taaactggct ygaatcacta gaaatcagat | 120 |
| cttgcacgag atcatatgac agcttgcagc atgaaaaaga taatggtatg accaatccag | 180 |
| cgattaacta tgctgccatg a | 201 |

<210> SEQ ID NO 292
<211> LENGTH: 201
<212> TYPE: DNA
<213> ORGANISM: Triticum aestivum

<400> SEQUENCE: 292

| | |
|---|---|
| acagcaacgt cttctaatgt ttcatcaagg aaccctaatc ggtgtatccc ctctgcacag | 60 |
| atgagaggca gagggcaaca accagcgaag caaaagtagt rcaactgtaa atgaacatta | 120 |
| gtcggaatct gttgtttgtt tatccattgt agtgtaatgt aatgtaatat attagtaggt | 180 |
| tgtacagtag agtaggtttg t | 201 |

<210> SEQ ID NO 293
<211> LENGTH: 201
<212> TYPE: DNA
<213> ORGANISM: Triticum aestivum

<400> SEQUENCE: 293

| | |
|---|---|
| cgaagcagaa gaagcgaaat gtccatactg tgctctcctc catgagtatg gcacacacaa | 60 |
| ctttacccca attcctatgg atgagtgtcc ggttgtcctt ygccttcttg atgaacactt | 120 |
| gaagatgata acagtgttgt tgctcatgat ttactattat gttccttcct catgagcaag | 180 |
| ccgatacttt gcgatgtaag a | 201 |

<210> SEQ ID NO 294
<211> LENGTH: 201
<212> TYPE: DNA
<213> ORGANISM: Triticum aestivum

<400> SEQUENCE: 294

| | |
|---|---|
| attgggttcg gatcactttc gccattgacc tgccatctct tgaggatggc cttgaaaggc | 60 |
| tgaaatcttt ctgcgagagg catgctatag tagaggccta rgctcaaaga tgattgagct | 120 |
| tttacactgc tgtggcgaat cgccagctat gcgttggatc gccctagtgt tgttttcaat | 180 |
| aatcgcttct ctttatgtca c | 201 |

<210> SEQ ID NO 295
<211> LENGTH: 201
<212> TYPE: DNA
<213> ORGANISM: Triticum aestivum

<400> SEQUENCE: 295

| | |
|---|---|
| catccagagc acctgcgctt acatcggaaa ctaccatttg gggatcactc tggaaagatc | 60 |
| ttctgtacca gattttccgt gcagtccgta gcattttgta yggttttgtt gccttctttt | 120 |
| caacgtgcaa taggcaccgg ctcagcatat acaatcacat agaagttctt ctccggcgcc | 180 |

```
tgtcccgcgc cttaaatggc a                                              201
```

<210> SEQ ID NO 296
<211> LENGTH: 201
<212> TYPE: DNA
<213> ORGANISM: Triticum aestivum

<400> SEQUENCE: 296

```
catcacgggt tccttgtcat gaacgatcgt tgtgttgtct ttgggctagg agttctcctg    60
tcgaacatca gaacttcacg ccgttacctt tgcctgtgta yggaaggcac tgtatatact   120
cgtagtggta catcctgtcc gtttctcgtc catggagtaa ataatttgtt caggctatac   180
aggtagaaca gtgcaacgca g                                              201
```

<210> SEQ ID NO 297
<211> LENGTH: 201
<212> TYPE: DNA
<213> ORGANISM: Triticum aestivum

<400> SEQUENCE: 297

```
tcaagtgtaa gacgyagatt gttgggaaca ctgtaaagac agctcagagt taacatggat    60
gcatatgatt ttggattgta cggatatgtt tgtactcctt ycaatatgct cggccaaacc   120
cttgagagac tcaactggtt cagattcttc tgaagcagtt tgatgtaata catccacaac   180
ttttcaaatt ccaaggtatg g                                              201
```

<210> SEQ ID NO 298
<211> LENGTH: 201
<212> TYPE: DNA
<213> ORGANISM: Triticum aestivum

<400> SEQUENCE: 298

```
agcagccttc ttccacttca gctgatgtta acaagctatt tgcattccca gttgatgtgc    60
cgaacgggat taaagaatca aaggatagtt ccagtgaatc ragtagtcaa gtaaaacctc   120
gagctatcat atctcaggat tttgagcatg atgcaagtca gagtccaaag aaactgagcg   180
atgatgtcgg tgcaaaagag g                                              201
```

<210> SEQ ID NO 299
<211> LENGTH: 201
<212> TYPE: DNA
<213> ORGANISM: Triticum aestivum

<400> SEQUENCE: 299

```
ttttgcaggc ccggagatag aagctgcttg tgattgcgag agatcagtag cagcattcag    60
agccaataca ggactgttgt gtacagtgtt accagttttc rtggagtttg gcttgataat   120
atttccatttt gcagcaagcc cttggtgatt tccctttgca accgtatttt gccccactcg   180
ctgaacagaa aactgtgctc c                                              201
```

<210> SEQ ID NO 300
<211> LENGTH: 201
<212> TYPE: DNA
<213> ORGANISM: Triticum aestivum

<400> SEQUENCE: 300

```
cgaagcggac cacaattttta tggagcgtct gtccgccggt ggcgccgaag gtgaaggcga    60
agaagggtat ccgagctgtc gccgcattct tttggtggat raaatgttgc aggtggccat   120
cctgtaccga tctcctgtgc tgtttggcta ccacagatgt atgaccgaaa taaaacgtcc   180
```

```
ctgaatcctg catttcagtg c                                              201
```

<210> SEQ ID NO 301
<211> LENGTH: 201
<212> TYPE: DNA
<213> ORGANISM: Triticum aestivum

<400> SEQUENCE: 301

```
ttagaatttt cacttgtgat ggttccattc caaaatacga gtttgattcc aaaagcttga     60
tggtcagtgc attcgtatca tcggaagtca taatagcaaa ygggatcttc gtatggcatt    120
cgccctccat tttgcagctc gcctcttgta aagccagaat agactctatg taatgttgaa    180
gaaaacattt cccagtggtt g                                              201
```

<210> SEQ ID NO 302
<211> LENGTH: 201
<212> TYPE: DNA
<213> ORGANISM: Triticum aestivum

<400> SEQUENCE: 302

```
cctcccctca tcaggaaatg aaaattctga atctccgcgg ggacagcagc agccgccgct     60
tgtgctgcag ccccttgtac aggaaagcca aacctcttta yccgttcagt cgttgcagtt    120
gatctctcct tgagttgggc aattttgtcg gcaaattcat catcggtcgt catcttggcg    180
ttgaagctgt ctatacagtc t                                              201
```

<210> SEQ ID NO 303
<211> LENGTH: 101
<212> TYPE: DNA
<213> ORGANISM: Triticum aestivum

<400> SEQUENCE: 303

```
ctcctaccat ttgctgacgc aaatgcaatt gtacttgaga tggccaatga rgtgttgcct     60
gtcgttaaag aagttcctgt tcttgctggg gtttgcgcta c                        101
```

<210> SEQ ID NO 304
<211> LENGTH: 201
<212> TYPE: DNA
<213> ORGANISM: Triticum aestivum

<400> SEQUENCE: 304

```
catccttctg atttcttgct cttataggta ccttgctcgt atatgcgagc ataatgagca     60
attttattc aagcacatca agcatgtttt tggggactg racatgtttt atttaaaaca     120
catatatatg tctagttgtt ccttggtgac atccaccatt tagacctctt ccacaatatc    180
ctgctcaagg atagccacca c                                              201
```

<210> SEQ ID NO 305
<211> LENGTH: 201
<212> TYPE: DNA
<213> ORGANISM: Triticum aestivum

<400> SEQUENCE: 305

```
atcgtcgcca cttgatgcct actattattt gccattcga gtgcaagatg gggtgatagc     60
aactgggaag cggcacattg ttttctttct atttttttctt yggttttgtt agaatagtcg   120
atcratctgc gccttttgta tgttattttt gctcacatca ggctggactg ggtcgctgg    180
agagggcgta aggtaaaggt t                                              201
```

<210> SEQ ID NO 306
<211> LENGTH: 201
<212> TYPE: DNA
<213> ORGANISM: Triticum aestivum

<400> SEQUENCE: 306
attatttgcc tattcgagtg caagatgggg tgatagcaac tgggaagcgg cacattgttt    60
tctttctatt ttttcttygg ttttgttaga atagtcgatc ratctgcgcc ttttgtatgt   120 tattttgct cacatcaggc tggactgggg tcgctggaga gggcgtaagg taaaggttgt   180
ycccatccag gcagagccta g                                             201

<210> SEQ ID NO 307
<211> LENGTH: 201
<212> TYPE: DNA
<213> ORGANISM: Triticum aestivum

<400> SEQUENCE: 307
ctgcaagcga aattgaacct gctctgaaga agcagctcat catytccact gctttgatga    60
ctatcggtgt tgcggtaatc agctggttgg ctctcccagc yaagttcacc atcttcaact   120
tcggtgctca gaaggatgtg tccaactggg gcctgttctt ctgtgtggca gttggtctgt   180
gggctggtct gattattggg t                                             201

<210> SEQ ID NO 308
<211> LENGTH: 201
<212> TYPE: DNA
<213> ORGANISM: Triticum aestivum

<400> SEQUENCE: 308
ataccctcgg gcccatcgtg atacagcctg atcacctcaa aagcatcaag cggttgtcaa    60
tcgtgtgcaa gccaaggcta gacataacaa tccaagctgg ygcgctgcct gatcttgtgt   120
cgcttcatat cctctgtgaa acactggatg ttcttcctgg aacaccggc attgagattg   180 cacatatgaa tcagctggat c                                             201

<210> SEQ ID NO 309
<211> LENGTH: 201
<212> TYPE: DNA
<213> ORGANISM: Triticum aestivum

<400> SEQUENCE: 309
ttttgttaga atagtcgatc ratctgcgcc ttttgtatgt tattttgct cacatcaggc    60 tggactgggg tcgctggaga gggcgtaagg taaaggttgt ycccatccag gcagagccta   120
gggatcgata tgtgtatatt atatataaca atgctacact gtaacatgaa atgaaatgca   180
gagaaaatta aaatgcgtga g                                             201

<210> SEQ ID NO 310
<211> LENGTH: 201
<212> TYPE: DNA
<213> ORGANISM: Triticum aestivum

<400> SEQUENCE: 310
gaagtgccgc tctcaagatg gttgaggagg tccgcaggca gttcaacacc atycctggac    60
tgatggaggg aactgccaag cccgactatg ccacctgtgt maagatctcc actgatgctt   120
ccatcaagga gatgatccct ccgggtgctt tggtcatgct caccccctc attgttggaa   180 ccctcttcgg cgtggaaacc c                                             201

<210> SEQ ID NO 311
<211> LENGTH: 201
<212> TYPE: DNA
<213> ORGANISM: Triticum aestivum

<400> SEQUENCE: 311
gcatcaccgg atttctctgg tataactagg aaggcgatgc caactgctca aaccatgcct      60
actgaagctg ctgcaactat acataattta cagttccctc rcgcactggc cctccttgaa     120
agtgccaraa aaattgttgg acaaagcaca tttctaaaag cttttcctgg gaatgtgaat     180
gacactgcgg agccagcttt a                                                201

<210> SEQ ID NO 312
<211> LENGTH: 201
<212> TYPE: DNA
<213> ORGANISM: Triticum aestivum

<400> SEQUENCE: 312
caacagaagg cttctcatct ttactatcat cctctgcttg cttcttaggc ctggtggcac      60
gtggaccccg gctttgctca ttgaggaagt caagtggacc rtcacagctg cataacaaag     120
aattacccct tcctctcctg cgccctttat caattggaat aaaacttctg ccattcatgc     180
catagccagg gaaaggaccc c                                                201

<210> SEQ ID NO 313
<211> LENGTH: 201
<212> TYPE: DNA
<213> ORGANISM: Triticum aestivum

<400> SEQUENCE: 313
tacctcctct gcggcactct attctcttgc aatttctata cctcacaacc aacagcaagc      60
aacaacggtc agcaagtgca ggcagcagag aaacaccaca rccacccttc ttctctagca     120
gcagcaccag aacaacaagc agctccagca aactcagcag tagcagtcac agaccaaacc     180
agctgcacac aacagcaatc g                                                201

<210> SEQ ID NO 314
<211> LENGTH: 201
<212> TYPE: DNA
<213> ORGANISM: Triticum aestivum

<400> SEQUENCE: 314
tctctctgtt gtatgctatc cgcagcaatg ccatcgttgt tctcagcagt atagttttct      60
gaacgcttcc cttcttggt agcagtaact cttgagtaat racgagtact agaaaaccat     120
ctagtgatct gatggaatgt caggccaagc tcttgtccca gactttcttt tgctgggcga     180
ctagggtaag gttctttttc g                                                201

<210> SEQ ID NO 315
<211> LENGTH: 149
<212> TYPE: DNA
<213> ORGANISM: Triticum aestivum

<400> SEQUENCE: 315
cttccaaaca tcaggggcag ggccgtcttt cttctttcag ggttactggg ccttgccctc      60
cgcgaccgct tccatcccag aagatgctcc catgccttcg ratggcttcc cggccgtaag     120
gtaccactct cgcttgtatc cactgcttc                                        149

<210> SEQ ID NO 316
<211> LENGTH: 201
<212> TYPE: DNA
<213> ORGANISM: Triticum aestivum

<400> SEQUENCE: 316

| | | | | |
|---|---|---|---|---|
| acgagaaaga ctgctgctgc tgctgctgct cttccaccct cttcgccgcg gcctcttcgg | 60 |
| acaccgactt cttctcctcc ttcaacgcca ccaccggctc rtgatcgaat acctggttcc | 120 |
| tgccgagcgc ggtgtcgctc ggcgacttrt ctactgcaga gacttttgag cagaggcctc | 180 |
| ccatccccct ccttgttaac c | 201 |

<210> SEQ ID NO 317
<211> LENGTH: 201
<212> TYPE: DNA
<213> ORGANISM: Triticum aestivum

<400> SEQUENCE: 317

| | |
|---|---|
| ctagaggaga tgcgaagcca tggaagcagg caccgaaacc aagcaaggat gagctgagac | 60 |
| aagctgtctt ctgtatattg ggtgctgcaa attttgccac katgactttt ggagaggttg | 120 |
| taaaagcagt tgacaagtac tttggcaagg atttgttcaa gagaaagccg ctggtaaggg | 180 |
| ccttgataga ggaggagctg t | 201 |

<210> SEQ ID NO 318
<211> LENGTH: 201
<212> TYPE: DNA
<213> ORGANISM: Triticum aestivum

<400> SEQUENCE: 318

| | |
|---|---|
| tgaggcgtcg gaaggaaatg ttgtccagcg aaggggggcga tttcaggtag cttcatcagc | 60 |
| aagcagcaac agcaggccta atttaccaag tggagtaaca yggccagctt ccaattcatc | 120 |
| cacaattctt ccgacactac aattcttgat gcagcaaaat tctatgcaaa aggaagtgct | 180 |
| aagtagattg atttcttcaa t | 201 |

<210> SEQ ID NO 319
<211> LENGTH: 201
<212> TYPE: DNA
<213> ORGANISM: Triticum aestivum

<400> SEQUENCE: 319

| | |
|---|---|
| gccgcacatg gagttgcttc aagctgtggc gagcgctgta ctctccttcc tgggctgacg | 60 |
| atcattcatc ttcatcttct tgtaatttat tcctcctaga ytgaaaccgt ctgcttaatt | 120 |
| tatgtaccca agtaaggaga cacatttatt tacagtttga tgattctgtt gtgaaatttg | 180 |
| gatatttttt cactcttatt a | 201 |

<210> SEQ ID NO 320
<211> LENGTH: 201
<212> TYPE: DNA
<213> ORGANISM: Triticum aestivum

<400> SEQUENCE: 320

| | |
|---|---|
| agagtcttct cggtgcggag gagcttcgtc ttcttagaga tgctctcagg gaagtatgca | 60 |
| tcccccctgaa gagtatgtcc gaagacgacg gtgctagctt yatggcccgg tggtggatga | 120 |
| agatagttcg ggagctttgt tatgatacgc aggattacct caacttcgtc caaagtgctc | 180 |
| gagatcgtcc tgaattttca g | 201 |

<210> SEQ ID NO 321
<211> LENGTH: 201
<212> TYPE: DNA
<213> ORGANISM: Triticum aestivum

<400> SEQUENCE: 321
gggttcacct tcgcgcccaa gcacaagtct aactcgtacg accgcgctga gaacggctaa    60
aagactgccg cgtgatggtt attcggcagt ttatatgatg mtgaataaga tcacgtctct   120
tctcagttag tttgaaactc agccagggct ccatgttgcc tgcctcataa tggttattca   180
gcagtgtgga gcaacatcat g                                             201

<210> SEQ ID NO 322
<211> LENGTH: 201
<212> TYPE: DNA
<213> ORGANISM: Triticum aestivum

<400> SEQUENCE: 322
gtaaatagat gctcttcttg ccaagctaat aagcaaacga tggttcacca ggccggaagc    60
tccggtagat ggaggctatc actgggacwa gacccagcag ygcgatctgg acctgctccg   120
atgtgcttgt cctgacggtg atctgtccgc tcagcttgtt gttgagccca aggcgaacag   180
ccatctttga accccttcca a                                             201

<210> SEQ ID NO 323
<211> LENGTH: 201
<212> TYPE: DNA
<213> ORGANISM: Triticum aestivum

<400> SEQUENCE: 323
ccagtaatag gggttcacta tgtatgaacc agaatactgg aacctccaat gttgacctgt    60
gatttgtatg ttctccttta agtgaagttt gctcacttaa yttctgtaac tggtgctgga   120
gaatggcaga atccaggtat gtacggactg tggacctata ggtaccattg accratagaa   180
gtggaaccgc ggctgcacgg c                                             201

<210> SEQ ID NO 324
<211> LENGTH: 201
<212> TYPE: DNA
<213> ORGANISM: Triticum aestivum

<400> SEQUENCE: 324
aaataagcag aagtgaagat ttaccacagt acatagacaa atataagtta aatcctgcat    60
ctgtatagta tgatcaacat cacaaggagg agaaattgag maggtagtgc tgcatttcct   120
gtcatcatgt atccctcgc aacactctag agctcgaact cctcctcacg gagagccatc   180
tccgcagcct cctcctcatc g                                             201

<210> SEQ ID NO 325
<211> LENGTH: 201
<212> TYPE: DNA
<213> ORGANISM: Triticum aestivum

<400> SEQUENCE: 325
tttgaatgat gaaaactcaa gacaacgtaa ratgaccaaa agtatttgca ctggtcatct    60
tgcatgtcga ccagtccctg gaaaatggtt aattacaaca kgtgaaaaag aacattagat   120
cactgatctt agttcccggt cagagacgtc aagaatgcta atcctgcgat cacgatcata   180

```
atgttgagga agtagttgga c                                              201

<210> SEQ ID NO 326
<211> LENGTH: 201
<212> TYPE: DNA
<213> ORGANISM: Triticum aestivum

<400> SEQUENCE: 326
ctgaagcagg tactgacgga ggaagaagaa gcggatgctg cagctagcac acggcgatgt      60
tgagcgccga tagcttgtgt gcatggttct tgccctgctt yttggatgag cttgctgcag     120
gatgttgttg ctgctgctgc tgctgccgtg gcttgctgct gctgtggtat ttgcagtggc     180
tgtcgtgtct gtcgcggctt g                                              201

<210> SEQ ID NO 327
<211> LENGTH: 201
<212> TYPE: DNA
<213> ORGANISM: Triticum aestivum

<400> SEQUENCE: 327
gacaccttcc ttaggtgcat cagggttcaa aaaaaatgga tgccaacgaa cctcgaaatc      60
gaacttgtcc atggtttgct ccatagcttt ctcaagattc yttttcccaa caaagcacca     120
agggcacact gtatctgagc tcacgtcgat ctgaatgagc ttcttgccag tatttgaagc     180
catatgttta gcaaatctga g                                              201

<210> SEQ ID NO 328
<211> LENGTH: 201
<212> TYPE: DNA
<213> ORGANISM: Triticum aestivum

<400> SEQUENCE: 328
agacagaccc tgggaaacta tattcactgg atcatctcat gctctcccgc ctctcacgaa      60
actgtgttct gttttcttgg catcattgct ggagaagaga ycggttacag acgagtgaga     120
agcacccacc gcagttttgt cgcaatatat aatggtatac ttgctagttg cagttgtcag     180
tgtagaagca aacgaaagcc g                                              201

<210> SEQ ID NO 329
<211> LENGTH: 201
<212> TYPE: DNA
<213> ORGANISM: Triticum aestivum

<400> SEQUENCE: 329
ttgatgtctg tgttccgaaa aatgttgaag gatgggacat caagccaaca gcgtctccga      60
atggacgacc aacgttggct tctgcacggc aactgggtcc rttcaatccc atcaagtacc     120
tccgccgttc aaggctatag tttgtgtttg ctgcaaagaa gagttttgtg tatataatgg     180
aggcaatatg ttaaataccg a                                              201

<210> SEQ ID NO 330
<211> LENGTH: 201
<212> TYPE: DNA
<213> ORGANISM: Triticum aestivum

<400> SEQUENCE: 330
aagcaatctt gggacatcgg caggtttgcc aagactctgt ttttcttcaa cgggcctcca      60
aaccctctca agattgtgga gtccataatg agcagcatca yagcctccgc tcctaccgag     120
gcgccgaaga agcagagac ttctgatttg gtgcttgtca ctggggctac cggcggtgtc     180
```

```
gggcgaagag ttgtcgatgt c                                              201
```

<210> SEQ ID NO 331
<211> LENGTH: 201
<212> TYPE: DNA
<213> ORGANISM: Triticum aestivum

<400> SEQUENCE: 331

```
tctttgaagg ttcagactca tcggatgatg ttataaaatc caggtcatca gaatctgatc      60
cttcatcccc atcctctgca gatgatttgt cttcatctac ygtgtcccct tcagctaaag     120
tagggtcata atcctcctct gaatcatcgg atggaagatc agatgcacca atttggttta     180
agccattcga agttgactca g                                              201
```

<210> SEQ ID NO 332
<211> LENGTH: 201
<212> TYPE: DNA
<213> ORGANISM: Triticum aestivum

<400> SEQUENCE: 332

```
caatcaaatg cttccgggga gatgacctgg tgtatgtgac ttagcagtgt atagctaggc      60
gaaggcttcc ttttggttgg agctgttttt tctcatcgca yaagggtctt cttatggtct     120
gttaggaaga atgccgctta ctgcgttttc ggtgtcaagt ctgttccatt gaagaaaagt     180
tggattcgta atgtattccc a                                              201
```

<210> SEQ ID NO 333
<211> LENGTH: 201
<212> TYPE: DNA
<213> ORGANISM: Triticum aestivum

<400> SEQUENCE: 333

```
tgagctgaga gcmgccactg aagagccaaa gttgagcata gaggaaggca gcggcggtgc      60
ttcggatgcg atggctgtag actgattaac gatcctagca ytagcgagtt gcttaccctg     120
cacgctcaag catgcytcgg tagtktctgg gcgyggtgtt tctttgtaag agatcccttt     180
ttttgtgttg ctgtggtatc t                                              201
```

<210> SEQ ID NO 334
<211> LENGTH: 201
<212> TYPE: DNA
<213> ORGANISM: Triticum aestivum

<400> SEQUENCE: 334

```
cccgaagtgc aggcagagga atagatatga caacattgtt caggtcaaac atctctgaag      60
cctcatattc aatgttgaca taggtttcat ttccagatac ygagggccag cagttaactg     120
acagaggtaa atycgattca ttcatcccct ggattctcca tttcacaagt ggtgtttcat     180
tttgaccact tgggaaaggc c                                              201
```

<210> SEQ ID NO 335
<211> LENGTH: 121
<212> TYPE: DNA
<213> ORGANISM: Triticum aestivum

<400> SEQUENCE: 335

```
aataacatgc cctagaaaaa tcatggtctg aataaatatt ctagtattat cgcagcgcag      60
yggaaggtga gttttggct attaatgcca gctaaggtca actggtcact atccctaaag     120
``` c                                                                           121

<210> SEQ ID NO 336
<211> LENGTH: 201
<212> TYPE: DNA
<213> ORGANISM: Triticum aestivum

<400> SEQUENCE: 336
cgggtcgtct ccaggcgccg gcaagtttgg ttacctgaag atccgacggc ggcgtcccaa      60
gttgacaatc cccgaatgaa gtggtcggct ttccaatcca ytgtgcccgg tgaagtcagg     120
tttgttgaga ggtcaggctg ctgaattgat tgaacacaga acatgtgaag cagcaattca     180
ttgtgtatgt gggactgcag c                                               201

<210> SEQ ID NO 337
<211> LENGTH: 201
<212> TYPE: DNA
<213> ORGANISM: Triticum aestivum

<400> SEQUENCE: 337
acaactttca ttcagcctca atgggaggtt gattgtgaat tttttgttt cttctcattt       60 acaaaaatca tataagtctt atgtacatca atcagattgc kcttttgtaa taataatgtg     120
gccagatggt tggacgtctg cctattgcca gaaggtcaag gaagttggtg aactgatgac     180
agggaagctg ccaaccctag t                                               201

<210> SEQ ID NO 338
<211> LENGTH: 201
<212> TYPE: DNA
<213> ORGANISM: Triticum aestivum

<400> SEQUENCE: 338
tgttagaatt tgacagagaa cgcattagat tggaacccctt aactattgta tttgccacct     60
caaaagccaa aatagatatt ttatttccct ttgctccaga rcttgacaca aagccactgc    120
tagcatttaa acttgccatg ctactaccaa gtgtgtctag aacctccaca gctttcccaa    180
gcccaacagt gctagctcta c                                              201

<210> SEQ ID NO 339
<211> LENGTH: 201
<212> TYPE: DNA
<213> ORGANISM: Triticum aestivum

<400> SEQUENCE: 339
aatgcattga gacaggtgac cagtcaagat cttaattggc gaggaatgag cgaagccatt      60
catgcttggc cacggaattt agtraggtat ctgcaagtga ycctttatac ttggacacac    120
tatccatcat tgggaactct ccccttcaac gtgttctgag ctaggtggca ctttcttgtg    180
ctaccatgtt ataccattta c                                              201

<210> SEQ ID NO 340
<211> LENGTH: 121
<212> TYPE: DNA
<213> ORGANISM: Triticum aestivum

<400> SEQUENCE: 340
ccgttcatca atcaatcgct gaagattggc cggagattga aatgaaaccg attgattatg      60
rcaccgagat gcatgttttc tgctgatttt tgacgcctct gttcttgtct gctgagctgc    120
t                                                                   121

<210> SEQ ID NO 341
<211> LENGTH: 201
<212> TYPE: DNA
<213> ORGANISM: Triticum aestivum

<400> SEQUENCE: 341

```
acttccagcg cgactctctt gtgaagttct gccagaagca tggaatctct gtcaccgcac      60
acacacccct gggcggctcc actgccaata ccgaatggtt yggctcggtc tcatgcctcg     120
acgatcctgt catcaagtcc ctggctgaga aatacggcaa gacgccggcc cagctggtcc     180
tccggtgggg cctccagagg a                                               201
```

<210> SEQ ID NO 342
<211> LENGTH: 201
<212> TYPE: DNA
<213> ORGANISM: Triticum aestivum

<400> SEQUENCE: 342

```
ggtccacagg actttttaga ttagttacag tggccatgta gccattcaga ccggcagcta      60
tgatgtgata gcatacatga ccgagaacat atgcgtaatc rcaatcaaag tttgacggca     120
gggcacctct tgcttggtag ccaaaaaagt ggcaaattgc attgaacttc tttcctttgt     180
aagtgccttc ctccagacgt t                                               201
```

<210> SEQ ID NO 343
<211> LENGTH: 201
<212> TYPE: DNA
<213> ORGANISM: Triticum aestivum

<400> SEQUENCE: 343

```
atagttatca cccctttgca tgctagggat taaaacacat gagttgtatt atgtgtttat      60
ataaagaata aacaaaattg gcgtcctaag cagtaaacca mtaaataagg aaaattttgt     120
agacctgaca attgacacac catctaccgc cacatcctct ctatckaagc tctacaactc     180
caaaagaaca aaggacatag g                                               201
```

<210> SEQ ID NO 344
<211> LENGTH: 201
<212> TYPE: DNA
<213> ORGANISM: Triticum aestivum

<400> SEQUENCE: 344

```
aaatttgttt tcgtcttggt gagactggac agaagtaacc aatggttttt tgtccacatg      60
tggaactata gaagtgaatt gaaagatagg tgaagaggtt rtatttcagg agctattggg     120
ttcagttttg gacttccagt taactcctaa ctgtaaaatg aatacttaat ataagtgaaa     180
tgtaatggga tgagattgca t                                               201
```

<210> SEQ ID NO 345
<211> LENGTH: 201
<212> TYPE: DNA
<213> ORGANISM: Triticum aestivum

<400> SEQUENCE: 345

```
ggaacggaat attggatggg tataaaagca gtaacccacc ctgcagggct ctagcgtcaa      60
gctctcaaat tcattgctct gaaagccata cccctcagt rgtcatccgg gtcatcagat      120
gcgtcgctga acccatcatc actctgtttg ctgtcagact cactcattgc gtaaggatca     180
```

```
tactctctcc attctggatt t                                              201

<210> SEQ ID NO 346
<211> LENGTH: 201
<212> TYPE: DNA
<213> ORGANISM: Triticum aestivum

<400> SEQUENCE: 346
tcctgtcatt cacacggcga ggagcgtyga aggacgacgc ctcatcggcg aagccagggg     60
cagccggttc ggacgaccag tactggaatt cccccgcgaa katgccccac gacaacaaca    120
acgtcgacaa gaggtccaaa gtgaggaagc agccgtggat gcccttcatc tgctgccact    180
ccgtgcactg atgctgccat t                                              201

<210> SEQ ID NO 347
<211> LENGTH: 201
<212> TYPE: DNA
<213> ORGANISM: Triticum aestivum

<400> SEQUENCE: 347
atagcagcgt tatattgagg aacaccaggc ctaccaatgc aagaagtaat atacacgaac     60
atgacttcaa atatcctagg gagggaaaag tttccagtag ygaggtcaat gctgacagta    120
aatttcaaag ataccagcaa agaacagaga attcaggaag aaatcttgta ggtagtttta    180
gagataataa tgtggactat a                                              201

<210> SEQ ID NO 348
<211> LENGTH: 201
<212> TYPE: DNA
<213> ORGANISM: Triticum aestivum

<400> SEQUENCE: 348
ggtggatgtt ctggtagcga atggtatcag ttcggacaag ataagtgtta cttcctacga     60
agatatcaaa atgagggcct ttgctgagga ggcacgcgcc kaagaggagc gtccaaagaa    120
gaagagggcg aagaaaaatc cagactggga agatgatgac tccgacgaac agagtgaccc    180
tgatgatcct agcggcgacg a                                              201

<210> SEQ ID NO 349
<211> LENGTH: 201
<212> TYPE: DNA
<213> ORGANISM: Triticum aestivum

<400> SEQUENCE: 349
atgaatcccc atgctgctga gtttgtgcct ggaaaaactg tgcaacaaac tgatttggct     60 gcagggggaac aagctaattc tgtgactgat ccagcggatc rgcggttggc atcgcatgcc   120
tcagatgaag tgaaagtcga tgttcgtgag gcagacaagg caggtcaagt ggagaagaca    180
actccaggta aagggaagga a                                              201

<210> SEQ ID NO 350
<211> LENGTH: 201
<212> TYPE: DNA
<213> ORGANISM: Triticum aestivum

<400> SEQUENCE: 350
tcatgcaatg cttgaaagca aaaagttcat atacatcaat ttctgccaat aggatatcca     60
ccgcatggta atcctcgcca acagaagaaa acctttctct rattgtatct tgtagacttt    120
cttcagcctc ttcctctgtg atttctgcga cagccccaac agttttttgcc acatttggca   180
```

```
gagtaagttc tgtacgaaca c                                              201
```

<210> SEQ ID NO 351
<211> LENGTH: 201
<212> TYPE: DNA
<213> ORGANISM: Triticum aestivum

<400> SEQUENCE: 351

```
ataggcagcg tttcctccaa gtcgtggtcg aatcttctga accggaacgc ggacctcctc     60
gaggaggaga gcgtcgccaa gcttgtccaa gaactcgatg rcttctcaag gccagggagt    120
tcctgccctt ccttgtatga aaatattctg agcagctgta cagaattcct tggtggttct    180
ggtggaaagg cagcttctga t                                              201
```

<210> SEQ ID NO 352
<211> LENGTH: 201
<212> TYPE: DNA
<213> ORGANISM: Triticum aestivum

<400> SEQUENCE: 352

```
gaacaygctc accattcctt cccgtgcatg gggggttgtc attgaagtat tgaaagagag     60
acttccaaag gatggaataa ggtgccgggt tccgcagaga ygatgttaca tggtagatga    120
cttgcacctg ctgatcatct gagtgtgctg ccatggcaac catcatagca ttgaccacca    180
tgtcccctgg aatcacatcc a                                              201
```

<210> SEQ ID NO 353
<211> LENGTH: 201
<212> TYPE: DNA
<213> ORGANISM: Triticum aestivum

<400> SEQUENCE: 353

```
acacgtagga gccaaccttt tgtacctggg agtcgaaacs aatttctgcc ttctgcatta     60
tttcagtgtt aaagatgatg attgcatgcc gcatttgctt ygattgctta ctttctctgt    120
caagtatgat aagaatggag acatctggac ctgccgaatt ctagagtcta gcgtgaatgg    180
ygcaaggtgg accaaatcac g                                              201
```

<210> SEQ ID NO 354
<211> LENGTH: 178
<212> TYPE: DNA
<213> ORGANISM: Triticum aestivum

<400> SEQUENCE: 354

```
cgaggttggg cgagatggcg aacttgatca tgggcggcgg cccgcaggcg agcgcgaggg     60
tgtcgtcgcc gccctcgggg acgtgcgccc gcaggatgtc ytccgtcacg aaccccacgc    120
tgaacctcca cccgtccccc ggccgtaagg taccactctc gcttgtatcc actgctta     178
```

<210> SEQ ID NO 355
<211> LENGTH: 201
<212> TYPE: DNA
<213> ORGANISM: Triticum aestivum

<400> SEQUENCE: 355

```
tacatcagaa gctttcaatt tgactcctgg aaaagtacca gtatttccat ccctcaattc     60
ttctttcatt tcatacaagt accatataat aaggaaatgc rcccattatt aactggagaa    120
caaacatata tgatttcctt cattaaggta gatgtatgta atccactaca taaaatgtat    180
```

```
gtagaaaatg aaatttttca g                                            201
```

<210> SEQ ID NO 356
<211> LENGTH: 201
<212> TYPE: DNA
<213> ORGANISM: Triticum aestivum

<400> SEQUENCE: 356

```
acattgttca ggtcaaacat ctctgaagcc tcatattcaa tgttgacata ggtttcattt    60
ccagatacyg agggccagca gttaactgac agaggtaaat ycgattcatt catccctgg   120
attctccatt tcacaagtgg tgtttcattt tgaccacttg ggaaaggcct gtttggatct   180
tttgctccaa caatttgctg g                                            201
```

<210> SEQ ID NO 357
<211> LENGTH: 201
<212> TYPE: DNA
<213> ORGANISM: Triticum aestivum

<400> SEQUENCE: 357

```
gggatgagaa tggctactat gctggatcga atggactgga gatgcaaccg acagtcgttc    60
aagctgagaa tgggtcttat ttgtgttatg ttccgggtta ygaaaatggt tatactgctt   120
atagtccagt cgttcctgga actggcgtgg atagtcagta tgtcaacaaa gagccatatt   180
actccgctgt gattcccgtg c                                            201
```

<210> SEQ ID NO 358
<211> LENGTH: 201
<212> TYPE: DNA
<213> ORGANISM: Triticum aestivum

<400> SEQUENCE: 358

```
atcttccttt cattactacc ttcgactcat ccatcggtat aacaccaacc tcagatgcaa    60
cataaacaaa accatctgat gttttccaat agcgtgctgg rcgcagccca tttcgatcaa   120
ggcatgcccc taccgtcctt ccgtcactaa acaaaagtaa agcaggccca tcccaagcct   180
ccatttgacc tttgtagtat t                                            201
```

<210> SEQ ID NO 359
<211> LENGTH: 201
<212> TYPE: DNA
<213> ORGANISM: Triticum aestivum

<400> SEQUENCE: 359

```
ggatcattga ttgcagaatc tatagaattg aatcccatgt cagcaactcc aagtgaatgt    60
gaaatcattg aagatgataa ctcttgttga gaatccttag rtgaaatgta gttagaaatg   120
ccatttccag ccatctcatc catgaattta tcattttcaa tgctatttgc aagcaaggca   180
tctgcattaa gtggtaagcc c                                            201
```

<210> SEQ ID NO 360
<211> LENGTH: 201
<212> TYPE: DNA
<213> ORGANISM: Triticum aestivum

<400> SEQUENCE: 360

```
gccgtgcagc ctttgcttga cgtccttgaa cgtaagaccc cacctcgggc tccaggccac    60
gcgtggccag acctctacct cttgaccatt gaaagtgctg rctacagggt cagatatgtg   120
tgcaccggcc tttcttaaaa taaggctgtt tgccctgtaa attgccatct ctcctgaggt   180
```

```
tgcactatga aaaggattac c                                              201

<210> SEQ ID NO 361
<211> LENGTH: 201
<212> TYPE: DNA
<213> ORGANISM: Triticum aestivum

<400> SEQUENCE: 361
aatattattt gagaaaaaat gcattctaca aggtattcaa tatgtcaggt aaaagtatcg     60
atgcagacca agactaaca cttgatgtgg ataagttgac mactgacctt gctagcttgg    120
ttactggaat ggtaaagcca ctagttgaca ttctttggtt tacatggaga atgaagcttt   180
tgtccggccg aagaggagtt g                                             201

<210> SEQ ID NO 362
<211> LENGTH: 201
<212> TYPE: DNA
<213> ORGANISM: Triticum aestivum

<400> SEQUENCE: 362
ctcaacatcc tcatcaagct catggccgtc gagtccctcg tgttcgcgcc cttttcgcc     60 acgtacggag gtgtgctgtt caagtacatc tagaagactc rttgagcgga cttagaatct  120
acggacacca tcaccatcac gaataactct gccccgcccg cccgccgttc gtatgttgtg   180
cgctgctgtt attttggtt c                                              201

<210> SEQ ID NO 363
<211> LENGTH: 177
<212> TYPE: DNA
<213> ORGANISM: Triticum aestivum

<400> SEQUENCE: 363
gtcgacacca gagaagtcct acttcatcat aaactttact tattctgtac tgaactacag    60
cacatgcaac tcgcatkcct aacacaggac gggtataaat ataagaacta atgtgtgcag   120
aacaaaaaat ataattacac aggcgaagcc aggaatcatg tacaagaaag cagcagt      177

<210> SEQ ID NO 364
<211> LENGTH: 121
<212> TYPE: DNA
<213> ORGANISM: Triticum aestivum

<400> SEQUENCE: 364
cagatgaatc tgctggaccg ggcagtaaag atggttgctg aactagatga gccaattgag    60
rtgaactatg tgcgcaagca tgcccaggag caggcagagg agctcggtgt ctcggtaaga   120
g                                                                   121

<210> SEQ ID NO 365
<211> LENGTH: 201
<212> TYPE: DNA
<213> ORGANISM: Triticum aestivum

<400> SEQUENCE: 365
aggaagccat caagggttag cctttttaat gcttttgagg ctatgagatc aagatgcatc    60
gcagagtcta tcaaattcaa gtcttctagg ccagggctcc rggcaatgaa tctgttcaga   120
gaaagctcat ccacttccac gtcgcgcaga gtaagtttct tgagagaagg aagattgatt   180
atgtcaggca gtacaagtcc c                                             201
```

<210> SEQ ID NO 366
<211> LENGTH: 201
<212> TYPE: DNA
<213> ORGANISM: Triticum aestivum

<400> SEQUENCE: 366
gcttagcgtt ctactgcaaa gcacactgcc aacaggacat gatgttggca aaccgtctgc    60
tccagttcct ggccgtgcca caactgatat ctcaggtccc ygcaaccaaa atggatcagt   120
tcgtagacct ccaaaaagga aggctgttga aaggcaagag gaagaagacg cagcagcagc   180
tgcgcagagt cgagccatgc c                                            201

<210> SEQ ID NO 367
<211> LENGTH: 121
<212> TYPE: DNA
<213> ORGANISM: Triticum aestivum

<400> SEQUENCE: 367
aactagatgc cctttggga aggttttatc tcctgattct agctatattt gtgctcgtgt     60
raagttttcc ctggaaatac tagtaactta gcttgtaata gaaacgatgt tccctaaaca   120
t                                                                  121

<210> SEQ ID NO 368
<211> LENGTH: 121
<212> TYPE: DNA
<213> ORGANISM: Triticum aestivum

<400> SEQUENCE: 368
gtcttgttat accctatata tcggcatctt acttaagagc atgatttaca gctatagaag    60
magaacctat atgcaatctt gtcgattctg atattacttt ctgtacatgt cacatcgact   120
g                                                                  121

<210> SEQ ID NO 369
<211> LENGTH: 121
<212> TYPE: DNA
<213> ORGANISM: Triticum aestivum

<400> SEQUENCE: 369
ttgcattcct tcatgattaa agggacacca taccatgttg cctgattaga catattcaaa    60
ycggttatgt tgatgcaata taatggtata cttggaatga tagcttcctt tctgtatatg   120
c                                                                  121

<210> SEQ ID NO 370
<211> LENGTH: 201
<212> TYPE: DNA
<213> ORGANISM: Triticum aestivum

<400> SEQUENCE: 370
ggcatccgag aggctggcac tagtggcagc tcaagcattg caagagagtr aggaggctac    60
aagctctgaa gattctccga gagtgacact tccggtaggc raataccacc ttcttagcaa   120
gagggttcat gaagccgaag agctcgccag cgaaagggtg gcggcatcgt tggcgcaaat   180
agagctggcg aaagagtctg a                                            201

<210> SEQ ID NO 371
<211> LENGTH: 201
<212> TYPE: DNA
<213> ORGANISM: Triticum aestivum

<400> SEQUENCE: 371

```
cttctgagac cggaatttcc aataggatgg cttcgttctc gttccaagat ggtgaatttg      60
aagacctgaa gaaactctgc tgygctatag ctgatgacct mgttacctaa gcctgcggca     120
tatgcaacca tcaacagttt gtgtagcggt tcattatgta aaatcaccca gaatgttact     180
gcaactataa acatatcgtg t                                               201
```

<210> SEQ ID NO 372
<211> LENGTH: 201
<212> TYPE: DNA
<213> ORGANISM: Triticum aestivum

<400> SEQUENCE: 372

```
aaggttttgc atgtttccaa tgtttccaaa gagtcctccc tttgacggtg cctcatcacc      60
attctcatct ttgtccttct ttcctccaaa taaactgtat rcgcggaagg atctattact     120
agctcttttc caagtagaac atggcaaaca gaatgcgcct tgtacattta tcctagtacg     180
agctggtctg gaggggagcg t                                               201
```

<210> SEQ ID NO 373
<211> LENGTH: 201
<212> TYPE: DNA
<213> ORGANISM: Triticum aestivum

<400> SEQUENCE: 373

```
gtatacctcc cagagtggat ctacgagaaa gtaatcagtg ggcatgaatg ggagctaact      60
ttggaaatga cagcaaaaga caaagaaaag atgagacagc ygaccattgt ggccctgtgg     120
tgcatccaat ggaacccgaa gaatcggcca tcaatgacaa aggtggtaaa catgttaaca     180
gggaggttgc agaacctgca g                                               201
```

<210> SEQ ID NO 374
<211> LENGTH: 201
<212> TYPE: DNA
<213> ORGANISM: Triticum aestivum

<400> SEQUENCE: 374

```
aggcagtgat cacagttcct gcttatttca atgactccca gaggacggct acaaaagatg      60
ccggccgcat tgcaggcctg gatgttctcc gtatcataaa ygagcctacc gcggcatcgt     120
tggcatatgg ttttagaaaa aagaacaatg aaacaattct ggtttttgac ctgggaggag     180
gcacctttga tgtttcagtt c                                               201
```

<210> SEQ ID NO 375
<211> LENGTH: 201
<212> TYPE: DNA
<213> ORGANISM: Triticum aestivum

<400> SEQUENCE: 375

```
ccaagataca tgtacttggg aacaagtgtc aaagtaagct acttgaaata attgatgcta      60
gtgaattgcc agaatttctt ggtggcactt gtacctgtcc ygaatatgga gggtgcctca     120
aagctgaaaa agggccatgg aaggatgcaa acatactgaa gaaagtcctt aatggcgagg     180
ctcagtgtgc tcggcagatt g                                               201
```

<210> SEQ ID NO 376
<211> LENGTH: 201
<212> TYPE: DNA

<213> ORGANISM: Triticum aestivum

<400> SEQUENCE: 376

```
ctttccttgc tgccatggaa atcatggcag agaaattccc tggtgcattt gcaggttaca      60
aactagaggt aatggagtct catcaagcga caaaattgga ygtttctggc actgccaaag     120
ctgtaatctc ttgctttcag aagttgggtg tctcattcga cttaraygag gtaaacttgg     180
ttagggaccc cgaagagcag c                                                201
```

<210> SEQ ID NO 377
<211> LENGTH: 201
<212> TYPE: DNA
<213> ORGANISM: Triticum aestivum

<400> SEQUENCE: 377

```
atgttggtct ggataatgag aaggcaattg aggagaccgg cagacgwttc agagaaacgg      60
ttcttgcact tggaggtgga aaatctcctc tcgaggtttt ygttgctttc agaggacggg     120
agccgtcgcc ggagccactg ctcaggcaca acggcctgct acctgtcgcc gcatagggtg     180
tcgatcgctc ctttttctct t                                                201
```

<210> SEQ ID NO 378
<211> LENGTH: 201
<212> TYPE: DNA
<213> ORGANISM: Triticum aestivum

<400> SEQUENCE: 378

```
ttagaaaggt tgctggggc ttaaggggac caacaggata aaaccttcag magtgcttcg      60
tctatgctgt ccagatgcaa attgttgcga aaaatgttga ytgcaaggaa catatatggt     120
cggttataga agtcgttata aacatcttag caatgtggaa tgtaaggaac aagggccata     180
ccatgaactt agacggattt g                                                201
```

<210> SEQ ID NO 379
<211> LENGTH: 201
<212> TYPE: DNA
<213> ORGANISM: Triticum aestivum

<400> SEQUENCE: 379

```
gatctccaga tcaaggacgg cgatgggaac accgcccagg acttgtgctc ctcggcctgg      60
cctttcatga agccggcaaa ctgatggcac aatgaacccg rtgatacgtt gacgcctgct     120
gctactacta ctagtgccga gaaactatac acaccgtgct tgattagctg aatcggatga     180
gccgttttac caacctcatc g                                                201
```

<210> SEQ ID NO 380
<211> LENGTH: 201
<212> TYPE: DNA
<213> ORGANISM: Triticum aestivum

<400> SEQUENCE: 380

```
attctagaag atgatctata tcactatggt agtaacagtg aggagatgct tctcgatgag      60
ttgaaggttt cacgagcaat gtcaaagcat tttattaagg ytacatcttc agccactatc     120
aaggaggcaa cactgcttat gcacgataag cagcaaggtt gtgttcttgt tgtagacaat     180
gaagattttc ttgaagggat t                                                201
```

<210> SEQ ID NO 381
<211> LENGTH: 201

```
<212> TYPE: DNA
<213> ORGANISM: Triticum aestivum

<400> SEQUENCE: 381
ctgtccaaga tatggaagac ctaaaagcct tgtgaaaga ttctggttct gcagaagcca      60
atgatctagc acactgggat cttaacttct ggagtgaacg rctgcgggaa tctaaatatg    120
acatcgatga ggaaggrctg cgtccttact ttgcactgcc caaggttatg gatggcctct    180
tcagtcttgc gaataagctc t                                              201

<210> SEQ ID NO 382
<211> LENGTH: 101
<212> TYPE: DNA
<213> ORGANISM: Triticum aestivum

<400> SEQUENCE: 382
cagaagcttg ttcttctagc ggtgagaact ctccagtgtt ctatgcagcc rttgctggta     60
atgagcatga gaacattcaa gataacgatt ctgagagagg t                        101

<210> SEQ ID NO 383
<211> LENGTH: 201
<212> TYPE: DNA
<213> ORGANISM: Triticum aestivum

<400> SEQUENCE: 383
ctcttccatg ctggaatcgc agcagtactg ttgctctatg ttctcttctg ggttaagctg     60
gatcttttca caactctgaa gtacctcagc ttcctcggcg ygttccttgt gttcgttggc    120
cataggaccc tatctcatct ttccaacacg acggcaaaac agaagactgc ttgatgggaa    180
gatgcgaaga atgtgtgatc a                                              201

<210> SEQ ID NO 384
<211> LENGTH: 201
<212> TYPE: DNA
<213> ORGANISM: Triticum aestivum

<400> SEQUENCE: 384
acattttata tggctgaaca aactcggttc ctacagtaag attccctgct gaaggaaaac     60
cagatggcct accactaaag cttggagtca taggactgtc ragaggtgtc gcagcagaac    120
tctggggaga ataactagtc ataacgggtg ggaaacttga accacccaaa gcatacccag    180
aagtcacata aggatttgcc a                                              201

<210> SEQ ID NO 385
<211> LENGTH: 201
<212> TYPE: DNA
<213> ORGANISM: Triticum aestivum

<400> SEQUENCE: 385
gccaaaggta tctctgaagg aaggccttcc cttgatggtg acagatttcc gcaaaaggat     60
cttggatgag taaccaaggc aacactgaga tgaatctatt yggttctgaa tgctgcgaat    120
ataggcaaac gtgcttcacc aactggatcc attcagtata attctgtgtt tgtataacga    180
ccttgtagaa tcatttaaat t                                              201

<210> SEQ ID NO 386
<211> LENGTH: 201
<212> TYPE: DNA
<213> ORGANISM: Triticum aestivum
```

<400> SEQUENCE: 386

```
caaccgctgc tattggaaag ggttttgcca ttggatcagc tgctcttgtg tccctggcac      60
tttttggtgc ttttgtcagc agagctggtg tgaaggtcgt ygatgtccta tctcccaagg    120
tgttcattgg tctgattgtc ggagccatgc ttccgtactg gttctctgcc atgaccatga    180
agagtgttgg aagtgcygct c                                              201
```

<210> SEQ ID NO 387
<211> LENGTH: 201
<212> TYPE: DNA
<213> ORGANISM: Triticum aestivum

<400> SEQUENCE: 387

```
acagatcttg atgcagccaa gagaagcgag gagaccaaca tggtgacagc agatgttgat     60
acatccaaga gaagcgagga acagagcaac atggtcgccg ygaagcttga tacagccaag   120
aaaagcgagg agcagaccag cagtgttgct gcggcaggct gattacagga tgggcgcatc   180
tgaacggaag ctacatccaa a                                              201
```

<210> SEQ ID NO 388
<211> LENGTH: 101
<212> TYPE: DNA
<213> ORGANISM: Triticum aestivum

<400> SEQUENCE: 388

```
cggaaaagcc aggtgtgcct ctcgttcttc gatgagaaga acaagcaccc rggctggttc     60
agcagcaaga ctgagagggt ttactgggaa caatggttca t                        101
```

<210> SEQ ID NO 389
<211> LENGTH: 201
<212> TYPE: DNA
<213> ORGANISM: Triticum aestivum

<400> SEQUENCE: 389

```
ttgttggagt ttgcttgact ctaagccttg caaacatcgt ggggttcacc aaatgcaaca     60
aagatgccaa gaagaacatc cgagcttttg ctgaaaatgc ygctcaaaac gccatcacat   120
cccgcatcac atcatccctt cagtcagcat tcggtatctg aagtccagat tacagaggcc   180
caaaattaca tacaactgtg t                                              201
```

<210> SEQ ID NO 390
<211> LENGTH: 201
<212> TYPE: DNA
<213> ORGANISM: Triticum aestivum

<400> SEQUENCE: 390

```
tcagctctgg tagggctgcc gacttggtct cgtcgagctg cattatagcg gagattttct     60
tggtctgcac atcttctggc aagcttcttc tccgtgggta rtccgagctc actgacttcg   120
gattyggagg gtggtcagtt gaagcattgc ttttaggttc agcaagcttt ttcaaccgct   180
caatcgagga ttcagttctc c                                              201
```

<210> SEQ ID NO 391
<211> LENGTH: 201
<212> TYPE: DNA
<213> ORGANISM: Triticum aestivum

<400> SEQUENCE: 391

```
cttgctgaac aaaagtctgc tcaaggatct ctctacacaa gtcaagccta gaccagagga     60
```

```
cectcaatgg cgcaagatat gtagaaccaa gaaggtgacc racttcacta ggtcggcggg    120
tattcttgtt atttctgggc tcacttatta tgccttgayt tcccgtcctg aaatcgtaag    180
gtatggtgac tatcttgtta c                                             201
```

<210> SEQ ID NO 392
<211> LENGTH: 201
<212> TYPE: DNA
<213> ORGANISM: Triticum aestivum

<400> SEQUENCE: 392

```
catcccttcc tggtagacag atgaatggga cagcaattgg tggccttgaa ctgagtaagg    60
aagctatgct gagccttgct gctgctgcac aatgggagaa rcaaagagag ataaaccaag   120
caaagataga crcaaactgc agtaaaattc aggaagccct caagtccctg aacgagtrca   180
aaagaacatg cgagctgcat g                                             201
```

<210> SEQ ID NO 393
<211> LENGTH: 201
<212> TYPE: DNA
<213> ORGANISM: Triticum aestivum

<400> SEQUENCE: 393

```
catagatgaa gctttctgta gttttccatc accactgatc ttgggaaatt ggccacaccc    60
ccacagtgct gaggctggta gctgcgaggt acagggcact rtgaagaaaa gtttggccag   120
caagtttggc actggggctg gccgtccaga atacattgca tacccactgc agtgatcatc   180
ttcaagcttt agctgtcagc a                                             201
```

<210> SEQ ID NO 394
<211> LENGTH: 201
<212> TYPE: DNA
<213> ORGANISM: Triticum aestivum

<400> SEQUENCE: 394

```
agaaacttgt ggggctgctg catcccacgg gtttgaacag gattrtagtc ttgtgccatg    60
gctttacggc ctccaagagt tctggcgtta ttgttgatct rgcagatgca ataataaaac   120
aagggattag tgttttttcgc tttgacttca gtggaaacgg agagagcgaa ggcgttttcc   180
agtatggcaa ctacaggaaa g                                             201
```

<210> SEQ ID NO 395
<211> LENGTH: 201
<212> TYPE: DNA
<213> ORGANISM: Triticum aestivum

<400> SEQUENCE: 395

```
ttccagcttc tgtgcttcag ggagctcaag acaaatgtta gaatatttac ccaatggatg    60
atgtaatctc taggtatctt ttgtgcgcta gctgtgccaa rcagccgtta tgtatgttca   120
tctaattgtc acttctcatt tctcctgtta acactggtct tacttatgct agtataattt   180
aggaaacctg catagtaaca t                                             201
```

<210> SEQ ID NO 396
<211> LENGTH: 201
<212> TYPE: DNA
<213> ORGANISM: Triticum aestivum

<400> SEQUENCE: 396

```
tatacagaac aaagacgctc tcccgtacgg cccaaccagt ttggaatgac aagtttgaat      60
ttgatgagat tggtggtggt gaatatctga aggtcaaatg ytataattta gatacattca     120
gtgatgatag cattggcagc gcaagagtaa atctggaggg acttctagat ggtgctagcc     180
gagatgtgtg ggtaccactt g                                               201

<210> SEQ ID NO 397
<211> LENGTH: 201
<212> TYPE: DNA
<213> ORGANISM: Triticum aestivum

<400> SEQUENCE: 397
cccgtaccgc aactgatgct ccgcccttttg atgcaagcaa tatcactgca ctacagctca     60
tgttcagcaa gtttgaatac gacggaaagc tcaacccaac rtttgcagaa ggtcaattcg    120
agctcccttt ttcaagtatc aaagcataca taagtgagcc aattactcca aggttcattc    180
atgtgagctc tgcaggagtt a                                               201

<210> SEQ ID NO 398
<211> LENGTH: 201
<212> TYPE: DNA
<213> ORGANISM: Triticum aestivum

<400> SEQUENCE: 398
ttctcgagga agaagatgga tgcgaccgcc caggagctgt cggaggagaa ggcgctggcc      60
tactcatgcc tcgcgtaaat ccacattgga agggcagctg mtcctctgga tgttttgaat    120
aatgaaacct tccgctcctt agaaactctc gtctccaccc agaacagccg cacatcgcga    180
tgcatgctcc ttttcgctgg t                                               201

<210> SEQ ID NO 399
<211> LENGTH: 169
<212> TYPE: DNA
<213> ORGANISM: Triticum aestivum

<400> SEQUENCE: 399
ttagcattgt tgaaccatat ctattcctca tccttgagta gtgtgcaagc atactgtggc      60
agtttggctc cagttttgaa agtcattttt gtttgtctga racatcttgg aaagaacagt    120
gtaagaatga agtatttctg tttaatgcca gttagtattt ttgtcgcsa                 169

<210> SEQ ID NO 400
<211> LENGTH: 201
<212> TYPE: DNA
<213> ORGANISM: Triticum aestivum

<400> SEQUENCE: 400
acaacgtcga caagaggtcc aaagtgagga agcagccgtg gatgcccttc atctgctgcc      60
actccgtgca ctgatgctgc cattcattct tcctcagcta ygatcttctt tctacacacg    120
ccatgcgcat cttgtttgaa tccgtggcac cctttttagt atatttgcgt gaggactgga    180
tattggataa gcttatgtct t                                               201

<210> SEQ ID NO 401
<211> LENGTH: 201
<212> TYPE: DNA
<213> ORGANISM: Triticum aestivum

<400> SEQUENCE: 401
tgacatcaag ccacacaaca tcctgcttga tagcaatttt gtcccaaaac ttgctgattt      60
```

```
tggtctcgcc aagctgtacc caagaaacaa cagtttcgta ycattgagcg tcctgcgcgg      120
aacaattggg tacatagctc ctgagatgat atctaggagc tttggcgtca tatcgagcaa      180
gtctgatgtt tacagctttg g                                                201
```

<210> SEQ ID NO 402
<211> LENGTH: 201
<212> TYPE: DNA
<213> ORGANISM: Triticum aestivum

<400> SEQUENCE: 402

```
ttggttgttt tgttctttt tagcagatcg catcattgtg gcagcttact tagctgtagg       60
atattcatat ggctcgctcc atgtaaattg gtgatcgacg rcggagtttt aacgccgaga      120
tgcgccggct cctttttgatg taacccggct tctataccga cagttgtagg acaaagatga    180
gagattttat gacatgtaac a                                                201
```

<210> SEQ ID NO 403
<211> LENGTH: 201
<212> TYPE: DNA
<213> ORGANISM: Triticum aestivum

<400> SEQUENCE: 403

```
tgtwgaatac tcaccttcgg ataaaggaat tatcactggt tcctctgacg ggcttatacg      60
tttttgggaa aacgaaggag gcataaaatg tgttaagaat ytgacgcttc actcggcatc     120
ggtcctgtcc attagtgctg gtgatcactg gcttggaatt ggtgctgctg acaattctat    180
gtctcttttc catcgaccac a                                                201
```

<210> SEQ ID NO 404
<211> LENGTH: 201
<212> TYPE: DNA
<213> ORGANISM: Triticum aestivum

<400> SEQUENCE: 404

```
ttctttgcat gtactgctcc attggtttgc agattttgg gggcattgtg tatgctggwa       60
acccaacact agaagaaacg gacctcttca ataatgacta ycttctttttt aacttcaatg    120 actatccaag tggtatggtt actctgttca atttgttagt gatgggcaat tggcaagtat    180
ggatggagag ttattggcaa c                                                201
```

<210> SEQ ID NO 405
<211> LENGTH: 201
<212> TYPE: DNA
<213> ORGANISM: Triticum aestivum

<400> SEQUENCE: 405

```
gastctggaa gctgtacagg agtcgtcgag agtcaagagg aggttgttct gctcatagga      60
cgacctgacc tgacctgatc cgaggcaccg accatgtcga mattaacagt gaagctgcca    120
gcgccatttt tgacctcccc gtccgtctcg agagaacagc gaaagagaag atagcatgag    180
acgatgctcg tcgcttcctt t                                                201
```

<210> SEQ ID NO 406
<211> LENGTH: 201
<212> TYPE: DNA
<213> ORGANISM: Triticum aestivum

<400> SEQUENCE: 406

```
gaagtcagca cccctctcat tgcaacatag gactgcgagt acgccatctt gggagagggt    60
gaggggtcga attctgacca gtccttaacc gaccccctctc kctgcattgc cccagcattt   120
cttcttgcca ttgcaggtgc tcaatatgtc acgcatgtac agttctagag tcaagcaaaa   180
gacatcacct ctctgatacc a                                              201

<210> SEQ ID NO 407
<211> LENGTH: 201
<212> TYPE: DNA
<213> ORGANISM: Triticum aestivum

<400> SEQUENCE: 407
ctgctcaagg ggttatgatt tttattttat ttgtttataa gttcattcta tcagttcgtt    60
ttgtacctaa taagtgaact agcacaagtc agtagaatga rctactgatg aatgagcttc   120
taatttatct gcaactgtaa gagaaattga gcttcatgtt ttcacttgca catatataaa   180
tgctgaataa gctggtaagg a                                              201

<210> SEQ ID NO 408
<211> LENGTH: 201
<212> TYPE: DNA
<213> ORGANISM: Triticum aestivum

<400> SEQUENCE: 408
tatctgggca tatttgaacc attcagcgtg catgcctcac tcccatggtt ttagaaaggt    60
ttgctggggc ttaaggggac caacaggata aaaccttcag magtgcttcg tctatgctgt   120
ccagatgcaa attgttgcga aaaatgttga ytgcaaggaa catatatggt cggttataga   180
agtcgttata aacatcttag c                                              201

<210> SEQ ID NO 409
<211> LENGTH: 201
<212> TYPE: DNA
<213> ORGANISM: Triticum aestivum

<400> SEQUENCE: 409
ttctcgcaac aatgccagaa tcattaacag aatgtacaat aggcaaggct tcaacaaaat    60
ctgcctcatc atccaacatt gcaggaactg ggggactctc mtcggcctgt ggctcattaa   120
ccgcttcaga ttcagcctcc gctacaaatg gctccagctt ggtgccttga tgttctgcca   180
tttgtcgtct atcaatcgca t                                              201

<210> SEQ ID NO 410
<211> LENGTH: 201
<212> TYPE: DNA
<213> ORGANISM: Triticum aestivum

<400> SEQUENCE: 410
gaatgatgca gaaaatgctg gtgactgtga acctgaagaa tctgaaacta atgaaccaga    60
agcagaagca gaagcagaag atgtcaaatc taaggaagcc mgtggcaatt agattgccct   120
atcccccatg gtgctaacta aatgtggcaa aacaaaatag atgccaggca atatgattac   180
tgaagcgagt cgcggatgat g                                              201

<210> SEQ ID NO 411
<211> LENGTH: 201
<212> TYPE: DNA
<213> ORGANISM: Triticum aestivum

<400> SEQUENCE: 411
```

```
gatttcacca gaggcagcaa cgccgaggtt atctccgctt tggtgggcag agcttgagat      60
actttcagtt gaatcctagg aagaaacatg ttgatatggt mtggttcttg cagcaacact     120
gaggtcctgt gcgtactgtc ttgcaatctt gtacatcttt gttgcgagtt tctactttc    180 tggcgatttc ggtgtatatg c                                                201
```

<210> SEQ ID NO 412
<211> LENGTH: 201
<212> TYPE: DNA
<213> ORGANISM: Triticum aestivum

<400> SEQUENCE: 412

```
ggctgagatg aaccatgggc ctcttctttt gtagttcaac acttgaacat ttacacttgt      60
agcacaacac ttgaatattt acacttgtag tccaacactt ragcatttta cacttcaggc     120
agaaagacca gattatagtt cattttttcac ttttcagttc tcaatgcaca tctgaataaa    180
ttgtttggtg tataacttcc a                                                201
```

<210> SEQ ID NO 413
<211> LENGTH: 201
<212> TYPE: DNA
<213> ORGANISM: Triticum aestivum

<400> SEQUENCE: 413

```
aatatggaag acaatacatt tgatatttgg caagatgttg ccgcaccacg tcaccaacag      60 gaaacatat ctaatcttgg gagagaaatg actggtgcct ygtctgtgcc tgctaaagaa     120
attgactcca tggatttgtg gctaaccagc aatatcaagg aatctaacag ctgcagcaaa    180
gatgttagtg gaaytcatga c                                                201
```

<210> SEQ ID NO 414
<211> LENGTH: 146
<212> TYPE: DNA
<213> ORGANISM: Triticum aestivum

<400> SEQUENCE: 414

```
ggagttccaa attatctgct ttttgamcma gaaaaaagct tgtcayaggc aacagcctaa      60
caatcacggg gagttaccac ttgtaatcga agccatacag ataaaataaa gacagactac     120
atttgttatg atagcgatat aaatgc                                           146
```

<210> SEQ ID NO 415
<211> LENGTH: 201
<212> TYPE: DNA
<213> ORGANISM: Triticum aestivum

<400> SEQUENCE: 415

```
gagttttctc tgctctacat gatagtcctt gcatgcatcg acagaagact caagagcatg      60
gattgcaatc tccgctggaa tcatccatcg ataagggacc rtatgttaat ctcatggaag     120
atggaatggt agctgcagtg acaaacgagg ataccaacac tcacgaatcc ttggataagc    180
ataatcaggc tgtcagtgaa a                                                201
```

<210> SEQ ID NO 416
<211> LENGTH: 201
<212> TYPE: DNA
<213> ORGANISM: Triticum aestivum

<400> SEQUENCE: 416

```
agtagcacat tcttttccag gttttctgct tgctgtgcca tagcacaggt gagctggaga    60
tcctggagat tagacagccc tccaagttgt aatacattct ytattgagta acggcggctg   120
agatcaaaat tccccaaagt gcgaagagat gtcatgtggg ctactccttg aggcaggata   180
gattcgctcg gaagacggag g                                             201
```

<210> SEQ ID NO 417
<211> LENGTH: 201
<212> TYPE: DNA
<213> ORGANISM: Triticum aestivum

<400> SEQUENCE: 417

```
caggaggtaa aacagtctta tcatatagac aaagtttcac gtcaagcact ttaacattat    60
gcttcaccgc atagccaatc cacattctga catcattgca rttcagggga ccatgaggat   120
tccaatgcag ctggaatgtt tgcaagtcta ctttccgacg acaagcaat aggttgttaa    180 caaaacgagt aaacttctcg a                                             201
```

<210> SEQ ID NO 418
<211> LENGTH: 201
<212> TYPE: DNA
<213> ORGANISM: Triticum aestivum

<400> SEQUENCE: 418

```
gcctgttggc tcttccaact ttgttgacca cccaacctca tctgacagca gattagaatc    60
aaaacaaaac aaagatgcac gggacaccaa ggttgacgac ygggaggcaa aagctgatgc   120
tcgggatgtc catagtgata gcaggattga atttcaaggc aataaagctg agactgatgt   180
gaagacaaac aacagagcag a                                             201
```

<210> SEQ ID NO 419
<211> LENGTH: 201
<212> TYPE: DNA
<213> ORGANISM: Triticum aestivum

<400> SEQUENCE: 419

```
tttgaggaac aatgcccaaa ggatcatgtg atgtgcatat ttctgggaa ctgtcatcta    60 gcttcatatt catgctttcc agtgatagcg aattgcatcc rttcccaagg tggcgcagat   120
tctgccagac tatcaagcca tgcgtcggtg tttcagacct cgttcgcgca caatgtacag   180
cggtgcctat ggtgcccctt t                                             201
```

<210> SEQ ID NO 420
<211> LENGTH: 201
<212> TYPE: DNA
<213> ORGANISM: Triticum aestivum

<400> SEQUENCE: 420

```
ggcagcctaa tcaggtggtt tgagatctat ctctctgttt taatcgtgaa atggttagtt    60
tttcatggca gggtattatc tatcaataaa cttgtatgtg ycatgcaag tgctacctta    120 gactggtcag tagaatttga gaattgtatg gaaggaactg gtttgttgct ttgatatcta   180
tcaaaatgag atgatgtcct g                                             201
```

<210> SEQ ID NO 421
<211> LENGTH: 201
<212> TYPE: DNA
<213> ORGANISM: Triticum aestivum

<400> SEQUENCE: 421

```
tgccaaggat gctttgatct cagacgccgg tgataaaaat caatgaagac attgcggatg      60
tgaatgaaca catctccagg gaagagcacc ctgagcccac rttggaacac tcatccacgc     120
taagaaatgt tgatgagatt atgccggtgg acgaacctcc tgtatcaaag gaacctcaaa     180
ggtgcgggtc tgcccgcagc c                                               201
```

```
<210> SEQ ID NO 422
<211> LENGTH: 201
<212> TYPE: DNA
<213> ORGANISM: Triticum aestivum

<400> SEQUENCE: 422
ccgacactct tcaaggtcag agtctgacgc ctcagattac agcagcgatg atgatgagcg      60
aaggtcaacc aggaaggacc attctaggag ccggaggcgt ygccaccggt cctcagacga     120
tgaatctgag gagaagatca ggtcgaggca taggaagcgt catcacagat caagtgacga     180
ggacaagccg tcagattctg a                                               201
```

```
<210> SEQ ID NO 423
<211> LENGTH: 201
<212> TYPE: DNA
<213> ORGANISM: Triticum aestivum

<400> SEQUENCE: 423
cactaaacat cacacgagct ttcagtaaca cacaattgca ttaagtagaa tttgaacaat      60
agtaaagaaa gattacaata taacaaatct ttggatccaa yagaattaca actggacact     120
ataggttcta tcatctgtgt tcatggtagc ttcagatgct atagagtgaa ccatagccag     180
acgaagaaca agagtgaagc a                                               201
```

```
<210> SEQ ID NO 424
<211> LENGTH: 201
<212> TYPE: DNA
<213> ORGANISM: Triticum aestivum

<400> SEQUENCE: 424
cagttggagt tgctagtcag agagaagagc tacgcgctag gttccctggt gttcctggtg      60
atcttgtgaa ttacttcctc tttgttgcag aggaggtacg rgccacatta gcccagttgg     120
gttatgagaa gctggatgat ataattgggc ggacagattt acttaagcca aagcatatct     180
ctttggtgaa aacgcagcac a                                               201
```

```
<210> SEQ ID NO 425
<211> LENGTH: 201
<212> TYPE: DNA
<213> ORGANISM: Triticum aestivum

<400> SEQUENCE: 425
atctccaagt tggtatggat atcttccatg acttctttac ccttcatcaa agctaagttg      60
gaatttgaag cttccctcgc catccgatgg tcttcattcc rtgagttggg aagcatcgaa     120
gaggggtatg ctttctttga aataccaaat gtggaatttg aatcatcctt taacactgcg     180
gaatattgat ccctagttga a                                               201
```

```
<210> SEQ ID NO 426
<211> LENGTH: 201
<212> TYPE: DNA
<213> ORGANISM: Triticum aestivum
```

<400> SEQUENCE: 426

```
aagagaagag aacaagggga agatgattgt gaccatgttc ccgagcgggg gcgagagata     60
catgaactct gacctctttg caactgtaag agaggagtgt rctgccatga ccttttgatc    120
tcacatttta tgaatacaaa acagttgtat gtgaagggta tatgccgtcg gttaccttaa    180
tgtgttccac tggacgacat t                                              201
```

<210> SEQ ID NO 427
<211> LENGTH: 201
<212> TYPE: DNA
<213> ORGANISM: Triticum aestivum

<400> SEQUENCE: 427

```
aagcaaatcc agaaaaacca attggaaatc gacgcggtat actgctcctc tggtttgtat     60
gccatccagt gacctgatca cccttacaaa gggggccttc yaaaaccaat ttatacttgg    120
tcccaacatg cgttgctact ggccatgtac caaagcgcct gatttcctc atttcttcaa     180
atagatcaac tgagtatgct c                                              201
```

<210> SEQ ID NO 428
<211> LENGTH: 201
<212> TYPE: DNA
<213> ORGANISM: Triticum aestivum

<400> SEQUENCE: 428

```
ttagggtgga tggcggattc aggagtggcc tagatgtcct tttggctgct gccatgggtg     60
ctgatgaata tggctttggt tctgtagcta tgatagctac yggatgtgtc atggcacgca    120
tttgccacac aaacaattgc ccagttggag ttgctagtca gagagaagag ctacgcgcta    180
ggttccctgg tgttcctggt g                                              201
```

<210> SEQ ID NO 429
<211> LENGTH: 201
<212> TYPE: DNA
<213> ORGANISM: Triticum aestivum

<400> SEQUENCE: 429

```
ccgcgtcgct gttcttgcgc acagtgaaaa ggttgtagct gttctctgca ccaacataga     60
tgtcatcgtc aatcatctca actgcagtca tccagttcgc rttgtagtcc ctagcgagct    120
cttcaatcgc actctcctca tgcttgtaca caagcaagga tatcgatttc atcaggtctc    180
cgactacgat gaaatcacca c                                              201
```

<210> SEQ ID NO 430
<211> LENGTH: 201
<212> TYPE: DNA
<213> ORGANISM: Triticum aestivum

<400> SEQUENCE: 430

```
tggatctcac ccggacggtg cgtgtataat atgagcaacg tcttggtgag atccgcagat     60
catcacaatg ggtgttacgc aaggcatgtg atagacttat rctactgggg gtaatgcttg    120
cttcagttt tggttctgca tatgttgtat ggcttttta atacaaaagg gtgtattttg     180
tcctaagaca cctgtatata t                                              201
```

<210> SEQ ID NO 431
<211> LENGTH: 201
<212> TYPE: DNA
<213> ORGANISM: Triticum aestivum

<400> SEQUENCE: 431

```
ttttactgc caccttctcg ccattcaact caaccttcac ggttttgcca agggtgcccg      60
ccatgtcaac cactcgcttc atcatgagtg ccacaacatc ygcttcgagc tcagtcattt    120
tgaactttc aagatcaggc ttgaaggtaa ctttagtcca gttctccgac tgcttgcact    180
ttttaatctc aggctccgac t                                              201
```

<210> SEQ ID NO 432
<211> LENGTH: 201
<212> TYPE: DNA
<213> ORGANISM: Triticum aestivum

<400> SEQUENCE: 432

```
acaccgagtc tgaaaggatt gtgcaggagg ctcttgatag ggtcatgaca aatcggacca     60
ctgtcatagt tgcacaccgt ttgacgactg taaggaatgc ygatacaatt gctgtcatct   120
gccgaggatc aatagttgaa aaaggtccac accatgacct tttgagggac ccagaaggag   180
cttacagcca actgatacgc t                                              201
```

<210> SEQ ID NO 433
<211> LENGTH: 201
<212> TYPE: DNA
<213> ORGANISM: Triticum aestivum

<400> SEQUENCE: 433

```
agtctgaccg tcgattattc gaatcgtttg tataatgtaa ttagtgcgaa tcttgatagt     60
aagttttgc aggatgtgct tgagctcatc tgctggtaca rtgattagtt cacctgcctg   120
ttgtctcctc cgtaacgagt tgacagagaa agtacacgcg acaaaatgta ctccaagaca   180
cgctaagagt aatggaatca g                                              201
```

<210> SEQ ID NO 434
<211> LENGTH: 201
<212> TYPE: DNA
<213> ORGANISM: Triticum aestivum

<400> SEQUENCE: 434

```
gccttgcctc aaacccgaat ccaaacaagt cattcgaggt ccttcctaat ccgggtgact     60
ccctctcaag cctcagtttt agcccgaaaa gtaatcttct kgtggcaact tcctgggata   120
accaggtgag gtgttgggag ataggtaatg gtaacagtca gccaaaggca tccatatcac   180
atgatcagcc agtgctctgc t                                              201
```

<210> SEQ ID NO 435
<211> LENGTH: 96
<212> TYPE: DNA
<213> ORGANISM: Triticum aestivum

<400> SEQUENCE: 435

```
ccagatgggt tccatgacct ggcttctctg tttcaygtga gttatttctt gtgcttgttg     60
tagtgatatt tagtgatatc tgcatgaaca tatgtg                               96
```

<210> SEQ ID NO 436
<211> LENGTH: 201
<212> TYPE: DNA
<213> ORGANISM: Triticum aestivum

<400> SEQUENCE: 436

```
tggtcattct ctgggggat aattgtatcc ttccatggcc caatcccaat tacatacttc    60
cttatgaacg cgagatagcc gttcgaagtt atctcatagt rtgactggtt ggtatcttga  120
gttggaactg tggtttcgtc tattagaagt agttttggag catttgtgat gtttgagatg  180
taaattagtg aagttggagc a                                            201

<210> SEQ ID NO 437
<211> LENGTH: 201
<212> TYPE: DNA
<213> ORGANISM: Triticum aestivum

<400> SEQUENCE: 437
gcatttatat cgctatcata acaaatgtag tctgtcttta ttttatctgt atggcttcga   60
ttacaagtgg taactccccg tgattgttag gctgttgcct rtgacaagct tttttcttgg  120
tcaaaaagca gataatttgg aacttctatc ccaattggac tcatgtatgg ttacgaggac  180
ttttgcctgg ccaggcagct g                                            201

<210> SEQ ID NO 438
<211> LENGTH: 201
<212> TYPE: DNA
<213> ORGANISM: Triticum aestivum

<400> SEQUENCE: 438
ggaggccgaa gcccaagatc aactgagcac agtaattttc aacttgggta tacagtttga   60
catgatcctt gtaaatgctt gcaccatggg tgatatcttc ygtggaggtc taaaaaggcg  120
acaggacaga ctcaagcaay gcctagatgc agcacacagg ggttcgaccc tcagtcacac  180
cctctttatt tagatgacaa g                                            201

<210> SEQ ID NO 439
<211> LENGTH: 201
<212> TYPE: DNA
<213> ORGANISM: Triticum aestivum

<400> SEQUENCE: 439
cagttgtacc gagaaggaca acaagggaga ggaaggcggc agtagtctac gtcgcttctg   60
aaagcgaaga tgatgagtct gaggatgaag atgtgtcaga rccaagtgac gatgatgact  120
tctccgaaga tgactagact ccttggctca actgtccaaa cattgcgtgt ggtgcagtga  180
ctctagtgtc ttgagacatt t                                            201

<210> SEQ ID NO 440
<211> LENGTH: 201
<212> TYPE: DNA
<213> ORGANISM: Triticum aestivum

<400> SEQUENCE: 440
ctcccaagtc cagagtgaag gcgcacgctc tgctcgacct gctgcgcaac tcgccctact   60
cgaggtcgaa gctgcagccc aacaccctgg agaacatcgt yagcaacatt gcttctcaga  120
tcgatgggga ggaccgtggt gggaaggcca agaagatgct cgccgagatg gtgaaggtca  180
gcatggagca gagcttgagg c                                            201

<210> SEQ ID NO 441
<211> LENGTH: 121
<212> TYPE: DNA
<213> ORGANISM: Triticum aestivum

<400> SEQUENCE: 441
```

```
aaaatatttt tgccaggtga atccacatac tcatcagttg aaattatgtg actttggaag      60
ygcgaaagtg ctggtatgat cacacattac ctgatattca cacttgcacg acattggcat     120
t                                                                     121
```

<210> SEQ ID NO 442
<211> LENGTH: 201
<212> TYPE: DNA
<213> ORGANISM: Triticum aestivum

<400> SEQUENCE: 442

```
atttcgccat gatttcctac ccatctactt acttacaagc aaccgctgat aaattatata     60
attatatagt tctgcgaaaa atgattagca cttttcgccat mttgtctgtg gagtgtattt    120
gttgatctaa ttactagcag gaggtccttg caggaccgga ggatgtcctg aggacttcag    180
aaccaaggtc acgtatcttt t                                               201
```

<210> SEQ ID NO 443
<211> LENGTH: 201
<212> TYPE: DNA
<213> ORGANISM: Triticum aestivum

<400> SEQUENCE: 443

```
tcaagatact ctcaaaaatg ggcatatcct tgctctcaag ttactgtgga gctcagatct     60
ttgaaatata tggtcttggc caagaagttg tcgaccttgc rttctgtggg agtgtatcga    120
aaattggagg actcaccctt aatgagctgg gtcgagaaac actatcattc tgggtgaggg    180
ctttctcaga agataccgca a                                               201
```

<210> SEQ ID NO 444
<211> LENGTH: 201
<212> TYPE: DNA
<213> ORGANISM: Triticum aestivum

<400> SEQUENCE: 444

```
ttgggatgtg tttactggag cttgttacat ttgagtaccc atattgtgaa tgctccaatg     60
cagcacagat atacaagaaa gtttctgatg gtgaaaggcc yggttcactg gctaagattg    120
aggatcctga agttaaattc tttatagaga aatgcatagc ccaagcttcc caaaggctct    180
cagcagaaga actattagtg g                                               201
```

<210> SEQ ID NO 445
<211> LENGTH: 201
<212> TYPE: DNA
<213> ORGANISM: Triticum aestivum

<400> SEQUENCE: 445

```
gtatcttttg cagcatcaag gccttctccc gctccagctg ctgtatgtac aaatcctgct     60
cgtcctggac gctctccacc tccgtcaggg ccaacgacag ygcctccgca tcgccgccgt    120
cgtccaccaa gcccgagcat ttcttcaggc tgtctctcat ctgtgctgat atcttgtgtc    180
ctttgccgag ggcggacgca t                                               201
```

<210> SEQ ID NO 446
<211> LENGTH: 201
<212> TYPE: DNA
<213> ORGANISM: Triticum aestivum

<400> SEQUENCE: 446

-continued

```
caacttgggt atacagtttg acatgatcct tgtaaatgct tgcaccatgg gtgatatctt    60
cygtggaggt ctaaaaaggc gacaggacag actcaagcaa ygcctagatg cagcacacag   120
gggttcgacc ctcagtcaca ccctctttat ttagatgaca aggggggcttg cgggcccatc  180 attttagaas agctgacaca g                                             201
```

<210> SEQ ID NO 447
<211> LENGTH: 201
<212> TYPE: DNA
<213> ORGANISM: Triticum aestivum

<400> SEQUENCE: 447

```
acggcatgta tgttgaagtg tcaatctgct caggcagctc cttgatgtcc acctcaaacc    60
gttcttgcac ctggttaagg acgtccgagt ccgaggccga ygaaacaaaa gttatggcga   120
gtcccttggt gccaaaacgc ccagcccttc caaccctgtg caagtaggta tcagctgaat   180
caggcatgtc atagtttatc a                                             201
```

<210> SEQ ID NO 448
<211> LENGTH: 201
<212> TYPE: DNA
<213> ORGANISM: Triticum aestivum

<400> SEQUENCE: 448

```
tttgtggcag aatcatgatt gaaaaatagt gtataatttc tcattcacat cggcagcatg    60
tatgtatagt tttgcaaccg gacaagatga tgaaattccc yagtgcccaa ttcccacatt   120
tcccgaggct ttgtagcaca taacatttaa gtatatgagt cgcgcatgca tcatatgtgc   180
ttctcttctt tctggaggag g                                             201
```

<210> SEQ ID NO 449
<211> LENGTH: 201
<212> TYPE: DNA
<213> ORGANISM: Triticum aestivum

<400> SEQUENCE: 449

```
gtggtacctt acggccgggg agagaaggcc atgaccttcg acctcgacga caagatcctc    60
gccgccgtcg gggcggcgcc ggtcggcgtc gccgcctagg ratgttcgtc cttcgatgcg   120
ccgcagcggg aaaaccattt tgaaaacaca gccgcccgat tatcatacat acagatgaca   180
cagagcatat ctaatcatgt t                                             201
```

<210> SEQ ID NO 450
<211> LENGTH: 201
<212> TYPE: DNA
<213> ORGANISM: Triticum aestivum

<400> SEQUENCE: 450

```
agttcccaat aagcaagttc tcgaactctc ttggatcttc tactttattg ttgtaaccat    60
agcgcaccac acatcggaat accctgtatt ctcttggctc yacatatcgg aagaggaacc   120
gttcatttgt ttctatattg ctgattggta agtactttat tgaggtaatc acaagaactg   180
aatggatgga aggtactttt t                                             201
```

MOLECULAR MARKERS FOR VARIOUS TRAITS IN WHEAT AND METHODS OF USE

CROSS-REFERENCE TO RELATED APPLICATIONS

This application claims priority to U.S. Provisional Application No. 61/671,423, filed Jul. 13, 2012, which is hereby incorporated herein in its entirety by reference.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 434334seqlist.txt, a creation date of Jul. 9, 2013 and a size of 156 Kb. The sequence listing filed via EFS-Web is part of the specification and is hereby incorporated in its entirety by reference herein.

FIELD OF THE INVENTION

The present disclosure relates to compositions and methods useful in identifying and/or selecting wheat plants or germplasm for heading date, flowering date, anther-extrusion, and/or *fusarium* head blight resistance.

BACKGROUND

Wheat is one of the most important crops worldwide. World demand for wheat requires that improvements continue to be made in both wheat yield and quality. While conventional wheat breeding has resulted in improved wheat yields in the past, the last decade has seen little to no improvement. This is largely due to lack of knowledge about the genetic architecture of most complex traits and our inability to select for traits in a cost effective manner as part of a conventional breeding program (Gupta et al. 2010. *Mol Breeding* 26:145-161).

Breeding for desirable traits in wheat has been performed largely by phenotyping in the field and/or greenhouse. However, to effectively and accurately phenotype traits, such as e.g. heading, anther-extrusion, flowering and *fusarium* head blight resistance, wheat lines often have to be selfed several times to obtain homozygous material. In addition, since these traits are influenced by environmental conditions, the wheat lines need to be phenotyped in several locations and across several years, thereby requiring significant time, monetary, and land resources.

The identification of genetic markers linked to a favorable phenotype (i.e. trait) of interest, such as e.g. heading, anther-extrusion, flowering and *fusarium* head blight resistance, permits wheat lines to be genotyped at relatively little expense and during earlier stages of development, thereby allowing for the retention of only the lines with favorable genotypic information. This process is known as marker assisted selection. Methods of marker assisted selection allow breeders to avoid several generations of selfing, eliminating a large part of the phenotyping efforts, and ultimately leads to more rapid improvements in wheat at a lower cost and with significantly less field resources.

As such, there is a continual need for wheat plants with improved phenotypic traits. Thus, it is desirable to provide compositions and methods for identifying and selecting such plants.

SUMMARY

Methods and compositions for identifying and/or selecting wheat plants or germplasm for flowering date, heading date, anther-extrusion, and/or *fusarium* head blight resistance are provided. In certain embodiments, the method comprises detecting at least one marker locus, marker profile or marker haplotype that is associated with flowering date, heading date, anther-extrusion, and/or *fusarium* head blight resistance. In further embodiments, the method further comprises crossing a selected wheat plant with a second wheat plant.

DETAILED DESCRIPTION

The identification and selection of wheat plants or germplasm with improved properties through the use of marker assisted selection can greatly enhance a breeding program and the improvement of wheat varieties. The present invention provides marker loci that demonstrate statistically significant cosegregation with a trait of interest. Detection of these loci or additional linked loci can be used to produce wheat plants with desirable characteristics, such as for example, with respect to flowering date, heading date, anther-extrusion, and/or *fusarium* head blight resistance.

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of:" Similarly, the term "consisting essentially of" is intended to include examples encompassed by the term "consisting of:"

Certain definitions used in the specification and claims are provided below. In order to provide a clear and consistent understanding of the specification and claims, including the scope to be given such terms, the following definitions are provided:

"Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance, branching, flowering, seed set, seed size, seed density, standability, threshability, and the like.

"Allele" means any of one or more alternative forms of a genetic sequence. In a diploid cell or organism, for example, the two alleles of a given sequence typically occupy corresponding loci on a pair of homologous chromosomes. With regard to a SNP marker, allele refers to the specific nucleotide base present at that SNP locus in that individual plant.

An allele is "associated with" a trait when it is part of or linked to a DNA sequence or allele that affects the expression of the trait. The presence of the allele is an indicator of how the trait will be expressed.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods, such as the ligase chain reaction (LCR), and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

An "ancestral line" is a parent line used as a source of genes, e.g., for the development of elite lines.

An "ancestral population" is a group of ancestors that have contributed the bulk of the genetic variation that was used to develop elite lines.

"Backcrossing" is a process in which a breeder crosses a progeny variety back to one of the parental genotypes one or more times.

The term "chromosome segment" designates a contiguous linear span of genomic DNA that resides in planta on a single chromosome.

The term "complement" refers to a nucleotide sequence that is complementary to a given nucleotide sequence, i.e. the sequences are related by the Watson-Crick base-pairing rules.

"Cultivar" and "variety" are used synonymously and mean a group of plants within a species (e.g., *Triticum aestivum*) that share certain genetic traits that separate them from other possible varieties within that species. Wheat cultivars are inbred lines produced after several generations of self-pollinations. Individuals within a wheat cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of wheat breeding.

An "elite population" is an assortment of elite individuals or lines that can be used to represent the state of the art in terms of agronomically superior genotypes of a given crop species, such as wheat.

An "exotic wheat strain" or an "exotic wheat germplasm" is a strain or germplasm derived from a wheat not belonging to an available elite wheat line or strain of germplasm. In the context of a cross between two wheat plants or strains of germplasm, an exotic germplasm is not closely related by descent to the elite germplasm with which it is crossed. Most commonly, the exotic germplasm is not derived from any known elite line of wheat, but rather is selected to introduce novel genetic elements (typically novel alleles) into a breeding program.

A "favorable allele" is the allele at a particular locus that confers, or contributes to, an agronomically desirable phenotype, e.g., improved resistance to *Fusarium* head blight, and that allows the identification of plants with that agronomically desirable phenotype. A favorable allele of a marker is a marker allele that segregates with the favorable phenotype.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detectedusing DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

"Introgression" means the entry or introduction of a gene, QTL, marker locus, haplotype, marker profile, trait, or trait locus from the genome of one plant into the genome of another plant.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual wheat plant selected at the F3 to F5 generation until the residual segregating loci are "fixed" or homozygous across most or all loci. Commercial wheat varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., anther-extrusion, flowering date, heading date and/or *fusarium* head blight resistance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a map distance of 1.0 centiMorgan (1.0 cM).

The genetic elements or genes located on a single chromosome segment are physically linked. Advantageously, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less.

The phrase "closely linked" with respect to loci, in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to resistance and a proximal marker, "coupling" phase linkage indicates the state where the "favorable" allele at the locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies. The state of being in linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

"Linkage group" (LG) refers to traits or markers that generally co-segregate. A linkage group generally corresponds to a chromosomal region containing genetic material that encodes the traits or markers. As such, a linkage group can generally be assigned to a certain chromosome.

"Locus" is a defined segment of DNA. For example, it can refer to a position on a chromosome, where a nucleotide, gene, sequence, or marker is located.

A "map location" is an assigned location on a genetic map relative to linked genetic markers where a specified marker can be found within a given species.

"Mapping" is the process of defining the linkage relationships of loci through the use of genetic markers, populations segregating for the markers, and standard genetic principles of recombination frequency.

"Marker" or "molecular marker" or "marker locus" is a term used to denote a nucleic acid or amino acid sequence that is sufficiently unique to characterize a specific locus on the genome. Examples include Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers are known in the art, and phenotypic traits may also be used as markers in the methods. All markers are used to define a specific locus on the wheat genome. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage where the trait can be expressed.

"Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

In certain examples, multiple marker loci or haplotypes are used to define a "marker profile". As used herein, "marker profile" means the combination of two or more marker locus or haplotypes within a particular plant's genome. For instance, in one example, a particular combination of marker locus or a particular combination of haplotypes define the marker profile of a particular plant.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene traitor a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "favorable trait" or "favorable phenotype", such as for instance, improved resistance to *fusarium* head blight is an agronomically desirable phenotype. In some cases, such as e.g. with flowering date and heading date, the desirable phenotype is region dependent.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

"Recombination frequency" is the frequency of a crossing over event (recombination) between two genetic loci. Recombination frequency can be observed by following the segregation of markers and/or traits during meiosis.

"Self crossing," "self pollination," or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the wheat genome. Many techniques for detecting SNPs are known in the art, including allele specific hybridization, primer extension, direct sequencing, and real-time PCR, such as the TaqMan™ assay.

"Transgenic plant" refers to a plant that comprises within its cells an exogenous polynucleotide. Generally, the exogenous polynucleotide is stably integrated within the genome such that the polynucleotide is passed on to successive generations. The exogenous polynucleotide may be integrated into the genome alone or as part of a recombinant expression cassette. "Transgenic" is used herein to refer to any cell, cell line, callus, tissue, plant part, or plant, the genotype of which has been altered by the presence of exogenous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

An "unfavorable allele" of a marker is a marker allele that segregates with the unfavorable plant phenotype, therefore providing the benefit of identifying plants that can be removed from a breeding program or planting.

The term "vector" is used in reference to polynucleotide or other molecules that transfer nucleic acid segment(s) into a cell. A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses.

The term "yield" refers to the productivity per unit area of a particular plant product of commercial value. For example, yield of wheat is commonly measured in bushels of seed per acre or metric tons of seed per hectare per season or head per acre or seed per head. Yield is affected by both genetic and environmental factors. Yield is the final culmination of all agronomic traits.

Turning now to the embodiments:

Identification of Markers, Haplotypes and/or Marker Profiles Associated with Traits of Interest A variety of methods well known in the art are available for detecting molecular markers or clusters of molecular markers that co-segregate with a trait of interest, such as heading date, flowering date, anther-extrusion, and/or *fusarium* head blight resistance. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present disclosure provides marker loci that demonstrate statistically significant co-segregation with at least one of the following traits: heading date, flowering date, anther-extrusion, and/or *fusarium* head blight resistance, as determined by a population based association analysis. Detection of these loci or additional linked loci can be used in marker assisted wheat breeding programs to produce plants with favorable characteristics.

Markers, Haplotypes and/or Marker Profiles Associated with Flowering Date, Anther-Extrusion, Heading Date and/or *Fusarium* Head Blight Resistance.

Flowering Date

As used herein, flowering date is when the anthers actually shed pollen, usually a few days after heading. Pollination starts in the center of the head and moves out to the bottom and top. "Flowering date" is assigned when an estimated 50% of spikes have anthers exerted from approximately 50% of the flowers, as evidenced by visible anthers.

Alleles of markers associated with flowering date are provided herein and include: WSNP_KU_C16547_25454123; WSNP_EX_C2920_5385184; WSNP_EX_C10717_17456391; WSNP_JD_C1316_1891903; WSNP_BG263758B_TA_2_1; WSNP_EX_C3501_6408181; WSNP_BE404354B_TA_2_1; WSNP_EX_C10555_17237000; WSNP_KU_C6758_11757213; WSNP_JD_C6544_7697578; WSNP_EX_C36325_44308589; WSNP_EX_C2580_4800027; WSNP_EX_C10555_17235832; WSNP_EX_C22089_31270140; WSNP_EX_C6590_11419735; WSNP_CAP11_C210_199161; WSNP_KU_C1818_3557408; WSNP_EX_REP_C66606_64905694; and/or WSNP_EX_REP_C102795_87883062, as well as any marker linked to any of these markers.

In specific embodiments, the alleles of marker locus associated with the favorable flowering date comprise the alleles set forth in Table 6 and includes, for example: (a) an A allele at WSNP_KU_C16547_25454123; (b) a T allele at WSNP_EX_C10555_17235832; (c) a A allele at WSNP_EX_C2580_4800027; (d) a T allele at WSNP_EX_C10717_17456391; (e) a G allele at WSNP_BG263758B_TA_2_1; (f) a G allele at WSNP_EX_C2920_5385184; (g) a T allele at WSNP_JD_C1316_1891903; (h) a C allele at WSNP_EX_C36325_44308589; and/or (i) a G allele at WSNP_EX_C6590_11419735.

Further provided are various haplotypes or marker profiles associated with a favorable flowering date. Such haplotypes can comprise any combination of marker locus associated with the favorable flowering date as disclosed herein, including at least 2, 3, 4, 5, 6, 7, 8, 9, 10, 12, 13, 14, 15 or more markers. Non-limiting examples of haplotypes associated with a favorable flowering date are set forth in Table 6 and include for example: (a) an A allele at WSNP_KU_C16547_25454123 and a T allele at WSNP_EX_C10555_17235832; (b) an A allele at WSNP_EX_C2580_4800027 and a T allele at WSNP_EX_C10717_17456391; (c) a G allele at WSNP_BG263758B_TA_2_1, a G allele at WSNP_EX_C2920_5385184 and a T allele at WSNP_JD_C1316_1891903; and/or, (d) a C allele at WSNP_EX_C36325_44308589 and a G allele at WSNP_EX_C6590_11419735.

Heading Date

As used herein, "heading date" is when the wheat head (spike) emerges from the last leaf sheath. This is not synchronized in a plot or even between main stems and tillers, but they will generally all "head" within a couple days. As used herein, the "heading date" is assigned as the day when 50% of the heads have emerged 50% from the leaf sheath.

Alleles of markers associated with heading date are provided herein and include:
WSNP_CAP7_C3472_1623955; WSNP_EX_REP_C108057_91436561; WSNP_CAP8_C458_368155; WSNP_EX_C16720_25268525; WSNP_RA_C32271_41304469; WSNP_EX_C25082_34346512; WSNP_EX_C55096_57733894; WSNP_EX_C11229_18163892; WSNP_EX_C55096_57733841; WSNP_EX_C3096_5709369; WSNP_EX_REP_C67404_65986980; WSNP_BQ168706B_TA_2_2; WSNP_BQ168706B_TA_2_1; WSNP_EX_C8208_13870372; WSNP_JD_C17082_16025440; WSNP_EX_C21499_30644485; WSNP_EX_C3096_5709257; WSNP_BE489326B_TA_22; WSNP_JD_C4413_5541190; WSNP_EX_C57007_58898157; WSNP_EX_C10347_16946522; WSNP_KU_C7180_12403155; WSNP_BF201102A_TA_2_1; WSNP_EX_C43578_49857984; WSNP_KU_C7890_13513783; WSNP_EX_C57209_59016692; WSNP_JD_C12221_12509932; WSNP_JD_C7718_8795833; WSNP_EX_C19467_28423946; WSNP_EX_C8643_14488961; WSNP_EX_C1143_2194680; WSNP_RA_C1417122234872; WSNP_EX_C53387_56639804; WSNP_KU_C28104_38042857; WSNP_CAP8_REP_C3844_1896355; WSNP_RA_C2325332762188; WSNP_EX_C9971_16412345; WSNP_EX_C11106_18003332; WSNP_EX_C35861_43928486; WSNP_EX_C5547_9774453; WSNP_KUC10377_17180909; WSNP_KU_C1853827857915; WSNP_RA_C11420_18529863; WSNP_EX_C41347_48189975; WSNP_EX_C53387_56641291; WSNP_EX_C23509_32746909; WSNP_BE497845D_TA_1_1; WSNP_BE445508B_TA_2_2; WSNP_EX_C44049_50205457; WSNP_BE591466B_TA_2_1;

WSNP_EX_C15084_23263641; WSNP_JD_C13903_13781269; WSNP_KU_C644_1332610; WSNP_EX_C35861_43926307; WSNP_EX_C5547_9772680; WSNP_KU_REP_C102220_89250165; WSNP_EX_C8802_14726148; WSNP_EX_C130_258776; WSNP_BE499016B_TA_2_1; WSNP_EX_REP_C69919_68881108; WSNP_EX_C361_708712; WSNP_KU_C1102_2211433; WSNP_RA_C323_681466; WSNP_EX_C916_1767286; WSNP_KUC16295_25149034; WSNP_JD_C12087_12411036; WSNP_EX_C22016_31191407; WSNP_KU_C16812_25759885; WSNP_JD_C5795_6955627; WSNP_EX_REP_C69342_68276256; WSNP_EX_C2718_5038582; WSNP_KU_C17726_26872129; WSNP_JD_C15974_15272598; WSNP_EX_C5239_9272511; WSNP_RA_C37745_45806931; WSNP_EX_REP_C105541_89932598; WSNP_EX_REP_C69526_68472665; WSNP_EX_C123_244117; WSNP_EX_C1988_3742291; WSNP_EX_C19134_28056012; WSNP_JD_C7404_8500079; WSNP_EX_C8303_14001708; WSNP_EX_C9927_16346100; WSNP_JD_C4621_5757201; WSNP_BE591684B_TA_2_1; WSNP_KU_C8722_14766699; WSNP_EX_C2330_4366134; WSNP_EX_REP_C101414_86780996; WSNP_EX_C29130_38196906; WSNP_RA_C17541_26430903; WSNP_JD_C12687_12877994; WSNP_EX_C10500_17163855; WSNP_EX_C2161_4059735; WSNP_EX_C5547_9774195; WSNP_EX_C4211_7606269; WSNP_EX_C6142_10746442; WSNP_EX_C12254_19575022; WSNP_RA_C2228_4310870; WSNP_RA_C12148_19539667; WSNP_KU_C8712_14751858; WSNP_EX_C34344_42677360; WSNP_RFL_CONTIG4236_4881643; WSNP_BE495786A_TA_2_1; WSNP_RA_REP_C71473_69552690; WSNP_BE490744B_TA_2_1; WSNP_EX_REP_C67660_66321934; WSNP_EX_C758_1488368; WSNP_EX_C12887_20427158; WSNP_EX_C33778_42210283; WSNP_RA_C10053_16636851; WSNP_EX_C31262_40077397; WSNP_KU_C854_1768062; WSNP_BE445431A_TD_2_2; WSNP_EX_REP_C101746_87053634; WSNP_EX_C4769_8510104; WSNP_EX_REP_C104141_88935451; WSNP_EX_C44587_50598716; WSNP_EX_C741_1456698; WSNP_EX_REP_C103972_88799335; WSNP_EX_C3309_6096114; WSNP_RA_C7112_12318340; WSNP_RA_C2063_4012957; WSNP_EX_C42282_48900922; WSNP_EX_C53983_57032627; WSNP_EX_C34842_43092205; WSNP_EX_C5446_9616983; WSNP_EX_C97184_84339976; WSNP_JD_C9902_10674725; WSNP_BE445348B_TA_2_1; WSNP_BE500291A_TA_2_1; WSNP_EX_REP_C115803_95396724; WSNP_KU_REP_C72821_72480395; WSNP_EX_C3906_7086162; WSNP_KU_C6825_11858665; WSNP_EX_C4605_8240189; WSNP_BF428726A_TA_2_5; WSNP_KU_C66980_66202298; WSNP_BE405599B_TA_2_1; WSNP_JD_C35319_26397591; WSNP_EX_C5378_9505087; WSNP_CAP11_C827_513472; WSNP_EX_C29648_38653339; WSNP_KUC854_1768346; WSNP_KU_C328_679106; WSNP_EX_C3096_5708642; WSNP_CAP7_C2282_1107112; WSNP_JD_C9902_10674626; WSNP_KU_C24239_34199356; WSNP_KU_C5071_9050628; WSNP_EX_C31830_40573624; WSNP_KU_REP_C101212_88410320; WSNP_KU_C39289_47757996; WSNP_EX_C19622_28607997; WSNP_EX_REP_C66733_65077608; WSNP_EX_C26818_36041748; WSNP_EX_C11684_18805687; WSNP_EX_C34344_42676379; WSNP_RA_C6788_11804894; WSNP_EX_C7756_13218814; WSNP_EX_C35861_43927741; WSNP_KU_C34643_43968242; WSNP_RA_REP_C75364_72953286; WSNP_EXC5192_9203682; WSNP_EX_C5378_9504586; WSNP_EX_C4710_8412517; WSNP_EX_REP_C66628_64934660; WSNP_CAP11_C1182_686503; WSNP_JD_C2863_3822253; WSNP_EX_C4927_8772847; WSNP_EX_C44049_50205904; WSNP_RFL_CONTIG2729_2446041; WSNP_BE496983B_TA_2_1; WSNP_KU_C30743_40542247; and/or WSNP_KU_REP_C103274_90057407, as well as any other marker linked to any of these markers.

In specific embodiments, the allele of the marker locus associated with the favorable heading date comprises at least one of the alleles set forth in Table 6 and includes, for example: (a) an A allele at WSNP_EX_REP_C105541_89932598; (b) a G allele at WSNP_KU_C17726_26872129; (c) an A allele at WSNP_EX_C4605_8240189; (d) a T allele at WSNP_EX_C44049_50205904; (e) a C allele at WSNP_EX_C3906_7086162; (f) a C allele at WSNP_EX_REP_C101746_87053634; (g) a G allele at WSNP_EX_REP_C101414_86780996; (h) a C allele at WSNP_EX_C44049_50205457; (i) an A allele at WSNP_EX_C5192_9203682; (j) a G allele at WSNP_JD_C13903_13781269; (k) a G allele at WSNP_RA_C12148_19539667; (l) a G allele at WSNP_BE495786A_TA_2_1; (m) a C allele at WSNP_KU_C24239_34199356; (n) an A allele at WSNP_RA_C377454_5806931; (o) a C allele at WSNP_EX_C34344_42676379; (p) a C allele at WSNP_EX_C34344_42677360; (q) an G allele at WSNP_EX_REP_C66628_64934660; (r) an C allele at WSNP_EX_C42282_48900922; (s) a G allele at WSNP_EX_REP_C108057_91436561; (t) a G allele at WSNP_EX_C16720_25268525; (u) a C allele at WSNP_CAP8_C458_368155; (v) a G allele at WSNP_EX_C741_1456698; (w) a C allele at WSNP_JD_C12687_12877994; (x) a G allele at WSNP_EX_C55096_57733841; (y) a C allele at WSNP_EX_REP_C104141_88935451; (z) a C allele at WSNP_EX_C25082_34346512; (aa) a T allele at WSNP_EX_C361_708712; (ab) a C allele at WSNP_EX_C55096_57733894; (ac) a C allele at WSNP_EX_C8802_14726148; (ad) a T allele at WSNP_EX_C4927_8772847; (ae) a G allele at WSNP_JD_C17082_16025440; (af) a T allele at WSNP_JD_C9902_10674626; (ag) a T allele at WSNP_JD_C9902_10674725; (ah) an A allele at WSNP_EX_C21499_30644485; (ai) a G allele at WSNP_BQ168706B_TA_2_2; (aj) a T allele at WSNP_KU_C18538_27857915; (ak) a G allele at WSNP_BE489326B_TA_2_2; (al) a T allele at WSNP_BQ168706B_TA_2_1; (am) a C allele at WSNP_EX_C123_244117; (an) C allele at WSNP_EX_C5378_9505087; (ao) a C allele at WSNP_EX_C2330_4366134; (ap) a C allele at WSNP_EX_C22016_31191407; (aq) a G allele at WSNP_KU_C8722_14766699; (ar) a T allele at WSNP_KU_C6825_11858665; (as) a C allele at WSNP_EX_C5378_9504586; (at) a C allele at WSNP_EX_C4769_8510104; (au) a C allele at WSNP_EX_C5547_9774453; (av) a G allele at WSNP_EX_C5547_9772680; (aw) a T allele at WSNP_EX_C5547_9774195; (ax) a C allele at WSNP_BE445348B_TA_2_1; (ay) an A allele at WSNP_EX_C7756_13218814; (az) a C allele at WSNP_EX_C3096_5709369; (ba) an A allele at WSNP_EX_C3096_5709257; (bb) a G allele at WSNP_EX_C12887_20427158; (bc) a T allele at WSNP_KU_REP_C72821_72480395; (bd) an A allele at WSNP_EX_C3096_5708642; (be) a T allele at WSNP_EX_C57007_58898157; (bf) an A allele at WSNP_EX_C8208_13870372; (bg) an A allele at WSNP_JD_C4413_5541190; (bh) a C allele at WSNP_KU_C7180_12403155; (bi) a T allele at WSNP_EX_C10347_16946522; (bj) a T allele at WSNP_KU_REP_C102220_89250165; (bk) a C allele at WSNP_KU_C328_679106; (bl) a G allele at WSNP_RA_C323_681466; (bm) an A allele at WSNP_KU_C644_1332610; (bn) a T allele at WSNP_RA_C17541_26430903; (bo) a T allele at WSNP_KU_C7890_13513783; (bp) an A allele at WSNP_RA_C6788_11804894; (bq) a C allele at WSNP_EX_REP_C69526_68472665; (br) a T allele at WSNP_EX_C31830_40573624; (bs) a T allele at WSNP_CAP7_C2282_1107112; (bt) a T allele at WSNP_BF201102A_TA_2_1; (bu) a T allele at WSNP_EX_C19134_28056012; (by) a T allele at WSNP_EX_C4211_7606269; (bw) a T allele at WSNP_EX_C2718_5038582; (bx) a C allele at WSNP_RA_C11420_18529863; (by) a C allele at WSNP_KU_C1102_2211433; (bz) an A allele at WSNP_EX_C23509_32746909; (ca) a C allele at WSNP_RA_REP_C75364_72953286; (cb) an A allele at WSNP_EX_REP_C66733_65077608; (cd) a C allele at WSNP_BE500291A_TA_2_1; (ce) an A allele at WSNP_KU_C16812_25759885; (cf) a G allele at WSNP_EX_C130_258776; (cg) a C allele at WSNP_RA_C10053_16636851; (ch) a C allele at WSNP_EX_C15084_23263641; (ci) an A allele at WSNP_RA_C2228_4310870; (cj) an A allele at WSNP_EX_C43578_49857984; (ck) a G allele at WSNP_KU_C30743_40542247; (cl) an A allele at WSNP_JD_C5795_6955627; (cm) a G allele at WSNP_KU_REP_C101212_88410320; (cn) a G allele at WSNP_JD_C12221_12509932; (co) an A allele at WSNP_EX_C57209_59016692; (cp) a G allele at WSNP_EX_C2161_4059735; (cq) an A allele at WSNP_EX_C29648_38653339; (cr) a C allele at WSNP_EX_C19467_28423946; (cs) a G allele at WSNP_RA_C14171_22234872; (ct) a T allele at WSNP_EX_C53387_56641291; (cu) a G allele at WSNP_RA_C2063_4012957; (cv) a T allele at WSNP_EX_C6142_10746442; (cw) a T allele at WSNP_EX_C916_1767286; (cx) a C allele at WSNP_EX_C53387_56639804; (cy) a T allele at WSNP_EX_C10500_17163855; (cz) a C allele at WSNP_EX_C3309_6096114; (da) a G allele at WSNP_RFL_CONTIG42364881643; and/or (db) a C allele at WSNP_EX_C758_1488368.

Further provided are various haplotypes or marker profiles associated with a favorable heading date. Such haplotypes or marker profiles can comprise any combination of marker locus associated with the favorable heading date as disclosed herein, including at least 2, 3, 4, 5, 6, 7, 8, 9, 10, 12, 13, 14, 15 or more markers. Non-limiting examples of haplotypes associated with a favorable heading date are set forth in Table 6 and include, for example, (a) an A allele at WSNP_EX_REP_C105541_89932598 and a G allele at WSNP_KU_C17726_26872129; (b) an A allele at WSNP_EX_C4605_8240189, a T allele at WSNP_EX_C44049_50205904, a C allele at WSNP_EX_C3906_7086162, a C allele at WSNP_EX_REP_C101746_87053634, a G allele at WSNP_EX_REP_C101414_86780996, and a C allele at WSNP_EX_C44049_50205457; (c) an A allele at WSNP_EX_C5192_9203682, a G allele at WSNP_JD_C13903_13781269; a G allele at WSNP_RA_C12148_19539667, a G allele at WSNP_BE495786A_TA_2_1, and a C allele at WSNP_KU_C24239_34199356; (d) an A allele at WSNP_RA_C37745_45806931 and a C allele at WSNP_EX_C34344_42676379, a C allele at WSNP_EX_C34344_42677360, an G allele at WSNP_EX_REP_C66628_64934660 and a C allele at WSNP_EX_C42282_48900922; (e) a G allele at WSNP_EX_REP_C108057_91436561, a G allele at WSNP_EX_C16720_25268525, and a C allele at WSNP_CAP8C458_368155; (f) a G allele at WSNP_EX_C741_1456698 and a C allele at WSNP_JD_C12687_12877994; (g) a G allele at WSNP_EX_C55096_57733841, a C allele at WSNP_EX_REP_C104141_88935451, a C allele at WSNP_EX_C25082_34346512, a T allele at WSNP_EX_C361_708712, and a C allele at WSNP_EX_C55096_57733894; (h) a C allele at WSNP_EX_C8802_14726148 and a T allele at WSNP_EX_C4927_8772847; (i) a G allele at WSNP_JD_C17082_16025440, a T allele at WSNP_JD_C9902_10674626, and a T allele at WSNP_JD_C9902_10674725; (j) an A allele at WSNP_EX_C21499_30644485, a G allele at WSNP_BQ168706B_TA_2_2, a T allele at WSNP_KU_C18538_27857915, a G allele at WSNP_BE489326B_TA_2_2, and a T allele at WSNP_BQ168706B_TA_2_1; (k) a C allele at WSNP_EX_C123_244117, a C allele at WSNP_EX_C5378_9505087, a C allele at WSNP_EX_C2330_4366134, a C allele at WSNP_EX_C22016_31191407, a G allele at WSNP_KU_C8722_14766699, a T allele at WSNP_KU_C6825_11858665, a C allele at WSNP_EX_C5378_9504586, and a C allele at WSNP_EX_C4769_8510104; (l) a C allele at WSNP_EX_C5547_9774453, a G allele at WSNP_EX_C5547_9772680, a T allele at WSNP_EX_C5547_9774195, a C allele at WSNP_BE445348B_TA_2_1, an A allele at WSNP_EX_C7756_13218814, a C allele at WSNP_EX_C3096_5709369, and, an A allele at WSNP_EX_C3096_5709257; (m) a G allele at WSNP_EX_C12887_20427158, a T allele at WSNP_KU_REP_C72821_72480395, and an A allele at WSNP_EX_C3096_5708642; (n) a T allele at WSN- P_EX_C57007_58898157, an A allele at WSNP_EX_C8208_13870372, and, an A allele at WSN-P_JD_C4413_5541190; (o) a C allele at WSN-P_KU_C7180_12403155 and a T allele at WSN-P_EX_C10347_16946522; (p) a T allele at WSNP_KU_REP_C102220_89250165, a C allele at WSN-P_KU_C328_679106, a G allele at WSNP_RA_C323 681466, an A allele at WSNP_KU_C644_1332610, a T allele at WSNP_RA_C17541_26430903, a T allele at WSN-P_KU_C7890_13513783, and, an A allele at WSN-P_RA_C6788_11804894; (q) a C allele at WSN-P_EX_REP_C69526_68472665, a T allele at WSNP_EX_C31830_40573624, a T allele at WSNP_CAP7_C2282_1107112, a T allele at WSNP_BF201102A_TA_2_1, a T allele at WSN-P_EX_C19134_28056012, and a T allele at WSN-P_EX_C4211_7606269; (r) a T allele at WSN-P_EX_C2718_5038582, a C allele at WSNP_RA_C11420_18529863, a C allele at WSN-P_KU_C1102_2211433, an A allele at WSN-P_EX_C23509_32746909, a C allele at WSN-P_RA_REP_C75364_72953286, an A allele at WSNP_EX_REP_C66733_65077608, and, a C allele at WSNP_BE500291A_TA_2_1; (s) an A allele at WSN-P_KU_C16812_25759885, a G allele at WSN-P_EX_C130_258776, a C allele at WSN-P_RA_C10053_16636851, a C allele at WSNP_EX_C15084_23263641, and an A allele at WSN-P_RA_C2228_4310870; (t) an A allele at WSN-P_EX_C43578_49857984 and a G allele at WSN-P_KU_C30743_40542247; (u) an A allele at WSNP_JD_C5795_6955627 and a G allele at WSN-P_KU_REP_C101212_88410320; (v) a G allele at WSN-P_JD_C12221_12509932 and an A allele at WSN-P_EX_C57209_59016692; (w) a G allele at WSNP_EX_C2161_4059735 and an A allele at WSN-P_EX_C29648_38653339; (x) a C allele at WSN-P_EX_C19467_28423946 and a G allele at WSN-P_RA_C14171_22234872; (y) a T allele at WSNP_EX_C53387_56641291, a G allele at WSN-P_RA_C2063_4012957, a T allele at WSN-P_EX_C6142_10746442, a T allele at WSN-P_EX_C916_1767286, and a C allele at WSNP_EX_C53387_56639804; (z) a T allele at WSN-P_EX_C10500_17163855 and a C allele at WSN-P_EX_C3309_6096114; and/or, (aa) a G allele at WSN-P_RFL_CONTIG4236_4881643 and a C allele at WSNP_EX_C758_1488368.

Anther Extrusion

As used herein "anther extrusion" refers to the extrusion of anthers resulting from the separation of the lemma and palea of the wheat spikelet in response to a sudden elongation of the anther filaments. Anther extrusion occurs during flowering (Devries (1971) *Euphytica* 20:152-170) and is dependent on temperature and humidity (i.e. low temperatures and adequate humidity promote anther extrusion, while high temperatures and drought decrease it).

Anther extrusion can be assessed, for example, by evaluating anther retention (anthers held within the spikelet) and/or trapped anthers (partially extruded and trapped between the lemma and palea of the wheat spikelet), e.g. as described in Graham and Browne (2009) *Journal of Phytopatholo* 157:580-582.

Alleles from a marker associated with anther extrusion are provided herein and include WSN-P_EX_REP_C66893_65301351 as well as any marker linked to WSNP_EX_REP_C66893_65301351.

*Fusarium* Head Blight Resistance

Plant resistance is a phenotypic spectrum consisting of extremes in resistance and susceptibility, as well as a continuum of intermediate resistance phenotypes. Evaluation of these intermediate phenotypes using reproducible assays are of value to scientists who seek to identify genetic loci that impart resistance, to conduct marker assisted selection for resistance populations, and to use introgression techniques to breed a resistance trait into an elite wheat line, for example.

"*Fusarium* head blight" or "FHB" is a fungal disease caused by infection of fungal species in the genus *Fusarium*. Common species of *Fusarium* that cause *fusarium* head blight in wheat are *Fusarium graminearum* and *Fusarium culmorum*.

By "improved resistance" is intended that the plants show a decrease in the disease symptoms that are the outcome of plant/fungal interactions that result in *fusarium* head blight. That is, the damage caused by the fungus is prevented, or alternatively, the disease symptoms caused by the fungus is minimized or lessened. Thus, improved resistance to *fusarium* head blight can result in the suppressing, controlling, and/or killing the pathogen causing the disease, or alternatively, the improved resistance can reduce the disease symptoms of the *fusarium* head blight disease by at least about 2% to at least about 6%, at least about 5% to about 50%, at least about 10% to about 60%, at least about 30% to about 70%, at least about 40% to about 80%, or at least about 50% to about 90% or greater. Hence, the methods provided herein can be utilized to protect plants from *fusarium* head blight disease.

"Tolerance" refers to the plant's ability to withstand heavy infestation without significant yield loss. A "resistant plant" or "resistant plant variety" need not possess absolute or complete resistance to *fusarium* head blight. Instead, a "resistant plant," "resistant plant variety," or a plant or plant variety with "improved resistance" will have a level of resistance to *fusarium* head blight which is higher than that of a comparable susceptible plant or variety.

Screening and selection of resistant wheat plants may be performed, for example, by exposing plants to fungus such as *Fusarium graminearum, F. roseum, F. culmorum*, and the like under conditions which permit the *fusarium* head blight and selecting those plants showing resistance to the disease. Various assays can be used to measure improved resistance. For example, two types of resistance to *fusarium* head blight, Type I and Type II, can occur. Type I resistance reduces the number of initial infections and can be measured by the number of infected spikelets following a spray inoculation. Type II resistance restricts spread of the fungus in infected tissue and can measured by the number of spikelets infected in a spike beyond an initial infection site (a single spikelet) inoculated near the center of the spike. Other types of resistance or tolerance also have been recognized in some wheat lines, based on the ability to resist kernel infection, to degrade mycotoxins (DON and others) or to maintain yield despite the presence of FHB (tolerance).

Alleles of markers associated with resistance to *fusarium* head blight are provided herein and include: WSN-P_EX_C5550_9779698; WSNP_EX_C46670_52108070; WSNP_EX_C5060_8985678; WSN-P_RA_C8484_14372815; WSNP_EX_C1197619193550; WSNP_EX_C2097530093113; WSN-P_EX_C16581_25100502; WSNP_EX_C1745226163465; WSNP_KU_C4951_8856170; WSN-P_EX_C1873327607958; WSNP_KU_C3986248205590; WSNP_KUC16938_25916279; WSN- P_EX_REP_C6703665492436; WSNP_JD_C4485_5618761; WSNP_KU_C1693825916260; WSNP_JD_REP_C6320140318622; WSNP_RA_C10861_17763060; WSNP_BE517627ATA_2_1; WSNP_EX_C25924822528; WSNP_EX_C21092_30220342; WSNP_EX_C56928_58852277; WSNP_EX_C10642034431; WSNP_BE399936ATA_2_1; WSNP_EX_C3319641722217; WSNP_EX_C7091_12199032; WSNP_EX_C342_670415; WSNP_RA_C58188_60005934; WSNP_EX_C1064_2034518; WSNP_CD452951A_TA_2_1; WSNP_RA_C19083_28215239; WSNP_CAP7_C7742_3467376; WSNP_EX_C45617 51361414; WSNP_EX_C23720_32957892; WSNP_RA_C58188_60004916; WSNP_RA_REP_C106961_90622638; WSNP_EX_C21786_30948397; WSNP_CAP12_C5344_2430233; WSNP_EX_C20649_29731279; WSNP_EX_C1064_2034730; WSNP_EX_C21721_30882221; WSNP_KU_C44873_52048221; WSNP_EX_C11437_18454413; WSNP_EX_C3044_5620102; WSNP_EX_REP_C67635_66291944; WSNP_EX_REP_C67635_66292689; WSNP_CAP11_REP_C7339_3306558; WSNP_EX_C11229_18163892; WSNP_BF293133A_TA_2_2; WSNP_BF292295A_TA_2_1; WSNP_KU_C18473_27773912; WSNP_KU_C663_1368085; WSNP_EX_C7021_12096881; WSNP_RA_REP_C72670_70836439; WSNP_EX_REP_C66331_64502558; WSNP_BE489326B_TA_2_1; WSNP_JD_REP_C63654_40605158; WSNP_JD_REP_C50820_34666611; WSNP_EX_C19773_28772235; WSNP_BE638137B_TA_2_2; WSNP_EX_C5461_9636197; WSNP_RA_C21347_30731133; WSNP_EX_REP_C68829_67704044; WSNP_RA_C21347_30731229; WSNP_EX_REP_C101757_87064771; WSNP_EX_REP_C101757_87065169; WSNP_KU_C38543_47157828; WSNP_EX_REP_C101757_87065032; WSNP_EX_C3838_6980909; WSNP_EX_C49211_53875600; WSNP_CAP11_C299_251533; WSNP_EX_C49211_53875575; WSNP_EX_REP_C68600_67449494; WSNP_EX_C9362_15546626; WSNP_RA_C20970_30293078; WSNP_RA_C20970_30293227; WSNP_EX_REP_C68600_67448893; WSNP_JD_C7718_8795833; WSNP_EX_REP_C68165_66935041; WSNP_EX_C16491_24996576; WSNP_EX_C15378_23638822; WSNP_EX_C9763_16125630; WSNP_EX_C3530_6459643; WSNP_EX_C3530_6459532; WSNP_EX_REP_C68165_66935014; WSNP_KU_C38351_47009610; WSNP_CAP11_C2142_1128735; WSNP_EX_C15378_23639387; WSNP_EX_REP_C68165_66935148; WSNP_KU_C38351_47009641; WSNP_EX_C52849_56297163; WSNP_BE490200B_TA_2_1; WSNP_EX_C31256_40071875; WSNP_RA_C14498_22667649; WSNP_EX_C5936_10412246; WSNP_CAP12REP_C8688_3644383; WSNP_RA_C24962_34524602; WSNP_EX_C46160_51746546; WSNP_KU_C11690_19042937; WSNP_EX_C5744_10088287; WSNP_EX_C17349_26035281; WSNP_JD_REP_C63108_40258378; WSNP_EX_C5744_10087877; WSNP_KU_C1876_3666308; WSNP_EX_REP_C106072_90285324; WSNP_EX_C23716_32952372; WSNP_EX_C16836_25401702; WSNP_EX_C38198_45786860; WSNP_EX_C1146_2201722; WSNP_KU_C707_1465779; WSNP_RFL_CONTIG3854_4205716; WSNP_CAP11REP_C6622_3044459; WSNP_EX_REP_C69954_68913284; WSNP_EX_REP_C69954_68913307; WSNP_EX_C46274_51831129; WSNP_EX_C351_689415; WSNP_RA_C31052_40235870; WSNP_RA_REP_C71101_69119989; WSNP_EX_REP_C69816_68774932; WSNP_EX_C10783_17555091; WSNP_KU_C18780_28136150; WSNP_EX_C5457_9631220; WSNP_CAP11_C1711_934478; WSNP_EX_C6611_11452297; WSNP_EX_C8386_14127329; WSNP_JD_C9040_9947841; WSNP_EX_C10231_16783750; WSNP_JD_C17128_16056425; WSNP_KU_C23598_33524490; WSNP_JD_C5757_6915127; WSNP_EX_C23968_33209660; WSNP_JD_C6974_8084450; WSNP_CAP7_C5487_2464864; WSNP_EX_C8360_14085858; WSNP_KU_C4067_7419106; WSNP_EX_C5267_9318903; WSNP_EX_C22753_31958639; WSNP_JD_C13086_13174510; WSNP_EX_C5457_9632050; WSNP_RA_C18364_27416387; WSNP_KU_C26784_36748247; WSNP_EX_REP_C69986_68942834; WSNP_BQ169669B_TA_2_2; WSNP_EX_C19582_28564743; WSNP_JD_C5919_7081809; WSNP_EX_C6611_11451949; WSNP_EX_C3201_5910659; WSNP_BE496826A_TA_2_3; WSNP_JD_C2180_3000498; WSNP_EX_C27373_36578273; WSNP_EX_C18800_27681277; WSNP_JD_C9360_10216526; WSNP_EX_C40060_47197384; WSNP_EX_C1279_2451582; WSNP_EX_C22016_31191407; WSNP_EX_C15399_23662312; WSNP_EX_REP_C70299_69243835; WSNP_EX_C23968_33210344; WSNP_EX_C7172_12318529; WSNP_EX_C2723_5047696; WSNP_EX_C123_244117; WSNP_CAP7_C1339_673581; WSNP_KU_C8722_14766699; WSNP_EX_REP_C69986_68942866; WSNP_EX_C2330_4366134; WSNP_JD_C12088_12411845; WSNP_EX_C26747_35974837; WSNP_EX_C1146_2200823; WSNP_EX_REP_C67198_65702998; WSNP_CAP8REP_C8295_3722232; WSNP_CAP11_REP_C8768_3788007; WSNPBQ168329A_TD2_1; WSNP_EX_REP_C10350588446868; WSNP_EX_C40947399975; WSNP_BG314532ATA_21; WSNP_BF292596A_TA_1_3; WSNP_BF292596A_TA_1_1; WSNP_RA_C2027_3945764; WSNP_RA_REP_C69221_66574148; WSNP_EX_C17667_26408733; WSNP_EX_C16919_25506076; WSN- P_EX_REP_C70593_69508988; WSNP_EX_C22089_31270140; WSNP_KU_C14842_23275194; WSNP_EX_C2325_4355706; WSNP_EX_C10630_17338753; WSNP_KU_C53501_58106782; WSNP_EX_C4408_7939986; WSNP_KU_REP_C71567_71302010; WSNP_RFL_CONTIG2167_1484520; WSNP_EX_REP_C66407_64613374; WSNP_EX_C25755_35018674; WSNP_JD_C9360_10216330; WSNP_EX_REP_C67369_65940505; WSNP_EX_C4769_8510104; WSNP_RFL_CONTIG3917_4326857; WSNP_JD_C626_945114; WSNP_EX_C11055_17927668; WSNP_EX_C6476_11246531; WSNP_EX_C15163_23357477; WSNP_EX_C5780_10153638; WSNP_JD_C119_190135; WSNP_EX_C97184_84339976; WSNP_EX_C4548_8166555; WSNP_EX_REP_C68113_66877517; WSNP_EX_REP_C69266_68192954; WSNP_CAP11C847_522893; WSNP_EX_C1279_2451699; WSNP_EX_C7316_12552186; WSNP_EX_REP_C68515_67349904; WSNP_JD_C3463_4479210; WSNP_KU_C6825_11858665; WSNP_EX_C1790_3378771; WSNP_EX_C5378_9505533; WSNP_CAP7_C444_237594; WSNP_EX_C10630_17338703; WSNP_EX_C5378_9505087; WSNP_EX_C8386_14128029; WSNP_JD_REP_C63942_40788045; WSNP_EX_C4661_8344663; WSNP_RA_C9209_15425473; WSNP_JD_C43389_30288993; WSNP_EX_C30969_39821293; WSNP_EX_C3738_6809767; WSNP_EX_REP_C103505_88447145; WSNP_EX_REP_C67897_66613415; WSNP_EX_C33765_42199371; WSNP_EX_REP_C66606_64905694; WSNP_EX_C14248_22204549; WSNP_EX_REP_C66766_65123941; WSNP_CAP11_C3968_1874257; WSNP_EX_C15325_23565935; WSNP_KU_C10939_17975681; WSNP_EX_C41073_47987034; WSNP_EX_C5378_9504586; WSNP_EX_C15325_23565794; WSNP_EX_REP_C67492_66096650; WSNP_EX_C21129_30256617; WSNP_EX_C31670_40433594; WSNP_EX_C2181_4089639; WSNP_CAP11_C923_558715; WSNP_KU_C8592_14575931; WSNP_BE490744A_TD_2_1; WSNP_JD_REP_C62985_40164465; WSNP_EX_C54655_57455562; WSNP_EX_C16295_24772663; WSNP_EX_C3940_7144946; WSNP_KU_C12698_20441325; WSNP_BF291549B_TA_1_1; WSNP_RA_C9738_16173810; WSNP_EX_C15325_23564654; WSNP_EX_C7705_13139890; WSNP_RA_C9738_16174002; WSNP_EX_C16295_24772702; WSNP_EX_C3887_7051325; WSNP_KU_C7471_12865509; and/or WSNP_CAP8_C6680_3136899 as well as any marker linked to any of these markers.

In specific embodiments, the allele from a marker locus associated with the improved *fusarium* blight head resistance comprises at least one of the alleles set forth in Table 6 and includes, for example, (a) a T allele at WSNP_EX_C2181_4089639; (b) a C allele at WSNP_EX_REP_C70593_69508988; (c) an A allele at WSNP_EX_REP_C67492_66096650; (d) a G allele at WSNP_EX_C6476_11246531; (e) an A allele at WSNP_EX_C46670_52108070; (f) a C allele at WSNP_EX_C3887_7051325; (g) an A allele at WSNP_EX_REP_C67198_65702998; (h) a T allele at WSNP_KU_C8592_14575931; (i) a T allele at WSNP_EX_C7705_13139890; (j) a G allele at WSNP_EX_C5780_10153638; (k) a T allele at WSNP_EX_C18733_27607958; (l) a G allele at WSNP_EX_C11976_19193550; (m) a T allele at WSNP_KU_C16938_25916260; (n) a G allele at WSNP_JD_REP_C62985_40164465; (o) a C allele at WSNP_BF291549B_TA_1_1; (p) a C allele at WSNP_RA_C8484_14372815; (q) an A allele at WSNP_EX_REP_C67036_65492436; (r) a G allele at WSNP_KU_C4951_8856170; (s) a T allele at WSNP_JD_C4485_5618761; (t) a C allele at WSNP_EX_C17452_26163465; (u) a G allele at WSNP_RA_C2027_3945764; (v) a C allele at WSNP_EX_REP_C69986_68942866; (w) a T allele at WSNP_EX_REP_C69986_68942834; (x) an A allele at WSNP_KU_C39862_48205590; (y) an A allele at WSNP_EX_C6611_11451949; (z) an A allele at WSNP_EX_C6611_11452297; (aa) a G allele at WSNP_EX_C30969_39821293; (ab) a C allele at WSNP_JD_C13086_13174510; (ac) a G allele at WSNP_EX_REP_C68113_66877517; (ad) an A allele at WSNP_EX_C15325_23565935; (ae) a G allele at WSNP_CAP11REP_C8768_3788007; (af) an A allele at WSNP_BG314532A_TA_2_1; (ag) a G allele at WSNP_JD_C12088_12411845; (ah) a T allele at WSNP_EX_C15325_23565794; (ai) a G allele at WSNP_EX_C15325_23564654; (aj) a T allele at WSNP_CAP7_C7742_3467376; (ak) a G allele at WSNP_BE399936A_TA_2_1; (al) a T allele at WSNP_RA_C10861_17763060; (am) a G allele at WSNP_EX_C11437_18454413; (an) a C allele at WSNP_RA_C58188_60005934; (ao) a G allele at WSNP_EX_C23720_32957892; (ap) a C allele at WSNP_EX_C1064_2034518; (aq) a T allele at WSNP_BF293133A_TA_2_2; (ar) a C allele at WSNP_EX_REP_C67635_66291944; (as) an A allele at WSNP_EX_REP_C67635_66292689; (at) an A allele at WSNP_RA_C9738_16173810; (au) a C allele at WSNP_EX_C4548_8166555; (av) a C allele at WSNP_RA_C9738_16174002; (aw) a T allele at WSNP_EX_C10630_17338753; (ax) an A allele at WSNP_EX_C10630_17338703; (ay) a C allele at WSNP_EX_C8360_14085858; (az) a T allele at WSNP_KU_C12698_20441325; (ba) an A allele at WSNP_EX_REP_C66331_64502558; (bb) a T allele at WSNP_EX_C2723_5047696; (bc) a G allele at WSNP_EX_C8386_14127329; (bd) a T allele at WSNP_EX_REP_C66766_65123941; (be) an A allele at WSNP_BE489326B_TA_2_1; (bf) an A allele at WSNP_JD_C119_190135; (bg) a C allele at WSNP_EX_C4769_8510104; (bh) a G allele at WSNP_EX_C5378_9505533; (bi) a G allele at WSNP_EX_C7172_12318529; (bj) a C allele at WSNP_EX_C22016_31191407; (bk) a G allele at WSNP_KU_C8722_14766699; (bl) a C allele at WSNP_EX_C123_244117; (bm) a C allele at WSNP_EX_C5378_9504586; (bn) a C allele at WSNP_EX_C5378_9505087; (bo) a T allele at WSNP_KU_C6825_11858665; (bp) a C allele at WSNP_EX_C2330_4366134; (bq) a T allele at WSNP_EX_C5457_9632050: (br) an A allele at WSNP_EX_C5457_9631220; (bs) a G allele at WSNP_JD_REP_C63654_40605158; (bt) a G allele at WSN- P_EX_C7021_12096881; (bu) a G allele at WSNP_EX_C40060_47197384; (bv) a T allele at WSNP_EX_C15399_23662312; (bw) a C allele at WSNP_RA_REP_C72670_70836439; (bx) an A allele at WSNP_JD_REP_C50820_34666611; (by) a T allele at WSNP_EX_REP_C101757_87065169; (bz) an A allele at WSNP_EX_REP_C101757_87064771; (ca) a G allele at WSNP_EX_REP_C101757_87065032; (cb) a T allele at WSNP_EX_C1279_2451699; (cc) a G allele at WSNP_EX_C1279_2451582; (cd) a T allele at WSNP_EX_C49211_53875600; (ce) a G allele at WSNP_EX_C49211_53875575; (cf) a T allele at WSNP_RA_C21347_30731133; (cg) a G allele at WSNP_RA_C21347_30731229; (ch) a T allele at WSNP_CAP11C299_251533; (ci) a G allele at WSNP_CAP11_C923 558715; (cj) an A allele at WSNP_EX_C54655_57455562; (ck) a T allele at WSNP_JD_C43389_30288993; (cl) a C allele at WSNP_EX_C23968_33209660; (cm) a C allele at WSNP_EX_C16295_24772663; (cn) a G allele at WSNP_EX_C23968_33210344; (co) a T allele at WSNP_EX_C16295_24772702; (cp) an A allele at WSNP_RA_C20970_30293227; (cq) an A allele at WSNP_RA_C20970_30293078; (cr) a G allele at WSNP_EX_REP_C68600_67448893; (cs) a C allele at WSNP_EX_REP_C68600_67449494; (ct) a T allele at WSNP_KU_C38351_47009610; (cu) an A allele at WSNP_EX_REP_C68165_66935014; (cv) a T allele at WSNP_EX_C3530_6459532; (cw) a T allele at WSNP_EX_C3530_6459643; (cx) a C allele at WSNP_EX_REP_C68165_66935041; (cy) a T allele at WSNP_EX_C52849_56297163; (cz) a G allele at WSNP_JD_C7718_8795833; (da) a C allele at WSNP_JD_C2180_3000498; (db) a T allele at WSNP_KU_C26784_36748247; (dc) a T allele at WSNP_EX_C15378_23638822; (dd) an A allele at WSNP_EX_C15378_23639387; (de) a G allele at WSNP_CAP7_C5487_2464864; (df) a C allele at WSNP_EX_C2325_4355706; (dg) a G allele at WSNP_KU_REP_C71567_71302010; (dh) a T allele at WSNP_EX_C17349_26035281; (di) a G allele at WSNP_EX_C46160_51746546; (dj) a G allele at WSNP_EX_C38198_45786860; (dk) an A allele at WSNP_EX_C17667_26408733; (dl) a G allele at WSNP_JD_REP_C63108_40258378; (dm) a G allele at WSNP_RA_C24962_34524602; (dn) a G allele at WSNP_EX_C31256_40071875; (do) an A allele at WSNP_EX_C5744_1008828; (dp) an A allele at WSNP_BE490200B_TA_2_1; (dq) a C allele at WSNP_EX_REP_C106072_90285324; (dr) an A allele at WSNP_EX_C1146_2200823; (ds) a T allele at WSNP_EX_C19582_28564743; (dt) a C allele at WSNP_EX_C1146_2201722; (du) a T allele at WSNP_EX_C46274_51831129; (dv) a C allele at WSNP_RA_REP_C71101_69119989; (dw) a C allele at WSNP_RA_C31052_40235870; (dx) a T allele at WSNP_EX_REP_C69954_68913284; (dy) an A allele at WSNP_EX_C18800_27681277; (dz) an A allele at WSNP_EX_C27373_36578273; (ea) an C allele at WSNP_JD_C9040_9947841; (eb) a G allele at WSNP_KU_C10939_17975681; (ec) a G allele at WSNP_EX_C25755_35018674; (ed) an A allele at WSNP_EX_C26747_35974837; (ee) a T allele at WSNP_KU_C4067_7419106; (ef) an A allele at WSNP_EX_C1790_3378771; (eg) an A allele at WSNP_EX_REP_C69954_68913307; (eh) T allele at WSNP_EX_C4408_7939986; (ei) an A allele at P_EX_C14248_22204549; (ej) a G allele at WSNP_CAP11_C847_522893; (ek) a G allele at WSNP_KU_C18780_28136150; (el) a T allele at WSNP_BQ169669B_TA_2_2; (em) a C allele at WSNP_EX_C351_689415; (en) a T allele at WSNP_JD_C17128_16056425; and/or, (eo) a C allele at WSNP_EX_C3738_6809767.

Further provided are various haplotypes or marker profiles associated with the improved *fusarium* blight head resistance. Such haplotypes or marker profiles can comprise any combination of marker locus associated with the improved *fusarium* blight head resistance as disclosed herein, including at least 2, 3, 4, 5, 6, 7, 8, 9, 10, 12, 13, 14, or more markers. Non-limiting examples of haplotypes associated with an improved *fusarium* blight head resistance are set forth in Table 6 and include, for example, (a) a T allele at WSNP_EX_C2181_4089639 and a C allele at WSNP_EX_REP_C70593_69508988; (b) an A allele at WSNP_EX_REP_C67492_66096650 and a G allele at WSNP_EX_C6476_11246531; (c) an A allele at WSNP_EX_C46670_52108070 and a C allele at WSNP_EX_C3887_7051325; (d) an A allele at WSNP_EX_REP_C67198_65702998, a T allele at WSNP_KU_C8592_14575931, a T allele at WSNP_EX_C7705_13139890, and a G allele at WSNP_EX_C5780_10153638; (e) a T allele at WSNP_EX_C18733_27607958, a G allele at WSNP_EX_C11976_19193550, a T allele at WSNP_KU_C16938_25916260, a G allele at WSNP_JD_REP_C62985_40164465, and a C allele at WSNP_BF291549B_TA_1_1; (f) a C allele at WSNP_RA_C8484_14372815, an A allele at WSNP_EX_REP_C67036_65492436, a G allele at WSNP_KU_C4951_8856170, a T allele at WSNP_JD_C4485_5618761, a C allele at WSNP_EX_C17452_26163465, a G allele at WSNP_RA_C2027_3945764, a C allele at WSNP_EX_REP_C69986_68942866, and, a T allele at WSNP_EX_REP_C69986_68942834; (g) an A allele at WSNP_KU_C39862_48205590, an A allele at WSNP_EX_C6611_11451949, an A allele at WSNP_EX_C6611_11452297, and a G allele at WSNP_EX_C30969_39821293; (h) a C allele at WSNP_JD_C13086_13174510, a G allele at WSNP_EX_REP_C68113_66877517, and an A allele at WSNP_EX_C15325_23565935; (i) a G allele at WSNP_CAP11_REP_C8768_3788007, an A allele at WSNP_BG314532A_TA_2_1, a G allele at WSNP_JD_C12088_12411845, a T allele at WSNP_EX_C15325_23565794, and a G allele at WSNP_EX_C15325_23564654; (j) a T allele at WSNP_CAP7_C7742_3467376, a G allele at WSNP_BE399936A_TA_2_1, a T allele at WSNP_RA_C10861_17763060, a G allele at WSNP_EX_C11437_18454413, a C allele at WSNP_RA_C58188_60005934, a G allele at WSNP_EX_C23720_32957892, and a C allele at WSNP_EX_C1064_2034518; (k) a T allele at WSNP_BF293133A_TA_2_2, a C allele at WSNP_EX_REP_C67635_66291944, and an A allele at WSNP_EX_REP_C67635_66292689; (l) an A allele at WSNP_RA_C9738_16173810, a C allele at WSNP_EX_C4548_8166555, and a C allele at WSNP_RA_C9738_16174002; (m) a T allele at WSNP_EX_C10630_17338753 and an A allele at WSNP_EX_C10630_17338703; (n) a C allele at WSNP_EX_C8360_14085858, a T allele at WSN- P_KU_C12698_20441325, an A allele at WSNP_EX_REP_C66331_64502558, and a T allele at WSNP_EX_C2723_5047696; (o) a G allele at WSNP_EX_C8386_14127329 and a T allele at WSNP_EX_REP_C66766_65123941; (p) an A allele at WSNP_BE489326B_TA_2_1 and an A allele at WSNP_JD_C119_190135; (q) a C allele at WSNP_EX_C4769_8510104, a G allele at WSNP_EX_C5378_9505533, a G allele at WSNP_EX_C7172_12318529, a C allele at WSNP_EX_C22016_31191407, a G allele at WSNP_KU_C8722_14766699, a C allele at WSNP_EX_C123_244117, a C allele at WSNP_EX_C5378_9504586, a C allele at WSNP_EX_C5378_9505087, a T allele at WSNP_KU_C6825_11858665, a C allele at WSNP_EX_C2330_4366134, a T allele at WSNP_EX_C5457_9632050, an A allele at WSNP_EX_C5457_9631220, a G allele at WSNP_J-D_REP_C63654_40605158, and a G allele at WSNP_EX_C7021_12096881; (r) a G allele at WSNP_EX_C40060_47197384 and a T allele at WSNP_EX_C15399_23662312; (s) a C allele at WSNP_RA_REP_C72670_70836439 and an A allele at WSNP_JD_REP_C50820_34666611; (t) a T allele at WSNP_EX_REP_C101757_87065169, an A allele at WSNP_EX_REP_C101757_87064771, and a G allele at WSNP_EX_REP_C101757_87065032; (u) a T allele at WSNP_EX_C1279_2451699 and a G allele at WSNP_EX_C1279_2451582; (v) a T allele at WSNP_EX_C49211_53875600, a G allele at WSNP_EX_C49211_53875575, and a T allele at WSNP_RA_C21347_30731133; (w) a G allele at WSNP_RA_C21347_30731229 and a T allele at WSNP_CAP11C299_251533; (x) a G allele at WSNP_CAP11 C923_558715, an A allele at WSNP_EX_C54655_57455562, a T allele at WSNP_JD_C43389_30288993, a C allele at WSNP_EX_C23968_33209660, a C allele at WSNP_EX_C16295_24772663, a G allele at WSNP_EX_C23968_33210344, and a T allele at WSNP_EX_C16295_24772702; (y) an A allele at WSNP_RA_C20970_30293227, an A allele at WSNP_RA_C20970_30293078, a G allele at WSNP_EX_REP_C68600_67448893, and a C allele at WSNP_EX_REP_C68600_67449494; (z) a T allele at WSNP_KU_C38351_47009610, an A allele at WSNP_EX_REP_C68165_66935014, a T allele at WSNP_EX_C3530_6459532, a T allele at WSNP_EX_C3530 6459643, a C allele at WSNP_EX_REP_C68165_66935041, a T allele at WSNP_EX_C52849_56297163, and a G allele at WSNP_JD_C7718_8795833; (aa) a C allele at WSNP_JD_C2180_3000498, a T allele at WSNP_KU_C26784_36748247, a T allele at WSNP_EX_C15378_23638822, and an A allele at WSNP_EX_C15378_23639387; (ab) a G allele at WSNP_CAP7_C5487_2464864, a C allele at WSNP_EX_C2325_4355706, and a G allele at WSNP_KU_REP_C71567_71302010; (ac) a T allele at WSNP_EX_C17349_26035281, a G allele at WSNP_EX_C46160_51746546, a C allele at WSNP_EX_C38198_45786860, and an A allele at WSNP_EX_C17667_26408733; (ad) a G allele at WSNP_J-D_REP_C63108_40258378 and a G allele at WSNP_RA_C24962_34524602; (ae) a G allele at WSNP_EX_C31256_40071875, an A allele at WSNP_EX_C5744_10088287, an A allele at WSNP_BE490200B_TA_2_1 and a C allele at WSNP_EX_REP_C106072_90285324; (af) an A allele at WSNP_EX_C1146_2200823, a T allele at WSNP_EX_C19582_28564743, and a C allele at WSNP_EX_C1146_2201722; (ag) a T allele at WSNP_EX_C46274_51831129 and a C allele at WSNP_RA_REP_C71101_69119989; (ah) a C allele at WSNP_RA_C31052_40235870 and a T allele at WSNP_EX_REP_C69954_68913284; (ai) an A allele at WSNP_EX_C18800_27681277, an A allele at WSNP_EX_C27373_36578273, a C allele at WSNP_JD_C9040_9947841, a G allele at WSNP_KU_C10939_17975681, a G allele at WSNP_EX_C25755_35018674, an A allele at WSNP_EX_C26747_35974837, a T allele at WSNP_KU_C4067_7419106, an A allele at WSNP_EX_C1790_3378771, an A allele at WSNP_EX_REP_C69954_68913307, a T allele at WSNP_EX_C4408_7939986, and an A allele at WSNP_EX_C14248_22204549; (aj) a G allele at WSNP_CAP11_C847_522893, a G allele at WSNP_KU_C18780_28136150, and a T allele at WSNP_BQ169669B_TA_2_2; and/or (ak) a C allele at WSNP_EX_C351_689415, a T allele at WSNP_JD_C17128_16056425, and, a C allele at WSNP_EX_C3738_6809767.

A common measure of linkage is the frequency with which traits cosegregate. This can be expressed as a percentage of cosegregation (recombination frequency) or in (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Methods for Identifying and/or Selecting Wheat Plants Using Disclosed Markers, Haplotypes and/or Marker Profiles Methods are provided for identifying and/or selecting wheat plants or germplasm by detecting in the wheat plants, parts thereof, or germplasm, at least one marker locus associated with flowering date, heading date, anther extrusion, and/or resistance to *fusarium* head blight.

In some examples, the detecting comprises amplifying at least one of said marker locus or a portion thereof and detecting the resulting amplified marker amplicon. In certain examples, the amplifying comprises: (a) admixing an amplification primer or amplification primer pair with a nucleic acid isolated from the first wheat plant or germplasm, wherein the primer or primer pair is complementary or partially complementary to at least a portion of the marker locus, and is capable of initiating DNA polymerization by a DNA polymerase using the wheat nucleic acid as a template; and, (b) extending the primer or primer pair in a DNA polymerization reaction comprising a DNA polymerase and a template nucleic acid to generate at least one amplicon.

In some examples, the method employs the target regions in Table 1 or a portion thereof. Table 1 provides SNP markers from wheat that are significantly associated with flowering date. SEQ ID NOS: 1-19 found within Table 1 comprise nucleotide sequences of regions of the wheat genome containing the polymorphism associated with flowering date and each of these sequences or a portion thereof can be used as a probe or primer, either alone or in combination, for the detection of the corresponding marker locus.

In some particular examples, the method comprises amplifying at least a portion of one or more genome regions selected from the group consisting of SEQ ID NOs: 1, 2, 3, 4, 5, 6, 7, 8, 9, 10, 11, 12, 13, 14, 15, 16, 17, 18, and/or 19. In other examples, the primer or primer pair comprises at least a portion of one or more genomic regions as set forth in any one or more of SEQ ID NOS: 1, 2, 3, 4, 5, 6, 7, 8, 9, 10, 11, 12, 13, 14, 15, 16, 17, 18, and/or 19 such that the primer pair is complementary or partially complementary to at least a portion of the marker locus, and is capable of initiating DNA polymerization by a DNA polymerase using the wheat nucleic acid as a template.

In certain other examples, the detecting further comprises providing a detectable probe suitable for detection of the marker locus of interest. In certain examples, the probe used for detection comprises a nucleic acid sequence having at least a portion of one or more sequences set forth in Table 1 or a portion thereof (i.e., any one of SEQ ID NOs: 1, 2, 3, 4, 5, 6, 7, 8, 9, 10, 11, 12, 13, 14, 15, 16, 17, 18, and/or 19 or a portion thereof).

In specific embodiments, methods are provided which provide for the amplification and/or detection of an allele of at least one marker locus associated with a favorable flowering date wherein the marker locus being amplified and/or detected comprises at least one allele set forth in Table 6 and includes, for example: (a) an A allele at WSN-P_KU_C16547_25454123; (b) a T allele at WSN-P_EX_C10555_17235832; (c) an A allele at WSN-P_EX_C2580_4800027; (d) a T allele at WSNP_EX_C10717_17456391; (e) a G allele at WSNP_BG263758B_TA_2_1; (f) a G allele at WSN-P_EX_C2920_5385184; (g) a T allele at WSN-P_JD_C1316_1891903; (h) a C allele at WSN-P_EX_C36325_44308589; and/or (i) a G allele at WSNP_EX_C6590_11419735.

Further provided are methods which provide for the amplification and/or detection of various haplotypes or marker profiles associated with a favorable flowering date. Such methods include the amplification and/or detection of at least one haplotype associated with a favorable flowering date as set forth in Table 6 and include, for example, the amplification and/or detection of (a) an A allele at WSN-P_KUC16547_25454123 and a T allele at WSN-P_EX_C10555_17235832; (b) an A allele at WSN-P_EX_C2580_4800027 and a T allele at WSNP_EX_C10717_17456391; (c) a G allele at WSNP_BG263758B_TA_2_1, a G allele at WSN-P_EX_C2920_5385184 and a T allele at WSN-P_JD_C1316_1891903; and/or, (d) a C allele at WSN-P_EX_C36325_44308589 and a G allele at WSNP_EX_C6590_11419735.

Thus, in specific embodiments, a method of identifying a wheat plant that displays a favorable flowering date is provided and comprises: (a) obtaining genetic material from a wheat plant; and, (B) analyzing the genetic material for the presence of at least one allele of a marker locus disclosed herein or analyzing the genetic material for the presence of at least one haplotype disclosed in Table 6, wherein said allele or said haplotype is associated with a favorable flowering date, the presence of the allele or the haplotype is determined by detecting the allele or the haplotype, and selecting the wheat plant that is displaying a favorable flowering date.

In some examples, the method employs the target regions in Table 2 or a portion thereof. Table 2 provides SNP markers from wheat that are significantly associated with heading date. SEQ ID NOS: 276-449 found within Table 2 comprise nucleotide sequences of regions of the wheat genome containing the polymorphism associated with heading date and each of these sequences or a portion thereof can be used as a probe or primer, either alone or in combination, for the detection of the corresponding marker locus.

In some particular examples, the method comprises amplifying at least a portion of one or more genome regions selected from the group consisting of SEQ ID NOs: 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, and/or 449.

In other examples, the primer or primer pair comprises at least a portion of one or more genomic regions as set forth in any one or more of SEQ ID NOS: 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, and/or 449 such that the primer pair is complementary or partially complementary to at least a portion of the marker locus, and is capable of initiating DNA polymerization by a DNA polymerase using the wheat nucleic acid as a template.

In certain other examples, the detecting further comprises providing a detectable probe suitable for detection of the marker locus of interest. In certain examples, the probe used for detection comprises a nucleic acid sequence having at least a portion of one or more sequences set forth in Table 2 or a portion thereof (i.e., any one of SEQ ID NOs: 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, and/or 449 or a portion thereof).

In specific embodiments, methods are provided which provide for the amplification and/or detection of an allele of at least one marker locus associated with the favorable heading date wherein the marker locus being amplified and/or detected comprises at least one allele set forth in Table 6 and includes, for example, (a) an A allele at WSNP_EX_REP_C105541_89932598; (b) a G allele at WSNP_KU_C17726_26872129; (c) an A allele at WSNP_EX_C4605_8240189; (d) a T allele at WSNP_EX_C44049_50205904; (e) a C allele at WSNP_EX_C3906_7086162; (f) a C allele at WSNP_EX_REP_C101746_87053634; (g) a G allele at WSNP_EX_REP_C101414_86780996; (h) a C allele at WSNP_EX_C44049_50205457; (i) an A allele at WSNP_EX_C5192_9203682; (j) a G allele at WSNP_JD_C13903_13781269; (k) a G allele at WSNP_RA_C12148_19539667; (l) a G allele at WSNP_BE495786A_TA_2_1; (m) a C allele at WSNP_KU_C24239_34199356; (n) an A allele at WSNP_RA_C37745_45806931; (o) a C allele at WSNP_EX_C34344_42676379; (p) a C allele at WSNP_EX_C34344_42677360; (q) an G allele at WSNP_EX_REP_C66628_64934660; (r) an C allele at WSNP_EX_C42282_48900922; (s) a G allele at WSNP_EX_REP_C108057_91436561; (t) a G allele at WSNP_EX_C16720_25268525; (u) a C allele at WSNP_CAP8_C458_368155; (v) a G allele at WSNP_EX_C741_1456698; (w) a C allele at WSNP_JD_C12687_12877994; (x) a G allele at WSNP_EX_C55096_57733841; (y) a C allele at WSNP_EX_REP_C104141_88935451; (z) a C allele at WSNP_EX_C25082_34346512; (aa) a T allele at WSNP_EX_C361_708712; (ab) a C allele at WSNP_EX_C55096_57733894; (ac) a C allele at WSNP_EX_C8802_14726148; (ad) a T allele at WSNP_EX_C4927_8772847; (ae) a G allele at WSNP_JD_C17082_16025440; (af) a T allele at WSNP_JD_C9902_10674626; (ag) a T allele at WSNP_JD_C9902_10674725; (ah) an A allele at WSNP_EX_C21499_30644485; (ai) a G allele at WSNP_BQ168706B_TA_2_2; (aj) a T allele at WSNP_KU_C18538_27857915; (ak) a G allele at WSNP_BE489326B_TA_2_2; (al) a T allele at WSNP_BQ168706B_TA_2_1; (am) a C allele at WSNP_EX_C123_244117; (an) C allele at WSNP_EX_C5378_9505087; (ao) a C allele at WSNP_EX_C2330_4366134; (ap) a C allele at WSNP_EX_C22016_31191407; (aq) a G allele at WSNP_KU_C8722_14766699; (ar) a T allele at WSNP_KU_C6825_11858665; (as) a C allele at WSNP_EX_C5378_9504586; (at) a C allele at WSNP_EX_C4769_8510104; (au) a C allele at WSNP_EX_C5547_9774453; (av) a G allele at WSNP_EX_C5547_9772680; (aw) a T allele at WSNP_EX_C5547_9774195; (ax) a C allele at WSNP_BE445348B_TA_2_1; (ay) an A allele at WSNP_EX_C7756_13218814; (az) a C allele at WSNP_EX_C3096_5709369; (ba) an A allele at WSNP_EX_C3096_5709257; (bb) a G allele at WSNP_EX_C12887_20427158; (bc) a T allele at WSNP_KU_REP_C72821_72480395; (bd) an A allele at WSNP_EX_C3096_5708642; (be) a T allele at WSNP_EX_C57007_58898157; (bf) an A allele at WSNP_EX_C8208_13870372; (bg) an A allele at WSNP_JD_C4413_5541190; (bh) a C allele at WSNP_KU_C7180_12403155; (bi) a T allele at WSNP_EX_C10347_16946522; (bj) a T allele at WSNP_KU_REP_C102220_89250165; (bk) a C allele at WSNP_KU_C328_679106; (bl) a G allele at WSNP_RA_C323_681466; (bm) an A allele at WSNP_KU_C644_1332610; (bn) a T allele at WSNP_RA_C1754126430903; (bo) a T allele at WSNP_KU_C7890_13513783; (bp) an A allele at WSNP_RA_C6788_11804894; (bq) a C allele at WSNP_EX_REP_C69526_68472665; (br) a T allele at WSNP_EX_C31830_40573624; (bs) a T allele at WSNP_CAP7C2282_1107112; (bt) a T allele at WSNP_BF201102A_TA_2_1; (bu) a T allele at WSNP_EX_C19134_28056012; (bv) a T allele at WSNP_EX_C4211_7606269; (bw) a T allele at WSNP_EX_C2718_5038582; (bx) a C allele at WSNP_RA_C11420_18529863; (by) a C allele at WSNP_KU_C1102_2211433; (bz) an A allele at WSNP_EX_C23509_32746909; (ca) a C allele at WSNP_RA_REP_C75364_72953286; (cb) an A allele at WSNP_EX_REP_C66733_65077608; (cd) a C allele at WSNP_BE500291A_TA_2_1; (ce) an A allele at WSNP_KU_C16812_25759885; (CO a G allele at WSNP_EX_C130_258776; (cg) a C allele at WSNP_RA_C10053_16636851; (ch) a C allele at WSNP_EX_C15084 23263641; (ci) an A allele at WSNP_RA_C2228_4310870; (cj) an A allele at WSNP_EX_C43578_49857984; (ck) a G allele at WSNP_KU_C30743_40542247; (cl) an A allele at WSNP_JD_C5795_6955627; (cm) a G allele at WSNP_KU_REP_C101212_88410320; (cn) a G allele at WSNP_JD_C12221_12509932; (co) an A allele at WSNP_EX_C57209_59016692; (cp) a G allele at WSNP_EX_C2161_4059735; (cq) an A allele at WSNP_EX_C29648_38653339; (cr) a C allele at WSNP_EX_C19467_28423946; (cs) a G allele at WSNP_RA_C14171_22234872; (ct) a T allele at WSNP_EX_C53387_56641291; (cu) a G allele at WSNP_RA_C2063_4012957; (cv) a T allele at WSN- P_EX_C6142_10746442; (cw) a T allele at WSNP_EX_C916_1767286; (cx) a C allele at WSNP_EX_C53387_56639804; (cy) a T allele at WSNP_EX_C10500_17163855; (cz) a C allele at WSNP_EX_C3309_6096114; (da) a G allele at WSNP_RFL_CONTIG4236_4881643; and/or (db) a C allele at WSNP_EX_C758_1488368.

Further provided are methods which provide for the amplification and/or detection of various haplotypes or marker profiles associated with a favorable heading date. Such methods include the amplification and/or detection of at least one haplotype associated with a favorable heading date as set forth in Table 6 and include, for example, the amplification and/or detection of (a) an A allele at WSNP_EX_REP_C105541_89932598 and a G allele at WSNP_KU_C17726_26872129; (b) an A allele at WSNP_EX_C4605_8240189, a T allele at WSNP_EX_C44049_50205904, a C allele at WSNP_EX_C3906_7086162, a C allele at WSNP_EX_REP_C101746_87053634, a G allele at WSNP_EX_REP_C101414_86780996, and a C allele at WSNP_EX_C44049_50205457; (c) an A allele at WSNP_EX_C5192_9203682, a G allele at WSNP_JD_C13903_13781269; a G allele at WSNP_RA_C12148_19539667, a G allele at WSNP_BE495786A_TA_2_1, and a C allele at WSNP_KU_C24239_34199356; (d) an A allele at WSNP_RA_C37745_45806931 and a C allele atWSNP_EX_C34344_42676379, a C allele at WSNP_EX_C34344_42677360, an G allele at WSNP_EX_REP_C66628_64934660 and a C allele at WSNP_EX_C42282_48900922; (e) a G allele at WSNP_EX_REP_C108057_91436561, a G allele at WSNP_EX_C16720_25268525, and a C allele at WSNP_CAP8_C458_368155; (f) a G allele at WSNP_EX_C741_1456698 and a C allele at WSNP_JD_C12687_12877994; (g) a G allele at WSNP_EX_C55096_57733841, a C allele at WSNP_EX_REP_C104141_88935451, a C allele at WSNP_EX_C25082_34346512, a T allele at WSNP_EX_C361_708712, and a C allele at WSNP_EX_C55096_57733894; (h) a C allele at WSNP_EX_C8802_14726148 and a T allele at WSNP_EX_C4927_8772847; (i) a G allele at WSNP_JD_C17082_16025440, a T allele at WSNP_JD_C9902_10674626, and a T allele at WSNP_JD_C9902_10674725; (j) an A allele at WSNP_EX_C21499_30644485, a G allele at WSNP_BQ168706B_TA_2_2, a T allele at WSNP_KU_C18538_27857915, a G allele at WSNP_BE489326B_TA_2_2, and a T allele at WSNP_BQ168706B_TA_2_1; (k) a C allele at WSNP_EX_C123_244117, a C allele at WSNP_EX_C5378_9505087, a C allele at WSNP_EX_C2330_4366134, a C allele at WSNP_EX_C22016_31191407, a G allele at WSNP_KU_C8722_14766699, a T allele at WSNP_KU_C6825_11858665, a C allele at WSNP_EX_C5378_9504586, and a C allele at WSNP_EX_C4769_8510104; (l) a C allele at WSNP_EX_C5547_9774453, a G allele at WSNP_EX_C5547_9772680, a T allele at WSNP_EX_C5547_9774195, a C allele at WSNP_BE445348B_TA_2_1, an A allele at WSNP_EX_C7756_13218814, a C allele at WSNP_EX_C3096_5709369, and, an A allele at WSNP_EX_C3096_5709257; (m) a G allele at WSNP_EX_C12887_20427158, a T allele at WSNP_KU_REP_C72821_72480395, and an A allele at WSNP_EX_C3096_5708642; (n) a T allele at WSNP_EX_C57007_58898157, an A allele at WSNP_EX_C8208_13870372, and, an A allele at WSNP_JD_C4413_5541190; (o) a C allele at WSNP_KU_C7180_12403155 and a T allele at WSNP_EX_C10347_16946522; (p) a T allele at WSNP_KU_REP_C102220_89250165, a C allele at WSNP_KU_C328_679106, a G allele at WSNP_RA_C323_681466, an A allele at WSNP_KU_C644_1332610, a T allele at WSNP_RA_C17541_26430903, a T allele at WSNP_KU_C7890_13513783, and, an A allele at WSNP_RA_C6788_11804894; (q) a C allele at WSNP_EX_REP_C69526_68472665, a T allele at WSNP_EX_C31830_40573624, a T allele at WSNP_CAP7_C2282_1107112, a T allele at WSNP_BF201102A_TA_2_1, a T allele at WSNP_EX_C19134_28056012, and a T allele at WSNP_EX_C4211_7606269; (r) a T allele at WSNP_EX_C2718_5038582, a C allele at WSNP_RA_C11420_18529863, a C allele at WSNP_KU_C1102_2211433, an A allele at WSNP_EX_C23509_32746909, a C allele at WSNP_RA_REP_C75364_72953286, an A allele at WSNP_EX_REP_C66733_65077608, and, a C allele at WSNP_BE500291A_TA_2_1; (s) an A allele at WSNP_KU_C16812_25759885, a G allele at WSNP_EX_C130_258776, a C allele at WSNP_RA_C10053_16636851, a C allele at WSNP_EX_C15084_23263641, and an A allele at WSNP_RA_C2228_4310870; (t) an A allele at WSNP_EX_C43578_49857984 and a G allele at WSNP_KU_C30743_40542247; (u) an A allele at WSNP_JD_C5795_6955627 and a G allele at WSNP_KU_REP_C101212_88410320; (v) a G allele at WSNP_JD_C12221_12509932 and an A allele at WSNP_EX_C57209_59016692; (w) a G allele at WSNP_EX_C2161_4059735 and an A allele at WSNP_EX_C29648_38653339; (x) a C allele at WSNP_EX_C19467_28423946 and a G allele at WSNP_RA_C14171_22234872; (y) a T allele at WSNP_EX_C53387_56641291, a G allele at WSNP_RA_C2063_4012957, a T allele at WSNP_EX_C6142_10746442, a T allele at WSNP_EX_C916_1767286, and a C allele at WSNP_EX_C53387_56639804; (z) a T allele at WSNP_EX_C10500_17163855 and a C allele at WSNP_EX_C3309_6096114; and/or, (aa) a G allele at WSNP_RFL_CONTIG4236_4881643 and a C allele at WSNP_EX_C758_1488368.

Thus, in specific embodiments, a method of identifying a wheat plant that displays a favorable heading date is provided and comprises: (a) obtaining genetic material from a wheat plant; and, (B) analyzing the genetic material for the presence of at least one allele of a marker locus disclosed herein or analyzing the genetic material for the presence of at least one haplotype disclosed in Table 6, wherein said allele or said haplotype is associated with a favorable heading date, the presence of the allele or the haplotype is determined by detecting the allele or the haplotype, and selecting the wheat plant that is displaying a favorable heading date.

In some examples, the method employs the target regions in Table 3 or a portion thereof. Table 3 provides SNP markers from wheat that are significantly associated with resistance to *fusarium* head blight. SEQ ID NOS: 20-275 found within Table 3 comprise nucleotide sequences of regions of the wheat genome containing the polymorphism associated with *fusarium* head blight resistance and each of these sequences or a portion thereof can be used as a probe or primer, either alone or in combination, for the detection of the corresponding marker locus.

In some particular examples, the method comprises amplifying at least a portion of one or more genome regions selected from the group consisting of SEQ ID NOs: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, and/or 275.

In other examples, the primer or primer pair comprises at least a portion of one or more genomic regions as set forth in any one or more of SEQ ID NOS: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, and/or 275, such that the primer pair is complementary or partially complementary to at least a portion of the marker locus, and is capable of initiating DNA polymerization by a DNA polymerase using the wheat nucleic acid as a template.

In certain other examples, the detecting further comprises providing a detectable probe suitable for detection of the at least one marker locus of interest. In certain examples, the probe used for detection comprises a nucleic acid sequence having at least a portion of one or more sequences set forth in Table 3 or a portion thereof (i.e., any one of SEQ ID NOs: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, and/or 275 or a portion thereof).

In specific embodiments, methods are provided which provide for the amplification and/or detection of an allele of at least one marker locus associated with the improved *fusarium* blight head resistance wherein the marker locus being amplified and/or detected comprises at least one allele set forth in Table 6 and includes, for example, (a) a T allele at WSNP_EX_C2181_4089639; (b) a C allele at WSNP_EX_REP_C70593_69508988; (c) an A allele at WSNP_EX_REP_C67492_66096650; (d) a G allele at WSNP_EX_C6476_11246531; (e) an A allele at WSNP_EX_C46670_52108070; (f) a C allele at WSNP_EX_C3887_7051325; (g) an A allele at WSNP_EX_REP_C67198_65702998; (h) a T allele at WSNP_KU_C8592_14575931; (i) a T allele at WSNP_EX_C7705_13139890; (j) a G allele at WSNP_EX_C5780_10153638; (k) a T allele at WSNP_EX_C18733_27607958; (l) a G allele at WSNP_EX_C11976_19193550; (m) a T allele at WSNP_KU_C16938_25916260; (n) a G allele at WSNP_JD_REP_C62985_40164465; (o) a C allele at WSNP_BF291549B_TA_1_1; (p) a C allele at WSNP_RA_C8484_14372815; (q) an A allele at WSNP_EX_REP_C67036_65492436; (r) a G allele at WSNP_KU_C4951_8856170; (s) a T allele at WSNP_JD_C4485_5618761; (t) a C allele at WSNP_EX_C17452_26163465; (u) a G allele at WSNP_RA_C2027_3945764; (v) a C allele at WSNP_EX_REP_C69986_68942866; (w) a T allele at WSNP_EX_REP_C69986_68942834; (x) an A allele at WSNP_KU_C39862_48205590; (y) an A allele at WSNP_EX_C6611_11451949; (z) an A allele at WSNP_EX_C6611_11452297; (aa) a G allele at WSNP_EX_C30969_39821293; (ab) a C allele at WSNP_JD_C13086_13174510; (ac) a G allele at WSNP_EX_REP_C68113_66877517; (ad) an A allele at WSNP_EX_C15325_23565935; (ae) a G allele at WSNP_CAP11_REP_C8768_3788007; (af) an A allele at WSNP_BG314532A_TA_2_1; (ag) a G allele at WSNP_JD_C12088_12411845; (ah) a T allele at WSNP_EX_C15325_23565794; (ai) a G allele at WSNP_EX_C15325_23564654; (aj) a T allele at WSNP_CAP7_C7742_3467376; (ak) a G allele at WSNP_BE399936A_TA_2_1; (al) a T allele at WSNP_RA_C10861_17763060; (am) a G allele at WSNP_EX_C11437_18454413; (an) a C allele at WSNP_RA_C58188_60005934; (ao) a G allele at WSNP_EX_C23720_32957892; (ap) a C allele at WSNP_EX_C1064_2034518; (aq) a T allele at WSNP_BF293133A_TA_2_2; (ar) a C allele at WSNP_EX_REP_C67635_66291944; (as) an A allele at WSN- P_EX_REP_C67635_66292689; (at) an A allele at WSN-P_RA_C9738_16173810; (au) a C allele at WSNP_EX_C4548_8166555; (av) a C allele at WSN-P_RA_C9738_16174002; (aw) a T allele at WSN-P_EX_C10630_17338753; (ax) an A allele at WSN-P_EX_C10630_17338703; (ay) a C allele at WSNP_EX_C8360_14085858; (az) a T allele at WSN-P_KU_C12698_20441325; (ba) an A allele at WSN-P_EX_REP_C66331_64502558; (bb) a T allele at WSN-P_EX_C2723_5047696; (bc) a G allele at WSNP_EX_C8386_14127329; (bd) a T allele at WSN-P_EX_REP_C66766_65123941; (be) an A allele at WSNP_BE489326B_TA_2_1; (bf) an A allele at WSN-P_JD_C119_190135; (bg) a C allele at WSN-P_EX_C4769_8510104; (bh) a G allele at WSN-P_EX_C5378_9505533; (bi) a G allele at WSNP_EX_C7172_12318529; (bj) a C allele at WSN-P_EX_C22016_31191407; (bk) a G allele at WSN-P_KU_C8722_14766699; (bl) a C allele at WSN-P_EX_C123_244117; (bm) a C allele at WSNP_EX_C5378_9504586; (bn) a C allele at WSN-P_EX_C5378_9505087; (bo) a T allele at WSN-P_KU_C6825_11858665; (bp) a C allele at WSN-P_EX_C2330_4366134; (bq) a T allele at WSNP_EX_C5457_9632050; (br) an A allele at WSN-P_EX_C5457_9631220; (bs) a G allele at WSNP_J-D_REP_C63654_40605158; (bt) a G allele at WSN-P_EX_C7021_12096881; (bu) a G allele at WSNP_EX_C40060_47197384; (bv) a T allele at WSN-P_EX_C15399_23662312; (bw) a C allele at WSN-P_RA_REP_C72670_70836439; (bx) an A allele at WSN-P_JD_REP_C50820_34666611; (by) a T allele at WSNP_EX_REP_C101757_87065169; (bz) an A allele at WSNP_EX_REP_C101757_87064771; (ca) a G allele at WSNP_EX_REP_C101757_87065032; (cb) a T allele at WSNP_EX_C1279_2451699; (cc) a G allele at WSN-P_EX_C1279_2451582; (cd) a T allele at WSN-P_EX_C49211_53875600; (ce) a G allele at WSN-P_EX_C49211_53875575; (cf) a T allele at WSNP_RA_C21347_30731133; (cg) a G allele at WSN-P_RA_C21347_30731229; (ch) a T allele at WSNP_CAP11C299_251533; (ci) a G allele at WSNP_CAP11_C923_558715; (cj) an A allele at WSN-P_EX_C54655_57455562; (ck) a T allele at WSN-P_JD_C43389_30288993; (cl) a C allele at WSN-P_EX_C23968_33209660; (cm) a C allele at WSNP_EX_C16295_24772663; (cn) a G allele at WSN-P_EX_C23968_33210344; (co) a T allele at WSN-P_EX_C16295_24772702; (cp) an A allele at WSN-P_RA_C20970_30293227; (cq) an A allele at WSNP_RA_C20970_30293078; (cr) a G allele at WSN-P_EX_REP_C68600_67448893; (cs) a C allele at WSN-P_EX_REP_C68600_67449494; (ct) a T allele at WSN-P_KU_C38351_47009610; (cu) an A allele at WSNP_EX_REP_C68165_66935014; (cv) a T allele at WSNP_EX_C3530_6459532; (cw) a T allele at WSN-P_EX_C3530_6459643; (cx) a C allele at WSN-P_EX_REP_C68165_66935041; (cy) a C allele at WSN-P_EX_C52849_56297163; (cz) a G allele at WSNP_JD_C7718_8795833; (da) a C allele at WSN-P_JD_C2180_3000498; (db) a T allele at WSN-P_KU_C26784_36748247; (dc) a T allele at WSN-P_EX_C15378_23638822; (dd) an A allele at WSNP_EX_C15378_23639387; (de) a G allele at WSN-P_CAP7_C5487_2464864; (df) a C allele at WSN-P_EX_C2325_4355706; (dg) a G allele at WSN-P_KU_REP_C71567_71302010; (dh) a T allele at WSN-P_EX_C17349_26035281; (di) a G allele at WSNP_EX_C46160_51746546; (dj) a G allele at WSN-P_EX_C38198_45786860; (dk) an A allele at WSN-P_EX_C17667_26408733; (dl) a G allele at WSNP_J-D_REP_C63108_40258378; (dm) a G allele at WSNP_RA_C24962_34524602; (dn) a G allele at WSN-P_EX_C31256_40071875; (do) an A allele at WSN-P_EX_C5744_1008828; (dp) an A allele at WSNP_BE490200B_TA_2_1; (dq) a C allele at WSN-P_EX_REP_C106072_90285324; (dr) an A allele at WSN-P_EX_C1146_2200823; (ds) a T allele at WSN-P_EX_C19582_28564743; (dt) a C allele at WSNP_EX_C1146_2201722; (du) a T allele at WSN-P_EX_C46274_51831129; (dv) a C allele at WSN-P_RA_REP_C71101_69119989; (dw) a C allele at WSN-P_RA_C31052_40235870; (dx) a T allele at WSNP_EX_REP_C69954_68913284; (dy) an A allele at WSNP_EX_C18800_27681277; (dz) an A allele at WSN-P_EX_C27373_36578273; (ea) a C allele at WSN-P_JD_C9040_9947841; (eb) a G allele at WSN-P_KU_C10939_17975681; (ec) a G allele at WSNP_EX_C25755_35018674; (ed) an A allele at WSN-P_EX_C26747_35974837; (ee) a T allele at WSN-P_KU_C4067_7419106; (ef) an A allele at WSN-P_EX_C1790_3378771; (eg) an A allele at WSNP_EX_REP_C69954_68913307; (eh) T allele at WSN-P_EX_C4408_7939986; (ei) an A allele at WSN-P_EX_C14248_22204549; (ej) a G allele at WSNP_CAP11_C847_522893; (ek) a G allele at WSN-P_KU_C18780_28136150; (el) a T allele at WSNPBQ169669B_TA_2_2; (em) a C allele at WSN-P_EX_C351_689415; (en) a T allele at WSN-P_JD_C17128_16056425; and/or, (eo) a C allele at WSN-P_EX_C3738_6809767.

Further provided are methods which provide for the amplification and/or detection of various haplotypes or marker profiles associated with an improved *fusarium* blight head resistance. Such methods include the amplification and/or detection of at least one haplotype associated with an improved *fusarium* blight head resistance as set forth in Table 6 and include, for example, the amplification and/or detection of (a) a T allele at WSNP_EX_C2181_4089639 and a C allele at WSNP_EX_REP_C70593_69508988; (b) an A allele at WSNP_EX_REP_C67492_66096650 and a G allele at WSNP_EX_C6476_11246531; (c) an A allele at WSNP_EX_C46670_52108070 and a C allele at WSN-P_EX_C3887_7051325; (d) an A allele at WSN-P_EX_REP_C67198_65702998, a T allele at WSN-P_KU_C8592_14575931, a T allele at WSNP_EX_C7705_13139890, and a G allele at WSN-P_EX_C5780_10153638; (e) a T allele at WSN-P_EX_C18733_27607958, a G allele at WSN-P_EX_C11976_19193550, a T allele at WSNP_KU_C16938_25916260, a G allele at WSNP_J-D_REP_C62985_40164465, and a C allele at WSNP_BF291549B_TA_1_1; (f) a C allele at WSN-P_RA_C8484_14372815, an A allele at WSN-P_EX_REP_C67036_65492436, a G allele at WSN-P_KU_C4951_8856170, a T allele at WSNP_JD_C4485_5618761, a C allele at WSN-P_EX_C17452_26163465, a G allele at WSN-P_RA_C2027_3945764, a C allele at WSN-P_EX_REP_C69986_68942866, and, a T allele at WSNP_EX_REP_C69986_68942834; (g) an A allele at WSNP_KU_C39862_48205590, an A allele at WSN-P_EX_C6611_11451949, an A allele at WSN-P_EX_C6611_11452297, and a G allele at WSN- P_EX_C30969_39821293; (h) a C allele at WSNP_JD_C13086_13174510, a G allele at WSNP_EX_REP_C68113_66877517, and an A allele at WSNP_EX_C15325_23565935; (i) a G allele at WSNP_CAP11_REP_C8768_3788007, an A allele at WSNP_BG314532A_TA_2_1, a G allele at WSNP_JD_C12088_12411845, a T allele at WSNP_EX_C15325_23565794, and a G allele at WSNP_EX_C15325_23564654; (j) a T allele at WSNP_CAP7_C7742_3467376, a G allele at WSNP_BE399936A_TA_2_1, a T allele at WSNP_RA_C10861_17763060, a G allele at WSNP_EX_C11437_18454413, a C allele at WSNP_RA_C58188_60005934, a G allele at WSNP_EX_C23720_32957892, and a C allele at WSNP_EX_C1064_2034518; (k) a T allele at WSNP_BF293133A_TA_2_2, a C allele at WSNP_EX_REP_C67635_66291944, and an A allele at WSNP_EX_REP_C67635_66292689; (l) an A allele at WSNP_RA_C9738_16173810, a C allele at WSNP_EX_C4548_8166555, and a C allele at WSNP_RA_C9738_16174002; (m) a T allele at WSNP_EX_C10630_17338753 and an A allele at WSNP_EX_C10630_17338703; (n) a C allele at WSNP_EX_C8360_14085858, a T allele at WSNP_KU_C12698_20441325, an A allele at WSNP_EX_REP_C66331_64502558, and a T allele at WSNP_EX_C2723_5047696; (o) a G allele at WSNP_EX_C8386_14127329 and a T allele at WSNP_EX_REP_C66766_65123941; (p) an A allele at WSNP_BE489326B_TA_2_1 and an A allele at WSNP_JD_C119_190135; (q) a C allele at WSNP_EX_C4769_8510104, a G allele at WSNP_EX_C5378_9505533, a G allele at WSNP_EX_C7172_12318529, a C allele at WSNP_EX_C22016_31191407, a G allele at WSNP_KU_C8722_14766699, a C allele at WSNP_EX_C123_244117, a C allele at WSNP_EX_C5378_9504586, a C allele at WSNP_EX_C5378_9505087, a T allele at WSNP_KU_C6825_11858665, a C allele at WSNP_EX_C2330_4366134, a T allele at WSNP_EX_C5457_9632050, an A allele at WSNP_EX_C5457_9631220, a G allele at WSNP_JD_REP_C63654_40605158, and a G allele at WSNP_EX_C7021_12096881; (r) a G allele at WSNP_EX_C40060_47197384 and a T allele at WSNP_EX_C15399_23662312; (s) a C allele at WSNP_RA_REP_C72670_70836439 and an A allele at WSNP_JD_REP_C50820_34666611; (t) a T allele at WSNP_EX_REP_C101757_87065169, an A allele at WSNP_EX_REP_C101757_87064771, and a G allele at WSNP_EX_REP_C101757_87065032; (u) a T allele at WSNP_EX_C1279_2451699 and a G allele at WSNP_EX_C1279_2451582; (v) a T allele at WSNP_EX_C49211_53875600, a G allele at WSNP_EX_C49211_53875575, and a T allele at WSNP_RA_C21347_30731133; (w) a G allele at WSNP_RA_C21347_30731229 and a T allele at WSNP_CAP11_C299_251533; (x) a G allele at WSNP_CAP11_C923_558715, an A allele at WSNP_EX_C54655_57455562, a T allele at WSNP_JD_C43389_30288993, a C allele at WSNP_EX_C23968_33209660, a C allele at WSNP_EX_C16295_24772663, a G allele at WSNP_EX_C23968_33210344, and a C allele at WSNP_EX_C16295_24772702; (y) an A allele at WSNP_RA_C20970_30293227, an A allele at WSNP_RA_C20970_30293078, a G allele at WSNP_EX_REP_C68600_67448893, and a C allele at WSNP_EX_REP_C68600_67449494; (z) a T allele at WSNP_KU_C38351_47009610, an A allele at WSNP_EX_REP_C68165_66935014, a T allele at WSNP_EX_C3530_6459532, a T allele at WSNP_EX_C3530_6459643, a C allele at WSNP_EX_REP_C68165_66935041, a T allele at WSNP_EX_C52849_56297163, and a G allele at WSNP_JD_C7718_8795833; (aa) a C allele at WSNP_JD_C2180_3000498, a T allele at WSNP_KU_C26784_36748247, a T allele at WSNP_EX_C15378_23638822, and an A allele at WSNP_EX_C15378_23639387; (ab) a G allele at WSNP_CAP7_C5487_2464864, a C allele at WSNP_EX_C2325_4355706, and a G allele at WSNP_KU_REP_C71567_71302010; (ac) a T allele at WSNP_EX_C17349_26035281, a G allele at WSNP_EX_C46160_51746546, a G allele at WSNP_EX_C38198_45786860, and an A allele at WSNP_EX_C17667_26408733; (ad) a G allele at WSNP_JD_REP_C63108_40258378 and a G allele at WSNP_RA_C24962_34524602; (ae) a G allele at WSNP_EX_C31256_40071875, an A allele at WSNP_EX_C5744_10088287, an A allele at WSNP_BE490200B_TA_2_1 and a C allele at WSNP_EX_REP_C106072_90285324; (af) an A allele at WSNP_EX_C1146_2200823, a T allele at WSNP_EX_C19582_28564743, and a C allele at WSNP_EX_C1146_2201722; (ag) a T allele at WSNP_EX_C46274_51831129 and a C allele at WSNP_RA_REP_C71101_69119989; (ah) a C allele at WSNP_RA_C31052_40235870 and a T allele at WSNP_EX_REP_C69954_68913284; (ai) an A allele at WSNP_EX_C18800_27681277, an A allele at WSNP_EX_C27373_36578273, a C allele at WSNP_JD_C9040_9947841, a G allele at WSNP_KU_C10939_17975681, a G allele at WSNP_EX_C25755_35018674, an A allele at WSNP_EX_C26747_35974837, a T allele at WSNP_KU_C4067_7419106, an A allele at WSNP_EX_C1790_3378771, an A allele at WSNP_EX_REP_C69954_68913307, a T allele at WSNP_EX_C4408_7939986, and an A allele at WSNP_EX_C14248_22204549; (aj) a G allele at WSNP_CAP11_C847_522893, a G allele at WSNP_KU_C18780_28136150, and a T allele at WSNP_BQ169669B_TA_2_2; and/or (ak) a C allele at WSNP_EX_C351_689415, a T allele at WSNP_JD_C17128_16056425, and, a C allele at WSNP_EX_C3738_6809767.

Thus, in specific embodiments, a method of identifying a wheat plant that displays an improved *fusarium* blight head resistance is provided and comprises: (a) obtaining genetic material from a wheat plant; and, (B) analyzing the genetic material for the presence of at least one allele of a marker locus disclosed herein or analyzing the genetic material for the presence of at least one haplotype disclosed in Table 6, wherein said allele or said haplotype is associated with an improved *fusarium* blight head resistance, the presence of the allele or the haplotype is determined by detecting the allele or the haplotype, and selecting the wheat plant that is displaying an improved *fusarium* blight head resistance.

In some examples, the method employs the target region in Table 4 or a portion thereof. Table 4 provides a SNP marker from wheat that is significantly associated with anther-extrusion. SEQ ID NO: 450 found within Table 4 comprises nucleotide sequences of a region of the wheat genome containing the polymorphism associated with anther-extrusion and this sequence or a portion thereof can be used as a probe or primer, either alone or in combination, for the detection of the corresponding marker locus.

In some particular examples, the method comprises amplifying at least a portion of the genome region of SEQ ID NO: 450. In other examples, the primer or primer pair comprises at least a portion of the genomic region as set forth in SEQ ID NO: 450 such that the primer pair is complementary or partially complementary to at least a portion of the marker locus, and is capable of initiating DNA polymerization by a DNA polymerase using the wheat nucleic acid as a template.

In certain other examples, the detecting further comprises providing a detectable probe suitable for detection of the marker locus of interest. In certain examples, the probe used for detection comprises a nucleic acid sequence having at least a portion of one or more the sequence set forth in Table 4 or a portion thereof (i.e., SEQ ID NO: 450 or a portion thereof).

Thus, in specific embodiments, a method of identifying a wheat plant that displays a favorable anther-extrusion is provided and comprises: (a) obtaining genetic material from a wheat plant; and, (B) analyzing the genetic material for the presence of at least one allele of a marker locus disclosed herein or analyzing the genetic material for the presence of at least one haplotype disclosed in Table 6, wherein said allele or said haplotype is associated with an anther-extrusion, the presence of the allele or the haplotype is determined by detecting the allele or the haplotype, and selecting the wheat plant that is displaying a favorable anther-extrusion.

Marker Assisted Selection

Molecular markers can be used in a variety of plant breeding applications (e.g. see Staub et al. (1996) Hortscience 31: 729-741; Tanksley (1983) Plant Molecular Biology Reporter. 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into an elite line. This is also sometimes referred to as "yield drag." The size of the flanking region can be decreased by additional backcrossing, although this is not always successful, as breeders do not have control over the size of the region or the recombination breakpoints (Young et al. (1998) Genetics 120:579-585). In classical breeding it is usually only by chance that recombinations are selected that contribute to a reduction in the size of the donor segment (Tanksley et al. (1989). Biotechnology 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6) Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396). SSRs are highly suited to mapping and MAS as they are multi-allelic, codominant, reproducible and amenable to high throughput automation (Rafalski et al. (1996) Generating and using DNA markers in plants. In: Non-mammalian genomic analysis: a practical guide. Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals.

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp. 475-492; Shi (2001) Clin Chem 47, pp. 164-172; Kwok (2000) Pharmacogenomics 1, pp. 95-100; Bhattramakki and Rafalski (2001) Discovery and application of single nucleotide polymorphism markers in plants. In: R. J. Henry, Ed, Plant Genotyping: The DNA Fingerprinting of Plants, CABI Publishing, Wallingford. A wide range of commercially available technologies utilize these and other methods to interrogate SNPs including Masscode™ (Qiagen), Invader®. (Third Wave Technologies) and Invader Plus®, SnapShot®. (Applied Biosystems), Taqman®. (Applied Biosystems) and Beadarrays®. (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than single SNPs and can be more descriptive of any particular genotype. For example, a single SNP may be allele 'T' for a specific line or variety with a favorable phenotype, but the allele 'T' might also occur in the wheat breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Other types of molecular markers are also widely used, including but not limited to expressed sequence tags (ESTs), SSR markers derived from EST sequences, randomly amplified polymorphic DNA (RAPD), and other nucleic acid based markers. Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers.

In general, MAS uses polymorphic markers that have been identified as having a significant likelihood of co-segregation with a phenotype, such as flowering date, heading date, anther extrusion, and resistance to *fusarium* head blight. Such markers are presumed to map near a gene or genes that give the plant a specific phenotype (or trait), and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with a favorable phenotype can be selected for by detecting alleles at one or more marker loci, and in addition, progeny plants derived from those plants can also be selected. Hence, a plant containing a desired genotype in a given chromosomal region is obtained and then crossed to another plant. The progeny of such a cross would then be evaluated genotypically using one or more markers and the progeny plants with the same genotype in a given chromosomal region would then be identified as having a favorable or unfavorable phenotype.

The markers identified herein could be used in MAS either alone or in combination to select wheat plants with favorable phenotypes.

Plants

Plants, including wheat plants, seeds, tissue cultures, variants and mutants, that are identified and/or selected by the foregoing methods are provided. In some examples, plants comprising a favorable allele at one or more marker loci selected from the group consisting of: WSNP_KU_C16547_25454123; WSNP_EX_C2920_5385184; WSNP_EX_C10717_17456391; WSNP_JD_C1316_1891903; WSNP_BG263758B_TA_2_1; WSNP_EX_C3501_6408181; WSNP_BE404354B_TA_2_1; WSNP_EX_C10555_17237000; WSNP_KU_C6758_11757213; WSNP_JD_C6544_7697578; WSNP_EX_C36325_44308589; WSNP_EX_C2580_4800027; WSNP_EX_C10555_17235832; WSNP_EX_C22089_31270140; WSNP_EX_C6590_11419735; WSNP_CAP11_C210_199161; WSNP_KU_C1818_3557408; WSNP_EX_REP_C66606_64905694; and/or WSNP_EX_REP_C102795_87883062 are provided.

Further provided are wheat plants, seeds, tissue culture, explants, and plant cells comprising, for example, (a) an A allele at WSNP_KU_C16547_25454123; (b) a T allele at WSNP_EX_C10555_17235832; (c) an A allele at WSNP_EX_C2580_4800027; (d) a T allele at WSNP_EX_C10717_17456391; (e) a G allele at WSNP_BG263758B_TA_2_1; (f) a G allele at WSNP_EX_C2920_5385184; (g) a T allele at WSNP_JD_C1316_1891903; (h) a C allele at WSNP_EX_C36325_44308589; or (i) a G allele at WSNP_EX_C6590_11419735. In still other embodiments, wheat plants, seeds, tissue culture, explants, and plant cells are provided that comprise at least one haplotype associated with a favorable flowering date as set forth in Table 6 and include, for example, (a) an A allele at WSNP_KU_C16547_25454123 and a T allele at WSNP_EX_C10555_17235832; (b) an A allele at WSNP_EX_C2580_4800027 and a T allele at WSNP_EX_C10717_17456391; (c) a G allele at WSNP_BG263758B_TA_2_1, a G allele at WSNP_EX_C2920_5385184 and a T allele at WSNP_JD_C1316_1891903; and/or, (d) a C allele at WSNP_EX_C36325_44308589 and a G allele at WSNP_EX_C6590_11419735.

Plants, including wheat plants, seeds, tissue cultures, variants and mutants, having that are identified and/or selected by the foregoing methods are provided. In some examples, plants comprising a favorable allele at one or more marker loci selected from the group consisting WSNP_CAP7_C3472_1623955; WSNP_EX_REP_C108057_91436561; WSNP_CAP8_C458_368155; WSNP_EX_C16720_25268525; WSNP_RA_C32271_41304469; WSN- P_EX_C25082_34346512; WSNP_EX_C55096_57733894; WSNP_EX_C11229_18163892; WSNP_EX_C55096_57733841; WSNP_EX_C3096_5709369; WSNP_EX_REP_C67404_65986980; WSNP_BQ168706B_TA_2_2; WSNP_BQ168706B_TA_2_1; WSNP_EX_C8208_13870372; WSNP_JD_C17082_16025440; WSNP_EX_C21499_30644485; WSNP_EX_C3096_5709257; WSNP_BE489326B_TA_2_2; WSNP_JD_C4413_5541190; WSNP_EX_C57007_58898157; WSNP_EX_C10347_16946522; WSNP_KU_C7180_12403155; WSNP_BF201102A_TA_2_1; WSNP_EX_C43578_49857984; WSNP_KU_C7890_13513783; WSNP_EX_C57209_59016692; WSNP_JD_C12221_12509932; WSNP_JD_C7718_8795833; WSNP_EX_C19467_28423946; WSNP_EX_C8643_14488961; WSNP_EX_C1143_2194680; WSNP_RA_C14171_22234872; WSNP_EX_C53387_56639804; WSNP_KU_C28104_38042857; WSNP_CAP8REP_C3844_1896355; WSNP_RA_C23253_32762188; WSNP_EX_C9971_16412345; WSNP_EX_C11106_18003332; WSNP_EX_C35861_43928486; WSNP_EX_C5547_9774453; WSNP_KU_C10377_17180909; WSNP_KU_C18538_27857915; WSNP_RA_C11420_18529863; WSNP_EX_C41347_48189975; WSNP_EX_C53387_56641291; WSNP_EX_C23509_32746909; WSNP_BE497845D_TA_1_1; WSNP_BE445508B_TA_2_2; WSNP_EX_C44049_50205457; WSNP_BE591466B_TA_2_1; WSNP_EX_C15084_23263641; WSNP_JD_C13903_13781269; WSNP_KU_C644_1332610; WSNP_EX_C35861_43926307; WSNP_EX_C5547_9772680; WSNP_KU_REP_C102220_89250165; WSNP_EX_C8802_14726148; WSNP_EX_C130_258776; WSNP_BE499016B_TA_2_1; WSNP_EX_REP_C69919_68881108; WSNP_EX_C361_708712; WSNP_KU_C1102_2211433; WSNP_RA_C323_681466; WSNP_EX_C916_1767286; WSNP_KU_C16295_25149034; WSNP_JD_C12087_12411036; WSNP_EX_C22016_31191407; WSNP_KU_C16812_25759885; WSNP_JD_C5795_6955627; WSNP_EX_REP_C69342_68276256; WSNP_EX_C2718_5038582; WSNP_KU_C17726_26872129; WSNP_JD_C15974_15272598; WSNP_EX_C5239_9272511; WSNP_RA_C37745_45806931; WSNP_EX_REP_C105541_89932598; WSNP_EX_REP_C69526_68472665; WSNP_EX_C123_244117; WSNP_EX_C1988_3742291; WSNP_EX_C19134_28056012; WSNP_JD_C7404_8500079; WSNP_EX_C8303_14001708; WSNP_EX_C9927_16346100; WSNP_JD_C4621_5757201; WSNP_BE591684B_TA_2_1; WSNP_KU_C8722_14766699; WSNP_EX_C2330_4366134; WSNP_EX_REP_C101414_86780996; WSNP_EX_C29130_38196906; WSNP_RA_C17541_26430903; WSNP_JD_C12687_12877994; WSNP_EX_C10500_17163855; WSNP_EX_C2161_4059735; WSNP_EX_C5547_9774195; WSNP_EX_C4211_7606269; WSNP_EX_C6142_10746442; WSNP_EX_C12254_19575022; WSNP_RA_C2228_4310870; WSNP_RA_C12148_19539667; WSNP_KU_C8712_14751858; WSNP_EX_C34344_42677360; WSNP_RFL_CONTIG4236_4881643; WSNP_BE495786A_TA_2_1; WSNP_RA_REP_C71473_69552690; WSNP_BE490744B_TA_21; WSNP_EX_REP_C67660_66321934; WSNP_EX_C758_1488368; WSNP_EX_C12887_20427158; WSNP_EX_C33778_42210283; WSNP_RA_C10053_16636851; WSNP_EX_C31262_40077397; WSNP_KU_C854_1768062; WSNP_BE445431A_TD_2_2; WSNP_EX_REP_C101746_87053634; WSNP_EX_C4769_8510104; WSNP_EX_REP_C104141_88935451; WSNP_EX_C44587_50598716; WSNP_EX_C741_1456698; WSNP_EX_REP_C103972_88799335; WSNP_EX_C3309_6096114; WSNP_RA_C7112_12318340; WSNP_RA_C2063_4012957; WSNP_EX_C42282_48900922; WSNP_EX_C53983_57032627; WSNP_EX_C34842_43092205; WSNP_EX_C5446_9616983; WSNP_EX_C97184_84339976; WSNP_JD_C9902_10674725; WSNP_BE445348B_TA_2_1; WSNP_BE500291ATA_2_1; WSNP_EX_REP_C115803_95396724; WSNP_KU_REP_C72821_72480395; WSNP_EX_C3906_7086162; WSNP_KU_C6825_11858665; WSNP_EX_C4605_8240189; WSNP_BF428726A_TA_2_5; WSNP_KU_C66980_66202298; WSNP_BE405599B_TA_2_1; WSNP_JD_C35319_26397591; WSNP_EX_C5378_9505087; WSNP_CAP11_C827_513472; WSNP_EX_C29648_38653339; WSNP_KU_C854_1768346; WSNP_KU_C328_679106; WSNP_EX_C3096_5708642; WSNP_CAP7_C2282_1107112; WSNP_JD_C9902_10674626; WSNP_KU_C24239_34199356; WSNP_KU_C5071_9050628; WSNP_EX_C31830_40573624; WSNP_KU_REP_C101212_88410320; WSNP_KU_C39289_47757996; WSNP_EX_C19622_28607997; WSNP_EX_REP_C66733_65077608; WSNP_EX_C26818_36041748; WSNP_EX_C11684_18805687; WSNP_EX_C34344_42676379; WSNP_RA_C6788_11804894; WSNP_EX_C7756_13218814; WSNP_EX_C35861_43927741; WSNP_KU_C34643_43968242; WSNP_RA_REP_C75364_72953286; WSNP_EX_C5192_9203682; WSNP_EX_C5378_9504586; WSNP_EX_C4710_8412517; WSNP_EX_REP_C66628_64934660; WSNP_CAP11_C1182_686503; WSNP_JD_C2863_3822253; WSNP_EX_C4927_8772847; WSNP_EX_C44049_50205904; WSNP_RFL_CONTIG2729_2446041; WSNP_BE496983B_TA_2_1; WSNP_KU_C30743_40542247; and/or WSNP_KU_REP_C103274_90057407 are provided.

Further provided are wheat plants, seeds, tissue culture, explants, and plant cells comprising, for example, (a) an A allele at WSNP_EX_REP_C105541_89932598; (b) a G allele at WSNP_KU_C17726_26872129; (c) an A allele atWSNP_EX_C4605_8240189; (d) a T allele at WSNP_EX_C44049_50205904; (e) a C allele at WSNP_EX_C3906_7086162; (f) a C allele at WSN- P_EX_REP_C101746_87053634; (g) a G allele at WSNP_EX_REP_C101414_86780996; (h) a C allele at WSNP_EX_C44049_50205457; (i) an A allele at WSN-P_EX_C5192_9203682; (j) a G allele at WSN-P_JD_C13903_13781269; (k) a G allele at WSN-P_RA_C12148_19539667; (l) a G allele at WSNP_BE495786A_TA_2_1; (m) a C allele at WSN-P_KU_C24239_34199356; (n) an A allele at WSN-P_RA_C37745_45806931; (o) a C allele atWSN-P_EX_C34344_42676379; (p) a C allele at WSNP_EX_C34344_42677360; (q) an G allele atWSN-P_EX_REP_C66628_64934660; (r) an C allele at WSN-P_EX_C42282 48900922; (s) a G allele at WSN-P_EX_REP_C108057_91436561; (t) a G allele at WSNP_EX_C1672025268525; (u) a C allele at WSNP_CAP8C458_368155; (v) a G allele at WSN-P_EX_C741_1456698; (w) a C allele at WSN-P_JD_C12687_12877994; (x) a G allele at WSN-P_EX_C5509657733841; (y) a C allele at WSNP_EX_REP_C104141_88935451; (z) a C allele at WSNP_EX_C25082_34346512; (aa) a T allele at WSN-P_EX_C361_708712; (ab) a C allele at WSN-P_EX_C55096_57733894; (ac) a C allele at WSN-P_EX_C8802_14726148; (ad) a T allele at WSNP_EX_C4927_8772847; (ae) a G allele at WSN-P_JD_C17082_16025440; (af) a T allele at WSN-P_JD_C9902_10674626; (ag) a T allele at WSN-P_JD_C9902_10674725; (ah) an A allele at WSNP_EX_C21499_30644485; (ai) a G allele at WSNP_BQ168706B_TA_2_2; (aj) a T allele at WSN-P_KU_C18538_27857915; (ak) a G allele at WSNP_BE489326B_TA_2_2; (al) a T allele at WSNPBQ168706B_TA_2_1; (am) a C allele at WSN-P_EX_C123_244117; (an) C allele at WSN-P_EX_C5378_9505087; (ao) a C allele at WSN-P_EX_C2330_4366134; (ap) a C allele at WSNP_EX_C22016_31191407; (aq) a G allele at WSN-P_KU_C8722_14766699; (ar) a T allele at WSN-P_KU_C6825_11858665; (as) a C allele at WSN-P_EX_C5378_9504586; (at) a C allele at WSNP_EX_C4769_8510104; (au) a C allele at WSN-P_EX_C5547_9774453; (av) a G allele at WSN-P_EX_C5547_9772680; (aw) a T allele at WSN-P_EX_C5547_9774195; (ax) a C allele at WSNP_BE445348B_TA_2_1; (ay) an A allele at WSN-P_EX_C7756_13218814; (az) a C allele at WSN-P_EX_C3096_5709369; (ba) an A allele at WSN-P_EX_C3096_5709257; (bb) a G allele at WSNP_EX_C12887_20427158; (bc) a T allele at WSN-P_KU_REP_C72821_72480395; (bd) an A allele at WSN-P_EX_C3096_5708642; (be) a T allele at WSN-P_EX_C57007_58898157; (bf) an A allele at WSNP_EX_C8208_13870372; (bg) an A allele at WSN-P_JD_C4413_5541190; (bh) a C allele at WSN-P_KU_C7180_12403155; (bi) a T allele at WSN-P_EX_C10347_16946522; (bj) a T allele at WSNP_KU_REP_C102220_89250165; (bk) a C allele at WSNP_KU_C328_679106; (bl) a G allele at WSN-P_RA_C323_681466; (bm) an A allele at WSN-P_KU_C644_1332610; (bn) a T allele at WSN-P_RA_C17541_26430903; (bo) a T allele at WSNP_KU_C7890_13513783; (bp) an A allele at WSN-P_RA_C6788_11804894; (bq) a C allele at WSN-P_EX_REP_C69526_68472665; (br) a T allele at WSN-P_EX_C31830_40573624; (bs) a T allele at WSNP_CAP7_C2282_1107112; (bt) a T allele at WSNP_BF201102A_TA_2_1; (bu) a T allele at WSN-P_EX_C19134_28056012; (bv) a T allele at WSN-P_EX_C4211_7606269; (bw) a T allele at WSN-P_EX_C2718_5038582; (bx) a C allele at WSNP_RA_C11420_18529863; (by) a C allele at WSN-P_KU_C1102_2211433; (bz) an A allele at WSN-P_EX_C23509_32746909; (ca) a C allele at WSN-P_RA_REP_C75364_72953286; (cb) an A allele at WSNP_EX_REP_C66733_65077608; (cd) a C allele at WSNP_BE500291ATA_2_1; (ce) an A allele at WSN-P_KU_C16812_25759885; (cf) a G allele at WSN-P_EX_C130_258776; (cg) a C allele at WSN-P_RA_C10053_16636851; (ch) a C allele at WSNP_EX_C15084_23263641; (ci) an A allele at WSN-P_RA_C2228_4310870; (cj) an A allele at WSN-P_EX_C43578_49857984; (ck) a G allele at WSN-P_KU_C30743_40542247; (Cl) an A allele at WSNP_JD_C5795_6955627; (cm) a G allele at WSN-P_KU_REP_C101212_88410320; (cn) a G allele at WSN-P_JD_C12221_12509932; (co) an A allele at WSN-P_EX_C57209_59016692; (cp) a G allele at WSNP_EX_C2161_4059735; (cq) an A allele at WSN-P_EX_C29648_38653339; (cr) a C allele at WSN-P_EX_C19467_28423946; (cs) a G allele at WSN-P_RA_C14171_22234872; (ct) a T allele at WSNP_EX_C53387_56641291; (cu) a G allele at WSN-P_RA_C2063_4012957; (cv) a T allele at WSN-P_EX_C6142_10746442; (cw) a T allele at WSN-P_EX_C916_1767286; (cx) a C allele at WSNP_EX_C53387_56639804; (cy) a T allele at WSN-P_EX_C10500_17163855; (cz) a C allele at WSN-P_EX_C3309_6096114; (da) a G allele at WSNP_RFL_CONTIG4236_4881643; and/or (db) a C allele at WSN-P_EX_C758_1488368.

In still other embodiments, wheat plants, seeds, tissue culture, explants, and plant cells are provided that comprise at least one haplotype associated with a favorable heading date as set forth in Table 6 and include, for example, (a) an A allele at WSNP_EX_REP_C105541_89932598 and a G allele at WSNP_KU_C17726_26872129; (b) an A allele atWSNP_EX_C4605_8240189, a T allele at WSN-P_EX_C44049_50205904, a C allele at WSN-P_EX_C3906_7086162, a C allele at WSN-P_EX_REP_C101746_87053634, a G allele at WSNP_EX_REP_C101414_86780996, and a C allele at WSNP_EX_C44049_50205457; (c) an A allele at WSN-P_EX_C5192_9203682, a G allele at WSN-P_JD_C13903_13781269; a G allele at WSN-P_RA_C12148_19539667, a G allele at WSNP_BE495786A_TA_2_1, and a C allele at WSN-P_KU_C24239_34199356; (d) an A allele at WSN-P_RA_C37745_45806931 and a C allele atWSN-P_EX_C34344_42676379, a C allele at WSNP_EX_C34344_42677360, an G allele at WSNP_EX_REP_C66628_64934660 and a C allele at WSN-P_EX_C42282_48900922; (e) a G allele at WSN-P_EX_REP_C108057_91436561, a G allele at WSNP_EX_C16720_25268525, and a C allele at WSNP_CAP8_C458_368155; (f) a G allele at WSN-P_EX_C741_1456698 and a C allele at WSN-P_JD_C12687_12877994; (g) a G allele at WSN-P_EX_C55096_57733841, a C allele at WSNP_EX_REP_C104141_88935451, a C allele at WSN-P_EX_C25082_34346512, a T allele at WSN-P_EX_C361_708712, and a C allele at WSN-P_EX_C55096_57733894; (h) a C allele at WSNP_EX_C8802_14726148 and a T allele at WSN-P_EX_C4927_8772847; (i) a G allele at WSN- P_JD_C17082_16025440, a T allele at WSNP_JD_C9902_10674626, and a T allele at WSNP_JD_C9902_10674725; (j) an A allele at WSNP_EX_C21499_30644485, a G allele at WSNP_BQ168706B_TA_2_2, a T allele at WSNP_KU_C18538_27857915, a G allele at WSNP_BE489326B_TA_2_2, and a T allele at WSNP_BQ168706B_TA_2_1; (k) a C allele at WSNP_EX_C123_244117, a C allele at WSNP_EX_C5378_9505087, a C allele at WSNP_EX_C2330_4366134, a C allele at WSNP_EX_C22016_31191407, a G allele at WSNP_KU_C8722_14766699, a T allele at WSNP_KU_C6825_11858665, a C allele at WSNP_EX_C5378_9504586, and a C allele at WSNP_EX_C4769_8510104; (l) a C allele at WSNP_EX_C5547_9774453, a G allele at WSNP_EX_C5547_9772680, a T allele at WSNP_EX_C5547_9774195, a C allele at WSNP_BE445348B_TA_2_1, an A allele at WSNP_EX_C7756_13218814, a C allele at WSNP_EX_C3096_5709369, and, an A allele at WSNP_EX_C3096_5709257; (m) a G allele at WSNP_EX_C12887_20427158, a T allele at WSNP_KU_REP_C72821_72480395, and an A allele at WSNP_EX_C3096_5708642; (n) a T allele at WSNP_EX_C57007_58898157, an A allele at WSNP_EX_C8208_13870372, and, an A allele at WSNP_JD_C4413_5541190; (o) a C allele at WSNP_KU_C7180_12403155 and a T allele at WSNP_EX_C10347_16946522; (p) a T allele at WSNP_KU_REP_C102220_89250165, a C allele at WSNP_KU_C328_679106, a G allele at WSNP_RA_C323_681466, an A allele at WSNP_KU_C644_1332610, a T allele at WSNP_RA_C17541_26430903, a T allele at WSNP_KU_C7890_13513783, and, an A allele at WSNP_RA_C6788_11804894; (q) a C allele at WSNP_EX_REP_C69526_68472665, a T allele at WSNP_EX_C31830_40573624, a T allele at WSNP_CAP7_C2282_1107112, a T allele at WSNP_BF201102A_TA_2_1, a T allele at WSNP_EX_C19134_28056012, and a T allele at WSNP_EX_C4211_7606269; (r) a T allele at WSNP_EX_C2718_5038582, a C allele at WSNP_RA_C11420_18529863, a C allele at WSNP_KU_C1102_2211433, an A allele at WSNP_EX_C23509_32746909, a C allele at WSNP_RA_REP_C75364_72953286, an A allele at WSNP_EX_REP_C66733_65077608, and, a C allele at WSNP_BE500291A_TA_2_1; (s) an A allele at WSNP_KU_C16812_25759885, a G allele at WSNP_EX_C130_258776, a C allele at WSNP_RA_C10053_16636851, a C allele at WSNP_EX_C15084_23263641, and an A allele at WSNP_RA_C2228_4310870; (t) an A allele at WSNP_EX_C43578_49857984 and a G allele at WSNP_KU_C30743_40542247; (u) an A allele at WSNP_JD_C5795_6955627 and a G allele at WSNP_KU_REP_C101212_88410320; (v) a G allele at WSNP_JD_C12221_12509932 and an A allele at WSNP_EX_C57209_59016692; (w) a G allele at WSNP_EX_C2161_4059735 and an A allele at WSNP_EX_C29648_38653339; (x) a C allele at WSNP_EX_C19467_28423946 and a G allele at WSNP_RA_C14171_22234872; (y) a T allele at WSNP_EX_C53387_56641291, a G allele at WSNP_RA_C2063_4012957, a T allele at WSNP_EX_C6142_10746442, a T allele at WSNP_EX_C916_1767286, and a C allele at WSNP_EX_C53387_56639804; (z) a T allele at WSNP_EX_C10500_17163855 and a C allele at WSNP_EX_C3309_6096114; and/or, (aa) a G allele at WSNP_RFL_CONTIG4236_4881643 and a C allele at WSNP_EX_C758_1488368.

Plants, including wheat plants, seeds, tissue cultures, variants and mutants, having resistance to *fusarium* head blight are also provided. In certain examples, plants identified and selected by the foregoing methods are provided. In yet further examples, plants comprising a favorable allele at one or more marker locus selected from the group consisting WSNP_EX_C5550_9779698; WSNP_EX_C46670_52108070; WSNP_EX_C5060_8985678; WSNP_RA_C8484_14372815; WSNP_EX_C11976_19193550; WSNP_EX_C20975_30093113; WSNP_EX_C16581_25100502; WSNP_EX_C17452_26163465; WSNP_KU_C4951_8856170; WSNP_EX_C18733_27607958; WSNP_KU_C39862_48205590; WSNP_KU_C16938_25916279; WSNP_EX_REP_C67036_65492436; WSNP_JD_C4485_5618761; WSNP_KU_C16938_25916260; WSNP_JD_REP_C63201_40318622; WSNP_RA_C10861_17763060; WSNP_BE517627A_TA_2_1; WSNP_EX_C2592_4822528; WSNP_EX_C21092_30220342; WSNP_EX_C56928_58852277; WSNP_EX_C1064_2034431; WSNP_BE399936A_TA_2_1; WSNP_EX_C33196_41722217; WSNP_EX_C7091_12199032; WSNP_EX_C342_670415; WSNP_RA_C58188_60005934; WSNP_EX_C1064_2034518; WSNP_CD452951A_TA_2_1; WSNP_RA_C19083_28215239; WSNP_CAP7_C7742_3467376; WSNP_EX_C45617_51361414; WSNP_EX_C23720_32957892; WSNP_RA_C58188_60004916; WSNP_RA_REP_C106961_90622638; WSNP_EX_C21786_30948397; WSNP_CAP12_C5344_2430233; WSNP_EX_C20649_29731279; WSNP_EX_C1064_2034730; WSNP_EX_C21721_30882221; WSNP_KU_C44873_52048221; WSNP_EX_C11437_18454413; WSNP_EX_C3044_5620102; WSNP_EX_REP_C67635_66291944; WSNP_EX_REP_C67635_66292689; WSNP_CAP11_REP_C7339_3306558; WSNP_EX_C11229_18163892; WSNP_BF293133A_TA_2_2; WSNP_BF292295A_TA_2_1; WSNP_KU_C18473_27773912; WSNP_KU_C663_1368085; WSNP_EX_C7021_12096881; WSNP_RA_REP_C72670_70836439; WSNP_EX_REP_C66331_64502558; WSNP_BE489326B_TA_2_1; WSNP_JD_REP_C63654_40605158; WSNP_JD_REP_C50820_34666611; WSNP_EX_C19773_28772235; WSNP_BE638137B_TA_2_2; WSNP_EX_C5461_9636197; WSNP_RA_C21347_30731133; WSNP_EX_REP_C68829_67704044; WSNP_RA_C21347_30731229; WSNP_EX_REP_C101757_87064771; WSNP_EX_REP_C101757_87065169; WSNP_KU_C38543_47157828; WSNP_

P_EX_REP_C101757_87065032; WSNP_EX_C3838_6980909; WSNP_EX_C49211_53875600; WSNP_CAP11C299_251533; WSNP_EX_C49211_53875575; WSNP_EX_REP_C68600_67449494; WSNP_EX_C9362_15546626; WSNP_RA_C20970_30293078; WSNP_RA_C20970_30293227; WSNP_EX_REP_C68600_67448893; WSNP_JD_C7718_8795833; WSNP_EX_REP_C68165_66935041; WSNP_EX_C16491_24996576; WSNP_EX_C15378_23638822; WSNP_EX_C9763_16125630; WSNP_EX_C3530_6459643; WSNP_EX_C3530_6459532; WSNP_EX_REP_C68165_66935014; WSNP_KU_C38351_47009610; WSNP_CAP11_C2142_1128735; WSNP_EX_C15378_23639387; WSNP_EX_REP_C68165_66935148; WSNP_KU_C38351_47009641; WSNP_EX_C52849_56297163; WSNP_BE490200B_TA_2_1; WSNP_EX_C31256_40071875; WSNP_RA_C14498_22667649; WSNP_EX_C5936_10412246; WSNP_CAP12REP_C8688_3644383; WSNP_RA_C24962_34524602; WSNP_EX_C46160_51746546; WSNP_KU_C11690_19042937; WSNP_EX_C5744_10088287; WSNP_EX_C17349_26035281; WSNP_JD_REP_C63108_40258378; WSNP_EX_C5744_10087877; WSNP_KU_C1876_3666308; WSNP_EX_REP_C106072_90285324; WSNP_EX_C23716_32952372; WSNP_EX_C16836_25401702; WSNP_EX_C38198_45786860; WSNP_EX_C1146_2201722; WSNP_KU_C707_1465779; WSNP_RFL_CONTIG3854_4205716; WSNP_CAP11_REP_C6622_3044459; WSNP_EX_REP_C69954_68913284; WSNP_EX_REP_C69954_68913307; WSNP_EX_C46274_51831129; WSNP_EX_C351_689415; WSNP_RA_C31052_40235870; WSNP_RA_REP_C71101_69119989; WSNP_EX_REP_C69816_68774932; WSNP_EX_C10783_17555091; WSNP_KU_C18780_28136150; WSNP_EX_C5457_9631220; WSNP_CAP11_C1711_934478; WSNP_EX_C6611_11452297; WSNP_EX_C8386_14127329; WSNP_JD_C9040_9947841; WSNP_EX_C10231_16783750; WSNP_JD_C17128_16056425; WSNP_KU_C23598_33524490; WSNP_JD_C5757_6915127; WSNP_EX_C23968_33209660; WSNP_JD_C6974_8084450; WSNP_CAP7_C5487_2464864; WSNP_EX_C8360_14085858; WSNP_KU_C4067_7419106; WSNP_EX_C5267_9318903; WSNP_EX_C22753_31958639; WSNP_JD_C13086_13174510; WSNP_EX_C5457_9632050; WSNP_RA_C18364_27416387; WSNP_KU_C26784_36748247; WSNP_EX_REP_C69986_68942834; WSNP_BQ169669B_TA_2_2; WSNP_EX_C19582_28564743; WSNP_JD_C5919_7081809; WSNP_EX_C6611_11451949; WSNP_EX_C3201_5910659; WSNP_BE496826A_TA_2_3; WSNP_JD_C2180_3000498; WSNP_EX_C27373_36578273; WSNP_EX_C18800_27681277; WSNP_JD_C9360_10216526; WSNP_EX_C40060_47197384; WSNP_EX_C1279_2451582; WSNP_EX_C22016_31191407; WSNP_EX_C15399_23662312; WSNP_EX_REP_C70299_69243835; WSNP_EX_C23968_33210344; WSNP_EX_C7172_12318529; WSNP_EX_C2723_5047696; WSNP_EX_C123_244117; WSNP_CAP7_C1339_673581; WSNP_KU_C8722_14766699; WSNP_EX_REP_C69986_68942866; WSNP_EX_C2330_4366134; WSNP_JD_C12088_12411845; WSNP_EX_C26747_35974837; WSNP_EX_C1146_2200823; WSNP_EX_REP_C67198_65702998; WSNP_CAP8 REP_C8295_3722232; WSNP_CAP11 REP_C8768_3788007; WSNP_BQ168329A_TD_2_1; WSNP_EX_REP_C103505_88446868; WSNP_EX_C4094_7399975; WSNP_BG314532A_TA_2_1; WSNP_BF292596A_TA_1_3; WSNP_BF292596A_TA_1_1; WSNP_RA_C20273_945764; WSNP_RA_REP_C69221_66574148; WSNP_EX_C17667_26408733; WSNP_EX_C16919_25506076; WSNP_EX_REP_C70593_69508988; WSNP_EX_C22089_31270140; WSNP_KU_C14842_23275194; WSNP_EX_C2325_4355706; WSNP_EX_C10630_17338753; WSNP_KU_C53501_58106782; WSNP_EX_C4408_7939986; WSNP_KU_REP_C71567_71302010; WSNP_RFL_CONTIG2167_1484520; WSNP_EX_REP_C66407_64613374; WSNP_EX_C25755_35018674; WSNP_JD_C9360_10216330; WSNP_EX_REP_C67369_65940505; WSNP_EX_C4769_8510104; WSNP_RFL_CONTIG3917_4326857; WSNP_JD_C626_945114; WSNP_EX_C11055_17927668; WSNP_EX_C6476_11246531; WSNP_EX_C15163_23357477; WSNP_EX_C5780_10153638; WSNP_JD_C119_190135; WSNP_EX_C97184_84339976; WSNP_EX_C4548_8166555; WSNP_EX_REP_C68113_66877517; WSNP_EX_REP_C69266_68192954; WSNP_CAP11_C847_522893; WSNP_EX_C1279_2451699; WSNP_EX_C7316_12552186; WSNP_EX_REP_C68515_67349904; WSNP_JD_C3463_4479210; WSNP_KU_C6825_11858665; WSNP_EX_C1790_3378771; WSNP_EX_C5378_9505533; WSNP_CAP7_C444_237594; WSNP_EX_C10630_17338703; WSNP_EX_C5378_9505087; WSNP_EX_C8386_14128029; WSNP_JD_REP_C63942_40788045; WSNP_EX_C4661_8344663; WSNP_RA_C9209_15425473; WSNP_JD_C43389_30288993; WSNP_EX_C30969_39821293; WSNP_EX_C3738_6809767; WSNP_EX_REP_C103505_88447145; WSNP_EX_REP_C67897_66613415; WSNP_EX_C33765_42199371; WSNP_EX_REP_C66606_64905694; WSNP_EX_C14248_22204549; WSNP_EX_REP_C66766_65123941; WSNP_CAP11_C3968_1874257; WSNP_EX_C15325_23565935; WSNP_KU_C10939_17975681; WSNP_EX_C41073_47987034; WSNP_EX_C5378_9504586; WSNP_EX_C15325_23565794; WSNP_EX_REP_C67492_66096650; WSN-

P_EX_C21129_30256617; WSNP_EX_C31670_40433594; WSNP_EX_C2181_4089639; WSNP_CAP11_C923_558715; WSNP_KU_C8592_14575931; WSNP_BE490744A_TD_2_1; WSNP_JD_REP_C62985_40164465; WSNP_EX_C54655_57455562; WSNP_EX_C16295_24772663; WSNP_EX_C3940_7144946; WSNP_KU_C12698_20441325; WSNP_BF291549B_TA_1_1; WSNP_RA_C9738_16173810; WSNP_EX_C15325 23564654; WSNP_EX_C7705_13139890; WSNP_RA_C9738_16174002; WSNP_EX_C16295_24772702; WSNP_EX_C3887_7051325; WSNP_KU_C7471_12865509; and/or WSNP_CAP8_C6680_3136899 are provided.

Further provided are wheat plants, seeds, tissue culture, explants, and plant cells comprising, for example, (a) a T allele at WSNP_EX_C2181_4089639; (b) a C allele at WSNP_EX_REP_C70593_69508988; (c) an A allele at WSNP_EX_REP_C67492_66096650; (d) a G allele at WSNP_EX_C6476_11246531; (e) an A allele at WSNP_EX_C46670_52108070; (f) a C allele at WSNP_EX_C3887_7051325; (g) an A allele at WSNP_EX_REP_C67198_65702998; (h) a T allele at WSNP_KU_C8592_14575931; (i) a T allele at WSNP_EX_C7705_13139890; (j) a G allele at WSNP_EX_C5780_10153638; (k) a T allele at WSNP_EX_C18733_27607958; (l) a G allele at WSNP_EX_C11976_19193550; (m) a T allele at WSNP_KU_C16938_25916260; (n) a G allele at WSNP_JD_REP_C62985_40164465; (o) a C allele at WSNP_BF291549B_TA_1_1; (p) a C allele at WSNP_RA_C8484_14372815; (q) an A allele at WSNP_EX_REP_C67036_65492436; (r) a G allele at WSNP_KU_C4951_8856170; (s) a T allele at WSNP_JD_C4485_5618761; (t) a C allele at WSNP_EX_C17452_26163465; (u) a G allele at WSNP_RA_C2027_3945764; (v) a C allele at WSNP_EX_REP_C69986_68942866; (w) a T allele at WSNP_EX_REP_C69986_68942834; (x) an A allele at WSNP_KU_C39862_48205590; (y) an A allele at WSNP_EX_C6611_11451949; (z) an A allele at WSNP_EX_C6611_11452297; (aa) a G allele at WSNP_EX_C30969_39821293; (ab) a C allele at WSNP_JD_C13086_13174510; (ac) a G allele at WSNP_EX_REP_C68113_66877517; (ad) an A allele at WSNP_EX_C15325_23565935; (ae) a G allele at WSNP_CAP11REP_C8768_3788007; (af) an A allele at WSNP_BG314532A_TA_2_1; (ag) a G allele at WSNP_JD_C12088_12411845; (ah) a T allele at WSNP_EX_C15325_23565794; (ai) a G allele at WSNP_EX_C15325_23564654; (aj) a T allele at WSNP_CAP7_C7742_3467376; (ak) a G allele at WSNP_BE399936A_TA_2_1; (al) a T allele at WSNP_RA_C10861_17763060; (am) a G allele at WSNP_EX_C11437_18454413; (an) a C allele at WSNP_RA_C58188_60005934; (ao) a G allele at WSNP_EX_C23720_32957892; (ap) a C allele at WSNP_EX_C1064_2034518; (aq) a T allele at WSNP_BF293133A_TA_2_2; (ar) a C allele at WSNP_EX_REP_C67635_66291944; (as) an A allele at WSNP_EX_REP_C67635_66292689; (at) an A allele at WSNP_RA_C9738_16173810; (au) a C allele at WSNP_EX_C4548_8166555; (av) a C allele at WSNP_RA_C9738_16174002; (aw) a T allele at WSNP_EX_C10630_17338753; (ax) an A allele at WSNP_EX_C10630_17338703; (ay) a C allele at WSNP_EX_C8360_14085858; (az) a T allele at WSNP_KU_C12698_20441325; (ba) an A allele at WSNP_EX_REP_C66331_64502558; (bb) a T allele at WSNP_EX_C2723_5047696; (bc) a G allele at WSNP_EX_C8386_14127329; (bd) a T allele at WSNP_EX_REP_C66766_65123941; (be) an A allele at WSNP_BE489326B_TA_2_1; (bf) an A allele at WSNP_JD_C119_190135; (bg) a C allele at WSNP_EX_C4769_8510104; (bh) a G allele at WSNP_EX_C5378_9505533; (bi) a G allele at WSNP_EX_C7172_12318529; (bj) a C allele at WSNP_EX_C22016_31191407; (bk) a G allele at WSNP_KU_C8722_14766699; (bl) a C allele at WSNP_EX_C123_244117; (bm) a C allele at WSNP_EX_C5378_9504586; (bn) a C allele at WSNP_EX_C5378_9505087; (bo) a T allele at WSNP_KU_C6825_11858665;

(bp) a C allele at WSNP_EX_C2330_4366134; (bq) a T allele at WSNP_EX_C5457_9632050: (br) an A allele at WSNP_EX_C5457_9631220; (bs) a G allele at WSNP_JD_REP_C63654 40605158; (bt) a G allele at WSNP_EX_C7021_12096881; (bu) a G allele at WSNP_EX_C40060_47197384; (by) a T allele at WSNP_EX_C15399_23662312; (bw) a T allele at WSNP_RA_REP_C72670_70836439; (bx) an A allele at WSNP_JD_REP_C50820_34666611; (by) a T allele at WSNP_EX_REP_C101757_87065169; (bz) an A allele at WSNP_EX_REP_C101757_87064771; (ca) a G allele at WSNP_EX_REP_C101757_87065032; (cb) a T allele at WSNP_EX_C1279_2451699; (cc) a G allele at WSNP_EX_C1279_2451582; (cd) a T allele at WSNP_EX_C49211_53875600; (ce) a G allele at WSNP_EX_C49211_53875575; (cf) a T allele at WSNP_RA_C21347_30731133; (cg) a G allele at WSNP_RA_C21347_30731229; (ch) a T allele at WSNP_CAP11C299_251533; (ci) a G allele at WSNP_CAP11_C923_558715; (cj) an A allele at WSNP_EX_C54655_57455562; (ck) a T allele at WSNP_JD_C43389_30288993; (cl) a C allele at WSNP_EX_C23968_33209660; (cm) a C allele at WSNP_EX_C16295_24772663; (cn) a G allele at WSNP_EX_C23968_33210344; (co) a T allele at WSNP_EX_C16295_24772702; (cp) an A allele at WSNP_RA_C20970_30293227; (cq) an A allele at WSNP_RA_C20970_30293078; (cr) a G allele at WSNP_EX_REP_C68600_67448893; (cs) a C allele at WSNP_EX_REP_C68600_67449494; (ct) a T allele at WSNP_KU_C38351_47009610; (cu) an A allele at WSNP_EX_REP_C68165_66935014; (cv) a T allele at WSNP_EX_C3530_6459532; (cw) a T allele at WSNP_EX_C3530_6459643; (cx) a C allele at WSNP_EX_REP_C68165_66935041; (cy) a T allele at WSNP_EX_C52849_56297163; (cz) a G allele at WSNP_JD_C77188_795833; (da) a C allele at WSNP_JD_C2180_3000498; (db) a T allele at WSNP_KU_C26784_36748247; (dc) a T allele at WSNP_EX_C15378_23638822; (dd) an A allele at WSNP_EX_C15378_23639387; (de) a G allele at WSNP_CAP7_C5487_2464864; (df) a C allele at WSNP_EX_C2325_4355706; (dg) a G allele at WSNP_KU_REP_C71567_71302010; (dh) a T allele at WSNP_EX_C17349_26035281;

(di) a G allele at WSNP_EX_C46160_51746546; (dj) a G allele at WSNP_EX_C38198_45786860; (dk) an A allele at WSNP_EX_C17667_26408733; (dl) a G allele at WSNP_JD_REP_C63108_40258378; (dm) a G allele at WSNP_RA_C24962_34524602; (dn) a G allele at WSN- P_EX_C31256_40071875; (do) an A allele at WSNP_EX_C5744_1008828; (dp) an A allele at WSNP_BE490200B_TA_2_1; (dq) a C allele at WSNP_EX_REP_C106072_90285324; (dr) an A allele at WSNP_EX_C1146_2200823; (ds) a T allele at WSNP_EX_C19582_28564743; (dt) a C allele at WSNP_EX_C1146_2201722; (du) a T allele at WSNP_EX_C46274_51831129; (dv) a C allele at WSNP_RA_REP_C71101_69119989; (dw) a C allele at WSNP_RA_C31052_40235870; (dx) a T allele at WSNP_EX_REP_C69954_68913284; (dy) an A allele at WSNP_EX_C18800_27681277; (dz) an A allele at WSNP_EX_C27373_36578273; (ea) a C allele at WSNP_JD_C9040_9947841; (eb) a G allele at WSNP_KU_C10939_17975681; (ec) a G allele at WSNP_EX_C25755_35018674; (ed) an A allele at WSNP_EX_C26747_35974837; (ee) a T allele at WSNP_KU_C4067_7419106; (ef) an A allele at WSNP_EX_C1790_3378771; (eg) an A allele at WSNP_EX_REP_C69954_68913307; (eh) T allele at WSNP_EX_C4408_7939986; (ei) an A allele at WSNP_EX_C14248_22204549; (ej) a G allele at WSNP_CAP11_C847_522893; (ek) a G allele at WSNP_KU_C18780 28136150; (el) a T allele at WSNP_BQ169669B_TA_22; (em) a C allele at WSNP_EX_C351_689415; (en) a T allele at WSNP_JD_C17128_16056425; and/or, (eo) a C allele at WSNP_EX_C3738_6809767.

In still other embodiments, wheat plants, seeds, tissue culture, explants, and plant cells are provided that comprise at least one haplotype associated with an improved *fusarium* blight head resistance as set forth in Table 6 and include, for example, (a) a T allele at WSNP_EX_C2181_4089639 and a C allele at WSNP_EX_REP_C70593_69508988; (b) an A allele at WSNP_EX_REP_C67492_66096650 and a G allele at WSNP_EX_C6476_11246531; (c) an A allele at WSNP_EX_C46670_52108070 and a C allele at WSNP_EX_C3887_7051325; (d) an A allele at WSNP_EX_REP_C67198_65702998, a T allele at WSNP_KU_C8592_14575931, a T allele at WSNP_EX_C7705_13139890, and a G allele at WSNP_EX_C5780_10153638; (e) a T allele at WSNP_EX_C18733_27607958, a G allele at WSNP_EX_C11976_19193550, a T allele at WSNP_KU_C16938_25916260, a G allele at WSNP_JD_REP_C62985 40164465, and a C allele at WSNP_BF291549B_TA_1_1; (f) a C allele at WSNP_RA_C8484_14372815, an A allele at WSNP_EX_REP_C67036_65492436, a G allele at WSNP_KU_C4951_8856170, a T allele at WSNP_JD_C4485_5618761, a C allele at WSNP_EX_C17452_26163465, a G allele at WSNP_RA_C2027_3945764, a C allele at WSNP_EX_REP_C69986_68942866, and, a T allele at WSNP_EX_REP_C69986_68942834; (g) an A allele at WSNP_KU_C39862_48205590, an A allele at WSNP_EX_C6611_11451949, an A allele at WSNP_EX_C6611_11452297, and a G allele at WSNP_EX_C30969_39821293; (h) a C allele at WSNP_JD_C13086_13174510, a G allele at WSNP_EX_REP_C68113_66877517, and an A allele at WSNP_EX_C15325_23565935; (i) a G allele at WSNP_CAP11_REP_C8768_3788007, an A allele at WSNP_BG314532A_TA_2_1, a G allele at WSNP_JD_C12088_12411845, a T allele at WSNP_EX_C15325_23565794, and a G allele at WSNP_EX_C15325_23564654; (j) a T allele at WSNP_CAP7_C7742_3467376, a G allele at WSNP_BE399936A_TA_2_1, a T allele at WSNP_RA_C10861_17763060, a G allele at WSNP_EX_C11437_18454413, a C allele at WSNP_RA_C58188_60005934, a G allele at WSNP_EX_C23720_32957892, and a C allele at WSNP_EX_C1064_2034518; (k) a T allele at WSNP_BF293133A_TA_2_2, a C allele at WSNP_EX_REP_C67635_66291944, and an A allele at WSNP_EX_REP_C67635_66292689; (l) an A allele at WSNP_RA_C9738_16173810, a C allele at WSNP_EX_C4548_8166555, and a C allele at WSNP_RA_C9738_16174002; (m) a T allele at WSNP_EX_C10630_17338753 and an A allele at WSNP_EX_C10630_17338703; (n) a C allele at WSNP_EX_C8360_14085858, a T allele at WSNP_KU_C12698_20441325, an A allele at WSNP_EX_REP_C66331_64502558, and a T allele at WSNP_EX_C2723_5047696; (o) a G allele at WSNP_EX_C8386_14127329 and a T allele at WSNP_EX_REP_C66766_65123941; (p) an A allele at WSNP_BE489326B_TA_2_1 and an A allele at WSNP_JD_C119_190135; (q) a C allele at WSNP_EX_C4769_8510104, a G allele at WSNP_EX_C5378_9505533, a G allele at WSNP_EX_C7172_12318529, a C allele at WSNP_EX_C22016_31191407, a G allele at WSNP_KU_C8722_14766699, a C allele at WSNP_EX_C123 244117, a C allele at WSNP_EX_C5378_9504586, a C allele at WSNP_EX_C5378_9505087, a T allele at WSNP_KU_C6825_11858665, a C allele at WSNP_EX_C2330_4366134, a T allele at WSNP_EX_C5457_9632050, an A allele at WSNP_EX_C5457_9631220, a G allele at WSNP_JD_REP_C63654_40605158, and a G allele at WSNP_EX_C7021_12096881; (r) a G allele at WSNP_EX_C40060 47197384 and a T allele at WSNP_EX_C15399_23662312; (s) a C allele at WSNP_RA_REP_C72670_70836439 and an A allele at WSNP_JD_REP_C50820_34666611; (t) a T allele at WSNP_EX_REP_C101757_87065169, an A allele at WSNP_EX_REP_C101757_87064771, and a G allele at WSNP_EX_REP_C101757_87065032; (u) a T allele at WSNP_EX_C1279_2451699 and a G allele at WSNP_EX_C1279_2451582; (v) a T allele at WSNP_EX_C49211_53875600, a G allele at WSNP_EX_C49211_53875575, and a T allele at WSNP_RA_C21347_30731133; (w) a G allele at WSNP_RA_C21347_30731229 and a T allele at WSNP_CAP11_C299_251533; (x) a G allele at WSNP_CAP11_C923_558715, an A allele at WSNP_EX_C54655_57455562, a T allele at WSNP_JD_C43389_30288993, a C allele at WSNP_EX_C23968_33209660, a C allele at WSNP_EX_C16295_24772663, a G allele at WSNP_EX_C23968_33210344, and a T allele at WSNP_EX_C16295_24772702; (y) an A allele at WSNP_RA_C20970_30293227, an A allele at WSNP_RA_C20970_30293078, a G allele at WSNP_EX_REP_C68600_67448893, and a C allele at WSNP_EX_REP_C68600_67449494; (z) a T allele at WSNP_KU_C38351_47009610, an A allele at WSNP_EX_REP_C68165_66935014, a T allele at WSNP_EX_C3530_6459532, a G allele at WSNP_EX_C3530_6459643, a C allele at WSNP_EX_REP_C68165_66935041, a T allele at WSNP_EX_C52849_56297163, and a G allele at WSN- P_JD_C7718_8795833; (aa) a C allele at WSN-P_JD_C2180_3000498, a T allele at WSN-P_KU_C26784_36748247, a T allele at WSNP_EX_C15378_23638822, and an A allele at WSN-P_EX_C15378_23639387; (ab) a G allele at WSNP_CAP7_C5487_2464864, a C allele at WSN-P_EX_C2325_4355706, and a G allele at WSN-P_KU_REP_C71567_71302010; (ac) a T allele at WSN-P_EX_C17349_26035281, a G allele at WSNP_EX_C46160_51746546, a G allele at WSN-P_EX_C38198_45786860, and an A allele at WSN-P_EX_C17667_26408733; (ad) a G allele at WSNP_J-D_REP_C63108_40258378 and a G allele at WSNP_RA_C24962_34524602; (ae) a G allele at WSN-P_EX_C31256_40071875, an A allele at WSN-P_EX_C5744_10088287, an A allele at WSNP_BE490200B_TA_2_1 and a C allele at WSN-P_EX_REP_C106072_90285324; (af) an A allele at WSN-P_EX_C1146_2200823, a T allele at WSN-P_EX_C19582_28564743, and a C allele at WSNP_EX_C1146_2201722; (ag) a T allele at WSN-P_EX_C46274_51831129 and a C allele at WSN-P_RA_REP_C71101_69119989; (ah) a C allele at WSN-P_RA_C31052_40235870 and a T allele at WSNP_EX_REP_C69954_68913284; (ai) an A allele at WSNP_EX_C18800_27681277, an A allele at WSN-P_EX_C27373_36578273, a C allele at WSN-P_JD_C9040_9947841, a G allele at WSN-P_KU_C10939_17975681, a G allele at WSNP_EX_C25755_35018674, an A allele at WSN-P_EX_C26747_35974837, a T allele at WSN-P_KU_C4067_7419106, an A allele at WSN-P_EX_C1790_3378771, an A allele at WSNP_EX_REP_C69954_68913307, a T allele at WSN-P_EX_C4408_7939986, and an A allele at WSN-P_EX_C14248_22204549; (aj) a G allele at WSNP_CAP11_C847_522893, a G allele at WSN-P_KU_C18780_28136150, and a T allele at WSNP_BQ169669B_TA_2_2; and/or (ak) a C allele at WSNP_EX_C351_689415, a T allele at WSN-P_JD_C17128_16056425, and, a C allele at WSN-P_EX_C3738_6809767.

Plants, including wheat plants, seeds, tissue cultures, variants and mutants, that are identified and selected by the foregoing methods are provided. In yet further examples, plants comprising a favorable allele at the marker locus WSNP_EX_REP_C66893_65301351 are provided.

Introgression:

At least one marker locus associated with a favorable phenotype in wheat or of a haplotype associated with a favorable phenotype in wheat can be introgressed into a wheat plant or germplasm lacking the favorable phenotype. A first wheat plant or germplasm that is identified or selected as a result of detection at one or more of the marker loci disclosed in Tables 1-4 may be crossed with the second wheat germplasm to provide progeny wheat germplasm. These progeny germplasm are screened to determine the presence of the favorable phenotype in wheat, with respect to flowering date, anther-extrusion, heading date and/or *fusarium* head blight resistance by detecting any one or a combination of alleles at marker loci set forth in Tables 1, 2, 3, and/or 4. The progeny that tests positive for the presence of the allele or alleles (i.e. haplotype) that are associated with the favorable phenotype are selected as having the introgressed region. Methods for performing such screening are well known in the art and any suitable method can be used.

In still further methods, the information disclosed herein regarding marker loci associated with flowering date, heading date, anther extrusion, and *fusarium* head blight resistance can be used to aid in the selection of breeding plants, lines, and populations containing favorable versions of these traits for use in introgression of the favorable traits into elite wheat germplasm, or germplasm of proven genetic superiority suitable for variety release.

Also provided is a method for producing a wheat plant adapted for conferring a favorable phenotype with respect to flowering date, heading date, anther extrusion, and/or resistance to *fusarium* head blight in wheat. First, donor wheat plants for a parental line containing an allele or combination of alleles (i.e. haplotype) at one or more of the marker loci presented in Tables 1, 2, 3, and/or 4, are selected. According to the method, selection can be accomplished via MAS as explained herein. Selected plant material may represent, among others, an inbred line, a hybrid line, a heterogeneous population of wheat plants, or an individual plant. According to techniques well known in the art of plant breeding, this donor parental line is crossed with a second parental line. In some examples, the second parental line is a high yielding line. This cross produces a segregating plant population composed of genetically heterogeneous plants. Plants of the segregating plant population are screened for the allele or alleles that are associated with the favorable phenotype. Further breeding may include, among other techniques, additional crosses with other lines, hybrids, backcrossing, or self-crossing. The result is a line of wheat plants that has the favorable phenotype and optionally also has other desirable traits from one or more other wheat lines.

Non-limiting embodiments include:

1. A method of identifying a first wheat plant or germplasm

A) wherein said first wheat plant or germplasm displays a favorable flowering date said method comprising detecting in the first wheat plant or germplasm at least one marker locus comprising: WSN-P_KU_C16547_25454123; WSN-P_EX_C2920_5385184; WSN-P_EX_C10717_17456391; WSNP_JD_C1316_1891903; WSNP_BG263758B_TA_2_1; WSN-P_EX_C3501_6408181; WSNP_BE404354B_TA_2_1; WSN-P_EX_C10555_17237000; WSN-P_KU_C6758_11757213; WSN-P_JD_C6544_7697578; WSNP_EX_C36325_44308589; WSN-P_EX_C2580_4800027; WSN-P_EX_C10555_17235832; WSN-P_EX_C22089_31270140; WSNP_EX_C6590_11419735; WSNP_CAP11_C210_199161; WSN-P_KU_C1818_3557408; WSN-P_EX_REP_C66606_64905694; WSN-P_EX_REP_C102795_87883062; or a maker locus that is closely linked to any one of said marker locus;

B) wherein said first wheat plant or germplasm that displays a favorable heading date said method comprising detecting in the first wheat plant or germplasm at least one marker locus comprising WSNP_CAP7_C3472_1623955; WSN-P_EX_REP_C108057_91436561; WSNP_CAP8_C458_368155; WSN-P_EX_C16720_25268525; WSN-P_RA_C32271_41304469; WSN- P_EX_C25082_34346512; WSNP_EX_C55096_57733894; WSNP_EX_C11229_18163892; WSNP_EX_C55096_57733841; WSNP_EX_C3096_5709369; WSNP_EX_REP_C67404_65986980; WSNP_BQ168706B_TA_2_2; WSNP_BQ168706B_TA_2_1; WSNP_EX_C8208_13870372; WSNP_JD_C17082_16025440; WSNP_EX_C21499_30644485; WSNP_EX_C3096_5709257; WSNP_BE489326B_TA_2_2; WSNP_JD_C4413_5541190; WSNP_EX_C57007_58898157; WSNP_EX_C10347_16946522; WSNP_KU_C7180_12403155; WSNP_BF201102A_TA_2_1; WSNP_EX_C43578_49857984; WSNP_KU_C7890_13513783; WSNP_EX_C57209_59016692; WSNP_JD_C12221_12509932; WSNP_JD_C7718_8795833; WSNP_EX_C19467_28423946; WSNP_EX_C8643_14488961; WSNP_EX_C1143_2194680; WSNP_RA_C14171_22234872; WSNP_EX_C53387_56639804; WSNP_KU_C28104_38042857; WSNP_CAP8_REP_C3844_1896355; WSNP_RA_C23253_32762188; WSNP_EX_C9971_16412345; WSNP_EX_C11106_18003332; WSNP_EX_C35861_43928486; WSNP_EX_C5547_9774453; WSNP_KU_C10377_17180909; WSNP_KU_C18538_27857915; WSNP_RA_C11420_18529863; WSNP_EX_C41347_48189975; WSNP_EX_C53387_56641291; WSNP_EX_C23509_32746909; WSNP_BE497845D_TA_1_1; WSNP_BE445508B_TA_2_2; WSNP_EX_C44049_50205457; WSNP_BE591466B_TA_2_1; WSNP_EX_C15084_23263641; WSNP_JD_C13903_13781269; WSNP_KU_C644_1332610; WSNP_EX_C35861_43926307; WSNP_EX_C5547_9772680; WSNP_KU_REP_C102220_89250165; WSNP_EX_C8802_14726148; WSNP_EX_C130_258776; WSNP_BE499016B_TA_2_1; WSNP_EX_REP_C69919_68881108; WSNP_EX_C361_708712; WSNP_KU_C1102_2211433; WSNP_RA_C323_681466; WSNP_EX_C916_1767286; WSNP_KU_C16295_25149034; WSNP_JD_C12087_12411036; WSNP_EX_C22016_31191407; WSNP_KU_C16812_25759885; WSNP_JD_C5795_6955627; WSNP_EX_REP_C69342_68276256; WSNP_EX_C2718_5038582; WSNP_KU_C17726_26872129; WSNP_JD_C15974_15272598; WSNP_EX_C5239_9272511; WSNP_RA_C37745_45806931; WSNP_EX_REP_C105541_89932598; WSNP_EX_REP_C69526_68472665; WSNP_EX_C123_244117; WSNP_EX_C1988_3742291; WSNP_EX_C19134_28056012; WSNP_JD_C7404_8500079; WSNP_EX_C8303_14001708; WSNP_EX_C9927_16346100; WSNP_JD_C4621_5757201; WSNP_BE591684B_TA_2_1; WSNP_KU_C8722_14766699; WSNP_EX_C2330_4366134; WSNP_EX_REP_C101414_86780996; WSNP_EX_C29130_38196906; WSNP_RA_C17541_26430903; WSNP_JD_C12687_12877994; WSNP_EX_C10500_17163855; WSNP_EX_C2161_4059735; WSNP_EX_C5547_9774195; WSNP_EX_C4211_7606269; WSNP_EX_C6142_10746442; WSNP_EX_C12254_19575022; WSNP_RA_C2228_4310870; WSNP_RA_C12148_19539667; WSNP_KU_C8712_14751858; WSNP_EX_C34344_42677360; WSNP_RFL_CONTIG4236_4881643; WSNP_BE495786A_TA_2_1; WSNP_RA_REP_C71473_69552690; WSNP_BE490744B_TA_2_1; WSNP_EX_REP_C67660_66321934; WSNP_EX_C758_1488368; WSNP_EX_C12887_20427158; WSNP_EX_C33778_42210283; WSNP_RA_C10053_16636851; WSNP_EX_C31262_40077397; WSNP_KU_C854_1768062; WSNP_BE445431A_TD_2_2; WSNP_EX_REP_C101746_87053634; WSNP_EX_C4769_8510104; WSNP_EX_REP_C104141_88935451; WSNP_EX_C44587_50598716; WSNP_EX_C741_1456698; WSNP_EX_REP_C103972_88799335; WSNP_EX_C3309_6096114; WSNP_RA_C7112_12318340; WSNP_RA_C2063_4012957; WSNP_EX_C42282_48900922; WSNP_EX_C53983_57032627; WSNP_EX_C34842_43092205; WSNP_EX_C5446_9616983; WSNP_EX_C97184_84339976; WSNP_JD_C9902_10674725; WSNP_BE445348B_TA_2_1; WSNP_BE500291A_TA_2_1; WSNP_EX_REP_C115803_95396724; WSNP_KU_REP_C72821_72480395; WSNP_EX_C3906_7086162; WSNP_KU_C6825_11858665; WSNP_EX_C4605_8240189; WSNP_BF428726A_TA_2_5; WSNP_KU_C66980_66202298; WSNP_BE405599B_TA_2_1; WSNP_JD_C35319_26397591; WSNP_EX_C5378_9505087; WSNP_CAP11C827_513472; WSNP_EX_C29648_38653339; WSNP_KU_C854_1768346; WSNP_KU_C328_679106;

WSNP_EX_C3096_5708642;
WSNP_CAP7_C2282_1107112; WSNP_JD_C9902_10674626; WSNP_KU_C24239_34199356;
WSNP_KU_C5071_9050628;
WSNP_EX_C31830_40573624; WSNP_KU_REP_C101212_88410320; WSNP_KU_C39289_47757996; WSNP_EX_C19622_28607997;
WSNP_EX_REP_C66733_65077608; WSNP_EX_C26818_36041748; WSNP_EX_C11684_18805687; WSNP_EX_C34344_42676379;
WSNP_RA_C6788_11804894; WSNP_EX_C7756_13218814; WSNP_EX_C35861_43927741; WSNP_KU_C34643_43968242;
WSNP_RA_REP_C75364_72953286; WSNP_EX_C5192_9203682; WSNP_EX_C5378_9504586; WSNP_EX_C4710_8412517;
WSNP_EX_REP_C66628_64934660;
WSNP_CAP11C1182_686503; WSNP_JD_C2863_3822253; WSNP_EX_C4927_8772847; WSNP_EX_C44049_50205904; WSNP_RFL_CONTIG2729_2446041; WSNP_BE496983B_TA_2_1; WSNP_KU_C30743_40542247; WSNP_KU_REP_C103274_90057407, or a marker locus that is closely linked to any one of said marker locus;

C) said first wheat plant or germplasm that displays improved *fusarium* blight head resistance, said method comprising detecting at least one marker locus comprising WSNP_EX_C5550_9779698; WSNP_EX_C46670_52108070; WSNP_EX_C5060_8985678;
WSNP_RA_C8484_14372815; WSNP_EX_C11976_19193550; WSNP_EX_C20975_30093113; WSNP_EX_C16581_25100502;
WSNP_EX_C17452_26163465; WSNP_KU_C4951_8856170; WSNP_EX_C18733_27607958; WSNP_KU_C39862_48205590;
WSNP_KU_C16938_25916279; WSNP_EX_REP_C67036_65492436; WSNP_JD_C4485_5618761; WSNP_KU_C16938_25916260;
WSNP_JD_REP_C63201_40318622; WSNP_RA_C10861_17763060;
WSNP_BE517627A_TA_2_1; WSNP_EX_C2592_4822528; WSNP_EX_C21092_30220342; WSNP_EX_C56928_58852277;
WSNP_EX_C1064_2034431;
WSNP_BE399936A_TA_2_1; WSNP_EX_C33196_41722217; WSNP_EX_C7091_12199032; WSNP_EX_C342_670415; WSNP_RA_C58188_60005934; WSNP_EX_C1064_2034518;
WSNP_CD452951A_TA_2_1; WSNP_RA_C19083_28215239;
WSNP_CAP7_C7742_3467376; WSNP_EX_C45617_51361414; WSNP_EX_C23720_32957892; WSNP_RA_C58188_60004916;
WSNP_RA_REP_C106961_90622638; WSNP_EX_C21786_30948397;

WSNP_CAP12C5344_2430233; WSNP_EX_C20649_29731279; WSNP_EX_C1064_2034730; WSNP_EX_C21721_30882221;
WSNP_KU_C44873_52048221; WSNP_EX_C11437_18454413; WSNP_EX_C3044_5620102; WSNP_EX_REP_C67635_66291944;
WSNP_EX_REP_C67635_66292689;
WSNP_CAP11_REP_C7339_3306558; WSNP_EX_C11229_18163892;
WSNP_BF293133A_TA_2_2;
WSNP_BF292295A_TA_2_1; WSNP_KU_C18473_27773912; WSNP_KU_C663_1368085; WSNP_EX_C7021_12096881;
WSNP_RA_REP_C72670_70836439; WSNP_EX_REP_C66331_64502558;
WSNP_BE489326B_TA_2_1; WSNP_J-D_REP_C63654_40605158; WSNP_J-D_REP_C50820_34666611; WSNP_EX_C19773_28772235;
WSNP_BE638137B_TA_2_2; WSNP_EX_C5461_9636197; WSNP_RA_C21347_30731133; WSNP_EX_REP_C68829_67704044;
WSNP_RA_C21347_30731229; WSNP_EX_REP_C101757_87064771; WSNP_EX_REP_C101757_87065169; WSNP_KU_C38543_47157828;
WSNP_EX_REP_C101757_87065032; WSNP_EX_C3838_6980909; WSNP_EX_C49211_53875600;
WSNP_CAP11_C299_251533; WSNP_EX_C49211_53875575; WSNP_EX_REP_C68600_67449494; WSNP_EX_C9362_15546626;
WSNP_RA_C20970_30293078; WSNP_RA_C20970_30293227; WSNP_EX_REP_C68600_67448893; WSNP_JD_C7718_8795833;
WSNP_EX_REP_C68165_66935041; WSNP_EX_C16491_24996576; WSNP_EX_C15378_23638822; WSNP_EX_C9763_16125630;
WSNP_EX_C3530_6459643; WSNP_EX_C3530_6459532; WSNP_EX_REP_C68165_66935014; WSNP_KU_C38351_47009610;
WSNP_CAP11_C2142_1128735; WSNP_EX_C15378_23639387; WSNP_EX_REP_C68165_66935148; WSNP_KU_C38351_47009641;
WSNP_EX_C52849_56297163;
WSNP_BE490200B_TA_2_1; WSNP_EX_C31256_40071875; WSNP_RA_C14498_22667649; WSNP_EX_C5936_10412246;
WSNP_CAP12REP_C8688_3644383; WSNP_RA_C24962_34524602; WSNP_EX_C46160_51746546; WSNP_KU_C11690_19042937;
WSNP_EX_C5744_10088287; WSNP_EX_C17349_26035281; WSNP_J-D_REP_C63108_40258378; WSNP_EX_C5744_10087877;
WSNP_KU_C1876_3666308; WSN-

P_EX_REP_C106072_90285324; WSN-P_EX_C23716_32952372; WSN-P_EX_C16836_25401702; WSNP_EX_C38198_45786860; WSN-P_EX_C1146_2201722; WSNP_KU_C707_1465779; WSNP_RFL_CONTIG3854_4205716; WSNP_CAP11_REP_C6622_3044459; WSN-P_EX_REP_C69954_68913284; WSN-P_EX_REP_C69954_68913307; WSN-P_EX_C46274_51831129; WSNP_EX_C351_689415; WSN-P_RA_C31052_40235870; WSN-P_RA_REP_C71101_69119989; WSN-P_EX_REP_C69816_68774932; WSNP_EX_C10783_17555091; WSN-P_KU_C18780_28136150; WSN-P_EX_C5457_9631220; WSNP_CAP11_C1711_934478; WSN-P_EX_C6611_11452297; WSN-P_EX_C8386_14127329; WSN-P_JD_C9040_9947841; WSNP_EX_C10231_16783750; WSN-P_JD_C17128_16056425; WSN-P_KU_C23598_33524490; WSN-P_JD_C5757_6915127; WSNP_EX_C23968_33209660; WSN-P_JD_C6974_8084450; WSNP_CAP7_C5487_2464864; WSN-P_EX_C8360_14085858; WSN-P_KU_C4067_7419106; WSN-P_EX_C5267_9318903; WSNP_EX_C22753_31958639; WSN-P_JD_C13086_13174510; WSN-P_EX_C5457_9632050; WSN-P_RA_C18364_27416387; WSNP_KU_C26784_36748247; WSN-P_EX_REP_C69986_68942834; WSNP_BQ169669B_TA_2_2; WSN-P_EX_C19582_28564743; WSN-P_JD_C5919_7081809; WSN-P_EX_C6611_11451949; WSNP_EX_C3201_5910659; WSNP_BE496826A_TA_2_3; WSN-P_JD_C2180_3000498; WSN-P_EX_C27373_36578273; WSN-P_EX_C18800_27681277; WSNP_JD_C9360_10216526; WSN-P_EX_C40060_47197384; WSN-P_EX_C1279_2451582; WSN-P_EX_C220163_1191407; WSNP_EX_C15399_23662312; WSN-P_EX_REP_C70299_69243835; WSN-P_EX_C23968_33210344; WSN-P_EX_C7172_12318529; WSNP_EX_C2723_5047696; WSN-P_EX_C123_244117; WSNP_CAP7_C1339_673581; WSNP_KU_C8722_14766699; WSN-P_EX_REP_C69986_68942866; WSN-P_EX_C2330_4366134; WSN-P_JD_C12088_12411845; WSNP_EX_C26747_35974837; WSN-P_EX_C1146_2200823; WSN-P_EX_REP_C67198_65702998; WSNP_CAP8_REP_C8295_3722232; WSNP_CAP11_REP_C8768_3788007; WSNP_BQ168329A_TD_2_1; WSN-P_EX_REP_C103505_88446868; WSN-P_EX_C4094_7399975; WSNP_BG314532A_TA_2_1; WSNP_BF292596A_TA_1_3; WSNP_BF292596A_TA_1_1; WSN-P_RA_C2027_3945764; WSN-P_RA_REP_C69221_66574148; WSN-P_EX_C17667_26408733; WSNP_EX_C16919_25506076; WSN-P_EX_REP_C70593_69508988; WSN-P_EX_C22089_31270140; WSN-P_KU_C14842_23275194; WSNP_EX_C2325_4355706; WSN-P_EX_C10630_17338753; WSN-P_KU_C53501_58106782; WSN-P_EX_C4408_7939986; WSNP_KU_REP_C71567_71302010; WSNP_RFL_CONTIG2167_1484520; WSN-P_EX_REP_C66407_64613374; WSN-P_EX_C25755_35018674; WSN-P_JD_C9360_10216330; WSNP_EX_REP_C67369_65940505; WSN-P_EX_C4769_8510104; WSNP_RFL_CONTIG3917_4326857; WSNP_JD_C626_945114; WSN-P_EX_C11055_17927668; WSNP_EX_C6476_11246531; WSN-P_EX_C15163_23357477; WSN-P_EX_C5780_10153638; WSNP_JD_C119_190135; WSNP_EX_C97184_84339976; WSN-P_EX_C4548_8166555; WSN-P_EX_REP_C68113_66877517; WSN-P_EX_REP_C69266_68192954; WSNP_CAP11C847_522893; WSN-P_EX_C1279_2451699; WSN-P_EX_C7316_12552186; WSN-P_EX_REP_C68515_67349904; WSNP_JD_C3463_4479210; WSN-P_KU_C6825_11858665; WSN-P_EX_C1790_3378771; WSN-P_EX_C5378_9505533; WSNP_CAP7_C444_237594; WSN-P_EX_C10630_17338703; WSN-P_EX_C5378_9505087; WSN-P_EX_C8386_14128029; WSNP_JD_REP_C63942_40788045; WSN-P_EX_C4661_8344663; WSN-P_RA_C9209_15425473; WSN-P_JD_C43389_30288993; WSNP_EX_C30969_39821293; WSN-P_EX_C3738_6809767; WSN-P_EX_REP_C103505_88447145; WSN-P_EX_REP_C67897_66613415; WSNP_EX_C33765_42199371; WSN-P_EX_REP_C66606_64905694; WSN-P_EX_C14248_22204549; WSN-P_EX_REP_C66766_65123941; WSNP_CAP11_C3968_1874257; WSN-P_EX_C15325_23565935; WSN-P_KU_C10939_17975681; WSN-P_EX_C41073_47987034; WSNP_EX_C5378_9504586; WSN-P_EX_C15325_23565794; WSN-P_EX_REP_C67492_66096650; WSN-P_EX_C21129_30256617; WSNP_EX_C31670_40433594; WSN-P_EX_C2181_4089639; WSNP_CAP11C923_558715; WSN-P_KU_C8592_14575931;

WSNP_BE490744A_TD_2_1; WSNP_J-D_REP_C62985_40164465; WSNP_EX_C54655_57455562; WSNP_EX_C16295_24772663; WSNP_EX_C3940_7144946; WSNP_KU_C12698_20441325; WSNP_BF291549B_TA_1_1; WSNP_RA_C9738_16173810; WSNP_EX_C15325_23564654; WSNP_EX_C7705_13139890; WSNP_RA_C9738_16174002; WSNP_EX_C16295_24772702; WSNP_EX_C3887_7051325; WSNP_KU_C7471_12865509; or WSNP_CAP8_C6680_3136899; or a marker that is closely linked to any of said marker locus; or, D) said first wheat plant or germplasm that displays improved anther extrusion, said method comprising detecting at least one marker locus comprising WSNP_EX_REP_C66893_65301351 or a marker closely linked thereto.

2. The method of embodiment 1(A), wherein the said marker locus associated with the favorable flowering date comprises:
(a) an A allele at WSNP_KU_C16547_25454123;
(b) a T allele at WSNP_EX_C10555_17235832;
(c) an A allele at WSNP_EX_C2580_4800027;
(d) a T allele at WSNP_EX_C10717_17456391;
(e) a G allele at WSNP_BG263758B_TA_2_1;
(f) a G allele at WSNP_EX_C2920_5385184;
(g) a T allele at WSNP_JD_C1316_1891903;
(h) a C allele at WSNP_EX_C36325_44308589; or
(i) a G allele at WSNP_EX_C6590_11419735.

3. The method of embodiment 1(A) or 2, wherein at least two marker loci are detected.

4. The method of embodiment 3, wherein the at least two marker loci comprise a haplotype that is associated with the favorable flowering date.

5. The method of embodiment 4, wherein said haplotype associated with said the favorable flowering date comprises:
(a) an A allele at WSNP_KU_C16547_25454123 and a T allele at WSNP_EX_C10555_17235832;
(b) an A allele at WSNP_EX_C2580_4800027 and a T allele at WSNP_EX_C10717_17456391;
(c) a G allele at WSNP_BG263758B_TA_2_1, a G allele at WSNP_EX_C2920_5385184 and a T allele at WSNP_JD_C1316_1891903; and/or,
(d) a C allele at WSNP_EX_C36325_44308589 and a G allele at WSNP_EX_C6590_11419735.

6. The method of embodiment 1(B), wherein the said marker locus associated with the favorable heading date comprise:
(a) an A allele at WSNP_EX_REP_C105541_89932598;
(b) a G allele at WSNP_KU_C17726_26872129;
(c) an A allele at WSNP_EX_C4605_8240189;
(d) a T allele at WSNP_EX_C44049_50205904;
(e) a C allele at WSNP_EX_C3906_7086162;
(f) a C allele at WSNP_EX_REP_C101746_87053634;
(g) a G allele at WSNP_EX_REP_C101414_86780996;
(h) a C allele at WSNP_EX_C44049_50205457;
(i) an A allele at WSNP_EX_C5192_9203682;
(j) a G allele at WSNP_JD_C13903_13781269;
(k) a G allele at WSNP_RA_C12148_19539667;
(l) a G allele at WSNP_BE495786A_TA_2_1;
(m) a C allele at WSNP_KU_C24239_34199356;
(n) an A allele at WSNP_RA_C37745_45806931;
(o) a C allele at WSNP_EX_C34344_42676379;
(p) a C allele at WSNP_EX_C34344_42677360;
(q) a G allele at WSNP_EX_REP_C66628_64934660;
(r) a C allele at WSNP_EX_C42282_48900922;
(s) a G allele at WSNP_EX_REP_C108057_91436561;
(t) a G allele at WSNP_EX_C16720_25268525;
(u) a C allele at WSNP_CAP8_C458_368155;
(v) a G allele at WSNP_EX_C741_1456698;
(w) a C allele at WSNP_JD_C12687_12877994;
(x) a G allele at WSNP_EX_C55096_57733841;
(y) a C allele at WSNP_EX_REP_C104141_88935451;
(z) a C allele at WSNP_EX_C25082_34346512;
(aa) a T allele at WSNP_EX_C361_708712;
(ab) a C allele at WSNP_EX_C55096_57733894;
(ac) a C allele at WSNP_EX_C8802_14726148;
(ad) a T allele at WSNP_EX_C4927_8772847;
(ae) a G allele at WSNP_JD_C17082_16025440;
(af) a T allele at WSNP_JD_C9902_10674626;
(ag) a T allele at WSNP_JD_C9902_10674725;
(ah) an A allele at WSNP_EX_C21499_30644485;
(ai) a G allele at WSNP_BQ168706B_TA_22;
(aj) a T allele at WSNP_KU_C18538_27857915;
(ak) a G allele at WSNP_BE489326B_TA_2_2;
(al) a T allele at WSNP_BQ168706B_TA_2_1;
(am) a C allele at WSNP_EX_C123_244117;
(an) C allele at WSNP_EX_C5378_9505087;
(ao) a C allele at WSNP_EX_C2330_4366134;
(ap) a C allele at WSNP_EX_C22016_31191407;
(aq) a G allele at WSNP_KU_C8722_14766699;
(ar) a T allele at WSNP_KU_C6825_11858665;
(as) a C allele at WSNP_EX_C5378_9504586;
(at) a C allele at WSNP_EX_C4769_8510104;
(au) a C allele at WSNP_EX_C5547_9774453;
(av) a G allele at WSNP_EX_C5547_9772680;
(aw) a T allele at WSNP_EX_C5547_9774195;
(ax) a C allele at WSNP_BE445348B_TA_2_1;
(ay) an A allele at WSNP_EX_C7756_13218814;
(az) a C allele at WSNP_EX_C3096_5709369;
(ba) an A allele at WSNP_EX_C3096_5709257;
(bb) a G allele at WSNP_EX_C12887_20427158;
(bc) a T allele at WSNP_KU_REP_C72821_72480395;
(bd) a C allele at WSNP_EX_C3096_5708642;
(be) a T allele at WSNP_EX_C57007_58898157;
(bf) an A allele at WSNP_EX_C8208_13870372;
(bg) an A allele at WSNP_JD_C4413_5541190;
(bh) a C allele at WSNP_KU_C7180_12403155;
(bi) a T allele at WSNP_EX_C10347_16946522;
(bj) a T allele at WSNP_KU_REP_C102220_89250165;
(bk) a C allele at WSNP_KU_C328_679106;
(bl) a G allele at WSNP_RA_C323_681466;
(bm) an A allele at WSNP_KU_C644_1332610;
(bn) a T allele at WSNP_RA_C17541_26430903;
(bo) a T allele at WSNP_KU_C7890_13513783;
(bp) an A allele at WSNP_RA_C6788_11804894;
(bq) a C allele at WSNP_EX_REP_C69526_68472665;
(br) a T allele at WSNP_EX_C31830_40573624;
(bs) a T allele at WSNP_CAP7_C2282_1107112;
(bt) a T allele at WSNP_BF201102A_TA 2_1;
(bu) a T allele at WSNP_EX_C19134_28056012;
(bv) a T allele at WSNP_EX_C4211_7606269;
(bw) a T allele at WSNP_EX_C2718_5038582;
(bx) a C allele at WSNP_RA_C11420_18529863;
(by) a C allele at WSNP_KU_C1102_2211433;
(bz) an A allele at WSNP_EX_C23509_32746909;
(ca) a C allele at WSNP_RA_REP_C75364_72953286;
(cb) an A allele at WSNP_EX_REP_C66733_65077608;
(cd) a C allele at WSNP_BE500291A_TA_2_1;
(ce) an A allele at WSNP_KU_C16812_25759885;

(cf) a G allele at WSNP_EX_C130258776;
(cg) a C allele at WSNP_RA_C10053_16636851;
(ch) a C allele at WSNP_EX_C15084_23263641;
(ci) an A allele at WSNP_RA_C2228_4310870;
(cj) an A allele at WSNP_EX_C43578_49857984;
(ck) a G allele at WSNP_KU_C30743_40542247;
(cl) an A allele at WSNP_JD_C5795_6955627;
(cm) a G allele at WSNP_KU_REP_C101212_88410320;
(cn) a G allele at WSNP_JD_C12221_12509932;
(co) an A allele at WSNP_EX_C57209_59016692;
(cp) a G allele at WSNP_EX_C2161_4059735;
(cq) an A allele at WSNP_EX_C29648_38653339;
(cr) a C allele at WSNP_EX_C19467_28423946;
(cs) a G allele at WSNP_RA_C14171_22234872;
(ct) a T allele at WSNP_EX_C53387_56641291;
(cu) a G allele at WSNP_RA_C2063_4012957;
(cv) a T allele at WSNP_EX_C6142_10746442;
(cw) a T allele at WSNP_EX_C916_1767286;
(cx) a C allele at WSNP_EX_C53387_56639804;
(cy) a T allele at WSNP_EX_C10500_17163855;
(cz) a C allele at WSNP_EX_C3309_6096114;
(da) a G allele at WSNP_RFL_CONTIG4236_4881643;
(db) a C allele at WSNP_EX_C758_1488368.

7. The method of embodiment 1(B) or 6, wherein at least two marker loci are detected.

8. The method of embodiment 7, wherein the at least two marker loci comprise a haplotype that is associated with the favorable heading date.

9. The method of embodiment 8, wherein said haplotype associated with said the favorable heading date comprises:

(a) an A allele at WSNP_EX_REP_C105541_89932598 and a G allele at WSNP_KU_C17726_26872129;

(b) an A allele at WSNP_EX_C4605_8240189, a T allele at WSNP_EX_C44049_50205904, a C allele at WSNP_EX_C3906_7086162, a C allele at WSNP_EX_REP_C101746_87053634, a G allele at WSNP_EX_REP_C101414_86780996, and a C allele at WSNP_EX_C44049_50205457;

(c) an A allele at WSNP_EX_C5192_9203682, a G allele at WSNP_JD_C13903_13781269; a G allele at WSNP_RA_C12148_19539667, a G allele at WSNP_BE495786A_TA_2_1, and a C allele at WSNP_KU_C24239_34199356;

(d) an A allele at WSNP_RA_C37745_45806931 and a C allele at WSNP_EX_C34344_42676379, a C allele at WSNP_EX_C34344_42677360, an G allele at WSNP_EX_REP_C66628_64934660 and a C allele at WSNP_EX_C4228248900922;

(e) a G allele at WSNP_EX_REP_C108057_91436561, a G allele at WSNP_EX_C16720_25268525, and a C allele at WSNP_CAP8_C458_368155;

(f) a G allele at WSNP_EX_C741_1456698 and a C allele at WSNP_JD_C12687_12877994;

(g) a G allele at WSNP_EX_C55096_57733841, a C allele at WSNP_EX_REP_C104141_88935451, a C allele at WSNP_EX_C25082_34346512, a T allele at WSNP_EX_C361_708712, and a C allele at WSNP_EX_C55096_57733894;

(h) a C allele at WSNP_EX_C8802_14726148 and a T allele at WSNP_EX_C4927_8772847;

(i) a G allele at WSNP_JD_C17082_16025440, a T allele at WSNP_JD_C9902_10674626, and a T allele at WSNP_JD_C9902_10674725;

(j) an A allele at WSNP_EX_C21499_30644485, a G allele at WSNP_BQ168706B_TA_2_2, a T allele at WSNP_KU_C18538_27857915, a G allele at WSNP_BE489326B_TA_2_2, and a T allele at WSNP_BQ168706B_TA_2_1;

(k) a C allele at WSNP_EX_C123_244117, a C allele at WSNP_EX_C5378_9505087, a C allele at WSNP_EX_C2330_4366134, a C allele at WSNP_EX_C22016_31191407, a G allele at WSNP_KU_C8722_14766699, a T allele at WSNP_KU_C6825_11858665, a C allele at WSNP_EX_C5378_9504586, and a C allele at WSNP_EX_C4769_8510104;

(l) a C allele at WSNP_EX_C5547_9774453, a G allele at WSNP_EX_C5547_9772680, a T allele at WSNP_EX_C5547_9774195, a C allele at WSNP_BE445348B_TA_2_1, an A allele at WSNP_EX_C7756_13218814, a C allele at WSNP_EX_C3096_5709369, and, an A allele at WSNP_EX_C30965709257;

(m) a G allele at WSNP_EX_C12887_20427158, a T allele at WSNP_KU_REP_C72821_72480395, and an A allele at WSNP_EX_C3096_5708642;

(n) a T allele at WSNP_EX_C57007_58898157, an A allele at WSNP_EX_C8208_13870372, and, an A allele at WSNP_JD_C4413_5541190;

(o) a C allele at WSNP_KU_C7180_12403155 and a T allele at WSNP_EX_C10347_16946522;

(p) a T allele at WSNP_KU_REP_C102220_89250165, a C allele at WSNP_KU_C328_679106, a G allele at WSNP_RA_C323_681466, an A allele at WSNP_KU_C644_1332610, a T allele at WSNP_RA_C17541_26430903, a T allele at WSNP_KU_C7890_13513783, and, an A allele at WSNP_RA_C6788_11804894;

(q) a C allele at WSNP_EX_REP_C69526_68472665, a T allele at WSNP_EX_C31830_40573624, a T allele at WSNP_CAP7_C2282_1107112, a T allele at WSNP_BF201102A_TA_2_1, a T allele at WSNP_EX_C19134_28056012, and a T allele at WSNP_EX_C4211_7606269;

(r) a T allele at WSNP_EX_C2718_5038582, a C allele at WSNP_RA_C11420_18529863, a C allele at WSNP_KU_C1102_2211433, an A allele at WSNP_EX_C23509_32746909, a C allele at WSNP_RA_REP_C75364_72953286, an A allele at WSNP_EX_REP_C66733_65077608, and, a C allele at WSNP_BE500291A_TA_2_1;

(s) an A allele at WSNP_KU_C16812_25759885, a G allele at WSNP_EX_C130_258776, a C allele at WSNP_RA_C10053_16636851, a C allele at WSNP_EX_C15084_23263641, and an A allele at WSNP_RA_C2228_4310870;

(t) an A allele at WSNP_EX_C43578_49857984 and a G allele at WSNP_KU_C30743_40542247;

(u) an A allele at WSNP_JD_C5795_6955627 and a G allele at WSNP_KU_REP_C101212_88410320;

(v) a G allele at WSNP_JD_C12221_12509932 and an A allele at WSNP_EX_C57209_59016692;

(w) a G allele at WSNP_EX_C2161_4059735 and an A allele at WSNP_EX_C29648_38653339;

(x) a C allele at WSNP_EX_C19467_28423946 and a G allele at WSNP_RA_C14171_22234872;

(y) a T allele at WSNP_EX_C53387_56641291, a G allele at WSNP_RA_C2063_4012957, a T allele at WSNP_EX_C6142_10746442, a T allele at WSNP_EX_C916_1767286, and a C allele at WSNP_EX_C53387_56639804;

(z) a T allele at WSNP_EX_C10500_17163855 and a C allele at WSNP_EX_C3309_6096114; or, (aa) a G allele at WSNP_RFL_CONTIG4236_4881643 and a C allele at WSNP_EX_C758_1488368.

10. The method of embodiment 1(D), wherein the said marker locus associated with improved *fusarium* blight head resistance comprises:
(a) a T allele at WSNP_EX_C2181_4089639;
(b) a C allele at WSNP_EX_REP_C70593_69508988;
(c) an A allele at WSNP_EX_REP_C67492_66096650;
(d) a G allele at WSNP_EX_C6476_11246531;
(e) an A allele at WSNP_EX_C46670_52108070;
(f) a C allele at WSNP_EX_C3887_7051325;
(g) an A allele at WSNP_EX_REP_C67198_65702998;
(h) a T allele at WSNP_KU_C8592_14575931;
(i) a T allele at WSNP_EX_C7705_13139890;
(j) a G allele at WSNP_EX_C5780_10153638;
(k) a T allele at WSNP_EX_C18733_27607958;
(l) a G allele at WSNP_EX_C11976_19193550;
(m) a T allele at WSNP_KU_C16938_25916260;
(n) a G allele at WSNP_JD_REP_C62985_40164465;
(o) a C allele at WSNP_BF291549B_TA_1_1;
(p) a C allele at WSNP_RA_C8484_14372815;
(q) an A allele at WSNP_EX_REP_C67036_65492436;
(r) a G allele at WSNP_KU_C4951_8856170;
(s) a T allele at WSNP_JD_C4485_5618761;
(t) a C allele at WSNP_EX_C17452_26163465;
(u) a G allele at WSNP_RA_C2027_3945764;
(v) a C allele at WSNP_EX_REP_C69986_68942866;
(w) a T allele at WSNP_EX_REP_C69986_68942834;
(x) an A allele at WSNP_KU_C39862_48205590;
(y) an A allele at WSNP_EX_C6611_11451949;
(z) an A allele at WSNP_EX_C6611_11452297;
(aa) a G allele at WSNP_EX_C30969_39821293;
(ab) a C allele at WSNP_JD_C13086_13174510;
(ac) a G allele at WSNP_EX_REP_C68113_66877517;
(ad) an A allele at WSNP_EX_C15325_23565935;
(ae) a G allele at WSNP_CAP11REP_C8768_3788007;
(af) an A allele at WSNP_BG314532A_TA_2_1;
(ag) a G allele at WSNP_JD_C12088_12411845;
(ah) a T allele at WSNP_EX_C15325_23565794;
(ai) a G allele at WSNP_EX_C15325_23564654;
(aj) a T allele at WSNP_CAP7_C7742_3467376;
(ak) a G allele at WSNP_BE399936A_TA_2_1;
(al) a T allele at WSNP_RA_C10861_17763060;
(am) a G allele at WSNP_EX_C11437_18454413;
(an) a C allele at WSNP_RA_C58188_60005934;
(ao) a G allele at WSNP_EX_C23720_32957892;
(ap) a C allele at WSNP_EX_C1064_2034518;
(aq) a T allele at WSNP_BF293133A_TA_2_2;
(ar) a C allele at WSNP_EX_REP_C67635_66291944;
(as) an A allele at WSNP_EX_REP_C67635_66292689;
(at) an A allele at WSNP_RA_C9738_16173810;
(au) a C allele at WSNP_EX_C4548_8166555;
(av) a C allele at WSNP_RA_C9738_16174002;
(aw) a T allele at WSNP_EX_C10630_17338753;
(ax) an A allele at WSNP_EX_C10630_17338703;
(ay) a C allele at WSNP_EX_C8360_14085858;
(az) a T allele at WSNP_KU_C12698_20441325;
(ba) an A allele at WSNP_EX_REP_C66331_64502558;
(bb) a T allele at WSNP_EX_C2723_5047696;
(bc) a G allele at WSNP_EX_C8386_14127329;
(bd) a T allele at WSNP_EX_REP_C66766_65123941;
(be) an A allele at WSNP_BE489326B_TA_2_1;
(bf) an A allele at WSNP_JD_C119_190135;
(bg) a C allele at WSNP_EX_C4769_8510104;
(bh) a G allele at WSNP_EX_C5378_9505533;
(bi) a G allele at WSNP_EX_C7172_12318529;
(bj) a C allele at WSNP_EX_C22016_31191407;
(bk) a G allele at WSNP_KU_C8722_14766699;
(bl) a C allele at WSNP_EX_C123_244117;
(bm) a C allele at WSNP_EX_C5378_9504586;
(bn) a C allele at WSNP_EX_C5378_9505087;
(bo) a T allele at WSNP_KU_C6825_11858665;
(bp) a C allele at WSNP_EX_C2330_4366134;
(bq) a T allele at WSNP_EX_C5457_9632050:
(br) an A allele at WSNP_EX_C5457_9631220;
(bs) a G allele at WSNP_JD_REP_C63654_40605158;
(bt) a G allele at WSNP_EX_C7021_12096881;
(bu) a G allele at WSNP_EX_C40060_47197384;
(bv) a T allele at WSNP_EX_C15399_23662312;
(bw) a C allele at WSNP_RA_REP_C72670_70836439;
(bx) an A allele at WSNP_JD_REP_C50820_34666611;
(by) a T allele at WSNP_EX_REP_C101757_87065169;
(bz) an A allele at WSNP_EX_REP_C101757_87064771;
(ca) a G allele at WSNP_EX_REP_C101757_87065032;
(cb) a T allele at WSNP_EX_C1279_2451699;
(cc) a G allele at WSNP_EX_C1279_2451582;
(cd) a T allele at WSNP_EX_C49211_53875600;
(ce) a G allele at WSNP_EX_C49211_53875575;
(cf) a T allele at WSNP_RA_C21347_30731133;
(cg) a G allele at WSNP_RA_C21347_30731229;
(ch) a T allele at WSNP_CAP11_C299_251533;
(ci) a G allele at WSNP_CAP11_C923_558715;
(cj) an A allele at WSNP_EX_C54655_57455562;
(ck) a T allele at WSNP_JD_C43389_30288993;
(cl) a C allele at WSNP_EX_C23968_33209660;
(cm) a C allele at WSNP_EX_C16295_24772663;
(cn) a G allele at WSNP_EX_C23968_33210344;
(co) a T allele at WSNP_EX_C16295_24772702;
(cp) an A allele at WSNP_RA_C20970_30293227;
(cq) an A allele at WSNP_RA_C20970_30293078;
(cr) a G allele at WSNP_EX_REP_C68600_67448893;
(cs) a C allele at WSNP_EX_REP_C68600_67449494;
(ct) a T allele at WSNP_KU_C38351_47009610;
(cu) an A allele at WSNP_EX_REP_C68165_66935014;
(cv) a T allele at WSNP_EX_C3530_6459532;
(cw) a T allele at WSNP_EX_C3530_6459643;
(cx) a C allele at WSNP_EX_REP_C68165_66935041;
(cy) a T allele at WSNP_EX_C52849_56297163;
(cz) a G allele at WSNP_JD_C7718_8795833;
(da) a C allele at WSNP_JD_C2180_3000498;
(db) a T allele at WSNP_KU_C26784_36748247;
(dc) a T allele at WSNP_EX_C15378_23638822;
(dd) an A allele at WSNP_EX_C15378_23639387;
(de) a G allele at WSNP_CAP7_C5487_2464864;
(df) a C allele at WSNP_EX_C2325_4355706;
(dg) a G allele at WSNP_KU_REP_C71567_71302010;
(dh) a T allele at WSNP_EX_C17349_26035281;
(di) a G allele at WSNP_EX_C46160_51746546;
(dj) a G allele at WSNP_EX_C38198_45786860;
(dk) an A allele at WSNP_EX_C17667_26408733;
(dl) a G allele at WSNP_JD_REP_C63108_40258378;
(dm) a G allele at WSNP_RA_C24962_34524602;
(dn) a G allele at WSNP_EX_C31256_40071875;
(do) an A allele at WSNP_EX_C5744_1008828;
(dp) an A allele at WSNP_BE490200B_TA_2_1;
(dq) a C allele at WSNP_EX_REP_C106072_90285324;
(dr) an A allele at WSNP_EX_C1146_2200823;
(ds) a T allele at WSNP_EX_C19582_28564743;
(dt) a C allele at WSNP_EX_C1146_2201722;
(du) a T allele at WSNP_EX_C46274_51831129;
(dv) a C allele at WSNP_RA_REP_C71101_69119989;
(dw) a C allele at WSNP_RA_C31052_40235870;
(dx) a T allele at WSNP_EX_REP_C69954_68913284;
(dy) an A allele at WSNP_EX_C18800_27681277;

(dz) an A allele at WSNP_EX_C27373_36578273
(ea) a C allele at WSNP_JD_C9040_9947841;
(eb) a G allele at WSNP_KU_C10939_17975681;
(ec) a G allele at WSNP_EX_C25755_35018674;
(ed) an A allele at WSNP_EX_C26747_35974837;
(ee) a T allele at WSNP_KU_C4067_7419106;
(ef) an A allele at WSNP_EX_C1790_3378771;
(eg) an A allele at WSNP_EX_REP_C69954_68913307;
(eh) T allele at WSNP_EX_C4408_7939986;
(ei) an A allele at WSNP_EX_C14248_22204549;
(ej) a G allele at WSNP_CAP11_C847_522893;
(ek) a G allele at WSNP_KU_C18780_28136150;
(el) a T allele at WSNP_BQ169669B_TA_2_2;
(em) a C allele at WSNP_EX_C351_689415;
(en) a T allele at WSNP_JD_C17128_16056425; or,
(eo) a C allele at WSNP_EX_C3738_6809767.

11. The method of embodiment 1(D) or 10, wherein at least two marker loci are detected.

12. The method of embodiment 11, wherein the at least two marker loci comprise a haplotype that is associated with improved *fusarium* blight head resistance.

13. The method of embodiment 12, wherein said haplotype associated with the improved *fusarium* blight head resistance comprises:

(a) a T allele at WSNP_EX_C2181_4089639 and a C allele at WSNP_EX_REP_C70593_69508988;
(b) an A allele at WSNP_EX_REP_C67492_66096650 and a G allele at WSNP_EX_C6476_11246531;
(c) an A allele at WSNP_EX_C46670_52108070 and a C allele at WSNP_EX_C3887_7051325;
(d) an A allele at WSNP_EX_REP_C67198_65702998, a T allele at WSNP_KU_C8592_14575931, a T allele at WSNP_EX_C7705_13139890, and a G allele at WSNP_EX_C5780_10153638;
(e) a T allele at WSNP_EX_C18733_27607958, a G allele at WSNP_EX_C11976_19193550, a T allele at WSNP_KU_C16938_25916260, a G allele at WSNP_JD_REP_C62985_40164465, and a C allele at WSNP_BF291549B_TA_1_1;
(f) a C allele at WSNP_RA_C8484_14372815, an A allele at WSNP_EX_REP_C67036_65492436, a G allele at WSNP_KU_C4951_8856170, a T allele at WSNP_JD_C4485_5618761, a C allele at WSNP_EX_C17452_26163465, a G allele at WSNP_RA_C2027_3945764, a C allele at WSNP_EX_REP_C69986_68942866, and, a T allele at WSNP_EX_REP_C69986_68942834;
(g) an A allele at WSNP_KU_C39862_48205590, an A allele at WSNP_EX_C6611_11451949, an A allele at WSNP_EX_C6611_11452297, and a G allele at WSNP_EX_C30969_39821293;
(h) a C allele at WSNP_JD_C13086_13174510, a G allele at WSNP_EX_REP_C68113_66877517, and an A allele at WSNP_EX_C15325_23565935;
(i) a G allele at WSNP_CAP11_REP_C8768_3788007, an A allele at WSNP_BG314532A_TA_2_1, a G allele at WSNP_JD_C12088_12411845, a T allele at WSNP_EX_C15325_23565794, and a G allele at WSNP_EX_C15325_23564654;
(j) a T allele at WSNP_CAP7_C7742_3467376, a G allele at WSNP_BE399936A_TA_2_1, a T allele at WSNP_RA_C10861_17763060, a G allele at WSNP_EX_C11437_18454413, a C allele at WSNP_RA_C58188_60005934, a G allele at WSNP_EX_C23720_32957892, and a C allele at WSNP_EX_C1064_2034518;
(k) a T allele at WSNP_BF293133A_TA_2_2, a C allele at WSNP_EX_REP_C67635_66291944, and an A allele at WSNP_EX_REP_C67635_66292689;
(l) an A allele at WSNP_RA_C9738_16173810, a C allele at WSNP_EX_C4548_8166555, and a C allele at WSNP_RA_C9738_16174002;
(m) a T allele at WSNP_EX_C10630_17338753 and an A allele at WSNP_EX_C10630_17338703;
(n) a C allele at WSNP_EX_C8360_14085858, a T allele at WSNP_KU_C12698_20441325, an A allele at WSNP_EX_REP_C66331_64502558, and a T allele at WSNP_EX_C2723_5047696;
(o) a G allele at WSNP_EX_C8386_14127329 and a T allele at WSNP_EX_REP_C66766_65123941;
(p) an A allele at WSNP_BE489326B_TA_2_1 and an A allele at WSNP_JD_C119_190135;
(q) a C allele at WSNP_EX_C4769_8510104, a G allele at WSNP_EX_C5378_9505533, a G allele at WSNP_EX_C7172_12318529, a C allele at WSNP_EX_C22016_31191407, a G allele at WSNP_KU_C8722_14766699, a C allele at WSNP_EX_C123_244117, a C allele at WSNP_EX_C5378_9504586, a C allele at WSNP_EX_C5378_9505087, a T allele at WSNP_KU_C6825_11858665, a C allele at WSNP_EX_C2330_4366134, a T allele at WSNP_EX_C5457_9632050, an A allele at WSNP_EX_C5457_9631220, a G allele at WSNP_JD_REP_C63654_40605158, and a G allele at WSNP_EX_C7021_12096881;
(r) a G allele at WSNP_EX_C40060_47197384 and a T allele at WSNP_EX_C15399_23662312;
(s) a C allele at WSNP_RA_REP_C72670_70836439 and an A allele at WSNP_JD_REP_C50820_34666611;
(t) a T allele at WSNP_EX_REP_C101757_87065169, an A allele at WSNP_EX_REP_C101757_87064771, and a G allele at WSNP_EX_REP_C101757_87065032;
(u) a T allele at WSNP_EX_C1279_2451699 and a G allele at WSNP_EX_C1279_2451582;
(v) a T allele at WSNP_EX_C49211_53875600, a G allele at WSNP_EX_C49211_53875575, and a T allele at WSNP_RA_C21347_30731133;
(w) a G allele at WSNP_RA_C21347_30731229 and a T allele at WSNP_CAP11_C299_251533;
(x) a G allele at WSNP_CAP11_C923_558715, an A allele at WSNP_EX_C54655_57455562, a T allele at WSNP_JD_C43389_30288993, a C allele at WSNP_EX_C23968_33209660, a C allele at WSNP_EX_C16295_24772663, a G allele at WSNP_EX_C23968_33210344, and a T allele at WSNP_EX_C16295_24772702;
(y) an A allele at WSNP_RA_C20970_30293227, an A allele at WSNP_RA_C20970_30293078, a G allele at WSNP_EX_REP_C68600_67448893, and a C allele at WSNP_EX_REP_C68600_67449494;
(z) a T allele at WSNP_KU_C38351_47009610, an A allele at WSNP_EX_REP_C68165_66935014, a T allele at WSNP_EX_C3530_6459532, a T allele at WSNP_EX_C3530_6459643, a C allele at WSNP_EX_REP_C68165_66935041, a T allele at WSNP_EX_C52849_56297163, and a G allele at WSNP_JD_C7718_8795833;
(aa) a C allele at WSNP_JD_C2180_3000498, a T allele at WSNP_KU_C26784_36748247, a T allele at WSNP_EX_C15378_23638822, and an A allele at WSNP_EX_C15378_23639387;

(ab) a G allele at WSNP_CAP7_C5487_2464864, a C allele at WSNP_EX_C2325_4355706, and a G allele at WSNP_KU_REP_C71567_71302010;

(ac) a T allele at WSNP_EX_C17349_26035281, a G allele at WSNP_EX_C46160_51746546, a G allele at WSNP_EX_C38198_45786860, and an A allele at WSNP_EX_C17667_26408733;

(ad) a G allele at WSNP_JD_REP_C63108_40258378 and a G allele at WSNP_RA_C24962_34524602;

(ae) a G allele at WSNP_EX_C31256_40071875, an A allele at WSNP_EX_C5744_10088287, an A allele at WSNP_BE490200B_TA_2_1 and a C allele at WSNP_EX_REP_C106072_90285324;

(af) an A allele at WSNP_EX_C1146_2200823, a T allele at WSNP_EX_C19582_28564743, and a C allele at WSNP_EX_C1146_2201722;

(ag) a T allele at WSNP_EX_C46274_51831129 and a C allele at WSNP_RA_REP_C71101_69119989;

(ah) a C allele at WSNP_RA_C31052_40235870 and a T allele at WSNP_EX_REP_C69954_68913284;

(ai) an A allele at WSNP_EX_C18800_27681277, an A allele at WSNP_EX_C27373_36578273, a C allele at WSNP_JD_C9040_9947841, a G allele at WSNP_KU_C10939_17975681, a G allele at WSNP_EX_C25755_35018674, an A allele at WSNP_EX_C26747_35974837, a T allele at WSNP_KU_C4067_7419106, an A allele at WSNP_EX_C1790_3378771, an A allele at WSNP_EX_REP_C69954_68913307, a T allele at WSNP_EX_C4408_7939986, and an A allele at WSNP_EX_C14248_22204549;

(aj) a G allele at WSNP_CAP11_C847_522893, a G allele at WSNP_KU_C18780_28136150, and a T allele at WSNP_BQ169669B_TA_2_2; and/or (ak) a C allele at WSNP_EX_C351_689415, a T allele at WSNP_JD_C17128_16056425, and, a C allele at WSNP_EX_C3738_6809767.

14. The method of any one of embodiments 1-13, wherein the detecting comprises amplification of said at least one marker loci or a portion thereof.

15. The method of embodiment 14, wherein the method further comprises providing one or more labeled nucleic acid probes suitable for detection of the at least one marker locus being amplified.

16. The method of any one of embodiments 14 or 15, further comprising selecting the first wheat plant or germplasm, or selecting a progeny of the first wheat plant or germplasm.

17. The method of embodiment 16, further comprising crossing the selected first wheat plant or germplasm with a second wheat plant or germplasm.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Genome Wide Association Study

An association mapping strategy was undertaken to identify markers associated with flowering date, heading date, anther extrusion, and resistance to *fusarium* head blight in wheat. In this association analysis, a collection of 240 wheat lines was analyzed by assessing SNPs at approximately 3,100 genetic loci. The SNP information was obtained using the Illumina Infinium HD assay. The lines encompassed elite germplasm, commercially released cultivars, and other public varieties.

Phenotypic scores were obtained for flowering date, heading date, anther extrusion, and resistance to *fusarium* head blight in wheat using protocols that are familiar to one of ordinary skill in the art.

The phenotypic scores and marker information for each of the 240 lines was input into the association analysis. A structure-based association analysis was conducted using standard association mapping methods, where the population structure is controlled using marker data. The model-based cluster analysis software, Structure, developed by Pritchard et al., (Genetics 155:945-959 (2000)) was used with haplotype data for 880 elite maize inbreds at two hundred markers to estimate admixture coefficients and assign the inbreds to seven subpopulations. This reduces the occurrence of false positives that can arise due to the effect of population structure on association mapping statistics. A t-test was used to test a given marker for association between haplotype and phenotype in a given subpopulation (Press et al., Numerical Recipes in C, second edition, Cambridge University Press, NY (2002)).

Markers that were significantly associated (at a level of p≤0.001) with flowering date, heading date, resistance to *fusarium* blight, and anther extrusion are shown in Tables 1, 2, 3, and 4, respectively. The tables also provide the p-value for each marker-trait association as well as the SEQ ID NO: and reference sequence for each marker. The reference sequence includes the SNP polymorphism within the marker that is associated with the respective trait.

TABLE 1

| SNP markers significantly associated with flowering date | | | |
|---|---|---|---|
| Marker Name | P-Value | SEQ ID NO | Reference Sequence |
| WSNP_KU_C16547_25454123 | 0.000196 | 1 | TGCCCTATTTGGTACATTAAAACTGCTCAG GTTTCAGTTTGGGAACACAAAACCTGGCCC CTCAACGAGAGAATCTGCAGCTACATCTTC TCTGAATGAA[A/G]CATCTCCGTCAGAAGG TTCTTTTATCAGTAGCAGAGTAAGGGAACA GTTTGAGAAGCTGTCAAAAATGCTTTGGTT GAACAATAGGGTCCATTTGAGAAG |

TABLE 1-continued

SNP markers significantly associated with flowering date

| Marker Name | P-Value | SEQ ID NO | Reference Sequence |
|---|---|---|---|
| WSNP_EX_C2920_5385184 | 0.000692 | 2 | CTCCAGGCATCTCACCTCGGACATGCACGC GAACGACTGGGACTTTCCGTCGTAGTATTT CGACAACCCTTTCTTGGCGGAGAGTTCGGC CTTCATGGAC[A/G]ACAGATCGTAGACGCT GTCAGAGTTGAGTCTCCGCACCGGCGGGG AAGCCGGCACAAACTGGTCCTCGCCGTCTG AGAACTGGGCCTCGTCGTCGGAGTC |
| WSNP_EX_C10717_17456391 | 0.000132 | 3 | AACTTTTWWWTTGTTGGAAGGCCAATAAT TGTGGAAATGATTTCAAGAGGCTTCACAAC ATAGTCATGGGTACAGATATAGAACCTACT GAGAAAACTTG[T/G]GCCAGTATGCAGAGC ACACCATTCATCATATTCAACCTCCATACTC TTAGAACAAATCTAAAAGCTGGAAACATA AACCAACGGATCCACAAAACAAGC |
| WSNP_JD_C1316_1891903 | 0.0009 | 4 | CTGGGCCTCGTCGTCGGAGTCGCAGGAGA AGGAGGAGGAGGTCTCGAACAGGTCCTCG TCTTCCTGGTGCACCGGAAGGGCCTGAGAA ACAGCAGATCTG[T/C]CCATGGCTGCGAGT TTCTTGTTTCTGCGATGAACCTCAAGGAGA AAGGCGAGGAAGGTATGCTTGCTGCTGTA TATGGATGGATATATTCCTGCTCTTGT |
| WSNP_BG263758B_TA_2_1 | 0.00067 | 5 | ACTCCAAATGACTGAGTCAAAATCCGTGCC ATAGGTGTGGCAATAGTATGGGTACCCTTG [A/G]TAACGAAATTTCAACATAATTTTGAAA CAGACACCAAGAACCATCTTGGGTTTCAAC TGT |
| WSNP_EX_C3501_6408181 | 0.000578 | 6 | GCTCACCAAGGCAGTTCAGTAGTTTAAGTA ACATGCAGAACTTTCACAATATAAGGATGG CCATAGCTGTTGTCATTTGTAAGTGCTATTG GCACCAACC[A/G]ATACCCTAAGACAGGGA ACAAAACTGTGGAACAAAATTTCCTGCCAT TAATTGACACTACGGCACTGCCTGTTAAATT AATCTGATATTAAGGACAAAGA |
| WSNP_BE404354B_TA_2_1 | 1.46E-05 | 7 | TGAATGGTGCAGGATTGGCAATGGCTACG ATGGACATCATTAAGCT[A/G]CATGGTGGT ACACCTGCCAATTTTCTTGATGTTGGTGGG AGTGCATCCGAGGGACAGGTA |
| WSNP_EX_C10555_17237000 | 0.000792 | 8 | GCGCTGGTAACCACATGCTTTTTGGATATCT AAAAGAAGCTCCTTTGCATAAGAGTTTGTA AGGCTTTCCTGCATCCCAATTTCTCTAAGAA TGGCAACA[A/G]ATGGAAGATACAGACTTG GAAGTTCAAAAGCAAAAGGTGACATGTTG ATAGTCAGACGAGCAAAAAGTGATTTCGCT TCTATTAAGCGAGTACCATTTGC |
| WSNP_KU_C6758_11757213 | 3.48E-05 | 9 | TGGGATAGAACGTCACTGGAAACTAGCAA GGATCTTCGGATATTTTCGCTGGAAACTCG AGAGCTCGCGGGCGGTCGTAGTCGGTCGC TGTTCTTCCTCC[T/C]CCGTGATGCTGCCGC TCGTCCTCCTCGTTGGTCTCGTGCTCCGGAT ATTATTCTTTCTGCCGTTGTTTTCTCCTTTTT ATTCCACACCAGTTCTTATTTC |
| WSNP_JD_C6544_7697578 | 0.000762 | 10 | GCTTTGTGGGAACTTAGCGGGGATCRTCTT GAGCACACTAAATTTGTTGAGATAAATATC GACAAGATGAGGCATGTTTGCAAATATGTT AATCACTTCT[A/G]ACGGGATATGGCTAAT CGCCCAAGAGAAGGTTGTTACTTGATTCAT CTGGCCCAAAAAAATAACCATGTTATGACG TCGGTATTTAGTTTCGGCACGCGT |
| WSNP_EX_C36325_44308589 | 0.000912 | 11 | CCAAGCCTTGGGACAAGCCCGCCAGACCG AGTCGCTAGACTTTGCTGAAAGAGATGGC GCCCCGAGGCTCCGTAGAAAGAGAAGAGA |

TABLE 1-continued

SNP markers significantly associated with flowering date

| Marker Name | P-Value | SEQ ID NO | Reference Sequence |
|---|---|---|---|
| | | | AGTGTTGTTGTAT[T/C]GCCAATTTTTCGAA ATATACCGTCTGCTGTTCCTTTTTTCCCGCCT TGTTGCTCCTTTTTTTCACCTTGTTGTTTGAC TAGACGGCTCGAAATAGACAGA |
| WSNP_EX_C2580_4800027 | 0.000676 | 12 | GATGCCACTTACTACTGCTGAAAAGATTAT GGATTCTCATGGAATGGACCAGGTTCCTGT AGTTTCAGAACATGTTAATCATCAGGATGG AGGAATCTTG[A/G]TTGGTTTTGTAGATAG AGAATGCATCACCATTGCTCGAAGAGCTTT GGCAGCAAAAGAATTTTTCAGTTTCACATC GGAGATCAGAGGGGAAGAGAGTTG |
| WSNP_EX_C10555_17235832 | 2.51E-05 | 13 | AGCTGACGGACGAGTGGCCCGGTTGTCCA ACGTCTGCCACTCTACCAACATCCGGTTGG GAAGGTGCAGAAGAGAGGTCAGCCGTTGA AACACTCTTAAA[T/C]GAGTAAACCTGACT GGAGAGTAGCATGCGAGTCTCGCCGGGGG CTGTCTCCACGGGAAACCTGTAAAGTGCTT GGCCAGCTGATGGCCTTACGTCTTCAG |
| WSNP_EX_C22089_31270140 | 0.00082 | 14 | CCAAGATACATGTACTTGGGAACAAGTGTC AAAGTAAGCTACTTGAAATAATTGATGCTA GTGAATTGCCAGAATTTCTTGGTGGCACTT GTACCTGTCC[T/C]GAATATGGAGGGTGCC TCAAAGCTGAAAAAGGGCCATGGAAGGAT GCAAACATACTGAAGAAAGTCCTTAATGGC GAGGCTCAGTGTGCTCGGCAGATTG |
| WSNP_EX_C6590_11419735 | 0.000266 | 15 | GTGCTGCTACCCCCAAAGAGCAAGTGGTAG ATGCCAGTGTCGAAGAAGCCAAGCCTCCAC AAGATGCAGGCGTTGCGGCGGCAAACGGT GTCGGGCCTTC[A/G]ACTGTAAAGCCGGAG GACAAAATGGAAATCGATGGTTGATATTTA GGGATAACTGTATCGGACCCCCTCTTCAGT TTAGTTGCTAAACTGGTTCTAGTGT |
| WSNP_CAP11_C210_199161 | 0.00096 | 16 | GTAACAACAATAGGTTGTTGATTCTTTGAG GGGGAGCTGTGTGCGTCCTCCGCATGGGTT TTCTGTAAATTTGGCGCGCTACCTGAGTTTG AGCAAGGTT[T/G]TAACGGCATTTCTTTTTT CCTCAATGCCACGCTTGCCAGATCATGCAA TGTTCATGAAGACTTGTTGTTTTGAAGAAA GTGGGATGAGCAATTTTATTTT |
| WSNP_KU_C1818_3557408 | 0.00082 | 17 | GCTTCATCTGCGAGGGAGATGAAGCTCTAG GGTCCATGAAGGAAGTTGAAGCTCAAACTA TTGGAGATCTTCTACCAACCGATGATGATTT GATATCGGG[T/C]GTTATCGATGGCTTTGA ACTCTCTGGCCTGTCTATCAACCAGGATGA CGCCGATGAAGATATATTTGGCACTGRCGG AGGGTTGGAGCTTGAGAATGATG |
| WSNP_EX_REP_C66606_64905694 | 0.000138 | 18 | GGCAGCCTAATCAGGTGGTTTGAGATCTAT CTCTCTGTTTTAATCGTGAAATGGTTAGTTT TTCATGGCAGGGTATTATCTATCAATAAACT TGTATGTG[T/C]GCATGCAAGTGCTACCTTA GACTGGTCAGTAGAATTTGAGAATTGTATG GAAGGAACTGGTTTGTTGCTTTGATATCTA TCAAAATGAGATGATGTCCTG |
| WSNP_EX_REP_C102795_87883062 | 0.000076 | 19 | CATCTGTTTCTGAGCATCAGCCAACAGCCT GGTCTTCTTTTATGTTTGATTTCCACATCCTT CTTTTCCTATTCCCAGCGGGCCTCTATTTCT GCTTCAA[A/G]CGCCTGTCAGATGCCACAA TATTTATAGTTATGTATGGCCTCACAAGTAT GTACTTTGCTGGTGTGATGGTGAGGTTGAT TCTTGTTGCAGCACCTGCTG |

TABLE 2

SNP markers significantly associated with heading date

| Marker Name | P-Value | SEQ ID NO | Reference Sequence |
|---|---|---|---|
| WSNP_CAP7_C3472_1623955 | 2.93E-06 | 276 | GTGTTCAAGTCACAACGGTTCACA TAGCGCGGGCAAGACCACTGGAG ATCACATCGTTTGTTTGTTTACAGC AGGTGAAATAGAGCGAGCG[A/G] GCAAACAACAGGCCAAATGAATTG GGATTCGCTGATTCTCCATTCCAG GTACAAAATGGAACTAGTCTACTA TTGTACTGTTAGCCTCTCATACGTA ATA |
| WSNP_EX_REP_C108057_91436561 | 4.28E-04 | 277 | AAACCAAGTCCCCTCAGTAGGTAA AAATCACGGCCTATGGCATCCTCG ATGCCAGGTCTTTGCACCTTGACA GCTACCAACTGCTCAGAGTATTTC AACC[A/G]TGCCTTGTAAACTTGA CCTAAACTTGCTGCAGCTATCGGT GAAGGTGACATTGCTGAGTACATT GAATCAAGAGGAAAGCCAAGCTC CCTCTCGACACAG |
| WSNP_CAP8_C458_368155 | 4.00E-05 | 278 | AAGCGCCTCACTCCAGATGTAGTA GGGCCTAAGAAGGAGACATAAAT TCAATGGCATGTACAATGAACCCR TGGCACTGGCAACTGTTAATTCAC AGTAT[T/C]GCCGACAGGGCGAAA TGACAATCGTATGCTTTTTTGTTCC CATACATCCAAAATTATTACAAAAT TTTGGAACTTCCTGAGACAAGTGA TAACAGAAAAA |
| WSNP_EX_C16720_25268525 | 3.72E-04 | 279 | AAGCCCGACCACCGGGCTTGCTGT CCTATGGAAGAAGGCGGTGACTAT TATGTTGTCAAGAAAGGGGACATG GTTGCTGTTTACAAAACTTTAAATG ATT[T/G]CCAGGCGCAAATTTGCTC TTCGGTATCTGGTCCTGCTGCAAG TGCCTACAAGGGTTACTGCTGGAG CAAAGAAAAGGCAGAATACCTCTC TTCACGTGGA |
| WSNP_RA_C32271_41304469 | 2.98E-04 | 280 | TGAGGATGTTTTATCGTGTCATTG AAGTAATATCTTGCCCTAGCTCTGT CACAGCAAATATATACTTTAATGA GGTTTGGAAAGTGAGGACGGTGT TGCA[A/C]GAAGAAGCATCAAATG GTAATGGAGAATTTTCCAGAATGG TTATGGAGATGCAGGAAGCGTTCC ATGGGTATTGGCAAAATACGTACT TGTGGTTGTCAA |
| WSNP_EX_C25082_34346512 | 1.28E-07 | 281 | GGAGGTGAAGAGGCAGTTGCAGC CATGGGACGCTTGCGATTTGTGGT GCTTGCCAATGGTGAGGCTTTATT TGTGCACGGTGCTTCTTCCCATTCA TCAA[T/C]TCCTCCAGCTGAGCGTA GCAAAGTAGATGATGAGTGGATA CCGACAAGCGAACTGGTTCTTGGT GCTCTGGTTGCTTTACCCTTGGTCA CAGGACTTAAG |
| WSNP_EX_C55096_57733894 | 4.71E-07 | 282 | ATTATGGTAATTTCTATGCCTCAAA GTCATTTTTCGACTCGAAGAAGRG CAGGAGGATCATATGGGGTTGGA CTAACGAGACAGACAGTTCTTCGG ACGA[T/C]GTTGCAAAAGGTTGGG CAGGAATCCATGCAATTCCCAGGA CAATTTGGTTAGACAGCCATGGCA AGCAGTTGCTGCAATGGCCAGTTG AAGAGGTCGAGT |
| WSNP_EX_C11229_18163892 | 6.96E-04 | 283 | GTGATGGCGTTCATGCCGGAGCTG GGGCCATTCGATGTCTCTGGTAGC TAGCTAGTGTTCTGCTCATTGTGG CTGCTGTTGCTGTGCACCGGTGGC ACTA[A/G]ATTCCTGGCAGCAGTA |

TABLE 2-continued

SNP markers significantly associated with heading date

| Marker Name | P-Value | SEQ ID NO | Reference Sequence |
|---|---|---|---|
| | | | TTTCAAGCTTACTCTTTTGTTCTTGT AATAAAACGTTTGTTGAATGTACC TCGCTCAAATAAGTGCTCTTAGTTA GAACTATCG |
| WSNP_EX_C55096_57733841 | 3.79E-07 | 284 | CASCTTTATTCCAGATACTGTCCTA GATGACCGCCGGCTATGGTTGAG GATCGATTATGGTAATTTCTATGCC TCAAAGTCATTTTTCGACTCGAAG AAG[A/G]GCAGGAGGATCATATG GGGTTGGACTAACGAGACAGACA GTTCTTCGGACGAYGTTGCAAAAG GTTGGGCAGGAATCCATGCAATTC CCAGGACAATTTG |
| WSNP_EX_C3096_5709369 | 2.02E-04 | 285 | ATTTTCTATTTGACGCTGCTCTTCT AAATACTGCACTCAACTTGAATATC CGCAAATAGTAGATACCATCAGAA AACATGGAAGAAGATAATAGTGT GTC[A/C]TGAACTGTACAATAGCC ACTGAAACCATGGTGGCAGCTGCT CTGGAGGTACGAGTTGTATCGGTA CAGATATGGGTTCCTCGTACCCTG TTTGTGTAAAT |
| WSNP_EX_REP_C67404_65986980 | 2.37E-05 | 286 | CGGGTAGTGGCAACTTGGAAAAG AAGAATGCTTCAGCCTCACACATG AAAAATGGTTTTTCAAGACCACTCT TGAAATGCTCAGAAGAGGCTAGG CGAAA[T/C]GGTAATGTTGCAAGT ACATCCGGGAAAGTTCCTGCAACT TTACAGGCTGAAGCATCTGATTTG GCGAACTTCCTTACCATGGATAGG AATGGGGGTTATC |
| WSNP_BQ168706B_TA_2_2 | 3.08E-08 | 287 | TTCTGATCATATTTGTAGGTTGTAT TGGTGCGACTTGCCCCTGCTTTCTC TTTGGAAAAA[A/G]TGCACAGTTC TTGGGATCTGGAACTCTCGCTGGA TCAT |
| WSNP_BQ168706B_TA_2_1 | 3.08E-08 | 288 | TGTTATCGGGACATGCATAAAAAT ACCCTTTAATCGCAGGAAAGGAAA ACTGTTCTTATG[T/C]CCTGGATTG TTCTGATCATATTTGTAGGTTGTAT TGGTGCGACTTGCCCCTGCTTTCTCT |
| WSNP_EX_C8208_13870372 | 7.40E-05 | 289 | GTCATCATCAAACTGAGCAGAAAC CGGTATTTGATCATCAGGACTCTTT TTCCAATGACCTTGAGGGTTATGC GCCATCTCATGTGCCTCAGAGATC AAC[A/G]TCGTTGGAGGACGATCC GTTCTCCTACCCCAACCTCTTCTCA TCGAAGCCTTGAGTTCTAGTTATCT GCAAATTAGTCGTTGAGCCTGGTT TGAAGTCAT |
| WSNP_JD_C17082_16025440 | 3.08E-07 | 290 | AGGGGTTAAGTCCAAGAATAAGA ACTAAAACGGTCGCTGCCCACGGT TTGAAGACGAGGTCGCACATGCCG TCTGTACTACTGCATGGTTTTCCTA TCCC[A/G]CAAGTAAAATCACCCG TTACTCTACCGTTTAAGATTTGCGA CATCTCCTAGAGACTTATGCTCTAT ATTTTGTTGTGCCCACGTTGTTGTA CGCGTGTTA |
| WSNP_EX_C21499_30644485 | 3.08E-08 | 291 | CAATCATTGTTGTAGAAACATCAA TATTAAGAGAAAGCCCACTCTGTG TGGCTCGAAAGCTTGAGTGGAAAC CTCTGCAGCCCATCACACCCCCACC CAA[A/G]TCCACAAAGTTTGAAGG ATTGTTGTGAAAAAATGACTGGCG |

TABLE 2-continued

SNP markers significantly associated with heading date

| Marker Name | P-Value | SEQ ID NO | Reference Sequence |
|---|---|---|---|
| | | | GACTAACAGGCAGCCCTGTTTGGC AGAGTGTTGTCTTAATATGATATC AATAACCCGAA |
| WSNP_EX_C3096_5709257 | 1.88E-04 | 292 | CACATCTGTGCTCTCAGGTGCCGT TGCAAACTTGAGAGGGTGCGGGA AAGAATCGGCCGCGATCTTGTTCT GGGTGCACATTTTTGCAGTGTTCT CCATG[A/G]CGGGATGGATTATTT TCTATTTGACGCTGCTCTTCTAAAT ACTGCACTCAACTTGAATATCCGC AAATAGTAGATACCATCAGAAAAC ATGGAAGAAGAT |
| WSNP_BE489326B_TA_2_2 | 3.94E-04 | 293 | GCATTGCAAAATTCAGTTGTGATG TCAACATTCTTACTGCGATTTCTAT TTTCTAAAGAT[A/G]RWTTAACCA TTTTTCATATGCAGAAACTCTTGTC CATTCA |
| WSNP_JD_C4413_5541190 | 8.34E-06 | 294 | TCTTCCAAGTCAGGTGGGTTTGAG AAATCATGAGCAGCCGACTGTGAG CTTTGCACATGTGGACCAATATCT GGGGTTGATTGAGTACCAGAAGCT GGAC[A/G]AATTGCTGCTTTTGGG ACTTCAGGCAAATCCAATGAGTCA AAGCCGCCATCAGATTGATAATCT TCACCAGGTTCGTCAGCGGCAGTT GCAGCTACTGGT |
| WSNP_EX_C57007_58898157 | 8.13E-06 | 295 | ATGCAACTGTGACAGCTACACATA GCACCATAAGGATCCAATTTATTTC AGGAATGTATATCTGCCCATGGAT CCACCTCGATGTGTGAACAATCTTC AC[T/C]CGTGGGAAACATCCCAAA GCATGGCACTGCTTTACAATAGAG AATGTTGCTGAAATCACAGCCTGG CTTCCAACAACTGCAGCAAGAGTG GCCACCACAA |
| WSNP_EX_C10347_16946522 | 2.53E-12 | 296 | CTAATGAGATATTTATGTGTTCATA GGGGAGTGCATCGGGGCATCGGG CGGTCGTATGAGAAGAAGTGCGTT CAGCTGAGGACCCATGATGCCAAC GGTG[T/C]AGAGCCGTTCACCATC GAGAGGATCAGGGCTGCCATTAG GACCTTCGAGACGAAGCTCAACAT CTCCGCCGCCTTTCTCGACGAAATC TCCCAAAGGCTC |
| WSNP_KU_C7180_12403155 | 1.50E-12 | 297 | GTTGTAAGTTTTTTGTATTCTAATT TGGTTGAGATACTTAAACAGTGAT TTGTTACTTCACCTGTCGATAAATG TAGGGCTAAAGCAATAACTGGGA AAT[T/C]ATGAATTCCATGTACTTG TCATAGCCGATTCTTTGTTGTTCAG TAGTTTGTTTCAAGAGTGCAGGTC GTTTTTCTATAAGCTGGATGAATA GCTCCCTTG |
| WSNP_BF201102A_TA_2_1 | 4.40E-05 | 298 | GGTTGTTCTCACATAGTTTATTCTG TATCTAGTACTTTTACTAACGACAT CTTTTACTAT[T/C]GCAGCCACTTT ATCGTCCCTGAATTGGCTCCTAGC ACCAAGTTCTCCTACTCTTCTCACA |
| WSNP_EX_C43578_49857984 | 4.94E-07 | 299 | ATATTTGCGAACAAGAGCATGGAG TGGTCAGAGTTTCAGCAGGCTGTA CAGGCAGGCCACAAAGGTAGATA CGGGCAGATCCGGCTGAGGAAGC CGAAGC[A/G]GTCTATCTATACTTA TCCTGCCCCGGATTGTATGTGCCA AGGGTAGATCGCCGAGTTTTCTGC AGTGCACCGACAAAAGAAATGTG CCGAGTTACTTGCA |

TABLE 2-continued

SNP markers significantly associated with heading date

| Marker Name | P-Value | SEQ ID NO | Reference Sequence |
|---|---|---|---|
| WSNP_KU_C7890_13513783 | 6.84E-04 | 300 | CGAATTAATTCTCCACCAAACTCAAGCTCAGAGAGCGTTGTCAGATGAGCGATTGAGCTGATTGGAAGGCTGTAACATTCCATTATCCGCAGCTTCTCTA[T/C]AACTGGGCTGCTCGGAACACTTGCAACCTTCGGACAGGCATACATACTTAGCTCTTCAAGCAGAGGAAACATCACCAAGCTATGAGGAGGTTCCCCTGCA |
| WSNP_EX_C57209_59016692 | 4.20E-04 | 301 | tttattctcttgaggaggcaacatttggagaaattctcacgtccagagcaataagagcggctcattgtttaacttccattcagttttcgcctacttcaga[A/G]CACATACTGTTGGCATATGGACGTCGTCATAGCTCGTTGCTCAGGAGCATTGTTATGGATGCGGAGACGACTGGAATTCCTGTATATACTATCTTAGAGG |
| WSNP_JD_C12221_12509932 | 4.38E-04 | 302 | GAAACTTGAGGATTAGGATTGCGAGCTTTCTAAAATACAACAGCGGTTGTTTTAAGCTGATTGGAGATTACATGTACAGTTTTATAATTACAGGGTCGTG[T/G]GAACTTGACAGCAACGATGACCATGACCATGCCAAATTTACATCTTCACACYGCCTGTGCACAGACCTGAGTTAAAAGTTGCAAAACGATGCACGATTAG |
| WSNP_JD_C7718_8795833 | 1.78E-06 | 303 | GAATGGGCGAGTGGCCATTGAAGGTGAAGGGGTTCACAAAGATGTGGTAACTGATGAAGCTGAGGGAAGCTTGATTGTGAATGGGCGATCGTCCATGGAA[T/G]GTGATGTGGATCATCCAGATCTTCCCATTTCCAAGGAGATAGCAGAAGACACAGTTAATGAGAGGGAGGATGAGGGTAATGCTTTCAGCAGTGAAAATAA |
| WSNP_EX_C19467_28423946 | 8.04E-04 | 304 | GAATCTTTCTCGTCAAATAGAGGATGAGAATGCTGATTGTTACCCTCACAAACAAACTCAGGACTTGTAATTGTTCTTTCAGCATTTTCAACAGTGATTT[T/C]CGATGAGGCCAGGCGATCATGTTTTTGACACACGACTGTCTCGGCTTGGTCTAGCACCACATTGCACTTAGCATTCAGCTCTTTTAATTACAGATTGGTA |
| WSNP_EX_C8643_14488961 | 7.86E-04 | 305 | AATCATTTATCTGCGATGAGTACTGCTTGTTGCTATCTTCAGTGGTTAATAGTTCATTAGTACTCCTTGTGACTTCTTGGCGCAGAAACGAGATCTCTGA[A/G]TCTCTCTCTTGCAATTGTGACTGAAGGCTTTCCACTTCTGCAAGAAGACTTTCAGACAAGCTATGCAACTCGTCAAACTTCTCGACAGTGGTTGCAAGTT |
| WSNP_EX_C1143_2194680 | 7.70E-04 | 306 | catgagttacagtggatatgatattgaagatgcaattgtaatgaataaatcatcccttgatcgaggttttggtcgctgcatagcaatcaaaaagtacaag[A/G]TCACTATGCAGAAGTATGGAAATAATATATCAGAAAAGAATGTTAAACCGGAGAGGGATAAAGATGGTGTTTTGATGAAAAAGAATATGCAGGCATTGGA |
| WSNP_RA_C14171_22234872 | 8.54E-04 | 307 | CAAAGTATTCAGTACACTCTTTGTCATCTCTACCAGTCTCTGATGTAGAAGCGTCGTTAGACAGCTTGGTTTCATCTAAATGAATTTCCTTCTCGGCA[A/G]CATTGCTTAGAGTCGACTCTGACAAAAGAGTTTCATAATGGTC |

TABLE 2-continued

SNP markers significantly associated with heading date

| Marker Name | P-Value | SEQ ID NO | Reference Sequence |
|---|---|---|---|
| | | | TAAAACTTTCCTCAAAAGTTCACCC AAGCACAGTACAGCACCACCACCA GATGGAAT |
| WSNP_EX_C53387_56639804 | 9.59E-11 | 308 | AAGCTCGGACTAACAGCCACAGCA GTATATGTGCATTTGATGACTGTC CCTTCAGATGTGGCAGCGGGTGAC TCATCATCATCCTCGCATACACGGA GCG[T/C]CGTATCTATGAGCCCTTG GTTTATCTCCTCRATCTCCTCCAAG AGAGCATGATTTACCTCAATTTTTC GCCGCTTGGCACGCGAGGTTGCG GTTGACTGT |
| WSNP_KU_C28104_38042857 | 9.46E-04 | 309 | TCCCAGCTGCAATAGCATCAGTCA GGTCCTTTGTGGCATGGGTGTGGC AGGTGCCTCCTACAGTAACGGCTT CATCATCTAAGAGGCACTTCACAC CACA[T/C]GTAGGCTTCCAATGGA ACTTAACAAGGTGCGCCTTTCCATC CCTGCTGATTAAGGTGTAGGTGTT GACACCAAAACCGTCCATGTGCCT GTAGTTGAGTG |
| WSNP_CAP8_REP_C3844_1896355 | 8.18E-04 | 310 | TGCGCCCGGCCAGCAAGATGCAA ATAYGTAAATGAATTAGTTACCCAT ATACTGTAAATTAACGGCCAAGGA ATATACCGCAGTAAATATGCAAGT AATA[A/G]TACTAGCTCTTTTTTTC TAACCTATATATAGTAGCTCTCTTT GATTCGTTTTCAAAAAAAAAAGA |
| WSNP_RA_C23253_32762188 | 8.10E-04 | 311 | CTTGATCTTCACTGTTGTTTTGTAT ATGTTTAATACCATCTTGCTTTTCA TACCATCTCCAAGAAGGGTAAACC TCCCCGAAGAACTCAATAACAAAG TC[A/G]TCCATGCCAAATCCACCCT TTTTGTTGCAAACAACTCCAAGACC CTTTCTATAAGCAACATAGTTATGT TCAGGGCGGCTCCTCATGGCCTTC AGCATTC |
| WSNP_EX_C9971_16412345 | 2.50E-04 | 312 | CATCCGTCTTGGACAAGTTCGTCTT YGCATATTGCGTATTTTAAGAAAAT CCGGTGCTGATATATATAAATATT ATATATATGGTTGGTTTCGTTCTTT C[A/G]TAGCGTCGGTCGGTCGGTC CCTAGGGTCTATCTATCTGTTCATA CCCCTTCATTGTTTCATACCTTGTA ATCATAAAATCATCAGCCCTCCCTC CCAACC |
| WSNP_EX_C11106_18003332 | 6.60E-04 | 313 | ATTATGTTACTGTACTTTCTCTTCTC TTCGAGCGGCAGGCGGAAAAAAT CCCTTGATGCGTTCATCACAGAATC CATGAGAGAGGTCTCCATTCCATG GT[T/C]AGAAACCTTGAAGAATCC CCAGGTCTGCAGCGCTGACCGCAG CTTGGCGGCCTCCTCCGCATCGTT GGATGCGGACAGCARGCCGAGAT CGATTGTTGGA |
| WSNP_EX_C35861_43928486 | 1.22E-04 | 314 | GCAGTGATTTTGGAAGTGCAATTC ATGGTGTTGACGCAGATTTTCTAC CCTATGATGATGATGGGACTTTG ATGAGGCAATTGATCTCGATGATG ATGA[T/C]GATGAGCCAAATCCTG ACGAATTCCAGTCTCATGATGCAC TTAGTGGCTGGTCTTCTCGTACCA AGGGTGCTGCAAGATATCTCAAGA CTCTGTTCGATG |
| WSNP_EX_C5547_9774453 | 1.79E-05 | 315 | TTTTTTTTCTTCTCCGTTTGAGGTTT TGACCGTTTGTATTCAATTTGATTC TATTTTTGCCCTTGCATTCTCTCCCT |

TABLE 2-continued

SNP markers significantly associated with heading date

| Marker Name | P-Value | SEQ ID NO | Reference Sequence |
|---|---|---|---|
| | | | CCGCTGTCTGTAATTTGTTAGCT[A/C]GGGCAGTGTGGTGTGGTGACAGGGAGAGAGAACAGTGGATTCTATCATGTAATGTAGATTATCTTTCGCTACTTGATGGAGGTGAGATGGTTTGATGTAA |
| WSNP_KU_C10377_17180909 | 1.52E-06 | 316 | ATAATGGCGATGCCTGATAGGATATACAGGAAGTTTGTCAAGCAATGCGAGCGCCAACGCGTCGAGCTTATAAGGCAAGTTCAGCAGATGCAAAAGGCAT[T/C]GAGAGAGAAGCAGCTGAAATCCATTTTCCAATGGCGCAAGAAGCTTTTGGAAGCACATTGGGCTATTCGTGATGCACGAATAACTCGTAACAGAGGGGTG |
| WSNP_KU_C18538_27857915 | 5.00E-04 | 317 | ACGCGAGAGAAGAGGGAGTCAAGGGCACAGATCTGGTCGACAGAGTGGTGGGCACGACAAGGCTGACCCGAGGACCTTACAAGGCGCTGGATCTCGGCGG[T/C]GACAAATCTCCTGGTGCTGCGACTGGTGATGATGGAGGAGGGGTGGCAAATCCCTTGTTGCGGTGGCTAGTGATGAGGGAGGAGAGAGGAGGGAGATGGT |
| WSNP_RA_C11420_18529863 | 3.68E-04 | 318 | CTAATGTGGCTCACGACTTGGACAAATTGCAAAACAACACCTACTCGCTGTGCATTGAAGGAAACTGCTATGTTCTGCTATCCCCCAGGGATGATGGTAC[T/C]GGGTCTCAATCCAGCAAGGAAAAACTTCTCGTGTTCCATGTGCAGAGCGAGTTGGTGACCAGCATTGACACGCCAGAGGATGGCACCCTGTTTTCAGGCA |
| WSNP_EX_C41347_48189975 | 2.40E-04 | 319 | GGTAGTGGTAGTACTAGCTGCAGCAGCTGAAACTTCGGTTGCACGGGAACTCAGATTGTTGGTACTTTCTAGTGAAGATTTTGGCTGCTGGGAGAAGATA[A/G]GTTGCTTCTTAACAGGGCTCACAGAAGGAATGGAAGACTCCGTCATTCTTAACTTGGAGGGGCTCGTAACATCAACATGCCGCTGTGCATTTTGCTTCTT |
| WSNP_EX_C53387_56641291 | 1.10E-09 | 320 | AGGGACATGCTGCATACCAGCTACACCAGAGGACTGTAATCCAGTGCTCATACTTGACAAACTTGCTTGAGGATTAGTATGACTATCATGCTGCTGCAAA[T/C]TCTGGGAAGTCTGTTGCTGCTGTAAAATGCTGGAATTAGGAGCTTGTCCTGCAGGTGGCTGGAACTGTTGCTGTATTTGTGGCTGCACTGGCTTCCTTCT |
| WSNP_EX_C23509_32746909 | 8.68E-04 | 321 | GGATATGTTGAGGGTGGAGATTACTAAGGAGTTGGTCATGGCTTCGCCTGCTGTGATTCACTTCAGGTCCTAATTAATAATTGAAAAATAAGATGCATGG[A/C]GTCATCAGTAAAATCTAGAGTCCATCTGTCCATGTAAATCATTCATGGCATATGTACTCTTATTTATCGTCTATGTAGTTTCAAGGAGCTTCGGTGCTCT |
| WSNP_BE497845D_TA_1_1 | 2.02E-06 | 322 | GCACAAGAAAATATTAGGATCTTTTTTTATAATACTTCACATTCTATTGACAGGAAGAAT[A/G]CAGGACGGAGATGGGTTCTCTTTTTCCAGGACACAAATGGATTGCTCTTTAATGTTTGTA |

TABLE 2-continued

SNP markers significantly associated with heading date

| Marker Name | P-Value | SEQ ID NO | Reference Sequence |
|---|---|---|---|
| WSNP_BE445508B_TA_2_2 | 3.08E-07 | 323 | TTTGTTTTTGCTGGTGATACAAACT GTTTTCCAGTCACTCTTTTTTTCAA ATAAGAAAGA[T/C]GTGGCAAGTG ATGTTTGTATGGAGCACCACTTAA TTTTATTTACCTTTGCACTAGACTAG |
| WSNP_EX_C44049_50205457 | 1.84E-04 | 324 | CACTAATTTTCCCTGGCACCATTAC ATCAAGAATCGATATACAAACAAC AATCATATATGCTATATAGAAAAC ATGCACTCTTTTTTATTCAATGGGA CT[T/C]ATGTTTCCATGACGTTTAC TTGGTCTCCGAAGCAGCGGCGGC GGCATCAGCCTGTGCCTGTCTCTTC TTGGCAAATTCGACCACCCTATCA ACTTCTGGC |
| WSNP_BE591466B_TA_2_1 | 2.72E-07 | 325 | GTTTCTATTTACTTCTGAATGCTAA TTTACCGTTCTTGATTTTTGTTCTCA GGGTTGATA[T/G]AGCATGCTAAA TCTTGTCTAATTTCCATGTGTATAT TTCTTTGTGTTTGCAGGGGCTGCC |
| WSNP_EX_C15084_23263641 | 3.14E-04 | 326 | GTCTGCACACCGAAATAGGATTTG CCTCATGCTCTGATGCTTGATGGCT TCTCGACAACAAGGGTAAGTAACA GGAACAAGCCAAAGGAGATGACG AGTG[A/C]TGTGGCCATCAAGATA AGCATTGCTTGTAGTGTGATGCTT GGGCTCAAGAAGAAGATGACTGC GATGGCACCTGATTGCCAAACCTT CAACTGTGCAAAA |
| WSNP_JD_C13903_13781269 | 1.58E-04 | 327 | CTGATGAGAAAGCCAGGCTAGAG GAGCTTAAGAAACAGCGGGAGCT GKCTGCCGCCACCAAAGAGGAAG AGAAGAAGAAGAGGGAGGAGGC AAAGGCCGC[A/G]GCAGCGGCTC GTGTGCAAGCCAAACTTGACGCCA AGAAGGGCAAGGGAAAAGGAAA GGGCAAATAGATTACTCCCAACTG ATGTATTAGTCGTTGCATTT |
| WSNP_KU_C644_1332610 | 1.82E-04 | 328 | CTCAACGTGGGCCACTTTCCTCATC TTGCGGATTTGGTCACGAGGATCA ACTACAACCACTATTACATGTCTGA CACCGGAAGTTTCACTGCGATCCC TG[A/G]GTCCCGCCCTCGGCAGCA GCCTTGATAGGGTTGTAGGTGCTT TTCACCTCCATTTGTGGGGAGTG TATATAAACCCGAGGTGGCCAGGC CCAGGTGGCA |
| WSNP_EX_C35861_43926307 | 5.80E-05 | 329 | ACATACGTGACAGGGAATCAAACA CATTTTAATGAGGGGTCAGTAAAC ATGCAAGGGTATAATTTTCTTGCTT CTAATGTATCTGTAGAGCCATACC CTG[A/G]TGGTTCTACCGAGCCAT GGGTGACAGGGCAACAACAACAA AGCTTCTTGTCCCAAGCAAGTTGG GGTAGGCCTAGTGGTTCTACCGAG CCACGCGTGACA |
| WSNP_EX_C5547_9772680 | 1.08E-05 | 330 | GCCCAAGTTCTTTGGTTGCTTCCTT GTGTCCTCCTGGTGTGAGTGGTTC CATCCAATCTCCATCGATTGAACCT AAAGATGTCTCAAACCCATTTTTTT C[T/G]GTGGCTTCTGAACCTGACA GGGTGGATATGATTGATATGAATG AAGAAATGACTTCTGATTATCTACT TGATTCTGATGATGATGATGCTAA TAGAATCT |
| WSNP_KU_REP_C102220_89250165 | 7.78E-04 | 331 | AAGGGGAGCGGCCGTTGCTTTCAA TCTGAAGCAAAGTGGTGGTGCTTT |

TABLE 2-continued

SNP markers significantly associated with heading date

| Marker Name | P-Value | SEQ ID NO | Reference Sequence |
|---|---|---|---|
| | | | CATTAATGCTGTAATTTGTCCAGAAGATAGCTGAGAAAAATGGCATATCTCT[T/C]GGCATCGGTTTTCTTAGTCATATAAAGATAGACCCAAACCAGAAACAGTCAAATGGAGCACTAGATATACCCGAGGCTTCCTTTTATAAGAATGGTCGCA |
| WSNP_EX_C8802_14726148 | 2.32E-04 | 332 | TCTCTCAAGGACTTGAAGGTGAAGGGCTGTGGGAAACTTAAGGGAATCCCTATCGGTGTCACTGAAAATAACCCGTTCTTCGCAACAATAATAGGAGAAA[T/C]GCAATGGTGGAACGATTTAGTCTGGGGTGATGGAAAGTGTCAAGCGCTGGATATTGTTTAGGAACTGGGCCCCTTGCTACCGCATTTTGCAACTGAAGGA |
| WSNP_EX_C130_258776 | 1.58E-04 | 333 | CACACACTGCGGTGTTGAAAGCACACTTACTCAAGGCTCAGGCTAAGATGAAGCACTATGCTGACAAGAACAGGACACCTAGGGTCTTCTCTGTGGGTGA[T/G]GCAGTCTACTTGAAATTACAACCTTATGCACAACACTCTGTGGTGAATAGACCCTGTGCAAAACTGGCCTACAAGTACTATGGACCATTTGAAATATTGG |
| WSNP_BE499016B_TA_2_1 | 8.50E-06 | 334 | TCGCCGTACTCGCGGGTATTCCCCTTCCCTCGAGGGCTCAGCCCTAGCTTATCCCTCTGT[T/C]CCATTCGGTTCACCTTCTTTTTGGAAGGAAT |
| WSNP_EX_REP_C69919_68881108 | 1.72E-04 | 335 | ACAGTTTTGCCTCCGAAGCATGAGAAGCTCCCTGTGAGCGTGTGAACTGGATCCGTAGCCACTTCGCCGTCAGTCTGGTGAATTGATGTTTTTGATGTTA[A/G]TAATGGTACCATGAGCCGCCGTGACGACGACCGGCATTGTAAATTTATAAGCAGCAGTTTATATTACACTTGTTAGCAGAAGTCTTCAGTCATTGGTCCA |
| WSNP_EX_C361_708712 | 6.16E-04 | 336 | GAACGAGAACCACGACAAGGTCTACGAGCGGTACGGCGTGAGGAGCTCCGAGCGGGTGTCGTCGGCCGCGTCRACCCGGTCAGCTCGGTGACTTGAGGAC[T/C]GACCTGCTCTGCCCCGGCAATCATCGGATATCGCATGAGCTTCCGGGAAGGCCTCAGTTTTGCTCCTGTAACTCCGATGAATCGTTTTCTTGTTTCGCGA |
| WSNP_KU_C1102_2211433 | 7.70E-04 | 337 | AAAGGCCTTAAGCATGTCTTCTGCAAGTTTTGTTAGTTATCACTTCATAGCTTGGTCAAACTTTTTGGCCGGTGACAAGTTATAGGTAAGGTCTCCATC[A/C]TCTCCTTTATTTCTTTGGATCACTACAGTTCTTATAGCTTTCCGAATCATGCATGCCATGGTGCAAACTCAAATATGTAAATAATGCGTTTCCTTTTTTT |
| WSNP_RA_C323_681466 | 4.50E-04 | 338 | TCTTAGAGAGGATGCAGGTTCTCAAGGCATCTATCGTGCGAACCCTCTCCAGGATGTTGAGTAGAACGTGATCTGGCAGCTTGCTAAGCCTATCAACTTC[A/G]GCTTCATCCGAAGCTGCTTCGTGGCAGCGAGCTTTGGCTTTATTATTGTTTTCCATCTCCCGCAAAGTCCCTCATTGGCCAGGGATAGCCTCATTAGATG |
| WSNP_EX_C916_1767286 | 2.71E-09 | 339 | GCCTCCAACAAGTTAAAACATGCATTGATATCGGGTCAAACTGTGTTG |

TABLE 2-continued

SNP markers significantly associated with heading date

| Marker Name | P-Value | SEQ ID NO | Reference Sequence |
|---|---|---|---|
| | | | AGATTGATAGGACAAAAAGACCTC GCATAGAAGAAATTGTTGACTCGC TCAA[T/C]GGACTACGTTCAAGCC AAAAAGTTACCGAGGTCTCCCGTC CGCCTACAACTGGCAAGAAGCTAA TGGGCTCCATTTTTGGTCTGAAGA AATGAAACATGC |
| WSNP_KU_C16295_25149034 | 5.62E-04 | 340 | CCAAAGTTCAAGTGGCATATGTAG GCATTCTGCATAGGCTTGGACTAA TTCACACCTCTCAAGAGATTTTCAA AGATGCATCTCAGCTCGCCGCAAA ATT[T/G]GATCAGTGTCCAACACAT TAGAAGCAACACCAAGTTGAGAA GACACTCACCTGTGTTCAATCATAC CTTGCCCACGAAAAAATAATCATC CCCAGTCGGC |
| WSNP_JD_C12087_12411036 | 1.56E-08 | 341 | TTCCTGCAACACCTCCTTCATTAAT TTGACATTGTCAGTCAAGTCTTTAC AAGGACGAGGGGCACATCGATAT GAAGGATTCCATGGATCGTTTTCT TCC[A/G]TGCTTGATACATCCTTAC CTTTACCATTATCTTCATCATAAGC AGATTCAGTTGCCTTGTGCATTATC TCCATTGGTGAAGAACAAGCGTGG GATTCCAG |
| WSNP_EX_C22016_31191407 | 8.78E-04 | 342 | ATAGCAGCGTTATATTGAGGAACA CCAGGCCTACCAATGCAAGAAGTA ATATACACGAACATGACTTCAAAT ATCCTAGGGAGGGAAAAGTTTCCA GTAG[T/C]GAGGTCAATGCTGACA GTAAATTTCAAAGATACCAGCAAA GAACAGAGAATTCAGGAAGAAAT CTTGTAGGTAGTTTTAGAGATAAT AATGTGGACTATA |
| WSNP_KU_C16812_25759885 | 5.92E-04 | 343 | tgccaaatgacccaaccgctggccagcattc aggcagagatgacgaccaggaggtggttag acaaaagctgatcaagggttctctgaaatt gatggtgg[A/G]CAGTTTATTGGGAT AAAGAAAATGGGGAAACTAAGTG AGAAGCCATTCCGGGATGCTTGTG CTGTCAAGCTGGCCCCTAAATATG CTGGCGCGAAATCTT |
| WSNP_JD_C5795_6955627 | 1.56E-04 | 344 | CAATGATCTGCTGCAGCTTTCTTAG AGARTGGTCTACCTTCTTGATCTTT CGTGATGGCCAGCGATTTATACCA TGCTGCCTGCATATTCTTTTCAGGG T[A/G]GTAGGGCACACTCCAAGGC TCCTTGCTGCATCTTTCAGGCTACC AGCAAAGTACTGCCGAAGAACCG GCAAGCTCACAGTCTTCTCCGTCTT TGTGCGCC |
| WSNP_EX_REP_C69342_68276256 | 6.27E-08 | 345 | GCAAGAGTGGCATGATATACATAC ATCTTACAAATATCTGTCACAGCACC ATCAACAACATACAGATCGTCTTCT TCATCYTTGTCATCGTCGTCGTGAC T[T/C]GGCCCCGTTTTTCGTTGTT TGTTGTTAAATTTATCCCCCTCCGT AGTAGTATCGTGCCCCCCGCACTA ATCTGTGCCTAGCAGAGCTGAGCC GAGCTGA |
| WSNP_EX_C2718_5038582 | 1.94E-04 | 346 | TTAACCAATACTACCCGGCGKCAT AGAGTTGTACTCCTTCAGACGGCT TGCTCCTGGTGTTACGTTGTCAAC ATGTCCTGGAGATTTAGTAATAGC TCTG[T/C]GATGTTCTACAAAATGA GATACCTGTGCACTTACATTTGTGA |

TABLE 2-continued

SNP markers significantly associated with heading date

| Marker Name | P-Value | SEQ ID NO | Reference Sequence |
|---|---|---|---|
| | | | AATGGTGGTGTACTTCTTAGTTCTC AAGTCGGCCTACATGGAGGTACAA CCAGTCAAG |
| WSNP_KU_C17726_26872129 | 1.28E-04 | 347 | GCCAAGTGAAACGCTTCAGACCAA TGCGACCGAGTATCGACTACCCAA GCATAGCGAAATCAAGCTGATCAC TTATGTACGTATATATGTATTTGGG AGT[T/G]TAGTTTCCATCAAGTCTC CGCACGCACTGAACACTTGCTCTA AACAACAATGCTTTGTGAGGGTAT AAGAGTGTATCATATGTTAAATAA CTTATGTTGG |
| WSNP_JD_C15974_15272598 | 4.32E-04 | 348 | CCCAATATCAATTTCCCATGCTGGT TGTGAAGACAGAGCAGCGGATCA TCCAGCTCCGACGCTATGCATGCG TGCAGCCTGCTGTATTTGTTTCGCA TAG[T/C]TGCAATACTTATCTGTTT AATAATACTAGGGAGTAGTAGGTT ATTGAGGCTGTAGCGGAAGTTGG AACCTGCCTGAATGTAAGTGAAAG GGGACAGTTGC |
| WSNP_EX_C5239_9272511 | 9.60E-05 | 349 | ACTAGACGTAGTAGATCATGCCGA CCTCGATGAGGCTGATGTGGGGTA TGTGCAGCGTCACCGACGGGCCCC TGCAGTTCTTGCGGAGGAACGAGT AGGC[A/G]TAGTCGATGGCGAAC GACTTCAAGAAGTTGGAGTTCTTC CTCGCCTTGACGTAGGAGTGGCCG ATGATGTACGCCACGCCGGCCTCC TTAGCCTCCAGGA |
| WSNP_RA_C37745_45806931 | 1.20E-04 | 350 | ACTGGATTCTGCGCAAATTGACAT CGTCGACAAAGCTGACAAAGGTG AAACTGTAAGGAATCCATCAGTTG AACACACTGAGATGGTCAAGCTTG CAGGA[A/C]AAGATGAAGGCAAT ACCGAGCGTGCTTTACATGCCGGA GGCAGAAATGAAGAGTCACCTGA TGTTCTCTCAGATACCATGCAAACT GGAATTGTAGATGA |
| WSNP_EX_REP_C105541_89932598 | 5.69E-06 | 351 | AGCCTGAAGAATCTTCACCAATCG TGGATATGATACTGTAGGAACTGC CCACTCCAAATCAGAATTGTTAGG AATAATTTCTTCCAACAGCTTCCTG TAA[A/G]GTATAGACGGGACAAAC TGTTCTTGGTTGTACAGAATCCTGT GCAGAGTCCTGACTGCTATTTCTCT TATCTTATCTATTTTCTCAACTGCCT GCTTTGC |
| WSNP_EX_REP_C69526_68472665 | 1.04E-04 | 352 | AGTGCAGACATTCTCGTACTCGTTC AACAGTTCCTCAACCATTGCCTTAG TCTTTGAGTAGAATGAACCAGTGA AGTTTGGTTTATCCTCTTCTTTGAA G[T/C]CGATGCCTGACCCTTCAGG ATGATTTGCATCATATTCAAATATG CACCCAGTGGCATAGTTTATCACC AATAACCCATGCTCCCGACAAACA TCAGCTAG |
| WSNP_EX_C123_244117 | 2.34E-04 | 353 | ACACGTAGGAGCCAACCTTTTGTA CCTGGGAGTCGAAACSAATTTCTG CCTTCTGCATTATTTCAGTGTTAAA GATGATGATTGCATGCCGCATTTG CTT[T/C]GATTGCTTACTTTCTCTGT CAAGTATGATAAGAATGGAGACAT CTGGACCTGCCGAATTCTAGAGTC TAGCGTGAATGGYGCAAGGTGGA CCAAATCACG |

TABLE 2-continued

SNP markers significantly associated with heading date

| Marker Name | P-Value | SEQ ID NO | Reference Sequence |
|---|---|---|---|
| WSNP_EX_C1988_3742291 | 3.22E-04 | 354 | AGGCACTCGTCAGACTTGAGCAGC GCRTAGTAGATCCACAACATCGCG CTGAAGAGCGCCACCACGTAAGG GACCGATTGGAACCCCTGCGTCGA CTTGC[T/C]CCGGTAGATTCGGTA GAATGTCGGCAGTGGGGCCAGGT AGGTCATGAACGAGATGACATTGC CTAGGAGGCCAAAGGCAAAGGCC CACGGGTGCTGAAGA |
| WSNP_EX_C19134_28056012 | 7.37E-06 | 355 | CCACCGGTGCTAGCAGCGAGTGAT ATGATAGAAAGTGTGTAACGGTCG AAGACATGAACCTGTGCGGGTTTC CTCTAGAACTTTTATGAGGATCGA CCAG[T/C]CAGACAAGCACTTTAA CGTGCATATGTGTCGCAGAAGAAG GGACGGCGGGTGTCGATAAGTTA GTCAGTGTTTGCTCAGGATTCGTG CCATTTTCCRTAG |
| WSNP_JD_C7404_8500079 | 8.08E-04 | 356 | ACGGCTTCCAACCTGAGGACAACT TTGTGCGATACGTTAGGCGTGTCA TGGAGATTGCAGTGAACCTGAAG GAGATATCTCTGTATGACTGGCAG GTCTG[T/G]AAGCGCTGCAGGGAC TTGGATCCCAGTATCAAGGTCTGT CCTTCTCGGTATCCACGGACCAGT GAGCARAAGGATATGTTGAGGGT GGAGATTACTAAGG |
| WSNP_EX_C8303_14001708 | 5.01E-07 | 357 | CGTGGAGCATGCCTTGGCCAATGG TGAGGCTGAGCGCGATGTGGAGA CATCGGTGTTTGCTAAACTTGCCAT ATTTGAACAGGAGCTCCGTGCAGT GCTT[T/C]CAAAGGAGGTCGAGGC TGCCCGAGGTGCCGTAGAGAATG GTACTGCTACACAACAAAACCGTA TCGCTGAGTGTCGATCATACCCTCT CTACCGGTTTGT |
| WSNP_EX_C9927_16346100 | 3.48E-04 | 358 | ACTTAGTTAGTGACTTGAGCTACT GCAGTTGAAAGATTGTGTTGGTCT GACTTGGGAGATTTTGATTCGACA TCATTTGTCCTGTCTTTTCGTATCG AGA[A/G]TGGAAATTAGACCTAGA AGTCATTTGTTCTGTTGTCGAATGA CTGACGATATGAGTATCTTCAGCT CTGTAAACCTGAGGATGAAATTAG CAGTGTCTTT |
| WSNP_JD_C4621_5757201 | 9.20E-05 | 359 | ACGCCCAGTCCCCTCGCCACTACG GGCGATGTTCTATAGTTAGGCCTC CATGCAATGAACCCTGTAAACAAA CTGCGTGGAGCTGAAAATAATGTA ACAT[T/C]GTATCAGAATTAAACTA GTTCGCCAACATGGAGTTGGGCTG AACTTTGTTACCAATTTTCTCCTTG TGTTTCACCCTGGTGCTCATCGGTC TTAAGGGCG |
| WSNP_BE591684B_TA_2_1 | 2.72E-07 | 360 | TACTAACATGTTAATTTTGTTTTCC AGGAGGCAATGAGGAAAGACACC CTAGAACGTGCG[A/C]GAGAGCCA GGGTTTGACCTGAAAACGTACCTG GCAAGTGCGTACATCCACCCGGTT TTCA |
| WSNP_KU_C8722_14766699 | 2.62E-04 | 361 | tacatcagaagctttcaatttgactcctggaa aagtaccagtatttccatccctcaattcttctt tcatttcatacaagtaccatataataaggaa atgc[A/G]CCCATTATTAACTGGAG AACAAACATATATGATTTCCTTCAT |

TABLE 2-continued

SNP markers significantly associated with heading date

| Marker Name | P-Value | SEQ ID NO | Reference Sequence |
|---|---|---|---|
| | | | TAAGGTAGATGTATGTAATCCACT ACATAAAATGTATGTAGAAAATGA AATTTTTCAG |
| WSNP_EX_C2330_4366134 | 3.36E-04 | 362 | gggatgagaatggctactatgctggatcgaa tggactggagatgcaaccgacagtcgttcaa gctgagaatgggtcttatttgtgttatgttccg ggtta[T/C]GAAAATGGTTATACTGC TTATAGTCCAGTCGTTCCTGGAACT GGCGTGGATAGTCAGTATGTCAAC AAAGAGCCATATTACTCCGCTGTG ATTCCCGTGC |
| WSNP_EX_REP_C101414_86780996 | 4.18E-04 | 363 | TCCATGTCCGAACTTCGAAATCCTT TTTTATTGTATGATCTAATGTACTT TGAAAACTATGTCGGAGGTAATCG TCAACATATTTGTCAACTTCTGCGA C[A/G]AGGTCTTCTCCCATTGGAG GTGCCCGTATGTCGTGTTTGAGAA ACGACAACCAAGAAGAGAGTCTA AAATATCTCTCCTGGATCTCTGTTA GAGCTTCGC |
| WSNP_EX_C29130_38196906 | 2.70E-04 | 364 | TTCGCCCTAAGGACGTTGTTCCTAT CAAAACTGATGGTCAGGTTCCTCC CATGATTCTGCGTGGGCCCATATT GGATGAAGTGCATCAGCAGATTAA TCC[A/G]TGGATATATCAGATAAC TAGAGTTTACAAGGGAAAGGACT ATATGGAAACCGAGTTCATAGTTG GACCAATACCAATCGACGATGAAA ATGGAAAAGAAC |
| WSNP_RA_C17541_26430903 | 6.40E-05 | 365 | TCTATTCAGAAAGCAGGTGCTTGA TGGTAATTGGGACAATGCAGTAGC TACCTTGAATAAACTTGGCCTTCTG GATGAAAACATTGTGAAGTCTGCT GCA[T/C]TTTTGTTATTGGAGCAGA AATTCTTTGACCTTTTGAGAAATGA CAACTTAATGGGTGCCATAAAGAC GTTGCAAAATGAAATCTCCCCCCTT GGTGTTAA |
| WSNP_JD_C12687_12877994 | 3.76E-04 | 366 | GCACGTTTAGCTGCAGCGTTGCAC AACTCGGACATGATGATCAACCGG ACGTGATGTTAGCCATTGGCAGCT ACGCGTAGCTGCATCCAGCAGAAG CATA[T/C]CGTTGTACAGACCTGA GCTCTCGTTGCAGGAAGCAAAGCA TGCGGCACAGGTTTCAGACCTATC GAGTGAAGGCTGCGGAGTCCCTCT CCTGTTCTACAG |
| WSNP_EX_C10500_17163855 | 9.18E-04 | 367 | cttcagtgctaggccaccgttgcgctgcggag aggtagatcaacactcatgtcctagagggat caagacacaattaggagaagacaagcctga aaatgtt[T/C]AGACTTGACCCTCCA CTTATGTAGGCATGAGTTAAATAC ATGGTCAAACCATCGCCTTGAGTT TTGCTACATGGGTGGTCAAATCAT CGCCTCAGATTTG |
| WSNP_EX_C2161_4059735 | 4.64E-04 | 368 | TCTGAACAATTAGATGCCAGAGCG CCGGTACACGTTACGTTAAAATTT GGAATGAAACTATTTGCTTGTTTCT AAATAAAGATAAAACATATGCGAT TGC[A/G]TTCAATATACATCGGAA ACTAAAATCCCGTATGATACTCCGT TGGTGGAGCGCGAGGCTCGCACC CCCCGCCCGAAATGGATGGCAGTG TTCTTCTTCCT |
| WSNP_EX_C5547_9774195 | 2.84E-06 | 369 | ATGACATGAATGCAGTGTTCAAGA AGCTGTCTGATGGCCATGAGGAAA GTACTGTAAAGGCAATGGAGTCCG |

TABLE 2-continued

SNP markers significantly associated with heading date

| Marker Name | P-Value | SEQ ID NO | Reference Sequence |
|---|---|---|---|
| | | | AGAATGATCATGACGGAAGAGAC GCAAC[T/C]GAACAACACTGAATT ACTATCGCATGATTGGTAAAAGGG AATGCAAGTTGAAGAAGCTTATTC TTGGTTACCTTATGAAGCACTCCAC GGTACTTGGGTT |
| WSNP_EX_C4211_7606269 | 6.60E-05 | 370 | tgtcggggttgtttgctttgatccttcgtatctc ttccttgatgaatctgttgtacgccgaaggaa cacgctgcctcttctccggaggacgtgcgtgc ag[T/C]GTTTGTTCCTGCAGCAGAT CGTTTTGCGACGAGAACATCATCG TCGGCATCCSGAATTTGGACGACG ATGAAGAAGAAGACGAACCAAAC TCCGGGTTAT |
| WSNP_EX_C6142_10746442 | 5.06E-09 | 371 | agaaggcacttctggaccatgggcagcaaat agaccctgcaaaattacagttggaaaagga gaggctggaaaaaaggcagcaagaagaga aagaaaggat[T/C]GAAGCCCAGGTG AAGGCCGCTGAAGCTGCTGCACA GTTCAAGTTAGATGAAGAATTAAG GAAGAAGAGGGAGCGAGAAAGA GAGGCAGCACGCCTGGCAC |
| WSNP_EX_C12254_19575022 | 1.16E-04 | 372 | TCCCCAGTTTTGCTATTTATTTTCT CCCCGGCAAGGCTGGGGTATGTA GCGAGTTCGAACGGTCTGCTGGCG ATTCGCCGTAAGTAAGTTGCGCAA GGG[T/C]GCCCTCGTGTTTGCCCC GCCGACGAACTAGAGTTCGGACG GGTGCAAGGAGGGATGGCGAAAT GCGCAAGAGGTGATGTGTGTTTTG GGTGTGTGTTCTG |
| WSNP_RA_C2228_4310870 | 1.88E-04 | 373 | TCTGATTTTGGGGCACTCTATAAG GCCTAACTTGTGGTGGAGCTGCAC CTTCTACCAAAGGTATTTTGTGGTC CAATGCTCTATGAGGTGGCAGTGT TTT[A/G]GGTTCCTCAAACAGATCA GCATATTGCAGCAATAACTGCTGT ATTTATGGTGGAGTTTTAAAATCCT CTGGTGCATCCAAGAGTATGTTGT GGATTTGAC |
| WSNP_RA_C12148_19539667 | 1.12E-04 | 374 | CTGATGGATGTTCAGAATCAAACT TAACCTTTTCCTGTGATATGTATAA ACCATCCAAAATGCCAGATTCCCA CACCTCGCCACCGCGGCTGAGATC GCC[A/G]CTCGAGCTCTCCCCAGG CCCCAAATGGAACTGGGGGTCACT TAGTTGCACATCCTCCATATTCTCC TCAGTTGAAGAAATGGGAGCAGTT AGAACACACC |
| WSNP_KU_C8712_14751858 | 1.00E-04 | 375 | TATCACGTAGAAGAAGGACGCAAT GCTGTTTTACCTGGTGGTGTCTTCC ACCTATAAAATCAATATATAGTCG GCGGCCCAGTGTAGCGACAGTTTG TTG[T/C]TTAGACGGCGGCTTTAG CCTTACTGTTGTATGACTTTGTAAG GTCTTGTGAGAATAATTAATAAAG TGGCCGTATGCATCGCCCAGATGC AGAGGCCGGG |
| WSNP_EX_C34344_42677360 | 1.09E-05 | 376 | CCAAAAGATGCAGTTAAAATTCCT TGTGATGTGAAGCTGGAGGATGA AGCATTGACTGAAGAATCTGTAGA TCAAGTTGTAACTGAGCAAGTCAA AGTTC[T/C]ATCAGATGCTGTACCC GACACTTCAAAAGTTCAACCAGAA ACACCAGTCGAACACGTGGGTACA GCAGCAGAAGGGGACACTGCTCA AGACCTAACTGAA |

TABLE 2-continued

SNP markers significantly associated with heading date

| Marker Name | P-Value | SEQ ID NO | Reference Sequence |
|---|---|---|---|
| WSNP_RFL_CONTIG4236_4881643 | 2.54E-06 | 377 | CCCGCTATTGGCTAAGAGTCTATG TTAATCAGATGTCCCGAGAAGACT TC[A/G]AATCCCTCTCCAGAGGCA TGAAGCATAAGATGCAAAAGTTCT TTGGGGAG |
| WSNP_BE495786A_TA_2_1 | 1.18E-04 | 378 | CCTAAATATTTTAGTTGCCTCTTCA ATGGAGTATAAAAGGAACATTAA GAGAATGATACA[T/G]AACAAGAA AGAACTAACCTTATTTTTAGAATTT TTGTCCATCTTTGTTACTGTTGCTTTC |
| WSNP_RA_REP_C71473_69552690 | 1.07E-05 | 379 | GCCCAAGTTCTTTGGTTGCTTCCTT GTGTCCTCCTGGTGTGAGTGGTTC CATCCAATCTCCATCGATTGAACCT AAAGATGTCTCAAACCCATTTTTTT C[T/G]GTGGCTTCTGAACCTGACA GGGTGGATATGATTGATATGAATG AAGAAATGACTTCTGATTATCTACT TGATTCTGATGATGATGATGCTAA TAGAATCT |
| WSNP_BE490744B_TA_2_1 | 5.92E-07 | 380 | CATCTTTTAATGGAGTTGTGATAT GGAAGATTAATAGTTTTTTTATGG GGAAATCCGGCA[A/G]GTGGAAG ATTAAAAATTAATCTGTAGAGATG TTGCTTTTATTCGCATAATCTGTAA GATG |
| WSNP_EX_REP_C67660_66321934 | 6.02E-04 | 381 | AAACGATTGGATTCACTGAGCTAC ACATCTGCCCTATCAGTTGCTCTCG CTGTGGTTTTTGTTGTTATTACTGC TGGGATTGCCATAATCAAAGTCAT CA[A/G]TGGAACTGTAGCAATGCC CAAGCTTTTTCCAGAAATAGATGA TCTTAGTTCTGTCTGGAAGCTTTTT ACAGCTGTCCCTGTCCTTGTCACTG CATATATC |
| WSNP_EX_C758_1488368 | 1.40E-06 | 382 | GACAGCCATTTCAGCGAGCCCTCA TCCTCCTCTCCTCCTTGATAAGGTA GCTCCCCAAAGAACTTTTGCATCTT ATGCTTCATGCCTCTGGAGAGGGA TT[T/C]GAAGTCTTCTCGGGACATC TGATTAACATAGACTCTTAGCCAAT AGCGGGCTTCTGGGGATAAAAAC AATGAATTGTAGAGAAGACGCCA AAGCTTAGGT |
| WSNP_EX_C12887_20427158 | 6.49E-06 | 383 | CCTTCTCCTGTTCATACAAAATCGA TAAGTAGCAAAACGGATTGTAATG AAGACGGCGCCTTCAGAGTCCAAG GAGACTCTGATTTGAGGTTACAAT CAG[A/G]TCAACAGACAGATAGAT TCCAATCCTCAGGGACATTGGATG CTCTCAGGGAAAGGATGAAGAGC ATCCAAGCCGCAGCTGTGGGGGG CAATTTCGATGTA |
| WSNP_EX_C33778_42210283 | 9.54E-04 | 384 | ATATTCACGGAAAAGATCAAGAAA TATACTCCATTAAACTGCCTGGGA ACCCCAAGCTTGGTGAGGGGAAA CCTGAAAAYCAAAATCATGCTATA ATTTT[T/C]ACTCGTGGAGATGCAA TACAGACTATCGATATGAATCAGG ATAACTACTTGGAGGAGGCAATGA AGTAAGGAATTTACTTGAAGAAT TTCGTGGTAACC |
| WSNP_RA_C10053_16636851 | 7.78E-04 | 385 | TGGCGGAGCAGCTTGAAATGGTA AAGAAGGAGCTTAAAGAAATAAA ATATGAGCATGTGGGAGCAAAGG AGGAGCTTGCTGTGGCAAAAGAG CAACTTGC[T/C]CAGAAGAACAAA GACCTGAAGGTTCTAAGGAAGAA |

TABLE 2-continued

SNP markers significantly associated with heading date

| Marker Name | P-Value | SEQ ID NO | Reference Sequence |
|---|---|---|---|
| | | | GCTTCAGGAGAGTGAAGCCATGC ACACTCAACATGAGCAGCAAATTG GAAGTGCTTCTGAGCCTG |
| WSNP_EX_C31262_40077397 | 1.24E-04 | 386 | GTATTGAGAAGAGTTTGGTAACCC TCTCTTCCACCCCAGAATACATAGT TCTCACCGCCTAGGTAGTGAGTAA CCTCCAAAGCTTTCTTCACTTGAGC AG[T/C]AGCATAAGCATACACCTT GACCTCTGGGCTAGTAGCAGCTCC GTGCATGTAACGTGGATGCATGAA AAGCTGTGCAGTCCCCCACAATGG CTTTATATTG |
| WSNP_KU_C854_1768062 | 8.80E-05 | 387 | TACTTCGGAGGAATGGAACTGTTT GTTTGTCTTTCCGTGTGTTGGTCTT TTTTCCACATCAGTGGGGTCTTAG ATAGCTTTTTTAGAATGCTAAACTT AG[A/G]AACGGAAGTACTGAACA AATCAATAGAGGTTGGTAACAAGT GTTTGAGAGGAAATTTTTGTCTGC AGTCTGCACTAACAAAATCTTGTG GCCCTTTGTTT |
| WSNP_BE445431A_TD_2_2 | 2.96E-04 | 388 | AAAGGTACTGTCTGCCCTAAGTGA AGCTGGGCTTTTTACCAGTGGCGG TTTGGTGAGAGA[T/G]AAGGTAAA CTTCATAATAAGACCTTGGAGACA GACATTTATCACTGCTTTAGTTTTG GAT |
| WSNP_EX_REP_C101746_87053634 | 6.34E-06 | 389 | GCCTGATGGAGTCAAACACTCAGT TGAGGGATATGTTCCAAAACCCAG AATTTCTTCGCCAGATGGCATCCCC AGAGGCTTTGCAGCAATTACTCTC ATT[A/C]CAGCAGACAATGTCATC ACAGCTTGGCCAAAATCAACCTAG CCAGGCTGGTAACCTAGGAGGCA ATGGCACAGGCACGCGGGGAAAT GTTGGTCTGGACA |
| WSNP_EX_C4769_8510104 | 3.82E-04 | 390 | ACAGATCTTGATGCAGCCAAGAGA AGCGAGGAGACCAACATGGTGAC AGCAGATGTTGATACATCCAAGAG AAGCGAGGAACAGAGCAACATGG TCGCCG[T/C]GAAGCTTGATACAG CCAAGAAAAGCGAGGAGCAGACC AGCAGTGTTGCTGCGGCAGGCTG ATTACAGGATGGGCGCATCTGAAC GGAAGCTACATCCAAA |
| WSNP_EX_REP_C104141_88935451 | 6.67E-07 | 391 | GCTGCCTTGTCCTGCTCCAGGACA TACTTAACACTAGTCCCATTCAGTG AAGCTATACGATCAGATATCCAAG TCCGAGATAGTACAAGTACTGCAA CTG[A/C]AAGCAATTGTGCCCCTT GCTTATCAACGATTTTAGGAACCA GTATTTTAGACATTGCAGCAACTCT AACAGGCAAAGGTCTCGGCGAGC ACTGCAATTGT |
| WSNP_EX_C44587_50598716 | 7.56E-04 | 392 | GACCATGCACATATGGGAAGGTG CGAACCATGGCAGACTGTTTCTGG TAATCCGCATTGAAACAAATGAAG AATGATCGTGGAGCAATTCACCAC GCTAC[A/G]TCTGTAACTCAGTGG CTTTGCCATTGGATATGCACTGGA CGGTGTGTGCGCGCATGATGTATC TCAAGATATCAGTTCTCACAGTGA CCAGTTGACTTGT |
| WSNP_EX_C741_1456698 | 1.32E-04 | 393 | agcccatgcaccctagtgccaacagaggata caaaactcaggggaatatcaatctcgtaaag gtcctcttccttcatgctagtgaaatcaagtgt atgat[A/G]CGTAGATTGAGAAATC |

TABLE 2-continued

SNP markers significantly associated with heading date

| Marker Name | P-Value | SEQ ID NO | Reference Sequence |
|---|---|---|---|
| | | | AACAATCTTGGATCAAATGCATCC ACCACGGGCTGTGAAAAGTATCCG TCAAACGCTGAGCCATGCAAGGGT GTAAGATCAACA |
| WSNP_EX_REP_C103972_88799335 | 9.80E-05 | 394 | TAGGCACCGGTAAAGAAGGAGGA AATTTTTTGCACAGAAGCAAAGCA AACTGACCTCTCTCTCTTCCTGATC TGGAACTGTACATAGTATAAAGAA GAAC[A/G]GCCTGTTAGGGGAGG GTAGTTAGTGCCATTTATAATATAT ATTATTAACAAAAAAGAAGTAAAG GAGGCTGATGG |
| WSNP_EX_C3309_6096114 | 2.34E-04 | 395 | AGGTTTCATTACCATAAAGAGGAA ATTTATCAGAAGTATTTGTTGTATA TACRTGCAAAATTAATGAATGATA CAGAGAATGATGAAGTGCATACAT GCG[T/C]GACAGAAATAGAACGAA TGTTGCCTCACCACCATTGTTACCT CCCATCAGTATGGCGACTAGGAAT ACAAAAGACATAATTCAGTCATTT CAGCCTGGAA |
| WSNP_RA_C7112_12318340 | 5.06E-09 | 396 | AAGCCAACCACCTGGGTGATCCAT GAGCTTCCCCAGAATATTTCTACA GACCCTTGTCTTGCTAGCATTCATG CTTCCAGCCTTGTTGTTAGAAGAT GGT[T/C]GATGCTCAGATGAAGAA ATTGACGTCGTTCCAGATTTTTGA GACCGTTTACTTCCCTCCACCTCTG AATCTGTACCAGAATCTTCCGATCC ACTGCTTAT |
| WSNP_RA_C2063_4012957 | 5.61E-07 | 397 | TCAAGTAGTATATTGTCAGGTTTCA TATCCATATGATATATTTGCTTTTC CTTGTGCAGATGATACAAACCTTC ACAAATGCCTCTAATAATTTCATAA C[A/G]TGTCTTCCATTCAAGTCCCC GTAATTCATCTGGAAGATCTGTTT GGGGATCCAGCTAGCTACTCGAG GAACATCCAAGTAGACGAGAGGC GCAGGAAGAT |
| WSNP_EX_C42282_48900922 | 1.26E-04 | 398 | CCAGAACTTTTCCAGGTCATCCTGC TTTAGATGATGTTGGAAGAAATGC CTTGAGACGCTTGCTTCTGGCTTAT GCTAGACACAATCCAACAGTTGGT TA[T/C]TGTCAGGCAATGAACTTCT TTGCTGGTCTCTTACTTCTATTGAT GCCAGAAGAGAACGCATTTTGGAC ATTGGCAGGAATTATTGATGACTA CTTTGATG |
| WSNP_EX_C53983_57032627 | 4.97E-06 | 399 | ATAACTCAACCCCAAGCGACCTTCT AACAAATTCACAGCATACAGCAGC AAACGCTGTCAGAGCTGATGCAAC AGTAACAGCTGACCAGACTGATAC ATT[T/C]GATGAAGAGCTTAAGAA GCTGGTTGCGATGGGCTTTGAAAG GACTCAGGCTGAAGTTGCTCTTGC CGCCGCGGACGGAGATCCAAACG TTGCCATTGAGA |
| WSNP_EX_C34842_43092205 | 4.00E-04 | 400 | GAACACTGGATTCCAGACACCACA GACAATTTYCCTGACCATATTCTCA CTTGAGAGGAATGAACCTCGACGA GTGGGTAGCACCGATACCAGGCCT CCC[A/G]TGCTTCACCGGCTTGTAC GACAGGGAGAACTCTGCCAGGTA GTGCCCGATCATCTCCGGCTTGAT CTCCACCTGGTTGAAGCACTTGCC ATTGTAGATGC |

TABLE 2-continued

SNP markers significantly associated with heading date

| Marker Name | P-Value | SEQ ID NO | Reference Sequence |
|---|---|---|---|
| WSNP_EX_C5446_9616983 | 1.34E-04 | 401 | gccggcagcgcccccttcgtccctccgtcgg cttccccggcgagctaccaagdaaggagga atggttcgtcccttggaagtgcggttcgttccc ttgtc[T/C]GGCTTTGCACCTGGAGG GGATCCACCACAAGGTCCTAGAGC AAAGAAAGTATCCAAGGCTGCACC TGTGTTTGAAGTCCCTGGGTTATG GACACCCGATG |
| WSNP_EX_C97184_84339976 | 3.32E-04 | 402 | TTCCAGCTTCTGTGCTTCAGGGAG CTCAAGACAAATGTTAGAATATTT ACCCAATGGATGATGTAATCTCTA GGTATCTTTTGTGCGCTAGCTGTG CCAA[A/G]CAGCCGTTATGTATGT TCATCTAATTGTCACTTCTCATTTCT CCTGTTAACACTGGTCTTACTTATG CTAGTATAATTTAGGAAACCTGCA TAGTAACAT |
| WSNP_JD_C9902_10674725 | 1.95E-07 | 403 | AYGAGTTCAATGATAATTTACTAAC TAGAGCATCCATCGACTTCTATAG CTTGTGCACTGGTGTTATGCCCAG CAGGTGGAAGCATTGCCGCATGAC GAC[T/C]GCCGACGCTTGGCACAG CAACAGGCGGCTCGTTTCCTCCGG TGACCCGACAACCTGGCAGTTGGT GTAAAATTGTGAGAATCTTTCAGA TAGGGTGTACA |
| WSNP_BE445348B_TA_2_1 | 8.58E-06 | 404 | ATCGATGTTGTTTGTCTATGGGAG ATGTACTACAATAGCTACTGAATCT TGCTTCTTTGC[A/C]AACACATCCA TGCTTCTATCACTTGTTGTTGCATG ACACCCTCTCCATTTTTCAGTAGTT |
| WSNP_BE500291A_TA_2_1 | 1.96E-04 | 405 | CTCCTATTCTCTCTGTCTCTCTCATG CCAATG[T/C]CGCTGTCTTGGTCTC ATTCTCTTCTCCTGATGTGACTG GAAGCAGCCATGCAGTGACC |
| WSNP_EX_REP_C115803_95396724 | 3.68E-04 | 406 | GAAGGAGGATGCCAAGGTCGATA ACTCACTGTAACTCACTTCTTTTAA GTTCGCCTTAAGTTATCTGTACACT GATCTTCAGTTATTTATCTATCCCT TT[A/G]CAGACATCAATGAGTGCA GTTTTCGTAGATCAGYATCCTTGCC ATGGAACCTGCAGCAACACAATTG GGGACGTACAGTTGCTCATGCGAC TCTGGGACT |
| WSNP_KU_REP_C72821_72480395 | 2.54E-06 | 407 | gacgacagtcttccagaaggaacacatcttg aaagtctacagaaacacctaccacgtgacg agccagaagtcacagaaacaccttcagtca atactccgt[T/C]GGAAGCATACTTAG CAGTTGGAGCAACTGAACTGGAA GTTACTAAAAATGAGCCTAGGACA GCTAAAACTGATGCTGAGATGATG GCTGTTGATGCCAAG |
| WSNP_EX_C3906_7086162 | 1.70E-06 | 408 | GATACACCATGTTTTCTCTCGCGGC AATCCGACAAGAGGCGAGCATGT CACATTCTTGCTGCAGAGGAGACG AAGCGTGAAGGCGCCGTGGTTGT GAATA[T/C]GCATTCTTTCCTCCAA CCCCCGGATCTCCCCTCTCCAAAG GAGCTTGGCGAAGCTGGAGGACA CGGGCTGGACACGGAACAGTTTTT CTTCATGCTCATA |
| WSNP_KU_C6825_11858665 | 2.96E-04 | 409 | ttctttgcatgtactgctccattggtttgcagat ttttgggggcattgtgtatgctggwaaccca acactagaagaaacggacctcttcaataatg acta[T/C]CTTCTTTTTAACTTCAAT GACTATCCAAGTGGTATGGTTACT |

TABLE 2-continued

SNP markers significantly associated with heading date

| Marker Name | P-Value | SEQ ID NO | Reference Sequence |
|---|---|---|---|
| | | | CTGTTCAATTTGTTAGTGATGGGC AATTGGCAAGTATGGATGGAGAG TTATTGGCAAC |
| WSNP_EX_C4605_8240189 | 6.60E-05 | 410 | tggttcttgctgctccaattcaacaatgctttc aggatagctcaacaagatttgarcrggttctt ttccttgctctgcttcctctaacatatctggcc gc[A/G]GGCTATCTCTGCATAGTTC TTCTGGGATGCAGACGATTTCAGA ACAGTCTATTTTGCCAATTCCTTCA ATAGATATGGCGTCTGCTACATCA GTAACATC |
| WSNP_BF428726A_TA_2_5 | 6.04E-04 | 411 | TACATAATATAGCATATAGCCTAG CTAATATTCTTGTTTACGCGATTTC TTGAGAACACT[T/C]GAGAGTTAC GTGTCATGTCTATTATCCATTTTGT AATACCCTTGTGATTGTTAGAAAG TA |
| WSNP_KU_C66980_66202298 | 1.07E-05 | 412 | GCCCAAGTTCTTTGGTTGCTTCCTT GTGTCCTCCTGGTGTGAGTGGTTC CATCCAATCTCCATCGATTGAACCT AAAGATGTCTCAAACCCATTTTTTT C[T/G]GTGGCTTCTGAACCTGACA GGGTGGATATGATTGATATGAATG AAGAAATGACTTCTGATTATCTACT TGATTCTGATGATGATGATGCTAA TAGAATCT |
| WSNP_BE405599B_TA_2_1 | 2.86E-07 | 413 | ATACAATAGTATGTTTATGCTTATT GTGGCAATGAAACATGTGATTAGC CTATATGCACG[T/C]ATATAACAGT AAAGCTAAACTTCAAGCTTGTCTT GTGTGGCGATGAGACAATTATGCC AT |
| WSNP_JD_C35319_26397591 | 8.17E-09 | 414 | TCTTTCAAGAGAGGAGCTTGGCTG GGCAAGTTTACCGCTAAATAAAGC TTGTCTACTAAATCATGCGACTTAA GAAAACCCTGGAGTTTGGTATTTC GCT[T/C]TGGTTTGGGTGAATGTA ATTATTAGCTTCTGTGAACAACTCT GTATCTGGGTTTCGTTTCGTCAGT GTGTCGTCGTGAATGTGAACTCTT CTGAATGCCT |
| WSNP_EX_C5378_9505087 | 3.26E-04 | 415 | TTCTCGCAACAATGCCAGAATCATT AACAGAATGTACAATAGGCAAGG CTTCAACAAAATCTGCCTCATCATC CAACATTGCAGGAACTGGGGGAC TCTC[A/C]TCGGCCTGTGGCTCATT AACCGCTTCAGATTCAGCCTCCGCT ACAAATGGCTCCAGCTTGGTGCCT TGATGTTCTGCCATTTGTCGTCTAT CAATCGCAT |
| WSNP_CAP11_C827_513472 | 9.80E-04 | 416 | atacaagcgagagtggtaccttacggccggg atattt[A/G]TTATATTAATTAAAAG AAAAGGGCAAAGTTAGTTAGGTT GTGCCGCCATAGAATGCAATGCAC GCTCCCTTCATCATCTTCATCATCA TCATAATGTGAT |
| WSNP_EX_C29648_38653339 | 9.40E-05 | 417 | TGAGCTCTGGGCGGTGACCGATG GCAAGGTCGCCCCGTTCCCRGGCA CGTTCAAGGAGTACAAGAAGATG CTCACGACATAAACCTTGAAAAAG GACGGG[A/G]CATAGGGGAAGGT GCTCACACAGACATACAGAGACTA TATGTATGATATGTACTCCCTGGCA TTGGAAACTGATGTAATATTATGC TTGTGGCCTACCTG |

TABLE 2-continued

SNP markers significantly associated with heading date

| Marker Name | P-Value | SEQ ID NO | Reference Sequence |
|---|---|---|---|
| WSNP_KU_C854_1768346 | 7.20E-05 | 418 | TACTGATGGGAGGTAACAATGGT GGTGAGGCAACATTCGTTCTATTT CTGTCGCGCATGTATGCACTTCATC ATTCTCTGTATCATTCATTAATTTT GCA[T/C]GTATATACAACAAATACT TCTGATAAATTTCCTCTTTATGGTA ATGAAACCTTTGTGCATACGACAC TCACGTGTCTGATTTCTGTCCAACA ATTGATCC |
| WSNP_KU_C328_679106 | 2.23E-05 | 419 | CGATGGTGATTTCTTGCCAAGGCC CTTCAGGGACAGGAAGTGGTTGA AGTAAACCTGGGGATTTAACATGT TCATGTTTTGCTTGCTGACAGACAT CACA[T/C]TGATGGACATAATCAA CTATGTCTTGCTTCAACCCAGTCCA CACAAACAGTTTCCGAATTTTGTAA TATGTAGCTTGAATGCTAGAATGC CCTCCCACAG |
| WSNP_EX_C3096_5708642 | 1.58E-04 | 420 | CACATATGTGTTCAAGATGCTTTCT CCACCACCAGGAGAGACCTTTGAT GGTGAAGAGGAGAAGCTTCCGGT TCTGGCATCTGAAGAAAACGCGAT GCCT[A/G]AACTAGGTAAATATCC AACAGGCACTCACACTAGTACTGT ACCCGAGGATGAGCCTTTGTTAGC TCTCGAGGGGAATCAAAAAGGCG CTACTTCTCTAGG |
| WSNP_CAP7_C2282_1107112 | 6.40E-05 | 421 | CCGTACACTTAAATGAATCACCCCC TTGCAATATTGCACATGTTGCAAG TCTTACACTTCTATGTATACATATT TACTATTTACATTCCTCCAATGAGG C[T/C]CATATATATGATGATGCTAT ATCCTAACAAATTGCAATTTACAC WGCTTCAGAACTTGTTGAATTCTT CAGACCTCATGTCCTGCCTTGCCAT GCAGGAT |
| WSNP_JD_C9902_10674626 | 1.75E-07 | 422 | CTCCCTCCGTCCCACAATATAAGAT CCTTTTTCAAGTTATACTGTGGGAC GAAGGGAGTAATATTTACAAGATC GCGTCCACTAAACCTATCATGTTA GA[T/C]GAGTTCAATGATAATTTAC TAACTAGAGCATCCATCGACTTCTA TAGCTTGTGCACTGGTGTTATGCC CAGCAGGTGAAGCATTGCCGCAT GACGACYG |
| WSNP_KU_C24239_34199356 | 1.04E-04 | 423 | cagcatgaactgcaagggcatgcttgacagc tccatcttgtttggcttcttttgacaagcttgcc attgatgacaacaggtcacgtttgttattaga gtg[T/C]AGCATGACGCAGAGCAA ATTGTAGGCTGAGAATTCAAAATA ACAACCATTGTTTCCCTCTCTATAT AGCCTCTTCAGTTGTGACTGGCAC TGGTTAAATT |
| WSNP_KU_C5071_9050628 | 1.78E-04 | 424 | GACTTTCGGTCCATAGGTTGAGTG GTAAATAGTCCAGTACCATCTTTTA AGGCTATCAAACCTGTGTACGGAC TTCGGCATCAGTATCGGGGCAGCT TCT[A/G]TATCAGACATAAGCATG GAATTTTGGAGSAACATATGCTAC AAGTATTTTGTTTTACTGTTGTTAT CAGCCCCTGATATTAGCCGACGAG AGACGACTGA |
| WSNP_EX_C31830_40573624 | 1.10E-04 | 425 | TCTTCCTAGCGCCCATCCTTCTACT TTTGAACCAGGATTCAGACATCGT TGCAGGATTCGGTGACAGACAGC GTTACTTCCCTGTGACAATTTCTAT TTC[T/C]GGGTATTTGCTATTGGCA |

TABLE 2-continued

SNP markers significantly associated with heading date

| Marker Name | P-Value | SEQ ID NO | Reference Sequence |
|---|---|---|---|
| | | | TCATTGTATAAGATATGGGAGGAG GCTTGGCCTGGCGCTGGCAGTGG AGGATGGGCTCTTGATATCGGGG GCTCAGTTTGGC |
| WSNP_KU_REP_C101212_88410320 | 3.54E-04 | 426 | TGGCTGGGTTGCGGATGACGTAG CCATCGACCAAGGTATAGAGATCA GACTGCACAAGCAACAAATCAGAT GTAGCCTTCACGGGCAGAAACCTT GAGCG[A/G]GGAACGTTGATGCC GATTGCCTTCTCAAAGAACCTGAT CGCTGCTCCAGCTGCGGTTTCTAG CTGCAGGACTTTCACGCCATCAAC TTCCTTAGGGTTGG |
| WSNP_KU_C39289_47757996 | 6.17E-09 | 427 | CATTGTTCCTTAGTGTTGAAGTATA GCTGTCTTGTGGTGGTAGCACACG AACAGTTGCACGCAGTTCTTGGAT GGCAGACGGTGGAGGTGATGATG TAGG[A/G]GAGCAGTAACCAGTAT GCATTAACACAGCCACAAGGTCTG AATCATTTGTATAAACATCTGTTCC CCAAAGCTGAGCGCCTTTTACTTG CCGATTCGTGG |
| WSNP_EX_C19622_28607997 | 4.54E-04 | 428 | AGTTTGGAGCATGGGGGTTTGCTG CTGCACTAATGGAGGCATTGGGG GTACTCTCTATACATGTATGTATAT TGTTAGTCTAGGATCCTAGGATGT AGAA[A/G]TGAGTCTCCCTCCCTCC CCCATCTGTGTGGAGAGATCGATC TTGTAACTTCACCATACATGTAAAT TTTGCTTAGCAGATGCCAGCAGGG ACGGAAAAGA |
| WSNP_EX_REP_C66733_65077608 | 8.30E-04 | 429 | CGAAGGAGGTGTGGCGAAAAGAC MGATTCCATAGTGTGTGGACCTG AATCCTCCATGCAGGGTCTTTTGG GATGCATGGAGAGCAAGCCTGAG AAGAGCT[A/G]CACTAGACAAGTT TTAAAGCCTACGAGTGTGCAGATT TGCATCATATTGTTGTGTAAGAAG CATTTGTATCTGGTGCTGTGCTGG GGCTTAGGGCCTGCT |
| WSNP_EX_C26818_36041748 | 0 | 430 | ACCCAATGGAGAACACGCCCGATG TAGTGATTCGGAATATCAAAGCT AGTGTTTGGGCACTAACCGGAGCA TTATGGTTAACTTTTTCGGAGATGT CTT[T/C]TCTGTCTTGCCATTTTCCA GGTTTTCGCATACATGAGAAAGTA GTGCATATGTTAGCAGTCACTTGA GTGTGTAAACTCAAGCTCCTTTTTG CTGCTGGC |
| WSNP_EX_C11684_18805687 | 3.08E-04 | 431 | TACTTTGCGATTTTTGGAAGGTGG TATGCTTGCGGGGTTGCATTAGAC TGACAAGCGGGTTCGTTTTGCGGG GTTGATGTGGCTTTCTGGTTATTG GTGA[A/G]AATCGGCCTACTAGCT GAAACGATAGGCGGCCAAACAAA AAGGTTTATCGTGTAGGGGGGCAT CAAATGCGATGAGGGGGAGAAGC TGAAGAAGAGGATG |
| WSNP_EX_C34344_42676379 | 8.40E-05 | 432 | TATGTTGTCTCTGTTGCTACTGAAG CAAGCATTATCGAAAAAAGTACAT CAAAGAGGAGGAGAAAGAAGAG GGTTTTGCCTTCTCCTGAGCTAGA GACTA[T/C]TGATCATATGCAGGA CTCCTACTGGTCTGGTTTGAGTTTG CTTAATCACCCGATTCATAGCCTCA AAAGAGCTTCTACCAACACGAGGC CAAGGCGTAGG |

TABLE 2-continued

SNP markers significantly associated with heading date

| Marker Name | P-Value | SEQ ID NO | Reference Sequence |
|---|---|---|---|
| WSNP_RA_C6788_11804894 | 2.10E-04 | 433 | TTGTTATCCTTGCTGCTGCTCCATT TCAGTTTTCATTGAGGCTGTGTGCT GGCGGGTTGAACAAGAACTGTCAT TGGTTTCGGGGTGGTTTTATTTTG GG[A/G]CAGCTGTGGAGTTGGATT TGTATATTTACGGGGACTGTATAA TTTGGCGGAACTCTGCCGACTCCT ATCTCATGTGTCAGTATCATTCGCT GTGTATACA |
| WSNP_EX_C7756_13218814 | 1.48E-04 | 434 | TGATCTGTTCCATGGCCTTCATGCT TATCGGCGGCTCCTTGCAGCAGCT GGAACTGCGTTTGATCTGTTCCAT GGCCTTCAGTACAGGTACGGGGG GCAT[A/G]GCTTCTTCCACGGCGG CACTAGCCAGTGGCTGCCACGGCG ATAACTTGTGATATTCAGGAACAC TAGTGTCAGTTCTGCTGGTAATGC TGCTGCCATATG |
| WSNP_EX_C35861_43927741 | 1.46E-04 | 435 | ATGACACTGCAGCTCTTGATCTGG GACGTACCAGATGGAGCTCACAAC GCTGGCATCTCTGGTGCAAATGAC AGTGCAGCTCTTGATCACCAACTTC ATA[T/C]GGGACTACCAGATGGTG CTCAATTAGATGCTACACCACAAG AAGCAACTGATGCAGTTGACGCTA CAGCTGCATTTGGTTTGCAAATGC CATCTGATGAA |
| WSNP_KU_C34643_43968242 | 5.84E-04 | 436 | GCGGCAGCTCAAGCTACAGCTCCT CAGACTCGGAGGACAAGAAGAAG CGCCGACGCAAGACGACGCAGAA GAAGAGAAGGCACCGTAGGGATA GCACGTC[A/G]TCCTCCTCCTCTGG ATCTGAATCTGAGTCCGAGTCTGA TTCCGATTCTGACGGCAAAGGCAG CCGGAAGAAGAGCAAGAAGCACG GCGACAAGCGCCGAT |
| WSNP_RA_REP_C75364_72953286 | 4.00E-05 | 437 | TGCGACAATTAAATATGTCCCCAG ATGAAGATCTGTCATTCTGTGATG ATAAAGGAGAAACTGCCAAGGCT AAAAGACCCTGGGATTTTATATCA GCAGG[A/C]CACAAAATAGGAAA GCCAGTTCCTCTATTTAAGGAACT GAAAGATGAAGAAGTTGAGGCGT TTAGGATCAAATTCGCTGGCAGCC AAGCTGAAAGGATCT |
| WSNP_EX_C5192_9203682 | 1.24E-04 | 438 | GGCTACCTGCTGACAGCCACATTT ATCTGTCAGGCCGCTCTCTGAGTG GAATGTTTACAGAAACCTCATATTT GTTTGTAAAAGTTTTAGAACAACT ATA[A/G]TTTTGTGTTTGTATCAGG CAATTTATACACTAGGTGTAGGGC AAAAGRTAGGGACAAGAAAGGTT CGGAAATTTATTTGTAAAACAGAC ACAGCCAATCC |
| WSNP_EX_C5378_9504586 | 6.22E-04 | 439 | AAGCAAATCCAGAAAAACCAATTG GAAATCGACGCGGTATACTGCTCC TCTGGTTTGTATGCCATCCAGTGA CCTGATCACCCTTACAAAGGGGC CTTC[T/C]AAAACCAATTTATACTT GGTCCCAACATGCGTTGCTACTGG CCATGTACCAAAGCGCCTGATTTTC CTCATTTCTTCAAATAGATCAACTG AGTATGCTC |
| WSNP_EX_C4710_8412517 | 8.80E-05 | 440 | GCACCAGTTCCATCAACGCGAGAT TCGATCAAGCGGTGCGAAAGAGA AGACTGATATGTGGCAAGCTTTGA AACTCTGAGCAGCAAGCTCTGTTA TTAGG[A/C]GGCTGCCTCAAGCGA |

TABLE 2-continued

SNP markers significantly associated with heading date

| Marker Name | P-Value | SEQ ID NO | Reference Sequence |
|---|---|---|---|
| | | | TCCCCATTAGGAAGCTGTAGGATC GTTTGACTCGGAGATTGTGGGGA GTGGTGGTAGAGCAATGGGTTCTC TTCCTATCTCGTTC |
| WSNP_EX_REP_C66628_64934660 | 3.16E-05 | 441 | GCCCAACCGGTTCTCCCCATCAGG ATGCCATGTTTTGTATAGGAAAAG GCGGGAGTCTGTCTGACCCTAGCA TCGCACCGCTGTTAGGTTAGCTAA GGCT[A/G]TAGCATATATTTGGGC CCTTTCACATAAGCTTCATCAATCA TCTAGGGTATTGGTGTAACCATAA AGCGGAGCTGTTGCGGAACTTCG GTTGGTGCGGCT |
| WSNP_CAP11_C1182_686503 | 7.56E-04 | 442 | CTCATCCTTCCGCGGCCCGGAAGG ATACCCCTGTACATTGCGTGGAAC GCGGTCCTCCTACAATAGTGGCAA TGCGCCTGCTTGCTTGGTTCGCCG GTTC[T/G]WGAGTAAATGATGCT GTGCTGCTGCGGCGGTGACAGCTT CGGGTGGATGACAGTTACAGTTTT GGGGAATAAGGAAGGGGGTGCTG CAGGAATGGTTAA |
| WSNP_JD_C2863_3822253 | 1.95E-07 | 443 | GTCTTAACAGATAACAGTAGCATG GTCACATTTTATTGTGTCAAATAAG CAAGTATGATTCAAAT[T/C]ACATT GTGACCTCAGAGCTCATGAAACTG AAAACAAAGCTCTAATTGTCCCAA TTTAATGGGATTCTGTTCCGATTTC TCAACCAATATCAAATGAACAG |
| WSNP_EX_C4927_8772847 | 7.70E-04 | 444 | GCAAGATACGCTCCTGAAGGTTTT CAGCGAGGACAAGGAGGAGTTTG CCAGAACGACAGCCCTTTCATCTTC CTCATCGTCGACGTCCCTCAGCAA GGAA[T/C]TTGACAGGTCGGCCTA GGAGCACCCTGGCTCATTCTTGCC ATATTGGTAGCTGATTTTTATTTTT CCGTCTGAAACTGCTCGCCAGATC TTTCTTTTCTG |
| WSNP_EX_C44049_50205904 | 3.72E-04 | 445 | tcagacttctcctcctctgtcttggccctcaac gactgtacccatggggtsacgagcttatcgtc aatgtaggcggcccaaaaacgggcaattgc acgtt[T/C]GTAGGGGTCAGAGGGA AGAAGAGAGGGGCCGACAAGGA ACGCCTCATCGATGTACTGAACGA TGATCATTGACTCGCAAATGGGTT TCCCGTTGTGGACG |
| WSNP_RFL_CONTIG2729_2446041 | 3.20E-04 | 446 | ATGAATGAATCTGGGAAGCACAAT GCCCATCCACAGGCAAGATGCTTC GG[A/G]TGTGTAGACAAGTAGTGT GTGTGCCGTTCGTCAGCCTGCGAT GCTGTTTA |
| WSNP_BE496983B_TA_2_1 | 9.98E-04 | 447 | CACCACAAGGTCCACAACTACAGC TAACTCGGTCGAGATGGCTCGCAC TGCAGCTACTAA[A/G]CTCGTGCT GGTCGCCCTGGTGGCGGCAATGAT CCTCGCAGCCTCCGACGCGGCCAT CAGC |
| WSNP_KU_C30743_40542247 | 8.80E-05 | 448 | CGAACCGCGCAAGGCTTAAAGAG GCAGTGGAAGAACGGGCGCTGAT GGATGAGAATTATCAGGAAGCAA CCGCCATGCTGAAGGCAAAGCTGA GAGAGAC[A/G]TGCCGTGAGGTC CTGAAGCTGAGAGAAGAGCTTAA ACGACCAGAAGCCGCATCAAACTG ACGCAGTAACCTTTCTTCTTCGCAG CTACGTGCTCCTAACC |

TABLE 2-continued

SNP markers significantly associated with heading date

| Marker Name | P-Value | SEQ ID NO | Reference Sequence |
|---|---|---|---|
| WSNP_KU_REP_C103274_90057407 | 3.46E-06 | 449 | TGTTTATAGGCTGCGGCATTTCGG TGCCTCCAAGCCGCTGATAGGGTC GATCGAGCATTTTACAGGCACCTC TCGAGCGTTTGCAGTGCGTTAAGC AATA[T/C]GCAACTTGTGACGATG TCTGAGAACTGCTGCTCTTTATGCT TTTGTTACAAGCAAATATATAGCG CGTACATTAGGGAAAATACATCCC ACTGTCGGGTG |

TABLE 3

SNP markers significantly associated with resistance to fusarium head blight

| Marker Name | P-Value | SEQ ID NO | Reference Sequence |
|---|---|---|---|
| WSNP_EX_C5550_9779698 | 3.36E-04 | 20 | ATGATCAGTGCCTTCGAGAGCGGCTCTT CGCAGGCTCCGCCTTCAGTGCCAAGGAT CAAGTCGGAAGGGTCGTTGGAAGGGAT GCTATCGGCTTCCACCA[A/G]TCCTCCA GACAAGTCATCTGGCAAAGTGACCGTTA CTTCTGGTGATATAGGTTCCGAGTCGCG GTTAGGAAGGCACATCATCAACAAGAA ACCAAGCGCG |
| WSNP_EX_C46670_52108070 | 8.20E-05 | 21 | CCGTAATCGCGTCTAGACCATGGCAGA GTGCAATAACACCGCGACCCGGGCGAC CTTTCAGTCGGTGTCGCCCTTGCCCTTGT CTCGTTCTGATGCAATA[A/G]GGCCCGA AGAAATTTAAAGAGCTTGTACCTTTGAA TATTATAGAGCGTGCACCGAGCAATCGT GATGTTCAAATCAAACCGTCGCCTTCAG GCACTTGAT |
| WSNP_EX_C5060_8985678 | 9.78E-04 | 22 | GTGAACTATCTCAGGGGTGGTTGTAAGT ATAGAAAGGCTGGTAATGTACATTATGT TTGTACTAGAGCATTGTGGTATCCTGTTT GCCGTGGTTAATTAA[T/G]GGCTTGGTA ATTAATAGATGGAAGATGATGTCGTTTT GTCTTGTGGCAAGTGTGATGACACATAT TGTAGGGTTGGTTGAAAAGTATATTATG TTACTAG |
| WSNP_RA_C8484_14372815 | 9.10E-04 | 23 | ACATTTGATCTTGTCTCCAAATCATCATT GATAGAATCATTGAACCCTTGTAAGATA RCTCCGCGCTTTGCTGAAGAATACCTAT CTGTCTCAGGTCCCT[T/C]ATTAAGTTTA CCGTAGCAGCTATCACAGACACGGTAA GGCTTGTTTGGGTTTGGTGCTAATGAAG CCTTCAGAGATTTCTTACTGCTGCAGGA ATGACAA |
| WSNP_EX_C11976_19193550 | 1.18E-04 | 24 | GTTTCACCATCAGCCCTCTCGACACCGA TGGGACTGAACCTCCCACCAGACAATCA CCGCCATGGGGGCACTGGCATAGGCAG TGCCCCTTTCTACTGGG[A/G]TGGTGTT AATCCTAGCAGCAGCGGTAGTACCGGG AGCAGCGGRAGCAACAGCATGGGGTTC GAGCCACAGAGCACGAACTCAATTCTG GAGAACAGTGTA |
| WSNP_EX_C20975_30093113 | 9.60E-05 | 25 | ATGCATGTCTGCTTTCTTGTGAGGARAA GTGCTCCGGTAGAGAAACTAATACAGTT TCTTCAGAAGTGCATCTAAGCTCATCAA CTTTAGGACTGGTGCA[A/G]TATTTTAT GAATTAGTTGGTATTAAACTGTATCTCC ACCAGAACTCAGAATGTTTCCTGATATG TTTGATGCTTAAATAGAAACAATGTTCC TCATGTCA |

TABLE 3-continued

SNP markers significantly associated with resistance to *fusarium* head blight

| Marker Name | P-Value | SEQ ID NO | Reference Sequence |
|---|---|---|---|
| WSNP_EX_C16581_25100502 | 2.40E-04 | 26 | CAGAAATCTGCAGCCCTTCAAAGATCGG CCCTCCCAGGGTATCTTGGGAATGGAAT GACATCTCTGATGTTCTCCAGGCCCGTG GCGAAAAGGATCATCC[T/G]CTCGAACC CCAGGCCGAACCCGCTGTGCTTCACTGA GCCAAAGCGTCGGAGGTCCAGGTACCA CTCGTACGGCTCCAGAGGAAGATCGGC GTCCAGTATC |
| WSNP_EX_C17452_26163465 | 3.36E-04 | 27 | TGAATGCATATTGCTGCAGTGAAGTTAA TTCCACAAACAACACTCCTGACTTGCTTA TCTTTCAGAGCTTCAACTAGTGTAGGAG AATTCCTATCATCAG[T/C]ATCACCATGT CCTAACCGGCCATTAGCACCYTTACCCC ATGTATACACCTCTGTCCTGGAAGTCAA AACAGCAACATGATAAGCGCCACATGA AATCTCC |
| WSNP_KU_C4951_8856170 | 2.86E-04 | 28 | TTTGATCCAGCTGGATAGAGCCCGCAGA ATGTTGCGGGTGCGATTCGATCTTCACT AGCCTGGTCTGGACAACTCAGGATGCTC CTGTATGTTATAGCAG[A/G]TTTGCATG GCGGTCATCCCATTATAAACGATGAACT TCCATGCGAATTTGAGAATGTTGTACGG TGGTGTGAAGCCTGTTGATATATTGGTT ATATGGCT |
| WSNP_EX_C18733_27607958 | 1.57E-09 | 29 | ACATTGATTTGTAGCTGTCCCCGTACAC CCAGATATCTTCAATAATTGGAGGGAAG ACATATACTTTCTCCAGATACTCAACTGC GACATACTCCCCTTG[T/C]GATAGCTTAA ATATGTTCTTCTTTCGGTCAATAACCTTC AGGATTCCATCTGGGCTCATCTCTCCAA TATCTCCTGTATGAAACCATCCATCAACC ATGA |
| WSNP_KU_C39862_48205590 | 7.98E-08 | 30 | ATTATATACCATGTTCTGAACAGAGGAG CGGAGTTATTGTAAAAACTATCTAATGT TTAGTTGCTTGTATAAAACACAAGTTTT GAAGAAAATAGGATAT[A/C]TGTGTTGT GAATACATGGCCTGCAAATTCCAGTG CTAACAGCATAATATTTCAAATGTGGAT GTAAGGCCGATCAGATTTCACCAAAGTA GCCATGGG |
| WSNP_KU_C16938_25916279 | 2.02E-04 | 31 | CTGCTTTCCACTGAAATCTCCTATCTGCA ACCATACACACTGTTGCTCTTCTTGCTCA ATTCTGCTCTCAGCAACCATTTCYCCATA TATAAGTCACTAT[A/C]CCCTCTGCATTT CCCACCCCTTCTTCAGCCATGGATTCCTG AAGAAGCTCCGTGCTACCAGAGGAGGC TTCTGCTGTGAGCAATTGCAAGCTGTGT GAGT |
| WSNP_EX_REP_C67036_65492436 | 6.06E-04 | 32 | CCCATTAGACCCGTTCAAATATGGCTCT CCTGAATTTCTTGGGCTACCTAAATTCTC AGTTGCCATTGATATGTCATTAACAGGC ACTCCAGAAAGTGGT[A/G]GCAGTCTAC TGTGCTTAACTGCCCCTGCCCCTGCTCCT GCTCCTGCTCCTGCTCCTTCAGGTAGCTT CTCTGCCATACCCTTCAATTGTGCAGTG AGCGA |
| WSNP_JD_C4485_5618761 | 5.42E-04 | 33 | GTGGGTTGACTATGCCAAGTTTATAGGC ATACAATAAGTTGAAGACAGACCTAGA ATTGCACAAATCATTCGCAATGTTGATT CGTCGCTACGCCATATC[T/C]CATATCCT TACCGTGCTTCCTATCCTGACTCATCTGC CTTCATAGGAGACACTAACGACAGAGG TCGATTGCTTTTGCTGGAAAAGAAAGAT GCGTGCAG |
| WSNP_KU_C16938_25916260 | 1.32E-04 | 34 | GTCGCCCCCTAACCTTTCCCTGCTTTCCA CTGAAATCTCCTATCTGCAACCATACAC |

TABLE 3-continued

SNP markers significantly associated with resistance to *fusarium* head blight

| Marker Name | P-Value | SEQ ID NO | Reference Sequence |
|---|---|---|---|
| | | | ACTGTTGCTCTTCTTGCTCAATTCTGCTC TCAGCAACCATTTC[T/C]CCATATATAAG TCACTATMCCCTCTGCATTTCCCACCCCT TCTTCAGCCATGGATTCCTGAAGAAGCT CCGTGCTACCAGAGGAGGCTTCTGCTGT GAGC |
| WSNP_JD_REP_C63201_40318622 | 9.12E-10 | 35 | TATGACTCAAAACTGTCRGAACAGACAT GGTAACATGAGCGCTGAAAGGCGAGCT TAACAAGTTTTACAGCTTAGTTGGCTGC CTGTTCTTCTTCTTGAT[T/C]CCAGACTTT GAAACCTGGAGGCTGCGGTACACGGCG CTCAGCCTTGCAAGGGCCGGCTTGGTCA GATCAGGCCTGTAGTAGTTGTCGCAGAC CTGGTTCT |
| WSNP_RA_C10861_17763060 | 1.43E-08 | 36 | TGAACGATGGCGTTAGTGAGAAGTCAG TGTCATCTACAGCTCAGGAGTCGTCACA AGCCGGAGGACATGGTGCGTCAACACC CTCGGATGCAGAAAGGGA[T/C]GAAGT CTCCATTTCAAGCCGATTGTTGGAAAAT AAAAATGCAGGTACTATGAACCAGGGC CTGTCTGCTTCTGATATCTCCCACACGGC GGAGAGCTACA |
| WSNP_BE517627A_TA_2_1 | 8.40E-05 | 37 | TTTACGGATTGTTTAATTAGTAGTTGGC ATAGTTGTAGTTTTCATAGTTTGCTGATG CAT[T/C]CTATTTATTCAGTTTTTGGACG CTGATTTAAGTACTATTACTATTTCTGGT TATGTAGCT |
| WSNP_EX_C2592_4822528 | 7.22E-04 | 38 | ATTTATCATTGCCAAATGGTTCAATCCCG GTGATGTCATTGCTGGATATGCAAGGTC TCATTGGGCAAGGTATTCGAAGTTCTTA AGTGCCTAGGAACCT[A/C]GCTGTGCTT TTGTATTGACGTGATTAGCAAGTGTATT TACCGAAGCATAGATGTAATGTGGGTTA TGTGTAGCACCGAATCTGAGATGGCTGC AATCCAG |
| WSNP_EX_C21092_30220342 | 1.94E-04 | 39 | ACTCCTACATGTCCCCTGGCAAGAAAGA GGGCAGCACATCCATTGATTTGAGCACT GGCAGTGCAAGCAGTAGAGGAAAACAT GAACATATTTCTTCTGA[A/G]CCAAAGA CATCCTTGCAGAAAAATCCCAATGGTCC TAATGCTTTAGGTGACTTCTCTGAGCAA AATAGTCCCTCCTTAGTTTATACATATCC TGATTCTG |
| WSNP_EX_C56928_58852277 | 1.56E-09 | 40 | GTGGTTTGCAATTGCCTGGTTTTAGCT ATATGGCATTGTGCTTGTAGGTGCATGT AGATGCTGGTACGGATCATGTTGTAAA GGCTAACAATAAGTGCT[A/G]CCTGGGC CAAAGACCAAATAGGAATTTTACCTTAC GTTTCATGGATTCTTTCATGTTTATGGTT AATTTGGTGGTTCCACAGGAAACT |
| WSNP_EX_C1064_2034431 | 7.19E-09 | 41 | CTTGAGTTGTAAAACAACTGTACATACT AGGTCAGGATGGTGTATATACTCCCTTT TTTCCTCCAAGTGTTCAGTCAGGGAGTA TTGTCAACTGGGAAAT[A/G]ATCCAGAT CATCCTATTTCTAGTTGAGATTACGTATA TGCAGAACCAAAACTATAAACAGACATG ACCCCCAGTAGCATAAGTCTAYTGCATG CCTTACA |
| WSNP_BE399936A_TA_2_1 | 8.82E-09 | 42 | AAGAACGTACTAAACATAAATCAAGAAC CACACCCTAAATCTACCGCTATTACGGC CAAC[A/G]AAGGCGCCCAGACCAACAC ATACTTGCAGGCATATAAAGGGTTACAG ATCAGACGAAATA |
| WSNP_EX_C33196_41722217 | 5.50E-04 | 43 | TAGAATTTGGACGCTAGTGTCAGAGTTT GAGCAGTATGGCACCATCAAGATCCCTT GTGATCTTCCCTACAAAAAAAAGATCCC |

TABLE 3-continued

SNP markers significantly associated with resistance to *fusarium* head blight

| Marker Name | P-Value | SEQ ID NO | Reference Sequence |
|---|---|---|---|
| | | | TTGTGATCCATTCTGC[A/G]ATGGGGCC<br>TGAACAGCCTTTTACGTTTGTGAGAGTC<br>GAATCTTGTGTTGCCATGTGGAATGTTT<br>GTCTTTGTTTCAGAGCAACTCGTGGTGC<br>AGTATCTG |
| WSNP_EX_C7091_12199032 | 1.90E-04 | 44 | AAAGGATACTGCTAAGCCAGTAGAAAG<br>TAAGGCCCAGTCTACATCGGGAATCGA<br>AGACTTATTTAAAGACTCGCCAGCTGTG<br>GCAGCGTCTTCAGCTCCA[A/G]TTGCTT<br>CCAAATCAAACCCACAGACAGATATCAT<br>GAGTCTGTTTGAGAAGTCGAATATGGTA<br>TCACCATTTGCTATCCATCAGCAGCAGC<br>TTGCTTTTAT |
| WSNP_EX_C342_670415 | 4.72E-04 | 45 | GGGGGCCATGGTGGGATTTGGACCAGG<br>TTTCACCATGGAGACGGTGGTGCTGCGC<br>GCAACTGGCTTTTTAAAGAAAAGTTAGA<br>ACTTCATTAAGCACAAA[T/C]GGGAGAA<br>CAAGAACAAAGTCCATGCTCTCAACTGA<br>AATAACTTCGATACTCTACTATTATGTGT<br>GCACACTCTAAGTGACTCATAACAATAA<br>GTGGTTAC |
| WSNP_RA_C58188_60005934 | 4.10E-09 | 46 | GACCTTTTTTCCAACCGCCAGAAGCAGT<br>CAGAGCTCATCAAATGAAAAAAAGCGA<br>CTCGTCTCAAAGTGCTCAGAGCACGAAA<br>GGTCCTGGTGTTCATGA[T/C]ATGCTTTC<br>CCCAAACAATGGTATTGGGCATCCTAAA<br>CCCTTCTTCCAATCTCAGGAACCAGTTGC<br>ACCACAGCCAAAAAATGAAGCTACATG<br>GGTGTACC |
| WSNP_EX_C1064_2034518 | 4.00E-09 | 47 | TCAACTGGGAAATRATCCAGATCATCCT<br>ATTTCTAGTTGAGATTACGTATATGCAG<br>AACCAAAACTATAAACAGACATGACCCC<br>CAGTAGCATAAGTCTA[T/C]TGCATGCC<br>TTACATAACACCCACTGTAATGATCTGT<br>AGATCTCACCAGGACGTTGCCTATTTTC<br>ATAGCTCAGAGGAAGCAACATTCCAGTC<br>ACAGAAAG |
| WSNP_CD452951A_TA_2_1 | 1.14E-04 | 48 | ATCAGATGACCAGGCAATACGAAATAAT<br>GTTTCTTGGAGAAATGCGGAAGATTACA<br>AGAT[A/C]TCTACGGTAACTTATAACAT<br>ATTACCTCCATCCCAAATTACTTGTCTTA<br>GATTTGTCTAA |
| WSNP_RA_C19083_28215239 | 3.00E-04 | 49 | GCTTGAGAACTGATCCTTGATCCTCTTCA<br>CTCAGCTACCAAGCTATGTGTATCTAGC<br>GCTCATCTTAATCCTTGATCCTTGATCTT<br>GTCAGTTCTTTCAA[A/G]GTTTGCAGCT<br>GGGCTCCCGGTGGCCTAAGAGTGGTTTT<br>TATCTGTGTTGCTTTAATGGTTCATGTGG<br>TTTGTACGGGCAGTGTGTTCTGCTCATG<br>TATCT |
| WSNP_CAP7_C7742_3467376 | 1.08E-04 | 50 | GATGGTGACATGCTGGTGCAATTCTTAG<br>AGCTCACCAGTGAGCAACAGCAAAACT<br>GTTCTTGATGATGGGTCTTCAGTAAAGG<br>CACCACACAGGTCTATC[T/C]CCGTTTTC<br>CAGGTCATGCGAATGTTGGAGCGGGTC<br>CACTATGCGCTGAACYGAGGTTTTCTGC<br>AACCAACTTGGTTCACTCATACCACTGG<br>ACATACCGT |
| WSNP_EX_C45617_51361414 | 1.42E-08 | 51 | GGAGCCTGAGCCATGGCTGACCCATTCA<br>CTGCTGTGCCTACCTCCTTGCCGGATTTG<br>GTGATGATGCCAAAGGAAACAATGGGT<br>TGTTGGGATACCCGGA[A/G]TTATCTTC<br>TATCAGCACTTGCATTCAAAACCCAAAC<br>TGACCTTTAATTTAATGGAACRTACGTA<br>CATTCACTGATTTGTATACTTATTAGGTT<br>GCCCAGA |

TABLE 3-continued

SNP markers significantly associated with resistance to *fusarium* head blight

| Marker Name | P-Value | SEQ ID NO | Reference Sequence |
|---|---|---|---|
| WSNP_EX_C23720_32957892 | 1.08E-04 | 52 | TCACCTTCTGCTTCTTCATTGGCTTAACG TCTTCATCAGACTTTTCATCCTCAAAGAA ATCATCATCTTCATCAGCACCATCTTCGT TGCTATCGTCGTC[A/G]TCATCATCATCA TCCTTCGACGACCTCTTCCTAGCTTTCCG CTTTTCCTTCATTTTTTCTTGATGCATCTC CCAGACAGTCTTCTTCTCGCTGCTCTTCC |
| WSNP_RA_C58188_60004916 | 8.60E-05 | 53 | GATGATCTAGGCGACTCCTGCAACGAA GAGATTGCTAAGCCATTTTGTTTGAATG GCCAAGACGCATTGGGTTCAAATGTCTC TCCTGCCACCATTGTTT[A/C]TGCAGGA GATGGCTCTGATGGCTTAAGCGTGTCAC AGGCTAACGGTGCTGAGCCCCCTGAATC TACTGCAGCCGATGGGTGTTCCAACAAA GACATCAGT |
| WSNP_RA_REP_C106961_90622638 | 8.20E-04 | 54 | TGCTTTTAAGATTTGTCATTATGCTGGA GAGGTTTCATATGATACAACTGGGTTCT TGGAGAAGAATAGAGATCCACTGCACA CCGAGTCAATTCAATTA[T/C]TCTCTTCG TGCAAAAGTGATCTTCCAAAAGATTTTG CGTCTGTCATGATTGCTGATTCTCAGAA TAAATCAAGTTTGTCACGTCACTTATTAG TTGATAC |
| WSNP_EX_C21786_30948397 | 3.22E-04 | 55 | TTTACTCTGAAACGGATGACATCTGTAC GAAGACCCAATGCCCGGCAACTTCTGAT TTTGAGCTATCTCACTCGCAAACCTTACC ATCAATCACTCCACC[A/G]GGTTCTTACA CCATTCAGATGAAGATGCTCGGAAAGC ACGATGAGGAATTGAGCTGCATCTCCTT CGGGTTCAACATTGGCTTCCTTGCGCCG GTTGCCT |
| WSNP_CAP12_C5344_2430233 | 6.18E-04 | 56 | AATCAAGATGCCCATCGAGGAGTCATG ATGCATTCGATTGGATGACATCACTTCT ACTCTTGTACAGTACAAGTTGTACCTGC TGTACGTCGAACGTCGA[T/C]ATGATCC ATAGCCACCCCATTAGTAAAGAAGTACT TCCTCCGTTCCCAATTACTTGTCRCAGAT ATGCATGTATCTAGATGTATTTTAGTTTT AKATACA |
| WSNP_EX_C20649_29731279 | 6.42E-04 | 57 | CTTGTCCACTTGCACATGCTAGCTCTTGT TCCGTCTGYGAAACTTGCATAAGCTTCCT TTCCTCCACCATTCTGCTCATCTCGCTCA CCAAAGCAACATG[T/C]TTTGTCACATTT CCATGTGTCTTTCGATATTCAGGATAGTT GCTCACAAATTTTGCCATATCATCTATAC TCTGAAAATTCTGGCTGCTTTTTGAAAG AT |
| WSNP_EX_C1064_2034730 | 4.86E-04 | 58 | ACTGCCTGACCACCATGGTTGGCCACTG AGGATCACTGCACCGTGCCTGGGATGTT AACCCACTCCAGGTGCAGGATGATCTCG CTGGTGTCGGTGTTCC[T/C]CAGCTTGA GGACAATGTTCTGAGAGACCTTGCCGTC TTTCCATGTGATGTGGCTCTCGGTGGAG AAGCAGTTGCCCTTGTCAGGGTGGATC GTCTTCATC |
| WSNP_EX_C21721_30882221 | 3.36E-04 | 59 | TCTGATTTATGCCAATGAAGTTGACCAA ATGAGAAACCTCAATGATAAGTAATTCT TTAATAAAACATCTAACTATAATTATGCT TAAGATATTCTAGCT[T/C]TCTACATGGT TAAATTATTATTCTATTACATCATTATAC ACTATCCTATAATTTTAAATGGCTAGAA ATTTCAGTCTTCTTCTGGCTAATTGTTTT TAA |
| WSNP_KU_C44873_52048221 | 5.06E-04 | 60 | AACTCTGCCCTGGCTCGGAGGCTCTTGT GTAGATCGGGCAACAATTTGTGCTGTAT GTTGTGAAAACAGTTTAACTAGGTGTGA CTCATGCCATCTTATC[A/G]CGCTCTTTT |

TABLE 3-continued

SNP markers significantly associated with resistance to *fusarium* head blight

| Marker Name | P-Value | SEQ ID NO | Reference Sequence |
|---|---|---|---|
| | | | TTACACTTCAATTCATGTTCATATGTTGT TAATAGCTATTTGATTGTTTGATACTTGG AAMMWWWRCCTACTTGCTGTGCTAAT TGATAAT |
| WSNP_EX_C11437_18454413 | 1.18E-04 | 61 | CCTCTACCTTCCTGTGGTAGCAGTATTTC TCAGGGAGGATCTGGCGAGGAATAAAG CAGCGAGAACCAAGATAGTGCTGGAGC AGCAGCACAGCTGCTTG[T/G]ATGCTCA TGAATGTTGTCACAGCTATGCACCATTT CTTGTCAGGCTCAATGCGCATGAAGTTG CTAGGACAACCAAATATATATAGCGCGA TGGCGACCC |
| WSNP_EX_C3044_5620102 | 2.24E-04 | 62 | AGGTGGGTGAGATATGTGACGCAGGCC AACTCGTATGTAGCTCGTCTATGAGGAC ATTGTACAATTCCAAAGGCATTTCCCAC CTGTTCCTTGTGCAATT[A/G]TCTTGGAC CGACTTGAAGCTTGGACAGAGTGACAT GTATTGTAACTCTATAGTGGGATCCCAA CATCACTCTGCTCCTCTAGCTTAACTTTC TTTTAGTG |
| WSNP_EX_REP_C67635_66291944 | 5.54E-04 | 63 | CTTTGAGGGATATTCATGATATATCACTT AACTTGAAGATCTCCTTGGACAGTGAAA AATCAGGCAGCATGTCAAAATATGGAA GGAGTTCAACCAGTGA[T/C]AGGAGAA ACCTTGAGGATGCTGTACAAAAATTTTC AGAAGCTGTTAGTGCTGGCACAAAGGA TGAGTCTGGTGAGAAAGCTGGGGCCAC CACAGGCTCCA |
| WSNP_EX_REP_C67635_66292689 | 4.06E-04 | 64 | tgtacagccatgatggcagcaagttgaacttcatac ctgttctagcatcacgatcccaagcactaaggtactt gtatataaggtggggcgtagagctgtc[A/G]AAC ATGACGGTGGTTGTTGGTGAAAGCGGC GATACAGATTATGAAGGGCTACTCGGA GGCGTGCAGAAGACCATCATACTCAAA GGCTCATTTAATTCCG |
| WSNP_CAP11_REP_C7339_3306558 | 4.13E-11 | 65 | GTACATCCATCAAGTTGCACTTCTTCTTA GCAGGGGTCGATCGATGTACATCATGT GAATAATAAGCAAGAACATGCTGCTAC GCTGTCTGTACTGTTTT[T/G]CACATAAA CGAAATGCAGTGATCAATTCGTTCGTCT TAGGG |
| WSNP_EX_C11229_18163892 | 3.68E-04 | 66 | GTGATGGCGTTCATGCCGGAGCTGGGG CCATTCGATGTCTCTGGTAGCTAGCTAG TGTTCTGCTCATTGTGGCTGCTGTTGCTG TGCACCGGTGGCACTA[A/G]ATTCCTGG CAGCAGTATTTCAAGCTTACTCTTTTGTT CTTGTAATAAAACGTTTGTTGAATGTAC CTCGCTCAAATAAGTGCTCTTAGTTAGA ACTATCG |
| WSNP_BF293133A_TA_2_2 | 9.94E-04 | 67 | CCCATCTTCTTCYCCGCTTCTTCTTCCAGC AATGGTGGTGGACGGTTTTCTGAATCCT GG[T/C]AGTGTCTCTGTTTCTTCTTCTTCT TCTTCAGGAAGGACAGGCCGCCGCTCA CCTTCTCGC |
| WSNP_BF292295A_TA_2_1 | 3.38E-04 | 68 | GGTTTTCATCTTTGTTTTTATATATATCC GCTCTTCTTCAGGAAAGCAAGCCTAAGC CAC[A/C]TCCGAAGAGGAGCCAGCCTG AGTTCCTGAGAAATATTACAGTTTCCGT GAAGCCACGAGC |
| WSNP_KU_C18473_27773912 | 6.66E-16 | 69 | AGGCGACAGATGATTTTGAACCACAAT CCAGTGAAGCCGTCCATGCATGGCAAC AAACGTGTTTGCAAACCGCTAGATGGGT CATCGTGCAATGGTCGT[T/C]CACCCTAT ATGTCATGTGCACAGTAGTTTCCTAGAC |

TABLE 3-continued

SNP markers significantly associated with resistance to *fusarium* head blight

| Marker Name | P-Value | SEQ ID NO | Reference Sequence |
|---|---|---|---|
| | | | CGACAGAGTGCAGCAAGGCAGTTTAAG AAGGAAGTGATTGGGATTTTGGACGAG ATGAATCGAT |
| WSNP_KU_C663_1368085 | 3.28E-04 | 70 | AGACGCGGCTGCTGCGATTCACAGGAT AAGGGATGCTCATGCACATTAAGGTATA CTAGATGACATAACGAGGAAGCCAATA AATATAAGATATAACTGC[A/G]CATAAA CGCAGGTCCTTTTTTGCTGAAACAAGTG TGTCACTCACGCGCTTAATTGGCTTTGTA GTGTTTATTATGTATTCCAGTCTAGGTGT GGTTTAGC |
| WSNP_EX_C7021_12096881 | 4.15E-13 | 71 | AATGTTTCTGGTCTGGAATCGCTGGACG GAAGCATTGTTAGCGAGATGGAAGGTG AGAGCACCATCGACCGGCTGAGACGAC AGATTGATCTAGACCGGA[A/G]GTCGAT ACACCTCCTCTGCAGGGAGCTGGAAGA AGAGAGGAACGCCGCGGCGATCGCTGC AAACCAAGCACTGGCCATGATCACCAG GCTGCAGGATGAG |
| WSNP_RA_REP_C72670_70836439 | 5.40E-05 | 72 | TGACATCACCTGTAGTCTCTTTCTCTCGT GCCATTTCTTTGCCTGGCAATGGCAGCC AGATGACCCGTATGCACAGATTATTTGG TCGTGCGTCGCAGCG[T/C]GGTTGTTCA TCTGGCCAAATATTRCTACAGATAGAAG GATTCTGGGAAGGAAGCCCTGTGAAAA GGATGATGGGCACCATCATTGCAATTGT GTATTGTT |
| WSNP_EX_REP_C66331_64502558 | 3.51E-14 | 73 | ATAAGCAATTGTGGGCAAAATGCCGTC AGAATGGTCTGGATAATATCCATCGATT TTCTTGGCCTGAACATTGCAAAAACTAT TTGTCACGGGTTGGTAC[A/G]CTCAAGT CTAGACATCCACGATGGCAAAAGAGCG ATGATGCTACTGAAGTTTCTGAAACAGA TTCACCTGGTGACTCTTTGAGGGATATT CATGATATAT |
| WSNP_BE489326B_TA_2_1 | 9.82E-04 | 74 | TGGAATTAAAACTGCAAGAAAATTGATGA TCAACTATTAAATAATAACCTGTGGGGA TTTG[A/G]TTATGCTCTCCTAAGATTAGG ATTGTTTAAATCAATCCCTGCAAGCCCC ATCAATATGTT |
| WSNP_JD_REP_C63654_40605158 | 7.60E-05 | 75 | GCCTGGAACTTGCCAACTTGAATTTGAA GAACAGTCGTGGGTACACAGCACTCCA CCTAGCTGCTATGAGGAGAGAACCAGC TATTATTATGTGTCTCTT[A/G]AGCAAAG GAGCAGTGGCGTCGCAATTGACAGATG ATGGCCGCCTTGCAAGTAATATTTGTCG AAGATTAACAAGACTAAAAGATTATAAT GCAAAGATGG |
| WSNP_JD_REP_C50820_34666611 | 1.18E-04 | 76 | TCTCGTGCCATTTCTTTGCCTGGCAATGG CAGCAGATGACCCGTATGCACAGATTAT TTGGTCGTGCGTCGCAGCGYGGTTGTTC ATCTGGCCAAATATT[A/G]CTACAGATA GAAGGATTCTGGGAAGGAAGCCCTGTG AAAAGGATGATGGGCACCATCATTGCA ATTGTGTATTGTTAATTGTACACTAGCG GCGGCATCA |
| WSNP_EX_C19773_28772235 | 4.66E-04 | 77 | CCCAGCTAAGCAGCCCAGCATCGATGGT GGATCTCTTGAGGTCGCCATCGCCATTG ATGACAAGCAGGGTGAGAAGGTTGCGA AGAGTCTCACTCCGCTG[T/C]GGAGGTG GAAGAGCTACCCCAACACCCAGAACTCC AACACGGGGAGCAGGAGGGGGAAATG GTCCAAAGACCAGTCGGACGTCCTCCAA GTGCACGAAGA |
| WSNP_BE638137B_TA_2_2 | 1.90E-04 | 78 | GAAGATGGAAGCAAATCTGGAAGAAGG AAGTTTGTCCCCGACCCAGCACGCCGCG |

TABLE 3-continued

SNP markers significantly associated with resistance to *fusarium* head blight

| Marker Name | P-Value | SEQ ID NO | Reference Sequence |
|---|---|---|---|
| | | | CAAAA[T/C]AAAATGATGACTCTAGGGA TGAGAGGAGCAGGGCCGTGCGTTCTCT GAATTCTRTGCTGA |
| WSNP_EX_C5461_9636197 | 8.63E-09 | 79 | GAATATATGTCGCCACCATCTGATAAGT CTACCACAATGCACTCACAACACGATCT ATGAGGTAAATAGGTACAGTAAAACAG CATCCACGGTTCAAACA[T/G]AAAAAAT AAGCCATGTCTAGCCAGAGCACCAAAGT TTCCCGCAAAACAACTATGCCGGCCTGT ATCAGAAGACACCTCCACCTCCCTACGG CTGTGGATG |
| WSNP_RA_C21347_30731133 | 9.00E-05 | 80 | AAAAAGGCATGTACTCAGACGATGATG TGGCAGATCCAGTCTACAGTGGCGTTTC TGGTGATGAAACTGATGAATACTATCAT CATGATGACTATGGTCA[T/C]TATGTGC GATCCCCATGAGCATGTTGTCCAGCCTG CTGAGCTATCTGGTCAACATGTGAAGCT CTATATGCATAGCTTCACCACGAAGGCT TGCTKCTTC |
| WSNP_EX_REP_C68829_67704044 | 1.64E-04 | 81 | atcgtgtgcgattgagattgcccattgaaccacaaa gtgcgctagttaaaataatatacgctggtgtaaatgc tagtgatgtaaacttcagctccggacg[A/G]TATT TCAGTGGTAGTGCTAAAGAAACTGCTGC ACGCCTTCCGTTCGATGCTGGTTTTGAG GCTGTGGGAATTGTTGCTTCTGTTGGAG ATGCAGTGAGCC |
| WSNP_RA_C21347_30731229 | 2.99E-08 | 82 | GTCAYTATGTGCGATCCCCATGAGCATG TTGTCCAGCCTGCTGAGCTATCTGGTCA ACATGTGAAGCTCTATATGCATAGCTTC ACCACGAAGGCTTGCT[T/G]CTTCTTAG CAAGAACCAGTCTGGTTACTATGTTTAG TCTACTGGTTTATCTAAATAAAATGTGA AGCTCTATGCTTACAGCTTCACTTTAGG AACTGTCT |
| WSNP_EX_REP_C101757_87064771 | 2.24E-04 | 83 | atatcatacaacactatcatcgcggcgtacgcgcag agc[A/G]GGAATTTCCGCAGCATGAATT ACTTCGTCCAAAAGATGCAGGACGCGG GGTTTCCGGTTTCTCTCGAGGCGTACAA CTGCATGCTGAATGCTTATGGGAA |
| WSNP_EX_REP_C101757_87065169 | 2.96E-04 | 84 | AGGCTTACGGGATAGCGGGAATGCCCG AAGATGCTGTCAAGCTGATGCAGGAGA TGAGGATCAAAGGTATCAATGCTGACC GAGTAACGTATACTAACCT[T/C]ATAGC AGCTCTACAGAGGAATGAGAATTTCCTG GAGGCAGTCAAGTGGTCCCTCTGGATG AAGCAAACCGGAGTTGTAGGCGTCGGA GCTCGCCCATAAT |
| WSNP_KU_C38543_47157828 | 8.64E-04 | 85 | GGCTCACGGATCAGCAGTGAAAGGTAT CTGGACGGACGGTGCCTGGGCTTTCTCC ACCGGGCTTGATCAGAGAATCAGATGTT GGAAGATGGGCCCGTCC[A/G]GCAAAT TCATGGAGCATTCCCATGTTATCATCAG CGTGCCCGAGCCGGAAACTCTGGATGTT TTCCATGACCGTGGGAGCGGGATATAC CACATCGCCGT |
| WSNP_EX_REP_C101757_87065032 | 4.62E-04 | 86 | CTTCGACCACTACACTTACAACATTATGA TGAACATATATGGGAGAAAGGGCTGGA TCGAAGGCGTCGCCTACGTTCTTTCAGA ACTAAAGAGCCGCGGC[A/G]TTGAGCC AGACCTGTACAGTTACAACACATTGATA AAGGCTTACGGGATAGCGGGAATGCCC GAAGATGCTGTCAAGCTGATGCAGGAG ATGAGGATCAA |
| WSNP_EX_C3838_6980909 | 9.39E-09 | 87 | TGCCAATCTAATAATGACCAGCCAGACA TTCTTGACGCATCAACTACGCGTGAAGA GCTAGTTTCTCTGACTGAGTATCCTTGCC |

TABLE 3-continued

SNP markers significantly associated with resistance to *fusarium* head blight

| Marker Name | P-Value | SEQ ID NO | Reference Sequence |
|---|---|---|---|
| | | | TGCCAGTTGTTACAT[T/C]GGAATCTGG<br>AGTTAAGGCTCCTCACACCGACAAGGC<br>GACAGGCACGTCAGATGAGACATCCAA<br>AGATACTGAAAATATAAATGCATGCAAT<br>ATATCTTCT |
| WSNP_EX_C49211_53875600 | 6.50E-04 | 88 | CTTCGGTGAAGTGTGAAGTCCAGCTGAC<br>TGGAATTGAGGAATGCCTGTTCATACAT<br>TGGAACATTTTGTCAATCTKTGTAGCGT<br>GTATCTAATGTTTTCA[T/C]TCAAGAACT<br>CCAGCTCCCTGCTTAGTTGTAGCTTCTTA<br>CTCGGTACTTCAGTTTTCGTCTCGAAAA<br>GATGTCTCGTTGATCACTGACAAAATTA<br>CAGTGC |
| WSNP_CAP11_C299_251533 | 1.10E-04 | 89 | GCGAGAGATTAGGCACAAGTTCTACAA<br>TCGTATCTTGCAGTCGGCTCACACCAAT<br>CCAGCGTCTCAAGTTGAAGGTGGAAGA<br>TGGACCATTCCTTTTGAT[T/C]CAGTAAT<br>AAGGTCTCCCTCATTATAGTGAAAAGTT<br>TTTCCCTGTCGAAATCAAGTGTTTAYGC<br>GCCAAACGCTATCTACCAAACGACATCC<br>ATATCCATA |
| WSNP_EX_C49211_53875575 | 4.86E-04 | 90 | TGTCCAAGATTCTCGCTCCAACAAGCTT<br>CGGTGAAGTGTGAAGTCCAGCTGACTG<br>GAATTGAGGAATGCCTGTTCATACATTG<br>GAACATTTTGTCAATCT[T/G]TGTAGCGT<br>GTATCTAATGTTTTCAYTCAAGAACTCCA<br>GCTCCCTGCTTAGTTGTAGCTTCTTACTC<br>GGTACTTCAGTTTTCGTCTCGAAAAGAT<br>GTCTCG |
| WSNP_EX_REP_C68600_67449494 | 1.78E-04 | 91 | cttgatgtggctgaggaagaacaaacctaggactttt<br>aattccaattatttatgcatgtgctctgcttctggcaa<br>caatgccatctatcaccagttacttg[A/C]GGAG<br>ATCATTGGAGTGGCAGACTCCCAAGGT<br>AGTCGGCTTCGAGCTCTTCTCCTCCCTG<br>GTTATGGCTTTCATCAGCTGGCAGCTGT<br>TCTCGGCTTGTCA |
| WSNP_EX_C9362_15546626 | 2.22E-04 | 92 | cgcgaggaggggcatctctggctgttcaacaccaat<br>taatttctagtcctgcaattgataattctattaatcag<br>gagtcttcaagtggtgaccatagaag[A/G]ACTG<br>AGCATGTTGAGCGACAGAGTGGTGTGG<br>GTTCGCAACCATTACCGGGAGAGACTG<br>ACCTTGCAGAAATGGAAGTTAACATCGA<br>CAATGGAGGCGGTA |
| WSNP_RA_C20970_30293078 | 3.23E-12 | 93 | ATTTCACTGTTAAAACAGAAGCTTAAAG<br>ATATGAGGATCTTAGACAACGTTGATCT<br>TCCAGCCTCTGTTGCTAAACTGTTTATTA<br>AACCTAAAGAGAAAA[A/C]GGGGAAGT<br>TGCTTGTTSAATCTTTGGAGTCTATTGCT<br>GAAGGTGACGAGAAAACTGAGTCACAA<br>GAGGAGGAAAACATTCTATCCGAGACA<br>GCAGAGAAA |
| WSNP_RA_C20970_30293228 | 3.58E-12 | 94 | GAAAACTGAGTCACAAGAGGAGGAAAA<br>CATTCTATCCGAGACAGCAGAGAAAAA<br>GGGCGGATCTGACTCTGAAGAAGCTCC<br>TGATGCAGAAAAGGAGGAT[A/C]CTGT<br>GTATGAGTTAGATCCATTTGCAAAATAC<br>GATCCTCAGTTACCTAGAGTTGTTCGAA<br>TGGCAAATCTCTGTGTTGTTGGTGGACA<br>TTCAGTTAATGG |
| WSNP_EX_REP_C68600_67448893 | 9.00E-05 | 95 | GACCCACCTGCATCTCGAAAGCATCGCG<br>CAGCATCAGGCGATTCGACCTCGCCGTT<br>GCTC[T/G]GGCGCCGGAGACGCCGACG<br>CCGACGAGATGACGGTGTTCCACTTCCT<br>CAACTGCGCGGTCCTCACCTTCGGCCCC<br>CACGTCGTCTACTACTCCGCCACCC |

TABLE 3-continued

SNP markers significantly associated with resistance to *fusarium* head blight

| Marker Name | P-Value | SEQ ID NO | Reference Sequence |
|---|---|---|---|
| WSNP_JD_C7718_8795833 | 3.36E-12 | 96 | GAATGGGCGAGTGGCCATTGAAGGTGA AGGGGTTCACAAAGATGTGGTAACTGA TGAAGCTGAGGGAAGCTTGATTGTGAA TGGGCGATCGTCCATGGAA[T/G]GTGAT GTGGATCATCCAGATCTTCCCATTTCCAA GGAGATAGCAGAAGACACAGTTAATGA GAGGGAGGATGAGGGTAATGCTTTCAG CAGTGAAAATAA |
| WSNP_EX_REP_C68165_66935041 | 4.70E-11 | 97 | CGGTCACCAAGATCCATTGCGACATGTC TGATGCGGTCAATATCCTAACACATACT GATGAAGTAAAGCTCAARGCAGAAAGG ATTACAGCGATTGAGAA[A/C]AAGAAA GAGAGTTTGGCCAGAGAAGAAGACAAC AGAAATCTTCAAGCTTCACAAATAGACC CTGATTGTGACATGTCAATAGCTCTCAG TGAAGGAACTG |
| WSNP_EX_C16491_24996576 | 5.64E-04 | 98 | CAAGAGATTGGAAAAATATTCTGTCCAA AGTGTGGCAATGGTGGCACCTTGCGAA AGGTTTCAGTAACAGTTGGTGAAAATG GGATCACTATGGCTTCAC[A/G]GCGCCC GCGTGTTACTCTCCGAGGCACAAAATTT TCCCTTCCAATGCCCCAAGGTGGAAGAG ATGCCGTCATTAAGAATCCCATTTTACGT GAAGACCAA |
| WSNP_EX_C15378_23638822 | 2.88E-04 | 99 | AGCCACATTCTCCTGACAACCGTGCTCT AGCAAGAGAGTGCAAAGATGTCAAGAT TGACCGAGTCTATATTGGTTCTTGCACT GGTGGTAAGACCGAGGA[T/C]TTTATTG CTGCTGCAAAGGTGTTCTTAGCTTCGGG CAAGAAGGTTAAGGTTCCCACTTTTCTC GTTCCTGCGACTCAAAAGGTGTGGATG GACGTGTATA |
| WSNP_EX_C9763_16125630 | 9.06E-04 | 100 | AGGATGAATTGAGGAACGGAGGAAGT GGAGATCTGGAGGATGACCTTGCTGGA AAGGACAGATACATGGGTTCAATCGAA AGTCTCATCCGCAATAATAT[A/C]CAAC AATACAAAATTGATATGGCAGATGAAGT CATTAATGCTGGTCGTTTTGATCAAAGA ACGACCCATGAGGAAAGGCGCATGACT CTGGAGACWCTGC |
| WSNP_EX_C3530_6459643 | 4.27E-12 | 101 | AGGCCATTCTGTCCATCAGGAATCTTTT GACTCACGGCATTATCATGACTACTTGT CTGTTGCAAATTTYCCTTGCCTTCTACCT CAGGTTGTGTAAGGA[T/C]CGTGATACT TGCAGCAGCAGCACCAGGACAACGCCC AAGACGAAGCTCCCGGCAGCAAATTAG GCAGAGATCATAGGAACACTTATTGCA GCTTCTGTGG |
| WSNP_EX_C3530_6459532 | 2.37E-12 | 102 | TGACTACTTGTCTGTTGCAAATCTTGCTT GCCTTCTACCTCAGGTTGTGCAAGGACC ATGCTACTTGCAGCAGCAGCACTATCCT CAACAGGAACTGCAC[T/C]GTCCCTCAA CAGGCCATTCTGTCCATCAGGAATCTTTT GACTCACGGCATTATCATGACTACTTGT CTGTTGCAAATTTYCCTTGCCTTCTACCT CAGGT |
| WSNP_EX_REP_C68165_66935014 | 2.25E-12 | 103 | TTGCTCAGGAATTAGGAATTGGTGATTC GGTCACCAAGATCCATTGCGACATGTCT GATGCGGTCAATATCCTAACACATACTG ATGAAGTAAAGCTCAA[A/G]GCAGAAA GGATTACAGCGATTGAGAAMAAGAAA GAGAGTTTGGCCAGAGAAGAAGACAAC AGAAATCTTCAAGCTTCACAAATAGACC CTGATTGTGACA |
| WSNP_KU_C38351_47009610 | 1.54E-11 | 104 | TTTTTTCTTCTCTGTGCTTGCTTTCTTTTT TCTTCTCTTTGCTTGCTTTCATTTCTCTCT |

TABLE 3-continued

SNP markers significantly associated with resistance to *fusarium* head blight

| Marker Name | P-Value | SEQ ID NO | Reference Sequence |
|---|---|---|---|
| | | | CTGATAAATTAGAATAACGAGCGCCACT TCGTCTGGGTCG[T/G]GTCTGATGACCA GTAGGTTCAAAAATAGCAYCTGTATTAT CTGGAGATTCACTTTTATTTTCACTGCTG AAAGCATTACCCTCATCCTCCCTCTCATT AA |
| WSNP_CAP11_C2142_1128735 | 4.96E-10 | 105 | ACGACATGGCCAATTCTTTCATCTCCTTC TGATGAAACATGTTCTCTAGCATGCAGC TGCCTAAGCTATATACCACCGCGTGGAC GCATCAATCTGTGGA[T/C]GTACCCAAT GTTTATACGTGTCTGTCCATCGTATTTGT TCATTAGAAGAACCGTACGTGCGTGCAT GCATGATTGCATGAATTATACAGTAGGT TGTACT |
| WSNP_EX_C15378_23639387 | 5.10E-04 | 106 | GTCATGTGTGTGTCGTGCTGAGAAATAA GCTACTCAACGAGTAGCAGTTGTAACTG AGAAAGGTTCTGTTGTATGCTTTTTCATT GGCATTACCAGTGTG[A/C]TGTCAGGAA CAAACATAACTGTTACATTATTCCAGAAT GATACTGTATCTTAGTACATGATCTGGT AGCTGTTGATGTGGAACGGCGAAGTAC ACCAGAG |
| WSNP_EX_REP_C68165_66935148 | 2.94E-138 | 107 | GAGAGTTTGGCCAGAGAAGAAGACAAC AGAAATCTTCAAGCTTCACAAATAGACC CTGATTGTGACATGTCAATAGCTCTCAG TGAAGGAACTGAACATG[A/G]CTCAGTC ATTGAGCAGGCATTATCTGATGCTCTTTT AGATGAGCGGCATGGGGCTCATCAAGA TGTGGTAGCAGATGAAGCTGAGGGAAA CTTGACTGTG |
| WSNP_KU_C38351_47009641 | 8.10E-12 | 108 | CTTCTCTTTGCTTGCTTTCATTTCTCTCTC TGATAAATTAGAATAACGAGCGCCACTT CGTCTGGGTCGKGTCTGATGACCAGTAG GTTCAAAAATAGCA[T/C]CTGTATTATCT GGAGATTCACTTTTATTTTCACTGCTGAA AGCATTACCCTCATCCTCCCTCTCATTAA CTGTGTCTTCTGCTATCTCCTTGGAAATG GG |
| WSNP_EX_C52849_56297163 | 2.20E-11 | 109 | CACGAGAATACCCATCAAAAAGAAGT GAGTGTTTACTTCAACCTCCATCCACGA CAGGCACTCAAGAGCTGTAACACATAGC CGCTCACGTTCATCCTT[T/C]TCTTTCTTT TCTCGTACAGCCCGCCACATAACCATTG GTTCCCAGCTCAACCCAGAAGTTAATTC AAGCACGTTACGAACAATAACAGGCTCA CCCTTCA |
| WSNP_BE490200B_TA_2_1 | 6.62E-04 | 110 | TGAGCATTGGTCATGTAGCCTTTATCTCT GCGCGATATAGCTGTCTCGTTTGGGAAC ACA[A/G]CATCTTATTGGTGGAAATGTT GTGACCAAGAACATGAGGCTCTCTTGCC ATTTGGGCTCC |
| WSNP_EX_C31256_40071875 | 6.22E-04 | 111 | CAACGATCGCACCGACAAATACGGTGG GAGCTTAGAGAACCGTTGCCGCTTTGCG CTAGAAGTAGTCCAGGCCGTAGCTGAT GAGATTGGAGCTGATAAG[A/G]TCGGC ATAAGGCTTTCACCCTTTGCAAGTTACTC GGATGCATCAGACTCAAACCCAGAAGCT CTGGGCCTATACATGGCACAGGCGCTG AACAAGCTTGG |
| WSNP_RA_C14498_22667649 | 5.86E-04 | 112 | CCCCTTGATCAAGAAGCGGATACGTGA GGTGTATGAGCCGATTTAATGCAGCGG GCCCAAACTCGCGAGGCAGGCTGTGAA GATTGCTGTTATGTTGCT[T/C]GTTTGTT TGACGGCTGGCGCTACTCCGAATTCACA CGGGCCATCGGTCCAGGATGTGCAACC CTTATGTTCCATGGTTTCCAGCCTGTAAC CGAGGACTC |

TABLE 3-continued

SNP markers significantly associated with resistance to fusarium head blight

| Marker Name | P-Value | SEQ ID NO | Reference Sequence |
|---|---|---|---|
| WSNP_EX_C5936_10412246 | 3.18E-04 | 113 | TTCTCCTCACTGGCACTCTCCAGGACAA CTTCTTTGCCAGCTTTGCTCTTGGTTGGT TGATCACCAATGGTGCAGGTCTTGCATC TTACCCCATTGACAC[T/C]GTCCGCAGA AGGATGATGATGACCTCCGGAGAGGCY GTCAAGTACAAGAGCTCCTTGGATGCTT TCCAGCAGATCCTGAAGAAGGAGGGTG CCAAGTCCC |
| WSNP_CAP12_REP_C8688_3644383 | 2.52E-04 | 114 | CGGSGTTCCTGCTGAAGCAGCAAAAGTT TGATCAGCCCCAAATTCAAGTCCACGAA TCGTTTCATCACCAACTCTATGAGAATG AGCATCCTCGCATTTC[T/C]TGTACCTAG TTTGAATATATTACAGCTAGAAGACGGT AGAAAGTTCACTGCAGAAGTCATGAAA ACCTGCATTTTGAACTTCTCGAAAATCCT CTCCATG |
| WSNP_RA_C24962_34524602 | 4.14E-04 | 115 | AYGTGCAGAACTGCCTGTTGCTTGTGGA CATTTTAAGCATGGAACATCAGACACAG CTAAAGAAGCTAATATGTTCTCCCAAAC TATTTCCTGTGCGAAA[A/G]GCAAGACA AAAAACTCGTATGAGATATATCCTAGGA AAGATGAAGTTTGGGCCCTGCACAAGG GATGGGACATCAGCTGGAGTTCGGATG CTGACAGCCA |
| WSNP_EX_C46160_51746546 | 5.94E-04 | 116 | CCAATTACTATGCCATCATAAAGAAAGT CGATCTCAAGAATAATAAAGTACAAGTG AAATGGCTTGATCTCTGTCCTCGGGGAG AGGAGGAGAAAAGATT[A/G]ACTGGTA AAGAGGATCGGACTCTTGCGTGTGGAA TCTTTAAGGTTTCCTCTGGCAATGATGG TACTACGACTTACACTGGTACAGAGTCA TTTTCTCATC |
| WSNP_KU_C11690_19042937 | 1.02E-04 | 117 | TTTTCGAGATCTCATAGAGGCATCGAAG AGACTTTATAACATCCTCATGTTTAAACA TGCCATGCACTTGAAGAGATGCAGCTGC AGATCTAAACTGGCT[T/C]GAATCACTA GAAATCAGATCTTGCACGAGATCATATG ACAGCTTGCAGCATGAAAAAGATAATG GTATGACCAATCCAGCGATTAACTATGC TGCCATGA |
| WSNP_EX_C5744_10088287 | 4.24E-04 | 118 | ACAGCAACGTCTTCTAATGTTTCATCAA GGAACCCTAATCGGTGTATCCCCTCTGC ACAGATGAGAGGCAGAGGGCAACAACC AGCGAAGCAAAAGTAGT[A/G]CAACTG TAAATGAACATTAGTCGGAATCGTTGT TGTTTATCCATTGTAGTGTAATGTAATG TAATATATTAGTAGGTTGTACAGTAGAG TAGGTTTGT |
| WSNP_EX_C17349_26035281 | 2.34E-04 | 119 | CGAAGCAGAAGAAGCGAAATGTCCATA CTGTGCTCTCCTCCATGAGTATGGCACA CACAACTTTACCCCAATTCCTATGGATG AGTGTCCGGTTGTCCTT[T/C]GCCTTCTT GATGAACACTTGAAGATGATAACAGTG TTGTTGCTCATGATTTACTATTATGTTCC TTCCTCATGAGCAAGCCGATACTTTGCG ATGTAAGA |
| WSNP_JD_REP_C63108_40258378 | 4.48E-04 | 120 | ATTGGGTTCGGATCACTTTCGCCATTGA CCTGCCATCTCTTGAGGATGGCCTTGAA AGGCTGAAATCTTTCTGCGAGAGGCAT GCTATAGTAGAGGCCTA[A/G]GCTCAAA GATGATTGAGCTTTTACACTGCTGTGGC GAATCGCCAGCTATGCGTTGGATCGCCC TAGTGTTGTTTTCAATAATCGCTTCTCTT TATGTCAC |
| WSNP_EX_C5744_10087877 | 6.28E-04 | 121 | CATCCAGAGCACCTGCGCTTACATCGGA AACTACCATTTGGGGATCACTCTGGAAA |

TABLE 3-continued

SNP markers significantly associated with resistance to *fusarium* head blight

| Marker Name | P-Value | SEQ ID NO | Reference Sequence |
|---|---|---|---|
| | | | GATCTTCTGTACCAGATTTTCCGTGCAGT CCGTAGCATTTTGTA[T/C]GGTTTTGTTG CCTTCTTTTCAACGTGCAATAGGCACCG GCTCAGCATATACAATCACATAGAAGTT CTTCTCCGGCGCCTGTCCCGCGCCTTAA ATGGCA |
| WSNP_KU_C1876_3666308 | 4.92E-04 | 122 | CATCACGGGTTCCTTGTCATGAACGATC GTTGTGTTGTCTTTGGGCTAGGAGTTCT CCTGTCGAACATCAGAACTTCACGCCGT TACCTTTGCCTGTGTA[T/C]GGAAGGCA CTGTATATACTCGTAGTGGTACATCCTG TCCGTTTCTCGTCCATGGAGTAAATAATT TGTTCAGGCTATACAGGTAGAACAGTGC AACGCAG |
| WSNP_EX_REP_C106072_90285324 | 6.04E-04 | 123 | TCAAGTGTAAGACGYAGATTGTTGGGA ACACTGTAAAGACAGCTCAGAGTTAACA TGGATGCATATGATTTTGGATTGTACGG ATATGTTTGTACTCCTT[T/C]CAATATGC TCGGCCAAACCCTTGAGAGACTCAACTG GTTCAGATTCTTCTGAAGCAGTTTGATG TAATACATCCACAACTTTTCAAATTCCAA GGTATGG |
| WSNP_EX_C23716_32952372 | 2.64E-04 | 124 | AGCAGCCTTCTTCCACTTCAGCTGATGTT AACAAGCTATTTGCATTCCCAGTTGATG TGCCGAACGGGATTAAAGAATCAAAGG ATAGTTCCAGTGAATC[A/G]AGTAGTCA AGTAAAACCTCGAGCTATCATATCTCAG GATTTTGAGCATGATGCAAGTCAGAGTC CAAAGAAACTGAGCGATGATGTCGGTG CAAAAGAGG |
| WSNP_EX_C16836_25401702 | 1.80E-04 | 125 | TTTTGCAGGCCCGGAGATAGAAGCTGCT TGTGATTGCGAGAGATCAGTAGCAGCA TTCAGAGCCAATACAGGACTGTTGTGTA CAGTGTTACCAGTTTTC[A/G]TGGAGTT TGGCTTGATAATATTTCCATTTGCAGCA AGCCCTTGGTGATTTCCCTTTGCAACCGT ATTTTGCCCCACTCGCTGAACAGAAAAC TGTGCTCC |
| WSNP_EX_C38198_45786860 | 3.70E-04 | 126 | CGAAGCGGACCACAATTTTATGGAGCG TCTGTCCGCCGGTGGCGCCGAAGGTGA AGGCGAAGAAGGGTATCCGAGCTGTCG CCGCATTCTTTTGGTGGAT[A/G]AAATG TTGCAGGTGGCCATCCTGTACCGATCTC CTGTGCTGTTTGGCTACCACAGATGTAT GACCGAAATAAAACGTCCCTGAATCCTG CATTTCAGTGC |
| WSNP_EX_C1146_2201722 | 9.88E-04 | 127 | TTAGAATTTTCACTTGTGATGGTTCCATT CCAAAATACGAGTTTGATTCCAAAAGCT TGATGGTCAGTGCATTCGTATCATCGGA AGTCATAATAGCAAA[T/C]GGGATCTTC GTATGGCATTCGCCCTCCATTTTGCAGCT CGCCTCTTGTAAAGCCAGAATAGACTCT ATGTAATGTTGAAGAAAACATTTCCCAG TGGTTG |
| WSNP_KU_C707_1465779 | 1.99E-11 | 128 | CCTCCCCTCATCAGGAAATGAAAATTCT GAATCTCCGCGGGGACAGCAGCAGCCG CCGCTTGTGCTGCAGCCCCTTGTACAGG AAAGCCAAACCTCTTA[T/C]CCGTTCAG TCGTTGCAGTTGATCTCTCCTTGAGTTG GGCAATTTTGTCGGCAAATTCATCATCG GTCGTCATCTTGGCGTTGAAGCTGTCTA TACAGTCT |
| WSNP_RFL_CONTIG3854_4205716 | 5.70E-04 | 129 | CTCCTACCATTTGCTGACGCAAATGCAA TTGTACTTGAGATGGCCAATGA[A/G]GT GTTGCCTGTCGTTAAAGAAGTTCCTGTT CTTGCTGGGGTTTGCGCTAC |

TABLE 3-continued

SNP markers significantly associated with resistance to *fusarium* head blight

| Marker Name | P-Value | SEQ ID NO | Reference Sequence |
|---|---|---|---|
| WSNP_CAP11_REP_C6622_3044459 | 4.72E-04 | 130 | CATCCTTCTGATTTCTTGCTCTTATAGGT ACCTTGCTCGTATATGCGAGCATAATGA GCAATTTTTATTCAAGCACATCAAGCAT GTTTTTGGGGGACTG[A/G]ACATGTTTT ATTTAAAACACATATATATGTCTAGTTGT TCCTTGGTGACATCCACCATTTAGACCTC TTCCACAATATCCTGCTCAAGGATAGCC ACCAC |
| WSNP_EX_REP_C69954_68913284 | 7.20E-05 | 131 | ATCGTCGCCACTTGATGCCTACTATTATT TGCCTATTCGAGTGCAAGATGGGGTGA TAGCAACTGGGAAGCGGCACATTGTTTT CTTTCTATTTTTTCTT[T/C]GGTTTTGTTA GAATAGTCGATCRATCTGCGCCTTTTGT ATGTTATTTTTGCTCACATCAGGCTGGA CTGGGGTCGCTGGAGAGGGCGTAAGGT AAAGGTT |
| WSNP_EX_REP_C69954_68913307 | 4.80E-05 | 132 | ATTATTTGCCTATTCGAGTGCAAGATGG GGTGATAGCAACTGGGAAGCGGCACAT TGTTTTCTTTCTATTTTTTCTTYGGTTTTG TTAGAATAGTCGATC[A/G]ATCTGCGCC TTTTGTATGTTATTTTTGCTCACATCAGG CTGGACTGGGGTCGCTGGAGAGGGCGT AAGGTAAAGGTTGTYCCCATCCAGGCA GAGCCTAG |
| WSNP_EX_C46274_51831129 | 2.67E-10 | 133 | CTGCAAGCGAAATTGAACCTGCTCTGAA GAAGCAGCTCATCATYTCCACTGCTTTG ATGACTATCGGTGTTGCGGTAATCAGCT GGTTGGCTCTCCCAGC[T/C]AAGTTCAC CATCTTCAACTTCGGTGCTCAGAAGGAT GTGTCCAACTGGGGCCTGTTCTTCTGTG TGGCAGTTGGTCTGTGGGCTGGTCTGAT TATTGGGT |
| WSNP_EX_C351_689415 | 5.53E-12 | 134 | ATACCCTCGGGCCCATCGTGATACAGCC TGATCACCTCAAAAGCATCAAGCGGTTG TCAATCGTGTGCAAGCCAAGGCTAGAC ATAACAATCCAAGCTGG[T/C]GCGCTGC CTGATCTTGTGTCGCTTCATATCCTCTGT GAAACACTGGATGTTCTTCCTGGAACAC CCGGCATTGAGATTGCACATATGAATCA GCTGGATC |
| WSNP_RA_C31052_40235870 | 8.00E-05 | 135 | TTTTGTTAGAATAGTCGATCRATCTGCG CCTTTTGTATGTTATTTTTGCTCACATCA GGCTGGACTGGGGTCGCTGGAGAGGG CGTAAGGTAAAGGTTGT[T/C]CCCATCC AGGCAGAGCCTAGGGATCGATATGTGT ATATTATATATAACAATGCTACACTGTAA CATGAAATGAAATGCAGAGAAAATTAA AATGCGTGAG |
| WSNP_RA_REP_C71101_69119989 | 2.49E-10 | 136 | GAAGTGCCGCTCTCAAGATGGTTGAGG AGGTCCGCAGGCAGTTCAACACCATYCC TGGACTGATGGAGGGAACTGCCAAGCC CGACTATGCCACCTGTGT[A/C]AAGATC TCCACTGATGCTTCCATCAAGGAGATGA TCCCTCCGGGTGCTTGGTCATGCTCAC CCCCCTCATTGTTGGAACCCTCTTCGGC GTGGAAACCC |
| WSNP_EX_REP_C69816_68774932 | 1.67E-09 | 137 | GCATCACCGGATTTCTCTGGTATAACTA GGAAGGCGATGCCAACTGCTCAAACCA TGCCTACTGAAGCTGCTGCAACTATACA TAATTTACAGTTCCCTC[A/G]CGCACTGG CCCTCCTTGAAAGTGCCARAAAAATTGT TGGACAAAGCACATTTCTAAAAGCTTTT CCTGGGAATGTGAATGACACTGCGGAG CCAGCTTTA |
| WSNP_EX_C10783_17555091 | 1.00E-04 | 138 | CAACAGAAGGCTTCTCATCTTTACTATCA TCCTCTGCTTGCTTCTTAGGCCTGGTGGC ACGTGGACCCCGGCTTTGCTCATTGAGG |

TABLE 3-continued

SNP markers significantly associated with resistance to *fusarium* head blight

| Marker Name | P-Value | SEQ ID NO | Reference Sequence |
|---|---|---|---|
| | | | AAGTCAAGTGGACC[A/G]TCACAGCTGC ATAACAAAGAATTACCCCTTCCTCTCCTG CGCCCTTTATCAATTGGAATAAAACTTCT GCCATTCATGCCATAGCCAGGGAAAGG ACCCC |
| WSNP_KU_C18780_28136150 | 9.40E-05 | 139 | TACCTCCTCTGCGGCACTCTATTCTCTTG CAATTTCTATACCTCACAACCAACAGCA AGCAACAACGGTCAGCAAGTGCAGGCA GCAGAGAAACACCACA[A/G]CCACCCTT CTTCTCTAGCAGCAGCACCAGAACAACA AGCAGCTCCAGCAAACTCAGCAGTAGC AGTCACAGACCAAACCAGCTGCACACAA CAGCAATCG |
| WSNP_EX_C5457_9631220 | 1.97E-11 | 140 | TCTCTCTGTTGTATGCTATCCGCAGCAAT GCCATCGTTGTTCTCAGCAGTATAGTTTT CTGAACGCTTCCCTTTCTTGGTAGCAGT AACTCTTGAGTAAT[A/G]ACGAGTACTA GAAAACCATCTAGTGATCTGATGGAATG TCAGGCCAAGCTCTTGTCCCAGACTTTCT TTTGCTGGGCGACTAGGGTAAGGTTCTT TTTCG |
| WSNP_CAP11_C1711_934478 | 5.88E-04 | 141 | CTTCCAAACATCAGGGGCAGGGCCGTCT TTCTTCTTTCAGGGTTACTGGGCCTTGCC CTCCGCGACCGCTTCCATCCCAGAAGAT GCTCCCATGCCTTCG[A/G]ATGGCTTCC CGGCCGTAAGGTACCACTCTCGCTTGTA TCCACTGCTTC |
| WSNP_EX_C6611_11452297 | 3.71E-13 | 142 | ACGAGAAAGACTGCTGCTGCTGCTGCT GCTCTTCCACCCTCTTCGCCGCGGCCTCT TCGGACACCGACTTCTTCTCCTCCTTCAA CGCCACCACCGGCTC[A/G]TGATCGAAT ACCTGGTTCCTGCCGAGCGCGGTGTCGC TCGGCGACTTRTCTACTGCAGAGACTTT TGAGCAGAGGCCTCCCATCCCCCTCCTT GTTAACC |
| WSNP_EX_C8386_14127329 | 0 | 143 | CTAGAGGAGATGCGAAGCCATGGAAGC AGGCACCGAAACCAAGCAAGGATGAGC TGAGACAAGCTGTCTTCTGTATATTGGG TGCTGCAAATTTTGCCAC[T/G]ATGACTT TTGGAGAGGTTGTAAAAGCAGTTGACA AGTACTTTGGCAAGGATTTGTTCAAGAG AAAGCCGCTGGTAAGGGCCTTGATAGA GGAGGAGCTGT |
| WSNP_JD_C9040_9947841 | 8.05E-09 | 144 | TGAGGCGTCGGAAGGAAATGTTGTCCA GCGAAGGGGCGATTTCAGGTAGCTTC ATCAGCAAGCAGCAACAGCAGGCCTAA TTTACCAAGTGGAGTAACA[T/C]GGCCA GCTTCCAATTCATCCACAATTCTTCCGAC ACTACAATTCTTGATGCAGCAAAATTCT ATGCAAAAGGAAGTGCTAAGTAGATTG ATTTCTTCAAT |
| WSNP_EX_C10231_16783750 | 2.06E-04 | 145 | GCCGCACATGGAGTTGCTTCAAGCTGTG GCGAGCGCTGTACTCTCCTTCCTGGGCT GACGATCATTCATCTTCATCTTCTTGTAA TTTATTCCTCCTAGA[T/C]TGAAACCGTC TGCTTAATTTATGTACCCAAGTAAGGAG ACACATTTATTTACAGTTTGATGATTCTG TTGTGAAATTTGGATATTTTTTCACTCTT ATTA |
| WSNP_JD_C17128_16056425 | 7.55E-11 | 146 | AGAGTCTTCTCGGTGCGGAGGAGCTTC GTCTTCTTAGAGATGCTCTCAGGGAAGT ATGCATCCCCCTGAAGAGTATGTCCGAA GACGACGGTGCTAGCTT[T/C]ATGGCCC GGTGGTGGATGAAGATAGTTCGGGAGC TTTGTTATGATACGCAGGATTACCTCAA CTTCGTCCAAAGTGCTCGAGATCGTCCT GAATTTTCAG |

TABLE 3-continued

SNP markers significantly associated with resistance to *fusarium* head blight

| Marker Name | P-Value | SEQ ID NO | Reference Sequence |
|---|---|---|---|
| WSNP_KU_C23598_33524490 | 3.92E-04 | 147 | GGGTTCACCTTCGCGCCCAAGCACAAGT CTAACTCGTACGACCGCGCTGAGAACG GCTAAAAGACTGCCGCGTGATGGTTATT CGGCAGTTTATATGATG[A/C]TGAATAA GATCACGTCTCTTCTCAGTTAGTTTGAAA CTCAGCCAGGGCTCCATGTTGCCTGCCT CATAATGGTTATTCAGCAGTGTGGAGCA ACATCATG |
| WSNP_JD_C5757_6915127 | 8.60E-05 | 148 | GTAAATAGATGCTCTTCTTGCCAAGCTA ATAAGCAAACGATGGTTCACCAGGCCG GAAGCTCCGGTAGATGGAGGCTATCAC TGGGACWAGACCCAGCAG[T/C]GCGAT CTGGACCTGCTCCGATGTGCTTGTCCTG ACGGTGATCTGTCCGCTCAGCTTGTTGT TGAGCCCAAGGCGAACAGCCATCTTTGA ACCCCTTCCAA |
| WSNP_EX_C23968_33209660 | 4.10E-04 | 149 | ccagtaatagggggttcactatgtatgaaccagaata ctggaacctccaatgttgacctgtgatttgtatgttct cctttaagtgaagtttgctcacttaa[T/C]TTCTG TAACTGGTGCTGGAGAATGGCAGAATC CAGGTATGTACGGACTGTGGACCTATA GGTACCATTGACCRATAGAAGTGGAAC CGCGGCTGCACGGC |
| WSNP_JD_C6974_8084450 | 2.58E-04 | 150 | AAATAAGCAGAAGTGAAGATTTACCAC AGTACATAGACAAATATAAGTTAAATCC TGCATCTGTATAGTATGATCAACATCAC AAGGAGGAGAAATTGAG[A/C]AGGTAG TGCTGCATTTCCTGTCATCATGTATCCCC TCGCAACACTCTAGAGCTCGAACTCCTC CTCACGGAGAGCCATCTCCGCAGCCTCC TCCTCATCG |
| WSNP_CAP7_C5487_2464864 | 1.70E-04 | 151 | TTTGAATGATGAAAACTCAAGCAACGT AARATGACCAAAAGTATTTGCACTGGTC ATCTTGCATGTCGACCAGTCCCTGGAAA ATGGTTAATTACAACA[T/G]GTGAAAAA GAACATTAGATCACTGATCTTAGTTCCC GGTCAGAGACGTCAAGAATGCTAATCCT GCGATCACGATCATAATGTTGAGGAAG TAGTTGGAC |
| WSNP_EX_C8360_14085858 | 4.91E-14 | 152 | CTGAAGCAGGTACTGACGGAGGAAGAA GAAGCGGATGCTGCAGCTAGCACACGG CGATGTTGAGCGCCGATAGCTTGTGTGC ATGGTTCTTGCCCTGCTT[T/C]TTGGATG AGCTTGCTGCAGGATGTTGTTGCTGCTG CTGCTGCTGCCGTGGCTTGCTGCTGCTG TGGTATTTGCAGTGGCTGTCGTGTCTGT CGCGGCTTG |
| WSNP_KU_C4067_7419106 | 1.44E-08 | 153 | GACACCTTCCTTAGGTGCATCAGGGTTC AAAAAAAATGGATGCCAACGAACCTCG AAATCGAACTTGTCCATGGTTTGCTCCA TAGCTTTCTCAAGATTC[T/C]TTTTCCCA ACAAAGCACCAAGGGCACACTGTATCTG AGCTCACGTCGATCTGAATGAGCTTCTT GCCAGTATTTGAAGCCATATGTTTAGCA AATCTGAG |
| WSNP_EX_C5267_9318903 | 7.70E-04 | 154 | AGACAGACCCTGGGAAACTATATTCACT GGATCATCTCATGCTCTCCCGCCTCTCAC GAAACTGTGTTCTGTTTTCTTGGCATCAT TGCTGGAGAAGAGA[T/C]CGGTTACAG ACGAGTGAGAAGCACCCACCGCAGTTTT GTCGCAATATATAATGGTATACTTGCTA GTTGCAGTTGTCAGTGTAGAAGCAAAC GAAAGCCG |
| WSNP_EX_C22753_31958639 | 3.78E-12 | 155 | TTGATGTCTGTGTTCCGAAAAATGTTGA AGGATGGGACATCAAGCCAACAGCGTC TCCGAATGGACGACCAACGTTGGCTTCT |

TABLE 3-continued

SNP markers significantly associated with resistance to *fusarium* head blight

| Marker Name | P-Value | SEQ ID NO | Reference Sequence |
|---|---|---|---|
| | | | GCACGGCAACTGGGTCC[A/G]TTCAATC CCATCAAGTACCTCCGCCGTTCAAGGCT ATAGTTTGTGTTTGCTGCAAAGAAGAGT TTTGTGTATATAATGGAGGCAATATGTT AAATACCGA |
| WSNP_JD_C13086_13174510 | 2.38E-10 | 156 | aagcaatcttgggacatcggcaggtttgccaagact ctgttttcttcaacgggcctccaaaccctctcaagat tgtggagtccataatgagcagcatca[T/C]AGCC TCCGCTCCTACCGAGGCGCCGAAGAAA GCAGAGACTTCTGATTTGGTGCTTGTCA CTGGGGCTACCGGCGGTGTCGGGCGAA GAGTTGTCGATGTC |
| WSNP_EX_C5457_9632050 | 2.87E-11 | 157 | TCTTTGAAGGTTCAGACTCATCGGATGA TGTTATAAAATCCAGGTCATCAGAATCT GATCCTTCATCCCCATCCTCTGCAGATGA TTTGTCTTCATCTAC[T/C]GTGTCCCCTTC AGCTAAAGTAGGGTCATAATCCTCCTCT GAATCATCGGATGGAAGATCAGATGCA CCAATTTGGTTTAAGCCATTCGAAGTTG ACTCAG |
| WSNP_RA_C18364_27416387 | 1.88E-04 | 158 | CAATCAAATGCTTCCGGGGAGATGACCT GGTGTATGTGACTTAGCAGTGTATAGCT AGGCGAAGGCTTCCTTTTGGTTGGAGCT GTTTTTTCTCATCGCA[T/C]AAGGGTCTT CTTATGGTCTGTTAGGAAGAATGCCGCT TACTGCGTTTTCGGTGTCAAGTCTGTTCC ATTGAAGAAAAGTTGGATTCGTAATGTA TTCCCA |
| WSNP_KU_C26784_36748247 | 1.34E-10 | 159 | TGAGCTGAGAGCMGCCACTGAAGAGCC AAAGTTGAGCATAGAGGAAGGCAGCGG CGGTGCTTCGGATGCGATGGCTGTAGA CTGATTAACGATCCTAGCA[T/C]TAGCG AGTTGCTTACCCTGCACGCTCAAGCATG CYTCGGTAGTKTCTGGGCGYGGTGTTTC TTTGTAAGAGATCCCTTTTTTTGTGTTGC TGTGGTATCT |
| WSNP_EX_REP_C69986_68942834 | 2.86E-04 | 160 | CCCGAAGTGCAGGCAGAGGAATAGATA TGACAACATTGTTCAGGTCAAACATCTC TGAAGCCTCATATTCAATGTTGACATAG GTTTCATTTCCAGATAC[T/C]GAGGGCC AGCAGTTAACTGACAGAGGTAAATYCG ATTCATTCATCCCCTGGATTCTCCATTTC ACAAGTGGTGTTTCATTTTGACCACTTG GGAAAGGCC |
| WSNP_BQ169669B_TA_2_2 | 2.92E-04 | 161 | AATAACATGCCCTAGAAAAATCATGGTC TGAATAAATATTCTAGTATTATCGCAGC GCAG[T/C]GGAAGGTGAGTTTTTGGCTA TTAATGCCAGCTAAGGTCAACTGGTCAC TATCCCTAAAGC |
| WSNP_EX_C19582_28564743 | 5.16E-04 | 162 | CGGGTCGTCTCCAGGCGCCGGCAAGTTT GGTTACCTGAAGATCCGACGGCGGCGT CCCAAGTTGACAATCCCCGAATGAAGTG GTCGGCTTTCCAATCCA[T/C]TGTGCCCG GTGAAGTCAGGTTTGTTGAGAGGTCAG GCTGCTGAATTGATTGAACACAGAACAT GTGAAGCAGCAATTCATTGTGTATGTGG GACTGCAGC |
| WSNP_JD_C5919_7081809 | 4.70E-04 | 163 | ACAACTTTCATTCAGCCTCAATGGGAGG TTGATTGTGAATTTTTTGTTTCTTCTCAT TTACAAAAATCATATAAGTCTTATGTACA TCAATCAGATTGC[T/G]CTTTTGTAATAA TAATGTGGCCAGATGGTTGGACGTCTGC CTATTGCCAGAAGGTCAAGGAAGTTGG TGAACTGATGACAGGGAAGCTGCCAAC CCTAGT |

TABLE 3-continued

SNP markers significantly associated with resistance to fusarium head blight

| Marker Name | P-Value | SEQ ID NO | Reference Sequence |
|---|---|---|---|
| WSNP_EX_C6611_11451949 | 1.45E-13 | 164 | TGTTAGAATTTGACAGAGAACGCATTAG ATTGGAACCCTTAACTATTGTATTTGCCA CCTCAAAAGCCAAAATAGATATTTTATTT CCCTTTGCTCCAGA[A/G]CTTGACACAA AGCCACTGCTAGCATTTAAACTTGCCAT GCTACTACCAAGTGTGTCTAGAACCTCC ACAGCTTTCCCAAGCCCAACAGTGCTAG CTCTAC |
| WSNP_EX_C3201_5910659 | 1.94E-04 | 165 | AATGCATTGAGACAGGTGACCAGTCAA GATCTTAATTGGCGAGGAATGAGCGAA GCCATTCATGCTTGGCCACGGAATTTAG TRAGGTATCTGCAAGTGA[T/C]CCTTTAT ACTTGGACACACTATCCATCATTGGAA CTCTCCCCTTCAACGTGTTCTGAGCTAG GTGGCACTTTCTTGTGCTACCATGTTATA CCATTTAC |
| WSNP_BE496826A_TA_2_3 | 6.92E-04 | 166 | CCGTTCATCAATCAATCGCTGAAGATTG GCCGGAGATTGAAATGAAACCGATTGA TTATG[A/G]CACCGAGATGCATGTTTTC TGCTGATTTTTGACGCCTCTGTTCTTGTC TGCTGAGCTGCT |
| WSNP_JD_C2180_3000498 | 1.71E-07 | 167 | ACTTCCAGCGCGACTCTCTTGTGAAGTT CTGCCAGAAGCATGGAATCTCTGTCACC GCACACACACCCCTGGGCGGCTCCACTG CCAATACCGAATGGTT[T/C]GGCTCGGT CTCATGCCTCGACGATCCTGTCATCAAG TCCCTGGCTGAGAAATACGGCAAGACG CCGGCCCAGCTGGTCCTCCGGTGGGGC CTCCAGAGGA |
| WSNP_EX_C27373_36578273 | 2.69E-10 | 168 | ggtccacaggactttttagattagttacagtggccat gtagccattcagaccggcagctatgatgtgatagca tacatgaccgagaacatatgcgtaatc[A/G]CAA TCAAAGTTTGACGGCAGGGCACCTCTTG CTTGGTAGCCAAAAAAGTGGCAAATTG CATTGAACTTCTTTCCTTTGTAAGTGCCT TCCTCCAGACGTT |
| WSNP_EX_C18800_27681277 | 3.06E-11 | 169 | ATAGTTATCACCCCTTTGCATGCTAGGG ATTAAAACACATGAGTTGTATTATGTGT TTATATAAAGAATAAACAAAATTGGCGT CCTAAGCAGTAAACCA[A/C]TAAATAAG GAAAATTTTGTAGACCTGACAATTGACA CACCATCTACCGCCACATCCTCTCTATCK AAGTCTACAACTCCAAAAGAACAAAG GACATAGG |
| WSNP_JD_C9360_10216526 | 7.70E-04 | 170 | AAATTTGTTTTCGTCTTGGTGAGACTGG ACAGAAGTAACCAATGGTTTTTTGTCCA CATGTGGAACTATAGAAGTGAATTGAA AGATAGGTGAAGAGGTT[A/G]TATTTCA GGAGCTATTGGGTTCAGTTTTGGACTTC CAGTTAACTCCTAACTGTAAAATGAATA CTTAATATAAGTGAAATGTAATGGGATG AGATTGCAT |
| WSNP_EX_C40060_47197384 | 8.12E-11 | 171 | GGAACGGAATATTGGATGGGTATAAAA GCAGTAACCCACCCTGCAGGGCTCTAGC GTCAAGCTCTCAAATTCATTGCTCTGAA AGCCATACCCCCTCAGT[A/G]GTCATCC GGGTCATCAGATGCGTCGCTGAACCCAT CATCACTCTGTTTGCTGTCAGACTCACTC ATTGCGTAAGGATCATACTCTCTCCATTC TGGATTT |
| WSNP_EX_C1279_2451582 | 2.80E-04 | 172 | TCCTGTCATTCACACGGCGAGGAGCGTY GAAGGACGACGCCTCATCGGCGAAGCC AGGGGCAGCCGGTTCGGACGACCAGTA CTGGAATTCCCCCGCGAA[T/G]ATGCCC CACGACAACAACAACGTCGACAAGAGG TCCAAAGTGAGGAAGCAGCCGTGGATG |

TABLE 3-continued

SNP markers significantly associated with resistance to *fusarium* head blight

| Marker Name | P-Value | SEQ ID NO | Reference Sequence |
|---|---|---|---|
| | | | CCCTTCATCTGCTGCCACTCCGTGCACTG ATGCTGCCATT |
| WSNP_EX_C22016_31191407 | 8.20E-05 | 173 | ATAGCAGCGTTATATTGAGGAACACCA GGCCTACCAATGCAAGAAGTAATATACA CGAACATGACTTCAAATATCCTAGGGAG GGAAAAGTTTCCAGTAG[T/C]GAGGTCA ATGCTGACAGTAAATTTCAAAGATACCA GCAAAGAACAGAGAATTCAGGAAGAAA TCTTGTAGGTAGTTTTAGAGATAATAAT GTGGACTATA |
| WSNP_EX_C15399_23662312 | 5.60E-04 | 174 | GGTGGATGTTCTGGTAGCGAATGGTAT CAGTTCGGACAAGATAAGTGTTACTTCC TACGAAGATATCAAAATGAGGGCCTTTG CTGAGGAGGCACGCGCC[T/G]AAGAGG AGCGTCCAAAGAAGAAGAGGGCGAAG AAAAATCCAGACTGGGAAGATGATGAC TCCGACGAACAGAGTGACCCTGATGATC CTAGCGGCGACGA |
| WSNP_EX_REP_C70299_69243835 | 4.32E-04 | 175 | ATGAATCCCCATGCTGCTGAGTTTGTGC CTGGAAAAACTGTGCAACAAACTGATTT GGCTGCAGGGGAACAAGCTAATTCTGT GACTGATCCAGCGGATC[A/G]GCGGTT GGCATCGCATGCCTCAGATGAAGTGAA AGTCGATGTTCGTGAGGCAGACAAGGC AGGTCAAGTGGAGAAGACAACTCCAGG TAAAGGGAAGGAA |
| WSNP_EX_C23968_33210344 | 8.78E-04 | 176 | tcatgcaatgcttgaaagcaaaaagttcatatacat caatttctgccaataggatatccaccgcatggtaatc ctcgccaacagaagaaaacctttctct[A/G]ATT GTATCTTGTAGACTTTCTTCAGCCTCTTC CTCTGTGATTTCTGCGACAGCCCCAACA GTTTTTGCCACATTTGGCAGAGTAAGTT CTGTACGAACAC |
| WSNP_EX_C7172_12318529 | 5.47E-10 | 177 | ATAGGCAGCGTTTCCTCCAAGTCGTGGT CGAATCTTCTGAACCGGAACGCGGACCT CCTCGAGGAGGAGAGCGTCGCCAAGCT TGTCCAAGAACTCGATG[A/G]CTTCTCA AGGCCAGGGAGTTCCTGCCCTTCCTTGT ATGAAAATATTCTGAGCAGCTGTACAGA ATTCCTTGGTGGTTCTGGTGGAAAGGCA GCTTCTGAT |
| WSNP_EX_C2723_5047696 | 4.44E-16 | 178 | GAACAYGCTCACCATTCCTTCCCGTGCAT GGGGGGTTGTCATTGAAGTATTGAAAG AGAGACTTCCAAAGGATGGAATAAGGT GCCGGGTTCCGCAGAGA[T/C]GATGTTA CATGGTAGATGACTTGCACCTGCTGATC ATCTGAGTGTGCTGCCATGGCAACCATC ATAGCATTGACCACCATGTCCCCTGGAA TCACATCCA |
| WSNP_EX_C123_244117 | 1.98E-04 | 179 | ACACGTAGGAGCCAACCTTTTGTACCTG GGAGTCGAAACSAATTTCTGCCTTCTGC ATTATTTCAGTGTTAAAGATGATGATTG CATGCCGCATTTGCTT[T/C]GATTGCTTA CTTTCTCTGTCAAGTATGATAAGAATGG AGACATCTGGACCTGCCGAATTCTAGAG TCTAGCGTGAATGGYGCAAGGTGGACC AAATCACG |
| WSNP_CAP7_C1339_673581 | 1.07E-10 | 180 | CGAGGTTGGGCGAGATGGCGAACTTGA TCATGGGCGGCGGCCCGCAGGCGAGCG CGAGGGTGTCGTCGCCGCCCTCGGGGA CGTGCGCCCGCAGGATGTC[T/C]TCCGT CACGAACCCCACGCTGAACCTCCACCCG TCCCCCGGCCGTAAGGTACCACTCTCGC TTGTATCCACTGCTTA |
| WSNP_KU_C8722_14766699 | 8.20E-05 | 181 | tacatcagaagctttcaatttgactcctggaaaagta ccagtatttccatccctcaattcttctttcatttcatac |

TABLE 3-continued

SNP markers significantly associated with resistance to *fusarium* head blight

| Marker Name | P-Value | SEQ ID NO | Reference Sequence |
|---|---|---|---|
| | | | aagtaccatataataaggaaatgc[A/G]CCCAT TATTAACTGGAGAACAAACATATATGAT TTCCTTCATTAAGGTAGATGTATGTAATC CACTACATAAAATGTATGTAGAAAATGA AATTTTTCAG |
| WSNP_EX_REP_C69986_68942866 | 2.44E-04 | 182 | acattgttcaggtcaaacatctctgaagcctcatatt caatgttgacataggtttcatttccagatacygaggg ccagcagttaactgacagaggtaaat[T/C]CGAT TCATTCATCCCCTGGATTCTCCATTTCAC AAGTGGTGTTTCATTTTGACCACTTGGG AAAGGCCTGTTTGGATCTTTTGCTCCAA CAATTTGCTGG |
| WSNP_EX_C2330_4366134 | 6.40E-05 | 183 | gggatgagaatggctactatgctggatcgaatggac tggagatgcaaccgacagtcgttcaagctgagaatg ggtcttatttgtgttatgttccgggtta[T/C]GAAA ATGGTTATACTGCTTATAGTCCAGTCGTT CCTGGAACTGGCGTGGATAGTCAGTAT GTCAACAAAGAGCCATATTACTCCGCTG TGATTCCCGTGC |
| WSNP_JD_C12088_12411845 | 1.75E-10 | 184 | ATCTTCCTTTCATTACTACCTTCGACTCAT CCATCGGTATAACACCAACCTCAGATGC AACATAAACAAAACCATCTGATGTTTTC CAATAGCGTGCTGG[A/G]CGCAGCCCAT TTCGATCAAGGCATGCCCCTACCGTCCT TCCGTCACTAAACAAAAGTAAAGCAGGC CCATCCCAAGCCTCCATTTGACCTTTGTA GTATT |
| WSNP_EX_C26747_35974837 | 4.01E-10 | 185 | GGATCATTGATTGCAGAATCTATAGAAT TGAATCCCATGTCAGCAACTCCAAGTGA ATGTGAAATCATTGAAGATGATAACTCT TGTTGAGAATCCTTAG[A/G]TGAAATGT AGTTAGAAATGCCATTTCCAGCCATCTC ATCCATGAATTTATCATTTTCAATGCTAT TTGCAAGCAAGGCATCTGCATTAAGTGG TAAGCCC |
| WSNP_EX_C1146_2200823 | 3.14E-04 | 186 | GCCGTGCAGCCTTTGCTTGACGTCCTTG AACGTAAGACCCCACCTCGGGCTCCAG GCCACGCGTGGCCAGACCTCTACCTCTT GACCATTGAAAGTGCTG[A/G]CTACAGG GTCAGATATGTGTGCACCGGCCTTTCTT AAAATAAGGCTGTTTGCCCTGTAAATTG CCATCTCTCCTGAGGTTGCACTATGAAA AGGATTACC |
| WSNP_EX_REP_C67198_65702998 | 7.61E-09 | 187 | AATATTATTTGAGAAAAAATGCATTCTA CAAGGTATTCAATATGTCAGGTAAAAGT ATCGATGCAGACCAAAGACTAACACTTG ATGTGGATAAGTTGAC[A/C]ACTGACCT TGCTAGCTTGGTTACTGGAATGGTAAAG CCACTAGTTGACATTCTTTGGTTTACATG GAGAATGAAGCTTTTGTCCGGCCGAAG AGGAGTTG |
| WSNP_CAP8_REP_C8295_3722232 | 7.54E-11 | 188 | CTCAACATCCTCATCAAGCTCATGGCCG TCGAGTCCCTCGTGTTCGCGCCCTTTTTC GCCACGTACGGAGGTGTGCTGTTCAAG TACATCTAGAAGACTC[A/G]TTGAGCGG ACTTAGAATCTACGGACACCATCACCAT CACGAATAACTCTGCCCCGCCCGCCCGC CGTTCGTATGTTGTGCGCTGCTGTTATTT TTGGTTC |
| WSNP_CAP11_REP_C8768_3788007 | 1.28E-10 | 189 | GTCGACACCAGAGAAGTCCTACTTCATC ATAAACTTTACTTATTCTGTACTGAACTA CAGCACATGCAACTCGCAT[T/G]CCTAA CACAGGACGGGTATAAATATAAGAACT AATGTGTGCAGAACAAAAAATATAATTA CACAGGCGAAGCCAGGAATCATGTACA AGAAAGCAGCAGT |

TABLE 3-continued

SNP markers significantly associated with resistance to fusarium head blight

| Marker Name | P-Value | SEQ ID NO | Reference Sequence |
|---|---|---|---|
| WSNP_BQ168329A_TD_2_1 | 1.08E-04 | 190 | CAGATGAATCTGCTGGACCGGGCAGTA AAGATGGTTGCTGAACTAGATGAGCCA ATTGAG[A/G]TGAACTATGTGCGCAAGC ATGCCCAGGAGCAGGCAGAGGAGCTCG GTGTCTCGGTAAGAG |
| WSNP_EX_REP_C103505_88446868 | 9.46E-11 | 191 | AGGAAGCCATCAAGGGTTAGCCTTTTTA ATGCTTTTGAGGCTATGAGATCAAGATG CATCGCAGAGTCTATCAAATTCAAGTCT TCTAGGCCAGGGCTCC[A/G]GGCAATG AATCTGTTCAGAGAAAGCTCATCCACTT CCACGTCGCGCAGAGTAAGTTTCTTGAG AGAAGGAAGATTGATTATGTCAGGCAG TACAAGTCCC |
| WSNP_EX_C4094_7399975 | 5.00E-05 | 192 | GCTTAGCGTTCTACTGCAAAGCACACTG CCAACAGGACATGATGTTGGCAAACCG TCTGCTCCAGTTCCTGGCCGTGCCACAA CTGATATCTCAGGTCCC[T/C]GCAACCA AAATGGATCAGTTCGTAGACCTCCAAAA AGGAAGGCTGTTGAAAGGCAAGAGGA AGAAGACGCAGCAGCAGCTGCGCAGAG TCGAGCCATGCC |
| WSNP_BG314532A_TA_2_1 | 4.74E-11 | 193 | AACTAGATGCCCTTTTGGGAAGGTTTTA TCTCCTGATTCTAGCTATATTTGTGCTCG TGT[A/G]AAGTTTTCCCTGGAAATACTA GTAACTTAGCTTGTAATAGAAACGATGT TCCCTAAACAT |
| WSNP_BF292596A_TA_1_3 | 6.44E-04 | 194 | GTCTTGTTATACCCTATATATCGGCATCT TACTTAAGAGCATGATTTACAGCTATAG AAG[A/C]AGAACCTATATGCAATCTTGT CGATTCTGATATTACTTTCTGTACATGTC ACATCGACTG |
| WSNP_BF292596A_TA_1_1 | 5.94E-04 | 195 | TTGCATTCCTTCATGATTAAAGGGACAC CATACCATGTTGCCTGATTAGACATATTC AAA[T/C]CGGTTATGTTGATGCAATATA ATGGTATACTTGGAATGATAGCTTCCTT TCTGTATATGC |
| WSNP_RA_C2027_3945764 | 6.30E-04 | 196 | GGCATCCGAGAGGCTGGCACTAGTGGC AGCTCAAGCATTGCAAGAGAGTRAGGA GGCTACAAGCTCTGAAGATTCTCCGAGA GTGACACTTCCGGTAGGC[A/G]AATACC ACCTTCTTAGCAAGAGGGTTCATGAAGC CGAAGAGCTCGCCAGCGAAAGGGTGGC GGCATCGTTGGCGCAAATAGAGCTGGC GAAAGAGTCTGA |
| WSNP_RA_REP_C69221_66574148 | 1.02E-04 | 197 | CTTCTGAGACCGGAATTTCCAATAGGAT GGCTTCGTTCTCGTTCCAAGATGGTGAA TTTGAAGACCTGAAGAAACTCTGCTGYG CTATAGCTGATGACCT[A/C]GTTACCTAA GCCTGCGGCATATGCAACCATCAACAGT TTGTGTAGCGGTTCATTATGTAAAATCA CCCAGAATGTTACTGCAACTATAAACAT ATCGTGT |
| WSNP_EX_C17667_26408733 | 5.44E-04 | 198 | AAGGTTTTGCATGTTTCCAATGTTTCCAA AGAGTCCTCCCTTTGACGGTGCCTCATC ACCATTCTCATCTTTGTCCTTCTTTCCTCC AAATAAACTGTAT[A/G]CGCGGAAGGA TCTATTACTAGCTCTTTTCCAAGTAGAAC ATGGCAAACAGAATGCGCCTTGTACATT TATCCTAGTACGAGCTGGTCTGGAGGG GAGCGT |
| WSNP_EX_C16919_25506076 | 0 | 199 | GTATACCTCCCAGAGTGGATCTACGAGA AAGTAATCAGTGGGCATGAATGGGAGC TAACTTTGGAAATGACAGCAAAAGACA AAGAAAAGATGAGACAGC[T/C]GACCA TTGTGGCCCTGTGGTGCATCCAATGGAA CCCGAAGAATCGGCCATCAATGACAAA |

TABLE 3-continued

SNP markers significantly associated with resistance to *fusarium* head blight

| Marker Name | P-Value | SEQ ID NO | Reference Sequence |
|---|---|---|---|
| | | | GGTGGTAAACATGTTAACAGGGAGGTT GCAGAACCTGCAG |
| WSNP_EX_REP_C70593_69508988 | 5.00E-05 | 200 | AGGCAGTGATCACAGTTCCTGCTTATTT CAATGACTCCCAGAGGACGGCTACAAA AGATGCCGGCCGCATTGCAGGCCTGGA TGTTCTCCGTATCATAAA[T/C]GAGCCTA CCGCGGCATCGTTGGCATATGGTTTTAG AAAAAAGAACAATGAAACAATTCTGGTT TTTGACCTGGGAGGAGGCACCTTTGATG TTTCAGTTC |
| WSNP_EX_C22089_31270140 | 7.96E-04 | 201 | ccaagatacatgtacttgggaacaagtgtcaaagta agctacttgaaataattgatgctagtgaattgccag aatttcttggtggcacttgtacctgtcc[T/C]GAAT ATGGAGGGTGCCTCAAAGCTGAAAAAG GGCCATGGAAGGATGCAAACATACTGA AGAAAGTCCTTAATGGCGAGGCTCAGT GTGCTCGGCAGATTG |
| WSNP_KU_C14842_23275194 | 7.40E-05 | 202 | ctttccttgctgccatggaaatcatggcagagaaatt ccctggtgcatttgcaggttacaaactagaggtaat ggagtctcatcaagcgacaaaattgga[T/C]GTT TCTGGCACTGCCAAAGCTGTAATCTCTT GCTTTCAGAAGTTGGGTGTCTCATTCGA CTTARAYGAGGTAAACTTGGTTAGGGAC CCCGAAGAGCAGC |
| WSNP_EX_C2325_4355706 | 2.44E-04 | 203 | atgttggtctggataatgagaaggcaattgaggaga ccggcagacgwttcagagaaacggttcttgcacttg gaggtggaaaatctcctctcgaggtttt[T/C]GTT GCTTTCAGAGGACGGGAGCCGTCGCCG GAGCCACTGCTCAGGCACAACGGCCTG CTACCTGTCGCCGCATAGGGTGTCGATC GCTCCTTTTTCTCTT |
| WSNP_EX_C10630_17338753 | 3.44E-10 | 204 | TTAGAAAGGTTTGCTGGGGCTTAAGGG GACCAACAGGATAAAACCTTCAGMAGT GCTTCGTCTATGCTGTCCAGATGCAAAT TGTTGCGAAAAATGTTGA[T/C]TGCAAG GAACATATATGGTCGGTTATAGAAGTCG TTATAAACATCTTAGCAATGTGGAATGT AAGGAACAAGGGCCATACCATGAACTT AGACGGATTTG |
| WSNP_KU_C53501_58106782 | 5.14E-04 | 205 | GATCTCCAGATCAAGGACGGCGATGGG AACACCGCCCAGGACTTGTGCTCCTCGG CCTGGCCTTTCATGAAGCCGGCAAACTG ATGGCACAATGAACCCG[A/G]TGATACG TTGACGCCTGCTGCTACTACTACTAGTG CCGAGAAACTATACACACCGTGCTTGAT TAGCTGAATCGGATGAGCCGTTTTACCA ACCTCATCG |
| WSNP_EX_C4408_7939986 | 7.27E-11 | 206 | attctagaagatgatctatatcactatggtagtaaca gtgaggagatgcttctcgatgagttgaaggtttcacg agcaatgtcaaagcatttattaagg[T/C]TACAT CTTCAGCCACTATCAAGGAGGCAACACT GCTTATGCACGATAAGCAGCAAGGTTGT GTTCTTGTTGTAGACAATGAAGATTTTCT TGAAGGGATT |
| WSNP_KU_REP_C71567_71302010 | 9.56E-04 | 207 | CTGTCCAAGATATGGAAGACCTAAAAGC CTTTGTGAAAGATTCTGGTTCTGCAGAA GCCAATGATCTAGCACACTGGGATCTTA ACTTCTGGAGTGAACG[A/G]CTGCGGG AATCTAAATATGACATCGATGAGGAAG GRCTGCGTCCTTACTTTGCACTGCCCAA GGTTATGGATGGCCTCTTCAGTCTTGCG AATAAGCTCT |
| WSNP_RFL_CONTIG2167_1484520 | 2.20E-04 | 208 | CAGAAGCTTGTTCTTCTAGCGGTGAGAA CTCTCCAGTGTTCTATGCAGCC[A/G]TTG CTGGTAATGAGCATGAGAACATTCAAG ATAACGATTCTGAGAGAGGT |

TABLE 3-continued

SNP markers significantly associated with resistance to fusarium head blight

| Marker Name | P-Value | SEQ ID NO | Reference Sequence |
|---|---|---|---|
| WSNP_EX_REP_C66407_64613374 | 2.72E-04 | 209 | ctcttccatgctggaatcgcagcagtactgttgctcta tgttctcttctgggttaagctggatcttttcacaactct gaagtacctcagcttcctcggcg[T/C]GTTCCTT GTGTTCGTTGGCCATAGGACCCTATCTC ATCTTTCCAACACGACGGCAAAACAGAA GACTGCTTGATGGGAAGATGCGAAGAA TGTGTGATCA |
| WSNP_EX_C25755_35018674 | 8.54E-11 | 210 | ACATTTTATATGGCTGAACAAACTCGGT TCCTACAGTAAGATTCCCTGCTGAAGGA AAACCAGATGGCCTACCACTAAAGCTTG GAGTCATAGGACTGTC[A/G]AGAGGTG TCGCAGCAGAACTCTGGGGAGAATAAC TAGTCATAACGGGTGGGAAACTTGAAC CACCCAAAGCATACCCAGAAGTCACATA AGGATTTGCCA |
| WSNP_JD_C9360_10216330 | 5.00E-05 | 211 | GCCAAAGGTATCTCTGAAGGAAGGCCT TCCCTTGATGGTGACAGATTTCCGCAAA AGGATCTTGGATGAGTAACCAAGGCAA CACTGAGATGAATCTATT[T/C]GGTTCT GAATGCTGCGAATATAGGCAAACGTGC TTCACCAACTGGATCCATTCAGTATAATT CTGTGTTTGTATAACGACCTTGTAGAAT CATTTAAATT |
| WSNP_EX_REP_C67369_65940505 | 4.40E-05 | 212 | CAACCGCTGCTATTGGAAAGGGTTTTGC CATTGGATCAGCTGCTCTTGTGTCCCTG GCACTTTTTGGTGCTTTTGTCAGCAGAG CTGGTGTGAAGGTCGT[T/C]GATGTCCT ATCTCCCAAGGTGTTCATTGGTCTGATT GTCGGAGCCATGCTTCCGTACTGGTTCT CTGCCATGACCATGAAGAGTGTTGGAA GTGCYGCTC |
| WSNP_EX_C4769_8510104 | 6.40E-05 | 213 | ACAGATCTTGATGCAGCCAAGAGAAGC GAGGAGACCAACATGGTGACAGCAGAT GTTGATACATCCAAGAGAAGCGAGGAA CAGAGCAACATGGTCGCCG[T/C]GAAG CTTGATACAGCCAAGAAAAGCGAGGAG CAGACCAGCAGTGTTGCTGCGGCAGGC TGATTACAGGATGGGCGCATCTGAACG GAAGCTACATCCAAA |
| WSNP_RFL_CONTIG3917_4326857 | 7.42E-04 | 214 | CGGAAAAGCCAGGTGTGCCTCTCGTTCT TCGATGAGAAGAACAAGCACCC[A/G]G GCTGGTTCAGCAGCAAGACTGAGAGGG TTTACTGGGAACAATGGTTCAT |
| WSNP_JD_C626_945114 | 8.00E-05 | 215 | ttgttggagtttgcttgactctaagccttgcaaacatc gtggggttcaccaaatgcaacaaagatgccaagaa gaacatccgagcttttgctgaaaatgc[T/C]GCTC AAAACGCCATCACATCCCGCATCACATC ATCCCTTCAGTCAGCATTCGGTATCTGA AGTCCAGATTACAGAGGCCCAAAATTAC ATACAACTGTGT |
| WSNP_EX_C11055_17927668 | 5.86E-04 | 216 | TCAGCTCTGGTAGGGCTGCCGACTTGGT CTCGTCGAGCTGCATTATAGCGGAGATT TTCTTGGTCTGCACATCTTCTGGCAAGCT TCTTCTCCGTGGGTA[A/G]TCCGAGCTC ACTGACTTCGGATTYGGAGGGTGGTCA GTTGAAGCATTGCTTTTAGGTTCAGCAA GCTTTTTCAACCGCTCAATCGAGGATTC AGTTCTCC |
| WSNP_EX_C6476_11246531 | 5.80E-05 | 217 | cttgctgaacaaaagtctgctcaaggatctctctaca caagtcaagcctagaccagaggaccctcaatggcg caagatatgtagaaccaagaaggtgacc[A/G]A CTTCACTAGGTCGGCGGGTATTCTTGTT ATTTCTGGGCTCACTTATTATGCCTTGAY TTCCCGTCCTGAAATCGTAAGGTATGGT GACTATCTTGTTAC |
| WSNP_EX_C15163_23357477 | 2.98E-04 | 218 | CATCCCTTCCTGGTAGACAGATGAATGG GACAGCAATTGGTGGCCTTGAACTGAG TAAGGAAGCTATGCTGAGCCTTGCTGCT |

TABLE 3-continued

SNP markers significantly associated with resistance to *fusarium* head blight

| Marker Name | P-Value | SEQ ID NO | Reference Sequence |
|---|---|---|---|
| | | | GCTGCACAATGGGAGAA[A/G]CAAAGA GAGATAAACCAAGCAAAGATAGACRCA AACTGCAGTAAAATTCAGGAAGCCCTCA AGTCCCTGAACGAGTRCAAAAGAACAT GCGAGCTGCATG |
| WSNP_EX_C5780_10153638 | 9.80E-05 | 219 | CATAGATGAAGCTTTCTGTAGTTTTCCAT CACCCACTGATCTTGGGAAATTGGCCACA CCCCCACAGTGCTGAGGCTGGTAGCTGC GAGGTACAGGGCACT[A/G]TGAAGAAA AGTTTGGCCAGCAAGTTTGGCACTGGG GCTGGCCGTCCAGAATACATTGCATACC CACTGCAGTGATCATCTTCAAGCTTTAG CTGTCAGCA |
| WSNP_JD_C119_190135 | 9.04E-04 | 220 | agaaacttgtggggctgctgcatcccacgggtttga acaggattrtagtcttgtgccatggctttacggcctcc aagagttctggcgttattgttgatct[A/G]GCAG ATGCAATAATAAAACAAGGGATTAGTGT TTTTCGCTTTGACTTCAGTGGAAACGGA GAGAGCGAAGGCGTTTTCCAGTATGGC AACTACAGGAAAG |
| WSNP_EX_C97184_84339976 | 1.85E-09 | 221 | TTCCAGCTTCTGTGCTTCAGGGAGCTCA AGACAAATGTTAGAATATTTACCCAATG GATGATGTAATCTCTAGGTATCTTTTGT GCGCTAGCTGTGCCAA[A/G]CAGCCGTT ATGTATGTTCATCTAATTGTCACTTCTCA TTTCTCCTGTTAACACTGGTCTTACTTAT GCTAGTATAATTTAGGAAACCTGCATAG TAACAT |
| WSNP_EX_C4548_8166555 | 3.32E-04 | 222 | TATACAGAACAAAGACGCTCTCCCGTAC GGCCCAACCAGTTTGGAATGACAAGTTT GAATTTGATGAGATTGGTGGTGGTGAA TATCTGAAGGTCAAATG[T/C]TATAATTT AGATACATTCAGTGATGATAGCATTGGC AGCGCAAGAGTAAATCTGGAGGGACTT CTAGATGGTGCTAGCCGAGATGTGTGG GTACCACTTG |
| WSNP_EX_REP_C68113_66877517 | 8.40E-05 | 223 | cccgtaccgcaactgatgctccgcccttttgatgcaag caatatcactgcactacagctcatgttcagcaagttt gaatacgacggaaagctcaacccaac[A/G]TTT GCAGAAGGTCAATTCGAGCTCCCTTTTT CAAGTATCAAAGCATACATAAGTGAGCC AATTACTCCAAGGTTCATTCATGTGAGC TCTGCAGGAGTTA |
| WSNP_EX_REP_C69266_68192954 | 9.01E-09 | 224 | TTCTCGAGGAAGAAGATGGATGCGACC GCCCAGGAGCTGTCGGAGGAGAAGGC GCTGGCCTACTCATGCCTCGCGTAAATC CACATTGGAAGGGCAGCTG[A/C]TCCTC TGGATGTTTTGAATAATGAAACCTTCCG CTCCTTAGAAACTCTCGTCTCCACCCAGA ACAGCCGCACATCGCGATGCATGCTCCT TTTCGCTGGT |
| WSNP_CAP11_C847_522893 | 4.92E-04 | 225 | TTAGCATTGTTGAACCATATCTATTCCTC ATCCTTGAGTAGTGTGCAAGCATACTGT GGCAGTTTGGCTCCAGTTTTGAAAGTCA TTTTTGTTTGTCTGA[A/G]ACATCTTGGA AAGAACAGTGTAAGAATGAAGTATTTCT GTTTAATGCCAGTTAGTATTTTGTCGCSA |
| WSNP_EX_C1279_2451699 | 1.60E-04 | 226 | ACAACGTCGACAAGAGGTCCAAAGTGA GGAAGCAGCCGTGGATGCCCTTCATCTG CTGCCACTCCGTGCACTGATGCTGCCAT TCATTCTTCCTCAGCTA[T/C]GATCTTCTT TCTACACACGCCATGCGCATCTTGTTTG AATCCGTGGCACCCTTTTTAGTATATTTG CGTGAGGACTGGATATTGGATAAGCTT ATGTCTT |
| WSNP_EX_C7316_12552186 | 0 | 227 | TGACATCAAGCCACACAACATCCTGCTT GATAGCAATTTTGTCCCAAAACTTGCTG ATTTTGGTCTCGCCAAGCTGTACCCAAG AAACAACAGTTTCGTA[T/C]CATTGAGC |

TABLE 3-continued

SNP markers significantly associated with resistance to *fusarium* head blight

| Marker Name | P-Value | SEQ ID NO | Reference Sequence |
|---|---|---|---|
| | | | GTCCTGCGCGGAACAATTGGGTACATA GCTCCTGAGATGATATCTAGGAGCTTTG GCGTCATATCGAGCAAGTCTGATGTTTA CAGCTTTGG |
| WSNP_EX_REP_C68515_67349904 | 1.49E-08 | 228 | TTGGTTGTTTGTGTTCTTTTTAGCAGATC GCATCATTGTGGCAGCTTACTTAGCTGT AGGATATTCATATGGCTCGCTCCATGTA AATTGGTGATCGACG[A/G]CGGAGTTTT AACGCCGAGATGCGCCGGCTCCTTTTGA TGTAACCCGGCTTCTATACCGACAGTTG TAGGACAAAGATGAGAGATTTTATGAC ATGTAACA |
| WSNP_JD_C3463_4479210 | 2.62E-04 | 229 | tgtwgaatactcaccttcggataaaggaattatcac tggttcctctgacgggcttatacgttttgggaaaac gaaggaggcataaaatgtgttaagaat[T/C]TGA CGCTTCACTCGGCATCGGTCCTGTCCATT AGTGCTGGTGATCACTGGCTTGGAATTG GTGCTGCTGACAATTCTATGTCTCTTTTC CATCGACCACA |
| WSNP_KU_C6825_11858665 | 1.44E-04 | 230 | ttctttgcatgtactgctccattggtttgcagattttttg ggggcattgtgtatgctggwaacccaacactagaa gaaacggacctcttcaataatgacta[T/C]CTTCT TTTTAACTTCAATGACTATCCAAGTGGTA TGGTTACTCTGTTCAATTTGTTAGTGATG GGCAATTGGCAAGTATGGATGGAGAGT TATTGGCAAC |
| WSNP_EX_C1790_3378771 | 7.34E-11 | 231 | GASTCTGGAAGCTGTACAGGAGTCGTC GAGAGTCAAGAGGAGGTTGTTCTGCTC ATAGGACGACCTGACCTGACCTGATCCG AGGCACCGACCATGTCGA[A/C]ATTAAC AGTGAAGCTGCCAGCGCCATTTTTGACC TCCCCGTCCGTCTCGAGAGAACAGCGAA AGAGAAGATAGCATGAGACGATGCTCG TCGCTTCCTTT |
| WSNP_EX_C5378_9505533 | 2.21E-11 | 232 | GAAGTCAGCACCCCTCTCATTGCAACAT AGGACTGCGAGTACGCCATCTTGGGAG AGGGTGAGGGGTCGAATTCTGACCAGT CCTTAACCGACCCCTCTC[T/G]CTGCATT GCCCCAGCATTTCTTCTTGCCATTGCAG GTGCTCAATATGTCACGCATGTACAGTT CTAGAGTCAAGCAAAAGACATCACCTCT CTGATACCA |
| WSNP_CAP7_C444_237594 | 8.76E-04 | 233 | CTGCTCAAGGGGTTATGATTTTTATTTTA TTTGTTTATAAGTTCATTCTATCAGTTCG TTTTGTACCTAATAAGTGAACTAGCACA AGTCAGTAGAATGA[A/G]CTACTGATGA ATGAGCTTCTAATTTATCTGCAACTGTAA GAGAAATTGAGCTTCATGTTTTCACTTG CACATATATAAATGCTGAATAAGCTGGT AAGGA |
| WSNP_EX_C10630_17338703 | 8.03E-10 | 234 | TATCTGGGCATATTTGAACCATTCAGCG TGCATGCCTCACTCCCATGGTTTTAGAA AGGTTTGCTGGGGCTTAAGGGGACCAA CAGGATAAAACCTTCAG[A/C]AGTGCTT CGTCTATGCTGTCCAGATGCAAATTGTT GCGAAAAATGTTGAYTGCAAGGAACAT ATATGGTCGGTTATAGAAGTCGTTATAA ACATCTTAGC |
| WSNP_EX_C5378_9505087 | 1.60E-04 | 235 | TTCTCGCAACAATGCCAGAATCATTAAC AGAATGTACAATAGGCAAGGCTTCAAC AAAATCTGCCTCATCATCCAACATTGCA GGAACTGGGGGACTCTC[A/C]TCGGCCT GTGGCTCATTAACCGCTTCAGATTCAGC CTCCGCTACAAATGGCTCCAGCTTGGTG CCTTGATGTTCTGCCATTTGTCGTCTATC AATCGCAT |

TABLE 3-continued

SNP markers significantly associated with resistance to *fusarium* head blight

| Marker Name | P-Value | SEQ ID NO | Reference Sequence |
|---|---|---|---|
| WSNP_EX_C8386_14128029 | 2.22E-16 | 236 | GAATGATGCAGAAAATGCTGGTGACTG TGAACCTGAAGAATCTGAAACTAATGAA CCAGAAGCAGAAGCAGAAGCAGAAGAT GTCAAATCTAAGGAAGCC[A/C]GTGGCA ATTAGATTGCCCTATCCCCCATGGTGCT AACTAAATGTGGCAAAACAAAATAGAT GCCAGGCAATATGATTACTGAAGCGAG TCGCGGATGATG |
| WSNP_JD_REP_C63942_40788045 | 6.09E-10 | 237 | GATTTCACCAGAGGCAGCAACGCCGAG GTTATCTCCGCTTTGGTGGGCAGAGCTT GAGATACTTTCAGTTGAATCCTAGGAAG AAACATGTTGATATGGT[A/C]TGGTTCT TGCAGCAACACTGAGGTCCTGTGCGTAC TGTCTTGCAATCTTGTACATCTTTGTTGC GAGTTTCTACTTTTCTGGCGATTTCGGTG TATATGC |
| WSNP_EX_C4661_8344663 | 7.00E-05 | 238 | GGCTGAGATGAACCATGGGCCTCTTCTT TTGTAGTTCAACACTTGAACATTTACACT TGTAGCACAACACTTGAATATTTACACTT GTAGTCCAACACTT[A/G]AGCATTTTAC ACTTCAGGCAGAAAGACCAGATTATAGT TCATTTTTCACTTTTCAGTTCTCAATGCA CATCTGAATAAATTGTTTGGTGTATAAC TTCCA |
| WSNP_RA_C9209_15425473 | 4.98E-04 | 239 | AATATGGAAGACAATACATTTGATATTT GGCAAGATGTTGCCGCACCACGTCACCA ACAGGAAAACATATCTAATCTTGGGAGA GAAATGACTGGTGCCT[T/C]GTCTGTGC CTGCTAAAGAAATTGACTCCATGGATTT GTGGCTAACCAGCAATATCAAGGAATCT AACAGCTGCAGCAAAGATGTTAGTGGA AYTCATGAC |
| WSNP_JD_C43389_30288993 | 8.70E-04 | 240 | ggagttccaaattatctgcttttttgamcmagaaaa aagcttgtca[T/C]AGGCAACAGCCTAACA ATCACGGGGAGTTACCACTTGTAATCGA AGCCATACAGATAAAATAAAGACAGAC TACATTTGTTATGATAGCGATATAAATGC |
| WSNP_EX_C30969_39821293 | 1.15E-07 | 241 | GAGTTTTCTCTGCTCTACATGATAGTCCT TGCATGCATCGACAGAAGACTCAAGAG CATGGATTGCAATCTCCGCTGGAATCAT CCATCGATAAGGGACC[A/G]TATGTTAA TCTCATGGAAGATGGAATGGTAGCTGC AGTGACAAACGAGGATACCAACACTCA CGAATCCTTGGATAAGCATAATCAGGCT GTCAGTGAAA |
| WSNP_EX_C3738_6809767 | 2.30E-11 | 242 | AGTAGCACATTCTTTTCCAGGTTTTCTGC TTGCTGTGCCATAGCACAGGTGAGCTG GAGATCCTGGAGATTAGACAGCCCTCCA AGTTGTAATACATTCT[T/C]TATTGAGTA ACGGCGGCTGAGATCAAAATTCCCCAAA GTGCGAAGAGATGTCATGTGGGCTACT CCTTGAGGCAGGATAGATTCGCTCGGA AGACGGAGG |
| WSNP_EX_REP_C103505_88447145 | 5.60E-05 | 243 | CAGGAGGTAAAACAGTCTTATCATATAG ACAAAGTTTCACGTCAAGCACTTTAACA TTATGCTTCACCGCATAGCCAATCCACAT TCTGACATCATTGCA[A/G]TTCAGGGGA CCATGAGGATTCCAATGCAGCTGGAAT GTTTGCAAGTCTACTTTCCGACGGACAA GCAATAGGTTGTTAACAAAACGAGTAA ACTTCTCGA |
| WSNP_EX_REP_C67897_66613415 | 3.02E-04 | 244 | GCCTGTTGGCTCTTCCAACTTTGTTGACC ACCCAACCTCATCTGACAGCAGATTAGA ATCAAAACAAAACAAAGATGCACGGGA CACCAAGGTTGACGAC[T/C]GGGAGGC AAAAGCTGATGCTCGGGATGTCCATAGT GATAGCAGGATTGAATTTCAAGGCAAT |

TABLE 3-continued

SNP markers significantly associated with resistance to *fusarium* head blight

| Marker Name | P-Value | SEQ ID NO | Reference Sequence |
|---|---|---|---|
| | | | AAAGCTGAGACTGATGTGAAGACAAAC AACAGAGCAGA |
| WSNP_EX_C33765_42199371 | 9.80E-05 | 245 | TTTGAGGAACAATGCCCAAAGGATCAT GTGATGTGCATATTTCTGGGAACTGTC ATCTAGCTTCATATTCATGCTTTCCAGTG ATAGCGAATTGCATCC[A/G]TTCCCAAG GTGGCGCAGATTCTGCCAGACTATCAAG CCATGCGTCGGTGTTTCAGACCTCGTTC GCGCACAATGTACAGCGGTGCCTATGG TGCCCCTTT |
| WSNP_EX_REP_C66606_64905694 | 4.40E-04 | 246 | GGCAGCCTAATCAGGTGGTTTGAGATCT ATCTCTCTGTTTTAATCGTGAAATGGTTA GTTTTTCATGGCAGGGTATTATCTATCA ATAAACTTGTATGTG[T/C]GCATGCAAG TGCTACCTTAGACTGGTCAGTAGAATTT GAGAATTGTATGGAAGGAACTGGTTTG TTGCTTTGATATCTATCAAAATGAGATG ATGTCCTG |
| WSNP_EX_C14248_22204549 | 1.94E-10 | 247 | TGCCAAGGATGCTTTGATCTCAGACGCC GGTGATAAAAATCAATGAAGACATTGC GGATGTGAATGAACACATCTCCAGGGA AGAGCACCCTGAGCCCAC[A/G]TTGGAA CACTCATCCACGCTAAGAAATGTTGATG AGATTATGCCGGTGGACGAACCTCCTGT ATCAAAGGAACCTCAAAGGTGCGGGTC TGCCCGCAGCC |
| WSNP_EX_REP_C66766_65123941 | 8.42E-11 | 248 | CCGACACTCTTCAAGGTCAGAGTCTGAC GCCTCAGATTACAGCAGCGATGATGAT GAGCGAAGGTCAACCAGGAAGGACCAT TCTAGGAGCCGGAGGCGT[T/C]GCCACC GGTCCTCAGACGATGAATCTGAGGAGA AGATCAGGTCGAGGCATAGGAAGCGTC ATCACAGATCAAGTGACGAGGACAAGC CGTCAGATTCTGA |
| WSNP_CAP11_C3968_1874257 | 1.10E-09 | 249 | CACTAAACATCACACGAGCTTTCAGTAA CACACAATTGCATTAAGTAGAATTTGAA CAATAGTAAAGAAAGATTACAATATAAC AAATCTTTGGATCCAA[T/C]AGAATTAC AACTGGACACTATAGGTTCTATCATCTG TGTTCATGGTAGCTTCAGATGCTATAGA GTGAACCATAGCCAGACGAAGAACAAG AGTGAAGCA |
| WSNP_EX_C15325_23565935 | 2.04E-10 | 250 | cagttggagttgctagtcagagagaagagctacgc gctaggttccctggtgttcctggtgatcttgtgaatta cttcctctttgttgcagaggaggtacg[A/G]GCCA CATTAGCCCAGTTGGGTTATGAGAAGCT GGATGATATAATTGGGCGGACAGATTT ACTTAAGCCAAAGCATATCTCTTTGGTG AAAACGCAGCACA |
| WSNP_KU_C10939_17975681 | 3.38E-10 | 251 | ATCTCCAAGTTGGTATGGATATCTTCCAT GACTTCTTTACCCTTCATCAAAGCTAAGT TGGAATTTGAAGCTTCCCTCGCCATCCG ATGGTCTTCATTCC[A/G]TGAGTTGGGA AGCATCGAAGAGGGGTATGCTTTCTTTG AAATACCAAATGTGGAATTTGAATCATC CTTTAACACTGCGGAATATTGATCCCTA GTTGAA |
| WSNP_EX_C41073_47987034 | 1.10E-04 | 252 | AAGAGAAGAGAACAAGGGGAAGATGA TTGTGACCATGTTCCCGAGCGGGGGCG AGAGATACATGAACTCTGACCTCTTTGC AACTGTAAGAGAGGAGTGT[A/G]CTGC CATGACCTTTTGATCTCACATTTTATGAA TACAAAACAGTTGTATGTGAAGGGTATA TGCCGTCGGTTACCTTAATGTGTTCCACT GGACGACATT |

TABLE 3-continued

SNP markers significantly associated with resistance to fusarium head blight

| Marker Name | P-Value | SEQ ID NO | Reference Sequence |
| --- | --- | --- | --- |
| WSNP_EX_C5378_9504586 | 7.20E-05 | 253 | AAGCAAATCCAGAAAAACCAATTGGAA ATCGACGCGGTATACTGCTCCTCTGGTT TGTATGCCATCCAGTGACCTGATCACCC TTACAAAGGGGGCCTTC[T/C]AAAACCA ATTTATACTTGGTCCCAACATGCGTTGCT ACTGGCCATGTACCAAAGCGCCTGATTT TCCTCATTTCTTCAAATAGATCAACTGAG TATGCTC |
| WSNP_EX_C15325_23565794 | 2.05E-10 | 254 | TTAGGGTGGATGGCGGATTCAGGAGTG GCCTAGATGTCCTTTTGGCTGCTGCCAT GGGTGCTGATGAATATGGCTTTGGTTCT GTAGCTATGATAGCTAC[T/C]GGATGTG TCATGGCACGCATTTGCCACACAAACAA TTGCCCAGTTGGAGTTGCTAGTCAGAGA GAAGAGCTACGCGCTAGGTTCCCTGGT GTTCCTGGTG |
| WSNP_EX_REP_C67492_66096650 | 2.28E-04 | 255 | CCGCGTCGCTGTTCTTGCGCACAGTGAA AAGGTTGTAGCTGTTCTCTGCACCAACA TAGATGTCATCGTCAATCATCTCAACTG CAGTCATCCAGTTCGC[A/G]TTGTAGTC CCTAGCGAGCTCTTCAATCGCACTCTCCT CATGCTTGTACACAAGCAAGGATATCGA TTTCATCAGGTCTCCGACTACGATGAAA TCACCAC |
| WSNP_EX_C21129_30256617 | 5.91E-09 | 256 | TGGATCTCACCCGGACGGTGCGTGTATA ATATGAGCAACGTCTTGGTGAGATCCGC AGATCATCACAATGGGTGTTACGCAAG GCATGTGATAGACTTAT[A/G]CTACTGG GGGTAATGCTTGCTTTCAGTTTTGGTTCT GCATATGTTGTATGGCTTTTTTAATACAA AAGGGTGTATTTTGTCCTAAGACACCTG TATATAT |
| WSNP_EX_C31670_40433594 | 2.38E-04 | 257 | TTTTTACTGCCACCTTCTCGCCATTCAAC TCAACCTTCACGGTTTTGCCAAGGGTGC CCGCCATGTCAACCACTCGCTTCATCAT GAGTGCCACAACATC[T/C]GCTTCGAGC TCAGTCATTTTGAACTTTTCAAGATCAG GCTTGAAGGTAACTTTAGTCCAGTTCTC CGACTGCTTGCACTTTTTAATCTCAGGCT CCGACT |
| WSNP_EX_C2181_4089639 | 1.72E-04 | 258 | ACACCGAGTCTGAAAGGATTGTGCAGG AGGCTCTTGATAGGGTCATGACAAATCG GACCACTGTCATAGTTGCACACCGTTTG ACGACTGTAAGGAATGC[T/C]GATACAA TTGCTGTCATCTGCCGAGGATCAATAGT TGAAAAAGGTCCACACCATGACCTTTTG AGGGACCCAGAAGGAGCTTACAGCCAA CTGATACGCT |
| WSNP_CAP11_C923_558715 | 9.58E-04 | 259 | AGTCTGACCGTCGATTATTCGAATCGTT TGTATAATGTAATTAGTGCGAATCTTGA TAGTAAGTTTTTGCAGGATGTGCTTGAG CTCATCTGCTGGTACA[A/G]TGATTAGT TCACCTGCCTGTTGTCTCCTCCGTAACGA GTTGACAGAGAAAGTACACGCGACAAA ATGTACTCCAAGACACGCTAAGAGTAAT GGAATCAG |
| WSNP_KU_C8592_14575931 | 7.74E-09 | 260 | GCCTTGCCTCAAACCCGAATCCAAACAA GTCATTCGAGGTCCTTCCTAATCCGGGT GACTCCCTCTCAAGCCTCAGTTTTAGCCC GAAAAGTAATCTTCT[T/G]GTGGCAACT TCCTGGGATAACCAGGTGAGGTGTTGG GAGATAGGTAATGGTAACAGTCAGCCA AAGGCATCCATATCACATGATCAGCCAG TGCTCTGCT |
| WSNP_BE490744A_TD_2_1 | 1.12E-09 | 261 | CCAGATGGGTTCCATGACCTGGCTTCTC TGTTTCA[T/C]GTGAGTTATTTCTTGTGC |

TABLE 3-continued

SNP markers significantly associated with resistance to *fusarium* head blight

| Marker Name | P-Value | SEQ ID NO | Reference Sequence |
|---|---|---|---|
| | | | TTGTTGTAGTGATATTTAGTGATATCTGC ATGAACATATGTG |
| WSNP_JD_REP_C62985_40164465 | 9.60E-05 | 262 | TGGTCATTCTCTGGGGGGATAATTGTAT CCTTCCATGGCCCAATCCCAATTACATAC TTCCTTATGAACGCGAGATAGCCGTTCG AAGTTATCTCATAGT[A/G]TGACTGGTT GGTATCTTGAGTTGGAACTGTGGTTTCG TCTATTAGAAGTAGTTTTGGAGCATTTG TGATGTTTGAGATGTAAATTAGTGAAGT TGGAGCA |
| WSNP_EX_C54655_57455562 | 6.88E-04 | 263 | GCATTTATATCGCTATCATAACAAATGT AGTCTGTCTTTATTTTATCTGTATGGCTT CGATTACAAGTGGTAACTCCCCGTGATT GTTAGGCTGTTGCCT[A/G]TGACAAGCT TTTTTCTTGGTCAAAAAGCAGATAATTT GGAACTTCTATCCCAATTGGACTCATGT ATGGTTACGAGGACTTTTGCCTGGCCAG GCAGCTG |
| WSNP_EX_C16295_24772663 | 4.44E-04 | 264 | GGAGGCCGAAGCCCAAGATCAACTGAG CACAGTAATTTTCAACTTGGGTATACAG TTTGACATGATCCTTGTAAATGCTTGCAC CATGGGTGATATCTTC[T/C]GTGGAGGT CTAAAAGGCGACAGGACAGACTCAAG CAAYGCCTAGATGCAGCACACAGGGGT TCGACCCTCAGTCACACCCTCTTTATTTA GATGACAAG |
| WSNP_EX_C3940_7144946 | 7.00E-05 | 265 | CAGTTGTACCGAGAAGGACAACAAGGG AGAGGAAGGCGGCAGTAGTCTACGTCG CTTCTGAAAGCGAAGATGATGAGTCTG AGGATGAAGATGTGTCAGA[A/G]CCAA GTGACGATGATGACTTCTCCGAAGATGA CTAGACTCCTTGGCTCAACTGTCCAAAC ATTGCGTGTGGTGCAGTGACTCTAGTGT CTTGAGACATTT |
| WSNP_KU_C12698_20441325 | 0 | 266 | CTCCCAAGTCCAGAGTGAAGGCGCACG CTCTGCTCGACCTGCTGCGCAACTCGCC CTACTCGAGGTCGAAGCTGCAGCCCAAC ACCCTGGAGAACATCGT[T/C]AGCAACA TTGCTTCTCAGATCGATGGGGAGGACC GTGGTGGGAAGGCCAAGAAGATGCTCG CCGAGATGGTGAAGGTCAGCATGGAGC AGAGCTTGAGGC |
| WSNP_BF291549B_TA_1_1 | 3.01E-09 | 267 | AAAATATTTTTGCCAGGTGAATCCACAT ACTCATCAGTTGAAATTATGTGACTTTG GAAG[T/C]GCGAAAGTGCTGGTATGATC ACACATTACCTGATATTCACACTTGCAC GACATTGGCATT |
| WSNP_RA_C9738_16173810 | 6.50E-04 | 268 | ATTTCGCCATGATTTCCTACCCATCTACT TACTTACAAGCAACCGCTGATAAATTAT ATAATTATATAGTTCTGCGAAAAATGAT TAGCACTTTCGCCAT[A/C]TTGTCTGTGG AGTGTATTTGTTGATCTAATTACTAGCA GGAGGTCCTTGCAGGACCGGAGGATGT CCTGAGGACTTCAGAACCAAGGTCACGT ATCTTTT |
| WSNP_EX_C15325_23564654 | 2.04E-10 | 269 | TCAAGATACTCTCAAAAATGGGCATATC CTTGCTCTCAAGTTACTGTGGAGCTCAG ATCTTTGAAATATATGGTCTTGGCCAAG AAGTTGTCGACCTTGC[A/G]TTCTGTGG GAGTGTATCGAAAATTGGAGGACTCAC CCTTAATGAGCTGGGTCGAGAAACACTA TCATTCTGGGTGAGGGCTTTCTCAGAAG ATACCGCAA |
| WSNP_EX_C7705_13139890 | 6.06E-09 | 270 | ttgggatgtgtttactggagcttgttacatttgagtac ccatattgtgaatgctccaatgcagcacagatatac aagaaagtttctgatggtgaaaggcc[T/C]GGTT |

TABLE 3-continued

SNP markers significantly associated with resistance to *fusarium* head blight

| Marker Name | P-Value | SEQ ID NO | Reference Sequence |
|---|---|---|---|
| | | | CACTGGCTAAGATTGAGGATCCTGAAGT TAAATTCTTTATAGAGAAATGCATAGCC CAAGCTTCCCAAAGGCTCTCAGCAGAAG AACTATTAGTGG |
| WSNP_RA_C9738_16174002 | 3.28E-04 | 271 | GTATCTTTTGCAGCATCAAGGCCTTCTCC CGCTCCAGCTGCTGTATGTACAAATCCT GCTCGTCCTGGACGCTCTCCACCTCCGT CAGGGCCAACGACAG[T/C]GCCTCCGCA TCGCCGCCGTCGTCCACCAAGCCCGAGC ATTTCTTCAGGCTGTCTCTCATCTGTGCT GATATCTTGTGTCCTTTGCCGAGGGCGG ACGCAT |
| WSNP_EX_C16295_24772702 | 6.00E-04 | 272 | CAACTTGGGTATACAGTTTGACATGATC CTTGTAAATGCTTGCACCATGGGTGATA TCTTCYGTGGAGGTCTAAAAAGGCGACA GGACAGACTCAAGCAA[T/C]GCCTAGAT GCAGCACACAGGGGTTCGACCCTCAGT CACACCCTCTTTATTTAGATGACAAGGG GGCTTGCGGGCCCATCATTTTAGAASAG CTGACACAG |
| WSNP_EX_C3887_7051325 | 5.20E-05 | 273 | acggcatgtatgttgaagtgtcaatctgctcaggca gctccttgatgtccacctcaaaccgttcttgcacctgg ttaaggacgtccgagtccgaggccga[T/C]GAA ACAAAAGTTATGGCGAGTCCCTTGGTGC CAAAACGCCCAGCCCTTCCAACCCTGTG CAAGTAGGTATCAGCTGAATCAGGCAT GTCATAGTTTATCA |
| WSNP_KU_C7471_12865509 | 9.35E-12 | 274 | TTTGTGGCAGAATCATGATTGAAAAATA GTGTATAATTTCTCATTCACATCGGCAG CATGTATGTATAGTTTTGCAACCGGACA AGATGATGAAATTCCC[T/C]AGTGCCCA ATTCCCACATTTCCCGAGGCTTTGTAGC ACATAACATTTAAGTATATGAGTCGCGC ATGCATCATATGTGCTTCTCTTCTTTCTG GAGGAGG |
| WSNP_CAP8_C6680_3136899 | 9.02E-11 | 275 | GTGGTACCTTACGGCCGGGGAGAGAAG GCCATGACCTTCGACCTCGACGACAAGA TCCTCGCCGCCGTCGGGGCGGCGCCGG TCGGCGTCGCCGCCTAGG[A/G]ATGTTC GTCCTTCGATGCGCCGCAGCGGGAAAA CCATTTTGAAAACACAGCCGCCCGATTA TCATACATACAGATGACACAGAGCATAT CTAATCATGTT |

TABLE 4

SNP markers significantly associated with anther-extrusion

| Marker Name | P-Value | SEQ ID NO | Reference Sequence |
|---|---|---|---|
| WSNP_EX_REP_C66893_65301351 | 3.34E-04 | 450 | AGTTCCCAATAAGCAAGTTCTCGAACT CTCTTGGATCTTCTACTTTATTGTTGTA ACCATAGCGCACCACACATCGGAATAC CCTGTATTCTCTTGGCTC[T/C]ACATATC GGAAGAGGAACCGTTCATTTGTTTCTA TATTGCTGATTGGTAAGTACTTTATTGA GGTAATCACAAGAACTGAATGGATGG AAGGTACTTTTT |

Example 2

Identification of Favorable and Unfavorable Marker Alleles

The wheat lines used in the association studies can be sorted by phenotype and assessed at each of the marker loci found to be associated with that respective phenotype. For flowering date, this includes any of the marker loci disclosed in Table 1. For heading date, this includes any of the marker loci disclosed in Table 2. For resistance to *fusarium* head blight, this includes any of the marker loci disclosed in Table 3. For anther extrusion, this includes the marker disclosed in Table 4. The allele at each marker locus that is associated with a favorable phenotype (or alternatively, an unfavorable phenotype) can then be identified.

Example 3

Marker Assisted Selection

Polymorphic markers identified herein as co-segregating with a phenotype, such as flowering date, heading date, anther extrusion, and resistance to *fusarium* head blight can be used in marker assisted selection for that respective trait. Wheat plants with a favorable phenotype can be selected for by detecting alleles at one or more marker loci, and in addition, progeny plants derived from those plants can also be selected. Hence, a plant containing a desired genotype in a given chromosomal region can be obtained and then crossed to another plant. The progeny could then be evaluated genotypically using one or more markers and the progeny plants with the same genotype in a given chromosomal region could then be identified as having a favorable or unfavorable phenotype.

Example 4

Genomic Map Positions for Various Markers

TABLE 5

Summary of Map Positions for Various Markers

| Marker Name | Trait | Reference Sequence (SEQ ID NO:) | Chromosome | Position |
|---|---|---|---|---|
| WSNP_EX_REP_C66893_65301351 | Anther Extrusion | 450 | 8 | 218.2 |
| WSNP_EX_C10783_17555091 | FHB | 138 | 1 | 50.31 |
| WSNP_CAP11_C3968_1874257 | FHB | 249 | 1 | 92.06 |
| WSNP_EX_C2181_4089639 | FHB | 258 | 1 | 104.58 |
| WSNP_EX_REP_C70593_69508988 | FHB | 200 | 1 | 106.37 |
| WSNP_RA_C9209_15425473 | FHB | 239 | 1 | 141.49 |
| WSNP_EX_C5060_8985678 | FHB | 22 | 1 | 165.36 |
| WSNP_EX_C3201_5910659 | FHB | 165 | 1 | 256.51 |
| WSNP_EX_REP_C67492_66096650 | FHB | 255 | 1 | 270.24 |
| WSNP_EX_C6476_11246531 | FHB | 217 | 1 | 271.95 |
| WSNP_EX_C46670_52108070 | FHB | 21 | 1 | 279.8 |
| WSNP_EX_C3887_7051325 | FHB | 273 | 1 | 279.8 |
| WSNP_EX_REP_C67198_65702998 | FHB | 187 | 2 | 17.12 |
| WSNP_KU_C8592_14575931 | FHB | 260 | 2 | 17.12 |
| WSNP_EX_C7705_13139890 | FHB | 270 | 2 | 18.13 |
| WSNP_EX_C5780_10153638 | FHB | 219 | 2 | 20.57 |
| WSNP_EX_C18733_27607958 | FHB | 29 | 2 | 42.67 |
| WSNP_EX_C11976_19193550 | FHB | 24 | 2 | 43.75 |
| WSNP_KU_C16938_25916260 | FHB | 34 | 2 | 43.75 |
| WSNP_EX_C16581_25100502 | FHB | 26 | 2 | 43.96 |
| WSNP_JD_REP_C62985_40164465 | FHB | 262 | 2 | 47.51 |
| WSNP_BF291549B_TA_1_1 | FHB | 267 | 2 | 47.51 |
| WSNP_RA_C8484_14372815 | FHB | 23 | 2 | 72.11 |
| WSNP_EX_C17452_26163465 | FHB | 27 | 2 | 72.11 |
| WSNP_KU_C4951_8856170 | FHB | 28 | 2 | 72.11 |
| WSNP_EX_REP_C67036_65492436 | FHB | 32 | 2 | 72.11 |
| WSNP_JD_C4485_5618761 | FHB | 33 | 2 | 72.11 |
| WSNP_RA_C2027_3945764 | FHB | 196 | 2 | 74.63 |
| WSNP_EX_REP_C69986_68942834 | FHB | 160 | 2 | 75.19 |
| WSNP_EX_REP_C69986_68942866 | FHB | 182 | 2 | 75.19 |
| WSNP_KU_C39862_48205590 | FHB | 30 | 2 | 88.42 |
| WSNP_EX_C6611_11451949 | FHB | 164 | 2 | 89.32 |
| WSNP_EX_C6611_11452297 | FHB | 142 | 2 | 89.82 |
| WSNP_EX_C30969_39821293 | FHB | 241 | 2 | 89.82 |
| WSNP_JD_REP_C63201_40318622 | FHB | 35 | 2 | 137.65 |
| WSNP_KU_C23598_33524490 | FHB | 147 | 4 | 0 |
| WSNP_EX_C342_670415 | FHB | 45 | 4 | 7.15 |
| WSNP_JD_C13086_13174510 | FHB | 156 | 4 | 100.03 |
| WSNP_EX_REP_C68113_66877517 | FHB | 223 | 4 | 100.03 |
| WSNP_EX_C15325_23565935 | FHB | 250 | 4 | 102.12 |
| WSNP_CAP11_REP_C8768_3788007 | FHB | 189 | 4 | 104.81 |
| WSNP_BG314532A_TA_2_1 | FHB | 193 | 4 | 105.31 |
| WSNP_JD_C12088_12411845 | FHB | 184 | 4 | 105.81 |
| WSNP_EX_C15325_23565794 | FHB | 254 | 4 | 105.81 |
| WSNP_EX_C15325_23564654 | FHB | 269 | 4 | 106.39 |
| WSNP_CAP7_C7742_3467376 | FHB | 50 | 4 | 141.06 |
| WSNP_RA_C10861_17763060 | FHB | 36 | 4 | 141.7 |
| WSNP_BE517627A_TA_2_1 | FHB | 37 | 4 | 141.7 |

TABLE 5-continued

Summary of Map Positions for Various Markers

| Marker Name | Trait | Reference Sequence (SEQ ID NO:) | Chromosome | Position |
|---|---|---|---|---|
| WSNP_EX_C2592_4822528 | FHB | 38 | 4 | 141.7 |
| WSNP_EX_C1064_2034431 | FHB | 41 | 4 | 141.7 |
| WSNP_BE399936A_TA_2_1 | FHB | 42 | 4 | 141.7 |
| WSNP_EX_C33196_41722217 | FHB | 43 | 4 | 141.7 |
| WSNP_EX_C7091_12199032 | FHB | 44 | 4 | 141.7 |
| WSNP_RA_C58188_60005934 | FHB | 46 | 4 | 141.7 |
| WSNP_EX_C1064_2034518 | FHB | 47 | 4 | 141.7 |
| WSNP_CD452951A_TA_2_1 | FHB | 48 | 4 | 141.7 |
| WSNP_EX_C45617_51361414 | FHB | 51 | 4 | 141.7 |
| WSNP_EX_C23720_32957892 | FHB | 52 | 4 | 141.7 |
| WSNP_EX_C21786_30948397 | FHB | 55 | 4 | 141.7 |
| WSNP_EX_C20649_29731279 | FHB | 57 | 4 | 141.7 |
| WSNP_EX_C1064_2034730 | FHB | 58 | 4 | 141.7 |
| WSNP_EX_C21721_30882221 | FHB | 59 | 4 | 141.7 |
| WSNP_KU_C44873_52048221 | FHB | 60 | 4 | 141.7 |
| WSNP_EX_C11437_18454413 | FHB | 61 | 4 | 141.7 |
| WSNP_CAP11C1711_934478 | FHB | 141 | 4 | 242.41 |
| WSNP_EX_REP_C70299_69243835 | FHB | 175 | 4 | 253.49 |
| WSNP_RA_C19083_28215239 | FHB | 49 | 5 | 55.26 |
| WSNP_EX_C21092_30220342 | FHB | 39 | 5 | 81.83 |
| WSNP_EX_C3044_5620102 | FHB | 62 | 5 | 163.67 |
| WSNP_RFL_CONTIG3917_4326857 | FHB | 214 | 5 | 313.6 |
| WSNP_EX_REP_C67635_66291944 | FHB | 63 | 7 | 6.46 |
| WSNP_EX_REP_C67635_66292689 | FHB | 64 | 7 | 6.46 |
| WSNP_BF293133A_TA_2_2 | FHB | 67 | 7 | 6.46 |
| WSNP_EX_C4548_8166555 | FHB | 222 | 7 | 26.09 |
| WSNP_RA_C9738_16173810 | FHB | 268 | 7 | 26.09 |
| WSNP_RA_C9738_16174002 | FHB | 271 | 7 | 26.09 |
| WSNP_EX_C33765_42199371 | FHB | 245 | 7 | 57.05 |
| WSNP_BF292295A_TA_2_1 | FHB | 68 | 7 | 76.96 |
| WSNP_EX_C4094_7399975 | FHB | 192 | 7 | 181.09 |
| WSNP_BF292596A_TA_1_3 | FHB | 194 | 7 | 195.69 |
| WSNP_BF292596A_TA_1_1 | FHB | 195 | 7 | 195.69 |
| WSNP_EX_C10630_17338753 | FHB | 204 | 7 | 250.46 |
| WSNP_EX_C10630_17338703 | FHB | 234 | 7 | 250.46 |
| WSNP_EX_C11229_18163892 | FHB | 66 | 7 | 282.88 |
| WSNP_EX_C8360_14085858 | FHB | 152 | 8 | 3.17 |
| WSNP_KU_C12698_20441325 | FHB | 266 | 8 | 4.83 |
| WSNP_EX_REP_C66331_64502558 | FHB | 73 | 8 | 6.52 |
| WSNP_EX_C2723_5047696 | FHB | 178 | 8 | 7.02 |
| WSNP_EX_C7316_12552186 | FHB | 227 | 8 | 9.52 |
| WSNP_EX_C8386_14128029 | FHB | 236 | 8 | 14.8 |
| WSNP_EX_C8386_14127329 | FHB | 143 | 8 | 24.42 |
| WSNP_EX_REP_C66766_65123941 | FHB | 248 | 8 | 24.42 |
| WSNP_EX_C16919_25506076 | FHB | 199 | 8 | 33.03 |
| WSNP_KU_C663_1368085 | FHB | 70 | 8 | 45.04 |
| WSNP_BE489326B_TA_2_1 | FHB | 74 | 8 | 124.4 |
| WSNP_JD_C119_190135 | FHB | 220 | 8 | 124.4 |
| WSNP_EX_C4769_8510104 | FHB | 213 | 8 | 139.28 |
| WSNP_EX_C22016_31191407 | FHB | 173 | 8 | 141.85 |
| WSNP_EX_C7172_12318529 | FHB | 177 | 8 | 141.85 |
| WSNP_EX_C123_244117 | FHB | 179 | 8 | 141.85 |
| WSNP_KU_C8722_14766699 | FHB | 181 | 8 | 141.85 |
| WSNP_EX_C2330_4366134 | FHB | 183 | 8 | 141.85 |
| WSNP_KU_C6825_11858665 | FHB | 230 | 8 | 141.85 |
| WSNP_EX_C5378_9505533 | FHB | 232 | 8 | 141.85 |
| WSNP_EX_C5378_9505087 | FHB | 235 | 8 | 141.85 |
| WSNP_EX_C5378_9504586 | FHB | 253 | 8 | 141.85 |
| WSNP_EX_C5457_9631220 | FHB | 140 | 8 | 143.44 |
| WSNP_EX_C5457_9632050 | FHB | 157 | 8 | 143.44 |
| WSNP_JD_REP_C63654_40605158 | FHB | 75 | 8 | 144.06 |
| WSNP_EX_C7021_12096881 | FHB | 71 | 8 | 144.61 |
| WSNP_EX_C40060_47197384 | FHB | 171 | 8 | 148.8 |
| WSNP_EX_C15399_23662312 | FHB | 174 | 8 | 149.14 |
| WSNP_JD_C9360_10216330 | FHB | 211 | 8 | 160.91 |
| WSNP_RA_REP_C72670_70836439 | FHB | 72 | 8 | 297.03 |
| WSNP_JD_REP_C50820_34666611 | FHB | 76 | 8 | 297.03 |
| WSNP_EX_C19773_28772235 | FHB | 77 | 10 | 145.91 |
| WSNP_BE638137B_TA_2_2 | FHB | 78 | 11 | 150.97 |
| WSNP_RA_REP_C69221_66574148 | FHB | 197 | 13 | 17.11 |
| WSNP_EX_C10231_16783750 | FHB | 145 | 13 | 65.62 |
| WSNP_EX_C15163_23357477 | FHB | 218 | 13 | 70.08 |
| WSNP_EX_REP_C68515_67349904 | FHB | 228 | 13 | 91.45 |
| WSNP_EX_REP_C101757_87065169 | FHB | 84 | 13 | 97.6 |
| WSNP_EX_REP_C101757_87064771 | FHB | 83 | 13 | 97.79 |

TABLE 5-continued

Summary of Map Positions for Various Markers

| Marker Name | Trait | Reference Sequence (SEQ ID NO:) | Chromosome | Position |
|---|---|---|---|---|
| WSNP_EX_REP_C101757_87065032 | FHB | 86 | 13 | 97.79 |
| WSNP_EX_REP_C68829_67704044 | FHB | 81 | 13 | 106.06 |
| WSNP_EX_C3838_6980909 | FHB | 87 | 13 | 114.67 |
| WSNP_EX_C1279_2451582 | FHB | 172 | 13 | 119.66 |
| WSNP_EX_C1279_2451699 | FHB | 226 | 13 | 119.66 |
| WSNP_EX_C49211_53875600 | FHB | 88 | 13 | 126.52 |
| WSNP_EX_C49211_53875575 | FHB | 90 | 13 | 126.52 |
| WSNP_RA_C21347_30731133 | FHB | 80 | 13 | 230.05 |
| WSNP_RA_C21347_30731229 | FHB | 82 | 13 | 237.93 |
| WSNP_CAP11_C299_251533 | FHB | 89 | 13 | 237.93 |
| WSNP_EX_C23968_33209660 | FHB | 149 | 13 | 256.65 |
| WSNP_EX_C23968_33210344 | FHB | 176 | 13 | 256.65 |
| WSNP_JD_C43389_30288993 | FHB | 240 | 13 | 256.65 |
| WSNP_CAP11_C923_558715 | FHB | 259 | 13 | 256.65 |
| WSNP_EX_C54655_57455562 | FHB | 263 | 13 | 256.65 |
| WSNP_EX_C16295_24772663 | FHB | 264 | 13 | 256.65 |
| WSNP_EX_C16295_24772702 | FHB | 272 | 13 | 256.65 |
| WSNP_KU_C38543_47157828 | FHB | 85 | 13 | 290.4 |
| WSNP_RA_C20970_30293078 | FHB | 93 | 14 | 214.66 |
| WSNP_RA_C20970_30293227 | FHB | 94 | 14 | 214.66 |
| WSNP_EX_REP_C68600_67449494 | FHB | 91 | 14 | 217.45 |
| WSNP_EX_REP_C68600_67448893 | FHB | 95 | 14 | 217.45 |
| WSNP_EX_C97184_84339976 | FHB | 221 | 14 | 246.03 |
| WSNP_EX_C9362_15546626 | FHB | 92 | 14 | 301.43 |
| WSNP_CAP11_C2142_1128735 | FHB | 105 | 16 | 17.16 |
| WSNP_KU_C7471_12865509 | FHB | 274 | 16 | 21.13 |
| WSNP_CAP8_C6680_3136899 | FHB | 275 | 16 | 25.44 |
| WSNP_JD_C7718_8795833 | FHB | 96 | 16 | 30.15 |
| WSNP_EX_REP_C68165_66935041 | FHB | 97 | 16 | 30.15 |
| WSNP_EX_C3530_6459643 | FHB | 101 | 16 | 30.15 |
| WSNP_EX_C3530_6459532 | FHB | 102 | 16 | 30.15 |
| WSNP_EX_REP_C68165_66935014 | FHB | 103 | 16 | 30.15 |
| WSNP_KU_C38351_47009610 | FHB | 104 | 16 | 30.15 |
| WSNP_EX_REP_C68165_66935148 | FHB | 107 | 16 | 30.15 |
| WSNP_EX_C52849_56297163 | FHB | 109 | 16 | 30.15 |
| WSNP_EX_C9763_16125630 | FHB | 100 | 16 | 43.61 |
| WSNP_EX_C16491_24996576 | FHB | 98 | 16 | 49.03 |
| WSNP_JD_C2180_3000498 | FHB | 167 | 16 | 71.99 |
| WSNP_KU_C26784_36748247 | FHB | 159 | 16 | 74.29 |
| WSNP_EX_C15378_23638822 | FHB | 99 | 16 | 75.3 |
| WSNP_EX_C15378_23639387 | FHB | 106 | 16 | 75.3 |
| WSNP_EX_C22089_31270140 | FHB | 201 | 16 | 89.32 |
| WSNP_EX_C21129_30256617 | FHB | 256 | 16 | 237.22 |
| WSNP_CAP7_C5487_2464864 | FHB | 151 | 16 | 251.27 |
| WSNP_EX_C2325_4355706 | FHB | 203 | 16 | 252.95 |
| WSNP_KU_REP_C71567_71302010 | FHB | 207 | 16 | 255.8 |
| WSNP_EX_C17349_26035281 | FHB | 119 | 17 | 92.77 |
| WSNP_EX_C46160_51746546 | FHB | 116 | 17 | 94.34 |
| WSNP_EX_C38198_45786860 | FHB | 126 | 17 | 94.85 |
| WSNP_EX_C17667_26408733 | FHB | 198 | 17 | 95.85 |
| WSNP_RA_C24962_34524602 | FHB | 115 | 17 | 99.21 |
| WSNP_JD_REP_C63108_40258378 | FHB | 120 | 17 | 99.21 |
| WSNP_RA_C14498_22667649 | FHB | 112 | 17 | 131.33 |
| WSNP_CAP12_REP_C8688_3644383 | FHB | 114 | 17 | 140.99 |
| WSNP_EX_C31670_40433594 | FHB | 257 | 17 | 141.11 |
| WSNP_EX_C3940_7144946 | FHB | 265 | 17 | 143.86 |
| WSNP_KU_C1876_3666308 | FHB | 122 | 17 | 145.15 |
| WSNP_EX_C16836_25401702 | FHB | 125 | 17 | 148.94 |
| WSNP_KU_C11690_19042937 | FHB | 117 | 17 | 158.94 |
| WSNP_EX_C31256_40071875 | FHB | 111 | 17 | 159.94 |
| WSNP_EX_C5744_10088287 | FHB | 118 | 17 | 159.94 |
| WSNP_BE490200B_TA_2_1 | FHB | 110 | 17 | 161.3 |
| WSNP_EX_REP_C106072_90285324 | FHB | 123 | 17 | 163.31 |
| WSNP_EX_C5744_10087877 | FHB | 121 | 17 | 165.32 |
| WSNP_EX_C1146_2200823 | FHB | 186 | 19 | 154.97 |
| WSNP_EX_C19582_28564743 | FHB | 162 | 19 | 155.47 |
| WSNP_EX_C1146_2201722 | FHB | 127 | 19 | 159.87 |
| WSNP_EX_C46274_51831129 | FHB | 133 | 20 | 32.15 |
| WSNP_RA_REP_C71101_69119989 | FHB | 136 | 20 | 32.15 |
| WSNP_RA_C31052_40235870 | FHB | 135 | 20 | 69.65 |
| WSNP_EX_REP_C69954_68913284 | FHB | 131 | 20 | 70.65 |
| WSNP_CAP11_REP_C6622_3044459 | FHB | 130 | 20 | 76.13 |
| WSNP_RFL_CONTIG3854_4205716 | FHB | 129 | 20 | 78.14 |
| WSNP_JD_C9040_9947841 | FHB | 144 | 20 | 78.86 |
| WSNP_EX_C27373_36578273 | FHB | 168 | 20 | 78.86 |

TABLE 5-continued

Summary of Map Positions for Various Markers

| Marker Name | Trait | Reference Sequence (SEQ ID NO:) | Chromosome | Position |
|---|---|---|---|---|
| WSNP_EX_C18800_27681277 | FHB | 169 | 20 | 78.86 |
| WSNP_KU_C4067_7419106 | FHB | 153 | 20 | 81.36 |
| WSNP_EX_C26747_35974837 | FHB | 185 | 20 | 81.36 |
| WSNP_EX_C25755_35018674 | FHB | 210 | 20 | 81.36 |
| WSNP_KU_C10939_17975681 | FHB | 251 | 20 | 81.36 |
| WSNP_EX_C1790_3378771 | FHB | 231 | 20 | 81.69 |
| WSNP_EX_REP_C69954_68913307 | FHB | 132 | 20 | 82.45 |
| WSNP_EX_C4408_7939986 | FHB | 206 | 20 | 83.46 |
| WSNP_EX_C14248_22204549 | FHB | 247 | 20 | 83.46 |
| WSNP_RFL_CONTIG2167_1484520 | FHB | 208 | 20 | 84.95 |
| WSNP_CAP11_C847_522893 | FHB | 225 | 20 | 85.46 |
| WSNP_KU_C18780_28136150 | FHB | 139 | 20 | 85.96 |
| WSNP_BQ169669B_TA_2_2 | FHB | 161 | 20 | 86.46 |
| WSNP_EX_C351_689415 | FHB | 134 | 20 | 226.41 |
| WSNP_JD_C17128_16056425 | FHB | 146 | 20 | 226.41 |
| WSNP_EX_C3738_6809767 | FHB | 242 | 20 | 226.41 |
| WSNP_EX_C11055_17927668 | FHB | 216 | 22 | 0 |
| WSNP_EX_C5550_9779698 | FHB | 20 | | |
| WSNP_EX_C20975_30093113 | FHB | 25 | | |
| WSNP_KU_C16938_25916279 | FHB | 31 | | |
| WSNP_EX_C56928_58852277 | FHB | 40 | | |
| WSNP_RA_C58188_60004916 | FHB | 53 | | |
| WSNP_RA_REP_C106961_90622638 | FHB | 54 | | |
| WSNP_CAP12_C5344_2430233 | FHB | 56 | | |
| WSNP_CAP11_REP_C7339_3306558 | FHB | 65 | | |
| WSNP_KU_C18473_27773912 | FHB | 69 | | |
| WSNP_EX_C5461_9636197 | FHB | 79 | | |
| WSNP_KU_C38351_47009641 | FHB | 108 | | |
| WSNP_EX_C5936_10412246 | FHB | 113 | | |
| WSNP_EX_C23716_32952372 | FHB | 124 | | |
| WSNP_KU_C707_1465779 | FHB | 128 | | |
| WSNP_EX_REP_C69816_68774932 | FHB | 137 | | |
| WSNP_JD_C5757_6915127 | FHB | 148 | | |
| WSNP_JD_C6974_8084450 | FHB | 150 | | |
| WSNP_EX_C5267_9318903 | FHB | 154 | | |
| WSNP_EX_C22753_31958639 | FHB | 155 | | |
| WSNP_RA_C18364_27416387 | FHB | 158 | | |
| WSNP_JD_C5919_7081809 | FHB | 163 | | |
| WSNP_BE496826A_TA_2_3 | FHB | 166 | | |
| WSNP_JD_C9360_10216526 | FHB | 170 | | |
| WSNP_CAP7_C1339_673581 | FHB | 180 | | |
| WSNP_CAP8_REP_C8295_3722232 | FHB | 188 | | |
| WSNP_BQ168329A_TD_2_1 | FHB | 190 | | |
| WSNP_EX_REP_C103505_88446868 | FHB | 191 | | |
| WSNP_KU_C14842_23275194 | FHB | 202 | | |
| WSNP_KU_C53501_58106782 | FHB | 205 | | |
| WSNP_EX_REP_C66407_64613374 | FHB | 209 | | |
| WSNP_EX_REP_C67369_65940505 | FHB | 212 | | |
| WSNP_JD_C626_945114 | FHB | 215 | | |
| WSNP_EX_REP_C69266_68192954 | FHB | 224 | | |
| WSNP_JD_C3463_4479210 | FHB | 229 | | |
| WSNP_CAP7_C444_237594 | FHB | 233 | | |
| WSNP_JD_REP_C63942_40788045 | FHB | 237 | | |
| WSNP_EX_C4661_8344663 | FHB | 238 | | |
| WSNP_EX_REP_C103505_88447145 | FHB | 243 | | |
| WSNP_EX_REP_C67897_66613415 | FHB | 244 | | |
| WSNP_EX_REP_C66606_64905694 | FHB | 246 | | |
| WSNP_EX_C41073_47987034 | FHB | 252 | | |
| WSNP_BE490744A_TD_2_1 | FHB | 261 | | |
| WSNP_KU_C1818_3557408 | Flowering | 17 | 1 | 12.43 |
| WSNP_JD_C6544_7697578 | Flowering | 10 | 1 | 150.34 |
| WSNP_KU_C16547_25454123 | Flowering | 1 | 5 | 363.51 |
| WSNP_EX_C10555_17235832 | Flowering | 13 | 5 | 366.25 |
| WSNP_EX_C2580_4800027 | Flowering | 12 | 8 | 129.62 |
| WSNP_EX_C10717_17456391 | Flowering | 3 | 8 | 130.52 |
| WSNP_BG263758B_TA_2_1 | Flowering | 5 | 8 | 141.85 |
| WSNP_EX_C2920_5385184 | Flowering | 2 | 8 | 142.46 |
| WSNP_JD_C1316_1891903 | Flowering | 4 | 8 | 142.46 |
| WSNP_EX_C22089_31270140 | Flowering | 14 | 16 | 89.32 |
| WSNP_EX_C36325_44308589 | Flowering | 11 | 20 | 41.19 |
| WSNP_EX_C6590_11419735 | Flowering | 15 | 20 | 42.34 |
| WSNP_EX_C3501_6408181 | Flowering | 6 | 20 | 48.78 |
| WSNP_BE404354B_TA_2_1 | Flowering | 7 | | |
| WSNP_EX_C10555_17237000 | Flowering | 8 | | |
| WSNP_KU_C6758_11757213 | Flowering | 9 | | |

TABLE 5-continued

Summary of Map Positions for Various Markers

| Marker Name | Trait | Reference Sequence (SEQ ID NO:) | Chromosome | Position |
|---|---|---|---|---|
| WSNP_CAP11_C210_199161 | Flowering | 16 | | |
| WSNP_EX_REP_C66606_64905694 | Flowering | 18 | | |
| WSNP_EX_REP_C102795_87883062 | Flowering | 19 | | |
| WSNP_KU_C17726_26872129 | Heading Date | 347 | 1 | 73.05 |
| WSNP_EX_REP_C105541_89932598 | Heading Date | 351 | 1 | 73.05 |
| WSNP_EX_C44049_50205457 | Heading Date | 324 | 1 | 108.65 |
| WSNP_EX_C44049_50205904 | Heading Date | 445 | 1 | 108.65 |
| WSNP_EX_REP_C101746_87053634 | Heading Date | 389 | 1 | 109.66 |
| WSNP_EX_REP_C101414_86780996 | Heading Date | 363 | 1 | 111.3 |
| WSNP_EX_C3906_7086162 | Heading Date | 408 | 1 | 111.3 |
| WSNP_EX_C4605_8240189 | Heading Date | 410 | 1 | 111.3 |
| WSNP_JD_C13903_13781269 | Heading Date | 327 | 1 | 126.95 |
| WSNP_BE495786A_TA_2_1 | Heading Date | 378 | 1 | 126.95 |
| WSNP_RA_C12148_19539667 | Heading Date | 374 | 1 | 127.92 |
| WSNP_KU_C24239_34199356 | Heading Date | 423 | 1 | 128.68 |
| WSNP_EX_C5192_9203682 | Heading Date | 438 | 1 | 128.68 |
| WSNP_RA_C37745_45806931 | Heading Date | 350 | 1 | 130.7 |
| WSNP_EX_REP_C66628_64934660 | Heading Date | 441 | 1 | 130.7 |
| WSNP_EX_C42282_48900922 | Heading Date | 398 | 1 | 131.7 |
| WSNP_EX_C34344_42676379 | Heading Date | 432 | 1 | 131.7 |
| WSNP_EX_C34344_42677360 | Heading Date | 376 | 1 | 133.39 |
| WSNP_CAP7_C3472_1623955 | Heading Date | 276 | 1 | 168.77 |
| WSNP_CAP8_C458_368155 | Heading Date | 278 | 3 | 54.28 |
| WSNP_EX_REP_C108057_91436561 | Heading Date | 277 | 3 | 57.66 |
| WSNP_EX_C16720_25268525 | Heading Date | 279 | 3 | 57.66 |
| WSNP_RFL_CONTIG2729_2446041 | Heading Date | 446 | 4 | 197.66 |
| WSNP_RA_C32271_41304469 | Heading Date | 280 | 4 | 218.07 |
| WSNP_JD_C12687_12877994 | Heading Date | 366 | 5 | 110.75 |
| WSNP_EX_C741_1456698 | Heading Date | 393 | 5 | 110.75 |
| WSNP_EX_C5239_9272511 | Heading Date | 349 | 5 | 170.65 |
| WSNP_EX_C26818_36041748 | Heading Date | 430 | 5 | 292.54 |
| WSNP_KU_C8712_14751858 | Heading Date | 375 | 6 | 69.1 |
| WSNP_EX_C8303_14001708 | Heading Date | 357 | 6 | 96.13 |
| WSNP_JD_C2863_3822253 | Heading Date | 443 | 7 | 78.46 |
| WSNP_EX_REP_C69919_68881108 | Heading Date | 335 | 7 | 193.71 |
| WSNP_EX_C35861_43926307 | Heading Date | 329 | 7 | 194.01 |
| WSNP_EX_REP_C69342_68276256 | Heading Date | 345 | 7 | 194.01 |
| WSNP_EX_C35861_43927741 | Heading Date | 435 | 7 | 194.01 |
| WSNP_EX_C361_708712 | Heading Date | 336 | 7 | 266.27 |
| WSNP_EX_C55096_57733894 | Heading Date | 282 | 7 | 267.79 |
| WSNP_EX_REP_C104141_88935451 | Heading Date | 391 | 7 | 268.79 |
| WSNP_EX_C55096_57733841 | Heading Date | 284 | 7 | 269.29 |
| WSNP_EX_C25082_34346512 | Heading Date | 281 | 7 | 269.84 |
| WSNP_EX_C11229_18163892 | Heading Date | 283 | 7 | 282.88 |
| WSNP_BE496983B_TA_2_1 | Heading Date | 447 | 8 | 88.96 |
| WSNP_EX_C8802_14726148 | Heading Date | 332 | 8 | 109.46 |
| WSNP_EX_C4927_8772847 | Heading Date | 444 | 8 | 113.75 |
| WSNP_JD_C9902_10674725 | Heading Date | 403 | 8 | 119.87 |
| WSNP_JD_C9902_10674626 | Heading Date | 422 | 8 | 120.78 |
| WSNP_JD_C17082_16025440 | Heading Date | 290 | 8 | 121.7 |
| WSNP_BQ168706B_TA_2_2 | Heading Date | 287 | 8 | 124.4 |
| WSNP_BQ168706B_TA_2_1 | Heading Date | 288 | 8 | 124.4 |
| WSNP_EX_C21499_30644485 | Heading Date | 291 | 8 | 124.4 |
| WSNP_BE489326B_TA_2_2 | Heading Date | 293 | 8 | 124.4 |
| WSNP_KU_C18538_27857915 | Heading Date | 317 | 8 | 124.4 |
| WSNP_EX_C4769_8510104 | Heading Date | 390 | 8 | 139.28 |
| WSNP_EX_C22016_31191407 | Heading Date | 342 | 8 | 141.85 |
| WSNP_EX_C123_244117 | Heading Date | 353 | 8 | 141.85 |
| WSNP_KU_C8722_14766699 | Heading Date | 361 | 8 | 141.85 |
| WSNP_EX_C2330_4366134 | Heading Date | 362 | 8 | 141.85 |
| WSNP_KU_C6825_11858665 | Heading Date | 409 | 8 | 141.85 |
| WSNP_EX_C5378_9505087 | Heading Date | 415 | 8 | 141.85 |
| WSNP_EX_C5378_9504586 | Heading Date | 439 | 8 | 141.85 |
| WSNP_EX_C5547_9774453 | Heading Date | 315 | 8 | 150.12 |
| WSNP_EX_C5547_9772680 | Heading Date | 330 | 8 | 150.12 |
| WSNP_EX_C5547_9774195 | Heading Date | 369 | 8 | 150.12 |
| WSNP_EX_C53983_57032627 | Heading Date | 399 | 8 | 150.12 |
| WSNP_BE445348B_TA_2_1 | Heading Date | 404 | 8 | 152.06 |
| WSNP_EX_C7756_13218814 | Heading Date | 434 | 8 | 153.17 |
| WSNP_EX_C3096_5709369 | Heading Date | 285 | 8 | 153.84 |
| WSNP_EX_C3096_5709257 | Heading Date | 292 | 8 | 153.84 |
| WSNP_EX_C12887_20427158 | Heading Date | 383 | 8 | 157.36 |
| WSNP_KU_REP_C72821_72480395 | Heading Date | 407 | 8 | 157.87 |
| WSNP_EX_C3096_5708642 | Heading Date | 420 | 8 | 158.37 |
| WSNP_BE499016B_TA_2_1 | Heading Date | 334 | 8 | 170.8 |

TABLE 5-continued

Summary of Map Positions for Various Markers

| Marker Name | Trait | Reference Sequence (SEQ ID NO:) | Chromosome | Position |
|---|---|---|---|---|
| WSNP_EX_C8208_13870372 | Heading Date | 289 | 8 | 223.93 |
| WSNP_EX_C57007_58898157 | Heading Date | 295 | 8 | 223.93 |
| WSNP_JD_C4413_5541190 | Heading Date | 294 | 8 | 224.43 |
| WSNP_EX_C33778_42210283 | Heading Date | 384 | 10 | 31.34 |
| WSNP_EX_C11684_18805687 | Heading Date | 431 | 10 | 127.02 |
| WSNP_EX_C10347_16946522 | Heading Date | 296 | 11 | 18.66 |
| WSNP_KU_C7180_12403155 | Heading Date | 297 | 11 | 18.66 |
| WSNP_KU_C7890_13513783 | Heading Date | 300 | 13 | 17.11 |
| WSNP_KU_C644_1332610 | Heading Date | 328 | 13 | 17.11 |
| WSNP_KU_REP_C102220_89250165 | Heading Date | 331 | 13 | 17.11 |
| WSNP_RA_C323_681466 | Heading Date | 338 | 13 | 17.11 |
| WSNP_RA_C17541_26430903 | Heading Date | 365 | 13 | 17.11 |
| WSNP_KU_C328_679106 | Heading Date | 419 | 13 | 17.11 |
| WSNP_RA_C6788_11804894 | Heading Date | 433 | 13 | 17.11 |
| WSNP_EX_REP_C69526_68472665 | Heading Date | 352 | 13 | 46.4 |
| WSNP_EX_C31830_40573624 | Heading Date | 425 | 13 | 47.41 |
| WSNP_CAP7_C2282_1107112 | Heading Date | 421 | 13 | 47.91 |
| WSNP_BF201102A_TA_2_1 | Heading Date | 298 | 13 | 48.41 |
| WSNP_EX_C19134_28056012 | Heading Date | 355 | 13 | 50.42 |
| WSNP_EX_C4211_7606269 | Heading Date | 370 | 13 | 50.42 |
| WSNP_RA_C11420_18529863 | Heading Date | 318 | 13 | 65.62 |
| WSNP_EX_C2718_5038582 | Heading Date | 346 | 13 | 65.62 |
| WSNP_KU_C1102_2211433 | Heading Date | 337 | 13 | 66.16 |
| WSNP_EX_C23509_32746909 | Heading Date | 321 | 13 | 66.7 |
| WSNP_BE500291A_TA_2_1 | Heading Date | 405 | 13 | 67.23 |
| WSNP_EX_REP_C66733_65077608 | Heading Date | 429 | 13 | 67.23 |
| WSNP_RA_REP_C75364_72953286 | Heading Date | 437 | 13 | 67.23 |
| WSNP_EX_C15084_23263641 | Heading Date | 326 | 13 | 82.64 |
| WSNP_EX_C130_258776 | Heading Date | 333 | 13 | 82.64 |
| WSNP_KU_C16812_25759885 | Heading Date | 343 | 13 | 82.64 |
| WSNP_RA_C2228_4310870 | Heading Date | 373 | 13 | 82.64 |
| WSNP_RA_C10053_16636851 | Heading Date | 385 | 13 | 82.64 |
| WSNP_KU_C5071_9050628 | Heading Date | 424 | 13 | 91.45 |
| WSNP_EX_C43578_49857984 | Heading Date | 299 | 13 | 100.33 |
| WSNP_KU_C30743_40542247 | Heading Date | 448 | 13 | 100.33 |
| WSNP_KU_REP_C103274_90057407 | Heading Date | 449 | 14 | 19.8 |
| WSNP_JD_C5795_6955627 | Heading Date | 344 | 14 | 168.46 |
| WSNP_KU_REP_C101212_88410320 | Heading Date | 426 | 14 | 171.36 |
| WSNP_EX_C34842_43092205 | Heading Date | 400 | 14 | 237.93 |
| WSNP_EX_C97184_84339976 | Heading Date | 402 | 14 | 246.03 |
| WSNP_EX_C29130_38196906 | Heading Date | 364 | 14 | 267.02 |
| WSNP_EX_C57209_59016692 | Heading Date | 301 | 14 | 301.19 |
| WSNP_JD_C12221_12509932 | Heading Date | 302 | 14 | 301.19 |
| WSNP_JD_C7718_8795833 | Heading Date | 303 | 16 | 30.15 |
| WSNP_KU_C10377_17180909 | Heading Date | 316 | 16 | 43.61 |
| WSNP_EX_C8643_14488961 | Heading Date | 305 | 16 | 89.32 |
| WSNP_EX_C2161_4059735 | Heading Date | 368 | 16 | 250.45 |
| WSNP_EX_C29648_38653339 | Heading Date | 417 | 16 | 251.27 |
| WSNP_EX_C1988_3742291 | Heading Date | 354 | 17 | 4.12 |
| WSNP_EX_REP_C115803_95396724 | Heading Date | 406 | 17 | 28.49 |
| WSNP_EX_C19467_28423946 | Heading Date | 304 | 17 | 80.93 |
| WSNP_RA_C14171_22234872 | Heading Date | 307 | 17 | 80.93 |
| WSNP_RA_C23253_32762188 | Heading Date | 311 | 19 | 124.21 |
| WSNP_EX_REP_C67660_66321934 | Heading Date | 381 | 19 | 150.04 |
| WSNP_KU_C34643_43968242 | Heading Date | 436 | 19 | 158.87 |
| WSNP_CAP11_C827_513472 | Heading Date | 416 | 19 | 160.63 |
| WSNP_EX_C9971_16412345 | Heading Date | 312 | 19 | 236.25 |
| WSNP_CAP8_REP_C3844_1896355 | Heading Date | 310 | 19 | 257.07 |
| WSNP_RA_C7112_12318340 | Heading Date | 396 | 19 | 262.44 |
| WSNP_EX_C53387_56641291 | Heading Date | 320 | 19 | 265.17 |
| WSNP_RA_C2063_4012957 | Heading Date | 397 | 19 | 265.29 |
| WSNP_EX_C916_1767286 | Heading Date | 339 | 19 | 265.42 |
| WSNP_EX_C6142_10746442 | Heading Date | 371 | 19 | 265.42 |
| WSNP_EX_C53387_56639804 | Heading Date | 308 | 19 | 268.03 |
| WSNP_KU_C28104_38042857 | Heading Date | 309 | 19 | 271.42 |
| WSNP_EX_C11106_18003332 | Heading Date | 313 | 20 | 32.15 |
| WSNP_KU_C16295_25149034 | Heading Date | 340 | 20 | 146.53 |
| WSNP_KU_C854_1768062 | Heading Date | 387 | 20 | 146.53 |
| WSNP_KU_C854_1768346 | Heading Date | 418 | 20 | 146.53 |
| WSNP_EX_C10500_17163855 | Heading Date | 367 | 20 | 148.58 |
| WSNP_EX_C3309_6096114 | Heading Date | 395 | 20 | 148.58 |
| WSNP_RFL_CONTIG4236_4881643 | Heading Date | 377 | 20 | 160.97 |
| WSNP_EX_C758_1488368 | Heading Date | 382 | 20 | 160.97 |
| WSNP_BE497845D_TA_1_1 | Heading Date | 322 | 21 | 85.69 |
| WSNP_EX_REP_C67404_65986980 | Heading Date | 286 | | |

TABLE 5-continued

Summary of Map Positions for Various Markers

| Marker Name | Trait | Reference Sequence (SEQ ID NO:) | Chromosome | Position |
|---|---|---|---|---|
| WSNP_EX_C1143_2194680 | Heading Date | 306 | | |
| WSNP_EX_C35861_43928486 | Heading Date | 314 | | |
| WSNP_EX_C41347_48189975 | Heading Date | 319 | | |
| WSNP_BE445508B_TA_2_2 | Heading Date | 323 | | |
| WSNP_BE591466B_TA_2_1 | Heading Date | 325 | | |
| WSNP_JD_C12087_12411036 | Heading Date | 341 | | |
| WSNP_JD_C15974_15272598 | Heading Date | 348 | | |
| WSNP_JD_C7404_8500079 | Heading Date | 356 | | |
| WSNP_EX_C9927_16346100 | Heading Date | 358 | | |
| WSNP_JD_C4621_5757201 | Heading Date | 359 | | |
| WSNP_BE591684B_TA_2_1 | Heading Date | 360 | | |
| WSNP_EX_C12254_19575022 | Heading Date | 372 | | |
| WSNP_RA_REP_C71473_69552690 | Heading Date | 379 | | |
| WSNP_BE490744B_TA_2_1 | Heading Date | 380 | | |
| WSNP_EX_C31262_40077397 | Heading Date | 386 | | |
| WSNP_BE445431A_TD_2_2 | Heading Date | 388 | | |
| WSNP_EX_C44587_50598716 | Heading Date | 392 | | |
| WSNP_EX_REP_C103972_88799335 | Heading Date | 394 | | |
| WSNP_EX_C5446_9616983 | Heading Date | 401 | | |
| WSNP_BF428726A_TA_2_5 | Heading Date | 411 | | |
| WSNP_KU_C66980_66202298 | Heading Date | 412 | | |
| WSNP_BE405599B_TA_2_1 | Heading Date | 413 | | |
| WSNP_JD_C35319_26397591 | Heading Date | 414 | | |
| WSNP_KU_C39289_47757996 | Heading Date | 427 | | |
| WSNP_EX_C19622_28607997 | Heading Date | 428 | | |
| WSNP_EX_C4710_8412517 | Heading Date | 440 | | |
| WSNP_CAP11_C1182_686503 | Heading Date | 442 | | |

*Map positions based on public map of Cavanagh et al. (2013) PNAS vol. 110: 8057-8062

Example 5

Summary of Various Haplotypes

TABLE 6

Haplotype Summary for Various Traits

| Trait | Marker | Ref. Seq. (SEQ ID NO:) | Haplotype Group | Favorable Allele | Unfavorable Allele |
|---|---|---|---|---|---|
| Fusarium Head Blight | WSNP_EX_REP_C70593_69508988 | 200 | 1 | C/C | T/T |
| Fusarium Head Blight | WSNP_EX_C2181_4089639 | 258 | 1 | T/T | C/C |
| Fusarium Head Blight | WSNP_EX_REP_C67492_66096650 | 255 | 2 | A/A | G/G |
| Fusarium Head Blight | WSNP_EX_C6476_11246531 | 217 | 2 | G/G | A/A |
| Fusarium Head Blight | WSNP_EX_C46670_52108070 | 21 | 3 | A/A | G/G |
| Fusarium Head Blight | WSNP_EX_C3887_7051325 | 273 | 3 | C/C | T/T |
| Fusarium Head Blight | WSNP_EX_REP_C67198_65702998 | 187 | 4 | A/A | C/C |
| Fusarium Head Blight | WSNP_KU_C8592_14575931 | 260 | 4 | T/T | G/G |
| Fusarium Head Blight | WSNP_EX_C7705_13139890 | 270 | 4 | T/T | C/C |
| Fusarium Head Blight | WSNP_EX_C5780_10153638 | 219 | 4 | G/G | A/A |
| Fusarium Head Blight | WSNP_EX_C18733_27607958 | 29 | 5 | T/T | C/C |
| Fusarium Head Blight | WSNP_EX_C11976_19193550 | 24 | 5 | G/G | A/A |
| Fusarium Head Blight | WSNP_KU_C16938_25916260 | 34 | 5 | T/T | C/C |
| Fusarium Head Blight | WSNP_JD_REP_C62985_40164465 | 262 | 5 | G/G | A/A |
| Fusarium Head Blight | WSNP_BF291549B_TA_1_1 | 267 | 5 | C/C | —/— |
| Fusarium Head Blight | WSNP_RA_C8484_14372815 | 23 | 6 | C/C | T/T |
| Fusarium Head Blight | WSNP_EX_REP_C67036_65492436 | 32 | 6 | A/A | G/G |
| Fusarium Head Blight | WSNP_KU_C4951_8856170 | 28 | 6 | G/G | A/A |
| Fusarium Head Blight | WSNP_JD_C4485_5618761 | 33 | 6 | T/T | C/C |
| Fusarium Head Blight | WSNP_EX_C17452_26163465 | 27 | 6 | C/C | T/T |
| Fusarium Head Blight | WSNP_RA_C2027_3945764 | 196 | 6 | G/G | A/A |
| Fusarium Head Blight | WSNP_EX_REP_C69986_68942866 | 182 | 6 | C/C | T/T |
| Fusarium Head Blight | WSNP_EX_REP_C69986_68942834 | 160 | 6 | T/T | C/C |
| Fusarium Head Blight | WSNP_KU_C39862_48205590 | 30 | 7 | A/A | C/C |
| Fusarium Head Blight | WSNP_EX_C6611_11451949 | 164 | 7 | A/A | G/G |
| Fusarium Head Blight | WSNP_EX_C6611_11452297 | 142 | 7 | A/A | G/G |
| Fusarium Head Blight | WSNP_EX_C30969_39821293 | 241 | 7 | G/G | A/A |
| Fusarium Head Blight | WSNP_JD_C13086_13174510 | 156 | 8 | C/C | T/T |
| Fusarium Head Blight | WSNP_EX_REP_C68113_66877517 | 223 | 8 | G/G | A/A |
| Fusarium Head Blight | WSNP_EX_C15325_23565935 | 250 | 8 | A/A | G/G |

TABLE 6-continued

Haplotype Summary for Various Traits

| | | | | | |
|---|---|---|---|---|---|
| Fusarium Head Blight | WSNP_CAP11_REP_C8768_3788007 | 189 | 9 | G/G | T/T |
| Fusarium Head Blight | WSNP_BG314532A_TA_2_1 | 193 | 9 | A/A | G/G |
| Fusarium Head Blight | WSNP_JD_C12088_12411845 | 184 | 9 | G/G | A/A |
| Fusarium Head Blight | WSNP_EX_C15325_23565794 | 254 | 9 | T/T | C/C |
| Fusarium Head Blight | WSNP_EX_C15325_23564654 | 269 | 9 | G/G | A/A |
| Fusarium Head Blight | WSNP_EX_C23720_32957892 | 52 | 10 | G/G | A/A |
| Fusarium Head Blight | WSNP_CAP7_C7742_3467376 | 50 | 10 | T/T | C/C |
| Fusarium Head Blight | WSNP_BE399936A_TA_2_1 | 42 | 10 | G/G | A/A |
| Fusarium Head Blight | WSNP_RA_C10861_17763060 | 36 | 10 | T/T | C/C |
| Fusarium Head Blight | WSNP_EX_C11437_18454413 | 61 | 10 | G/G | T/T |
| Fusarium Head Blight | WSNP_RA_C58188_60005934 | 46 | 10 | C/C | T/T |
| Fusarium Head Blight | WSNP_EX_C1064_2034518 | 47 | 10 | C/C | T/T |
| Fusarium Head Blight | WSNP_BF293133A_TA_2_2 | 67 | 11 | T/T | C/C |
| Fusarium Head Blight | WSNP_EX_REP_C67635_66291944 | 63 | 11 | C/C | T/T |
| Fusarium Head Blight | WSNP_EX_REP_C67635_66292689 | 64 | 11 | A/A | G/G |
| Fusarium Head Blight | WSNP_RA_C9738_16173810 | 268 | 12 | A/A | C/C |
| Fusarium Head Blight | WSNP_EX_C4548_8166555 | 222 | 12 | C/C | T/T |
| Fusarium Head Blight | WSNP_RA_C9738_16174002 | 271 | 12 | C/C | T/T |
| Fusarium Head Blight | WSNP_EX_C10630_17338753 | 204 | 13 | T/T | C/C |
| Fusarium Head Blight | WSNP_EX_C10630_17338703 | 234 | 13 | A/A | C/C |
| Fusarium Head Blight | WSNP_EX_C8360_14085858 | 152 | 14 | C/C | T/T |
| Fusarium Head Blight | WSNP_KU_C12698_20441325 | 266 | 14 | T/T | C/C |
| Fusarium Head Blight | WSNP_EX_REP_C66331_64502558 | 73 | 14 | A/A | G/G |
| Fusarium Head Blight | WSNP_EX_C2723_5047696 | 178 | 14 | T/T | C/C |
| Fusarium Head Blight | WSNP_EX_C8386_14127329 | 143 | 15 | G/G | T/T |
| Fusarium Head Blight | WSNP_EX_REP_C66766_65123941 | 248 | 15 | T/T | C/C |
| Fusarium Head Blight | WSNP_BE489326B_TA_2_1 | 74 | 16 | A/A | G/G |
| Fusarium Head Blight | WSNP_JD_C119_190135 | 220 | 16 | A/A | G/G |
| Fusarium Head Blight | WSNP_EX_C4769_8510104 | 213 | 17 | C/C | T/T |
| Fusarium Head Blight | WSNP_EX_C5378_9505533 | 232 | 17 | G/G | T/T |
| Fusarium Head Blight | WSNP_EX_C7172_12318529 | 177 | 17 | G/G | A/A |
| Fusarium Head Blight | WSNP_EX_C22016_31191407 | 173 | 17 | C/C | T/T |
| Fusarium Head Blight | WSNP_KU_C8722_14766699 | 181 | 17 | G/G | A/A |
| Fusarium Head Blight | WSNP_EX_C123_244117 | 179 | 17 | C/C | T/T |
| Fusarium Head Blight | WSNP_EX_C5378_9504586 | 253 | 17 | C/C | T/T |
| Fusarium Head Blight | WSNP_EX_C5378_9505087 | 235 | 17 | C/C | A/A |
| Fusarium Head Blight | WSNP_KU_C6825_11858665 | 230 | 17 | T/T | C/C |
| Fusarium Head Blight | WSNP_EX_C2330_4366134 | 183 | 17 | C/C | T/T |
| Fusarium Head Blight | WSNP_EX_C5457_9632050 | 157 | 17 | T/T | C/C |
| Fusarium Head Blight | WSNP_EX_C5457_9631220 | 140 | 17 | A/A | G/G |
| Fusarium Head Blight | WSNP_JD_REP_C63654_40605158 | 75 | 17 | G/G | A/A |
| Fusarium Head Blight | WSNP_EX_C7021_12096881 | 71 | 17 | G/G | A/A |
| Fusarium Head Blight | WSNP_EX_C40060_47197384 | 171 | 18 | G/G | A/A |
| Fusarium Head Blight | WSNP_EX_C15399_23662312 | 174 | 18 | T/T | G/G |
| Fusarium Head Blight | WSNP_RA_REP_C72670_70836439 | 72 | 19 | C/C | T/T |
| Fusarium Head Blight | WSNP_JD_REP_C50820_34666611 | 76 | 19 | A/A | G/G |
| Fusarium Head Blight | WSNP_CAP11_C923_558715 | 259 | 20 | G/G | A/A |
| Fusarium Head Blight | WSNP_EX_C54655_57455562 | 263 | 20 | A/A | G/G |
| Fusarium Head Blight | WSNP_JD_C43389_30288993 | 240 | 20 | T/T | C/C |
| Fusarium Head Blight | WSNP_EX_C23968_33209660 | 149 | 20 | C/C | T/T |
| Fusarium Head Blight | WSNP_EX_C16295_24772663 | 264 | 20 | C/C | T/T |
| Fusarium Head Blight | WSNP_EX_C23968_33210344 | 176 | 20 | G/G | A/A |
| Fusarium Head Blight | WSNP_EX_C16295_24772702 | 272 | 20 | T/T | C/C |
| Fusarium Head Blight | WSNP_EX_C49211_53875600 | 88 | 21 | T/T | C/C |
| Fusarium Head Blight | WSNP_EX_C49211_53875575 | 90 | 21 | G/G | T/T |
| Fusarium Head Blight | WSNP_EX_C1279_2451699 | 226 | 22 | T/T | C/C |
| Fusarium Head Blight | WSNP_EX_C1279_2451582 | 172 | 22 | G/G | T/T |
| Fusarium Head Blight | WSNP_EX_C3838_6980909 | 87 | 23 | | |
| Fusarium Head Blight | WSNP_RA_C21347_30731133 | 80 | 23 | T/T | C/C |
| Fusarium Head Blight | WSNP_RA_C21347_30731229 | 82 | 23 | G/G | T/T |
| Fusarium Head Blight | WSNP_CAP11_C299_251533 | 89 | 23 | T/T | C/C |
| Fusarium Head Blight | WSNP_EX_REP_C101757_87064771 | 83 | 24 | A/A | G/G |
| Fusarium Head Blight | WSNP_EX_REP_C101757_87065032 | 86 | 24 | G/G | A/A |
| Fusarium Head Blight | WSNP_EX_REP_C101757_87065169 | 84 | 24 | T/T | C/C |
| Fusarium Head Blight | WSNP_EX_REP_C68600_67448893 | 95 | 25 | G/G | T/T |
| Fusarium Head Blight | WSNP_EX_REP_C68600_67449494 | 91 | 25 | C/C | A/A |
| Fusarium Head Blight | WSNP_RA_C20970_30293227 | 94 | 25 | A/A | C/C |
| Fusarium Head Blight | WSNP_RA_C20970_30293078 | 93 | 25 | A/A | C/C |
| Fusarium Head Blight | WSNP_KU_C38351_47009610 | 104 | 26 | T/T | G/G |
| Fusarium Head Blight | WSNP_EX_REP_C68165_66935014 | 103 | 26 | A/A | G/G |
| Fusarium Head Blight | WSNP_EX_C3530_6459532 | 102 | 26 | T/T | C/C |
| Fusarium Head Blight | WSNP_EX_C3530_6459643 | 101 | 26 | T/T | C/C |
| Fusarium Head Blight | WSNP_EX_REP_C68165_66935041 | 97 | 26 | C/C | A/A |
| Fusarium Head Blight | WSNP_EX_C52849_56297163 | 109 | 26 | T/T | C/C |
| Fusarium Head Blight | WSNP_JD_C7718_8795833 | 96 | 26 | G/G | T/T |
| Fusarium Head Blight | WSNP_JD_C2180_3000498 | 167 | 27 | C/C | T/T |
| Fusarium Head Blight | WSNP_KU_C26784_36748247 | 159 | 27 | T/T | C/C |
| Fusarium Head Blight | WSNP_EX_C15378_23638822 | 99 | 27 | T/T | C/C |

TABLE 6-continued

Haplotype Summary for Various Traits

| Trait | Marker | | | | |
|---|---|---|---|---|---|
| *Fusarium* Head Blight | WSNP_EX_C15378_23639387 | 106 | 27 | A/A | C/C |
| *Fusarium* Head Blight | WSNP_CAP7_C5487_2464864 | 151 | 28 | G/G | —/— |
| *Fusarium* Head Blight | WSNP_EX_C2325_4355706 | 203 | 28 | C/C | T/T |
| *Fusarium* Head Blight | WSNP_KU_REP_C71567_71302010 | 207 | 28 | G/G | A/A |
| *Fusarium* Head Blight | WSNP_EX_C17349_26035281 | 119 | 29 | T/T | C/C |
| *Fusarium* Head Blight | WSNP_EX_C46160_51746546 | 116 | 29 | G/G | A/A |
| *Fusarium* Head Blight | WSNP_EX_C38198_45786860 | 126 | 29 | G/G | A/A |
| *Fusarium* Head Blight | WSNP_EX_C17667_26408733 | 198 | 29 | A/A | G/G |
| *Fusarium* Head Blight | WSNP_JD_REP_C63108_40258378 | 120 | 30 | G/G | A/A |
| *Fusarium* Head Blight | WSNP_RA_C24962_34524602 | 115 | 30 | G/G | A/A |
| *Fusarium* Head Blight | WSNP_EX_C31256_40071875 | 111 | 31 | G/G | A/A |
| *Fusarium* Head Blight | WSNP_EX_C5744_10088287 | 118 | 31 | A/A | G/G |
| *Fusarium* Head Blight | WSNP_BE490200B_TA_2_1 | 110 | 31 | A/A | G/G |
| *Fusarium* Head Blight | WSNP_EX_REP_C106072_90285324 | 123 | 31 | C/C | T/T |
| *Fusarium* Head Blight | WSNP_EX_C1146_2200823 | 186 | 32 | A/A | G/G |
| *Fusarium* Head Blight | WSNP_EX_C19582_28564743 | 162 | 32 | T/T | C/C |
| *Fusarium* Head Blight | WSNP_EX_C1146_2201722 | 127 | 32 | C/C | T/T |
| *Fusarium* Head Blight | WSNP_EX_C46274_51831129 | 133 | 33 | T/T | C/C |
| *Fusarium* Head Blight | WSNP_RA_REP_C71101_69119989 | 136 | 33 | C/C | A/A |
| *Fusarium* Head Blight | WSNP_RA_C31052_40235870 | 135 | 34 | C/C | T/T |
| *Fusarium* Head Blight | WSNP_EX_REP_C69954_68913284 | 131 | 34 | T/T | C/C |
| *Fusarium* Head Blight | WSNP_EX_C18800_27681277 | 169 | 35 | A/A | C/C |
| *Fusarium* Head Blight | WSNP_EX_C27373_36578273 | 168 | 35 | A/A | G/G |
| *Fusarium* Head Blight | WSNP_JD_C9040_9947841 | 144 | 35 | C/C | T/T |
| *Fusarium* Head Blight | WSNP_KU_C10939_17975681 | 251 | 35 | G/G | A/A |
| *Fusarium* Head Blight | WSNP_EX_C25755_35018674 | 210 | 35 | G/G | A/A |
| *Fusarium* Head Blight | WSNP_EX_C26747_35974837 | 185 | 35 | A/A | G/G |
| *Fusarium* Head Blight | WSNP_KU_C4067_7419106 | 153 | 35 | T/T | C/C |
| *Fusarium* Head Blight | WSNP_EX_C1790_3378771 | 231 | 35 | A/A | C/C |
| *Fusarium* Head Blight | WSNP_EX_REP_C69954_68913307 | 132 | 35 | A/A | G/G |
| *Fusarium* Head Blight | WSNP_EX_C4408_7939986 | 206 | 35 | T/T | C/C |
| *Fusarium* Head Blight | WSNP_EX_C14248_22204549 | 247 | 35 | A/A | G/G |
| *Fusarium* Head Blight | WSNP_CAP11_C847_522893 | 225 | 36 | G/G | A/A |
| *Fusarium* Head Blight | WSNP_KU_C18780_28136150 | 139 | 36 | G/G | A/A |
| *Fusarium* Head Blight | WSNP_BQ169669B_TA_2_2 | 161 | 36 | T/T | C/C |
| *Fusarium* Head Blight | WSNP_EX_C351_689415 | 134 | 37 | C/C | T/T |
| *Fusarium* Head Blight | WSNP_JD_C17128_16056425 | 146 | 37 | T/T | C/C |
| *Fusarium* Head Blight | WSNP_EX_C3738_6809767 | 242 | 37 | C/C | T/T |

| Trait | Marker | Reference Sequence (SEQ ID NO:) | haplotype group | Favorable Allele | Unfavorable Allele |
|---|---|---|---|---|---|
| Heading Date | WSNP_EX_REP_C105541_89932598 | 351 | 1 | A/A | G/G |
| HEADING DATE | WSNP_KU_C17726_26872129 | 347 | 1 | G/G | T/T |
| HEADING DATE | WSNP_EX_C44049_50205904 | 445 | 2 | T/T | |
| HEADING DATE | WSNP_EX_C44049_50205457 | 324 | 2 | C/C | T/T |
| HEADING DATE | WSNP_EX_REP_C101746_87053634 | 389 | 2 | C/C | —/— |
| HEADING DATE | WSNP_EX_C3906_7086162 | 408 | 2 | C/C | T/T |
| HEADING DATE | WSNP_EX_C4605_8240189 | 410 | 2 | A/A | G/G |
| HEADING DATE | WSNP_EX_REP_C101414_86780996 | 363 | 2 | G/G | A/A |
| HEADING DATE | WSNP_JD_C13903_13781269 | 327 | 3 | G/G | A/A |
| HEADING DATE | WSNP_BE495786A_TA_2_1 | 378 | 3 | G/G | T/T |
| HEADING DATE | WSNP_RA_C12148_19539667 | 374 | 3 | G/G | A/A |
| HEADING DATE | WSNP_EX_C5192_9203682 | 438 | 3 | A/A | G/G |
| HEADING DATE | WSNP_KU_C24239_34199356 | 423 | 3 | C/C | T/T |
| HEADING DATE | WSNP_RA_C37745_45806931 | 350 | 4 | A/A | C/C |
| HEADING DATE | WSNP_EX_REP_C66628_64934660 | 441 | 4 | G/G | A/A |
| HEADING DATE | WSNP_EX_C34344_42676379 | 432 | 4 | C/C | T/T |
| HEADING DATE | WSNP_EX_C42282_48900922 | 398 | 4 | C/C | T/T |
| HEADING DATE | WSNP_EX_C34344_42677360 | 376 | 4 | C/C | T/T |
| HEADING DATE | WSNP_CAP8_C458_368155 | 278 | 5 | C/C | T/T |
| HEADING DATE | WSNP_EX_REP_C108057_91436561 | 277 | 5 | G/G | A/A |
| HEADING DATE | WSNP_EX_C16720_25268525 | 279 | 5 | G/G | T/T |
| HEADING DATE | WSNP_EX_C741_1456698 | 393 | 6 | G/G | |
| HEADING DATE | WSNP_JD_C12687_12877994 | 366 | 6 | C/C | |

| Trait | Marker | Ref. Seq. (SEQ ID NO:) | Haplotype Group | Favorable Allele | Unfavorable Allele |
|---|---|---|---|---|---|
| HEADING DATE | WSNP_EX_C361_708712 | 336 | 7 | T/T | C/C |
| HEADING DATE | WSNP_EX_C55096_57733894 | 282 | 7 | C/C | T/T |
| HEADING DATE | WSNP_EX_REP_C104141_88935451 | 391 | 7 | C/C | A/A |
| HEADING DATE | WSNP_EX_C55096_57733841 | 284 | 7 | G/G | A/A |
| HEADING DATE | WSNP_EX_C25082_34346512 | 281 | 7 | C/C | T/T |
| HEADING DATE | WSNP_EX_C8802_14726148 | 332 | 8 | C/C | T/T |

TABLE 6-continued

Haplotype Summary for Various Traits

| | | | | | |
|---|---|---|---|---|---|
| HEADING DATE | WSNP_EX_C4927_8772847 | 444 | 8 | T/T | |
| HEADING DATE | WSNP_JD_C9902_10674725 | 403 | 9 | T/T | C/C |
| HEADING DATE | WSNP_JD_C9902_10674626 | 422 | 9 | T/T | C/C |
| HEADING DATE | WSNP_JD_C17082_16025440 | 290 | 9 | G/G | A/A |
| HEADING DATE | WSNP_EX_C21499_30644485 | 291 | 10 | A/A | |
| HEADING DATE | WSNP_BQ168706B_TA_2_2 | 287 | 10 | G/G | A/A |
| HEADING DATE | WSNP_KU_C18538_27857915 | 317 | 10 | T/T | C/C |
| HEADING DATE | WSNP_BE489326B_TA_2_2 | 293 | 10 | G/G | A/A |
| HEADING DATE | WSNP_BQ168706B_TA_2_1 | 288 | 10 | T/T | C/C |
| HEADING DATE | WSNP_EX_C4769_8510104 | 390 | 11 | C/C | T/T |
| HEADING DATE | WSNP_EX_C123_244117 | 353 | 11 | C/C | T/T |
| HEADING DATE | WSNP_EX_C5378_9505087 | 415 | 11 | C/C | A/A |
| HEADING DATE | WSNP_EX_C2330_4366134 | 362 | 11 | C/C | T/T |
| HEADING DATE | WSNP_EX_C22016_31191407 | 342 | 11 | C/C | T/T |
| HEADING DATE | WSNP_KU_C8722_14766699 | 361 | 11 | G/G | A/A |
| HEADING DATE | WSNP_KU_C6825_11858665 | 409 | 11 | T/T | C/C |
| HEADING DATE | WSNP_EX_C5378_9504586 | 439 | 11 | C/C | T/T |
| HEADING DATE | WSNP_EX_C5547_9774453 | 315 | 12 | CC | A/A |
| HEADING DATE | WSNP_EX_C5547_9772680 | 330 | 12 | G/G | T/T |
| HEADING DATE | WSNP_EX_C5547_9774195 | 369 | 12 | T/T | C/C |
| HEADING DATE | WSNP_BE445348B_TA_2_1 | 404 | 12 | CC | A/A |
| HEADING DATE | WSNP_EX_C7756_13218814 | 434 | 12 | A/A | G/G |
| HEADING DATE | WSNP_EX_C3096_5709369 | 285 | 12 | C/C | A/A |
| HEADING DATE | WSNP_EX_C3096_5709257 | 292 | 12 | A/A | G/G |
| HEADING DATE | WSNP_EX_C12887_20427158 | 383 | 13 | G/G | A/A |
| HEADING DATE | WSNP_KU_REP_C72821_72480395 | 407 | 13 | T/T | C/C |
| HEADING DATE | WSNP_EX_C3096_5708642 | 420 | 13 | A/A | G/G |
| HEADING DATE | WSNP_EX_C57007_58898157 | 295 | 14 | T/T | C/C |
| HEADING DATE | WSNP_EX_C8208_13870372 | 289 | 14 | A/A | G/G |
| HEADING DATE | WSNP_JD_C4413_5541190 | 294 | 14 | A/A | G/G |
| HEADING DATE | WSNP_KU_C7180_12403155 | 297 | 15 | C/C | T/T |
| HEADING DATE | WSNP_EX_C10347_16946522 | 296 | 15 | T/T | C/C |
| HEADING DATE | WSNP_EX_C43578_49857984 | 299 | 16 | A/A | G/G |
| HEADING DATE | WSNP_KU_C30743_40542247 | 448 | 16 | G/G | A/A |
| HEADING DATE | WSNP_KU_C328_679106 | 419 | 17 | C/C | T/T |
| HEADING DATE | WSNP_RA_C17541_26430903 | 365 | 17 | T/T | C/C |
| HEADING DATE | WSNP_RA_C6788_11804894 | 433 | 17 | A/A | G/G |
| HEADING DATE | WSNP_BE500291A_TA_2_1 | 405 | 17 | C/C | T/T |
| HEADING DATE | WSNP_KU_C16812_25759885 | 343 | 17 | A/A | G/G |
| HEADING DATE | WSNP_EX_C130_258776 | 333 | 17 | G/G | T/T |
| HEADING DATE | WSNP_RA_C10053_16636851 | 385 | 17 | C/C | T/T |
| HEADING DATE | WSNP_EX_C15084_23263641 | 326 | 17 | C/C | A/A |
| HEADING DATE | WSNP_RA_C2228_4310870 | 373 | 17 | A/A | G/G |
| HEADING DATE | WSNP_KU_REP_C102220_89250165 | 331 | 17 | T/T | C/C |
| HEADING DATE | WSNP_KU_C644_1332610 | 328 | 17 | A/A | G/G |
| HEADING DATE | WSNP_RA_REP_C75364_72953286 | 437 | 17 | C/C | A/A |
| HEADING DATE | WSNP_EX_REP_C66733_65077608 | 429 | 17 | A/A | G/G |
| HEADING DATE | WSNP_RA_C323_681466 | 338 | 17 | G/G | A/A |
| HEADING DATE | WSNP_EX_C23509_32746909 | 321 | 17 | A/A | C/C |
| HEADING DATE | WSNP_KU_C1102_2211433 | 337 | 17 | C/C | A/A |
| HEADING DATE | WSNP_EX_C2718_5038582 | 346 | 17 | T/T | C/C |
| HEADING DATE | WSNP_RA_C11420_18529863 | 318 | 17 | C/C | T/T |
| HEADING DATE | WSNP_EX_C19134_28056012 | 355 | 18 | T/T | C/C |
| HEADING DATE | WSNP_EX_C4211_7606269 | 370 | 18 | T/T | C/C |
| HEADING DATE | WSNP_KU_C7890_13513783 | 300 | 18 | T/T | C/C |
| HEADING DATE | WSNP_BF201102A_TA_2_1 | 298 | 18 | T/T | C/C |
| HEADING DATE | WSNP_CAP7_C2282_1107112 | 421 | 18 | T/T | C/C |
| HEADING DATE | WSNP_EX_C31830_40573624 | 425 | 18 | T/T | C/C |
| HEADING DATE | WSNP_EX_REP_C69526_68472665 | 352 | 18 | C/C | T/T |
| HEADING DATE | WSNP_JD_C12221_12509932 | 302 | 19 | G/G | |
| HEADING DATE | WSNP_EX_C57209_59016692 | 301 | 19 | A/A | |
| HEADING DATE | WSNP_KU_REP_C101212_88410320 | 426 | 20 | G/G | A/A |
| HEADING DATE | WSNP_JD_C5795_6955627 | 344 | 20 | A/A | G/G |
| HEADING DATE | WSNP_EX_C2161_4059735 | 368 | 21 | G/G | A/A |
| HEADING DATE | WSNP_EX_C29648_38653339 | 417 | 21 | A/A | G/G |
| HEADING DATE | WSNP_EX_C19467_28423946 | 304 | 22 | C/C | T/T |
| HEADING DATE | WSNP_RA_C14171_22234872 | 307 | 22 | G/G | A/A |
| HEADING DATE | WSNP_EX_C53387_56641291 | 320 | 23 | T/T | C/C |
| HEADING DATE | WSNP_RA_C2063_4012957 | 397 | 23 | G/G | A/A |
| HEADING DATE | WSNP_EX_C6142_10746442 | 371 | 23 | T/T | C/C |
| HEADING DATE | WSNP_EX_C916_1767286 | 339 | 23 | T/T | C/C |
| HEADING DATE | WSNP_EX_C53387_56639804 | 308 | 23 | C/C | T/T |
| HEADING DATE | WSNP_KU_C28104_38042857 | 309 | 23 | C/C | T/T |
| HEADING DATE | WSNP_EX_C10500_17163855 | 367 | 24 | T/T | C/C |
| HEADING DATE | WSNP_EX_C3309_6096114 | 395 | 24 | C/C | T/T |
| HEADING DATE | WSNP_RFL_CONTIG4236_4881643 | 377 | 25 | G/G | A/A |
| HEADING DATE | WSNP_EX_C758_1488368 | 382 | 25 | C/C | T/T |
| Days to Flower | WSNP_EX_C10555_17235832 | 13 | 1 | TT | CC |

TABLE 6-continued

Haplotype Summary for Various Traits

| Days to Flower | WSNP_KU_C16547_25454123 | 1 | 1 | AA | GG |
|---|---|---|---|---|---|
| Days to Flower | WSNP_EX_C2580_4800027 | 12 | 2 | A/A | G/G |
| Days to Flower | WSNP_EX_C10717_17456391 | 3 | 2 | T/T | G/G |
| Days to Flower | WSNP_BG263758B_TA_2_1 | 5 | 3 | G/G | A/A |
| Days to Flower | WSNP_EX_C2920_5385184 | 2 | 3 | G/G | A/A |
| Days to Flower | WSNP_JD_C1316_1891903 | 4 | 3 | T/T | C/C |
| Days to Flower | WSNP_EX_C36325_44308589 | 11 | 4 | CC | TT |
| Days to Flower | WSNP_EX_C6590_11419735 | 15 | 4 | GG | AA |

*Map positions based on public map of Cavanagh et al. (2013) PNAS vol. 110: 8057-8062
** Various haplotypes are denoted via numerical groupings in Table 6.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of producing a wheat plant or germplasm that displays improved *fusarium* head blight resistance, said method comprising:
   (a) isolating a nucleic acid from a wheat plant or part thereof;
   (b) detecting a C allele at nucleotide position 101 of SEQ ID NO:149,
   (c) thereby identifying and/or selecting a *fusarium* head blight resistant wheat plant;

(d) crossing the wheat plant of (c) with a second wheat plant not having the C allele at nucleotide position 101 of SEQ ID N0:149;

(e) collecting seed from the cross in step (d); and (f) growing a progeny wheat plant from said seed which comprises the C allele at nucleotide position 101 of SEQ ID N0:149, thereby producing a wheat plant with improved *fusarium* head blight resistance relative to a wheat plant not comprising the C allele at nucleotide position 101 of SEQ ID N0:149.

2. A method of producing a wheat plant or germplasm with improved *fusarium* head blight resistance, said method comprising:

(a) isolating a nucleic acid from a wheat plant or part thereof;

(b) detecting a haplotype associated with the improved *fusarium* head blight resistance, wherein said haplotype comprises: a G allele at nucleotide position 101 of SEQ ID NO:259, an A allele at nucleotide position 101 of SEQ ID NO:263, a T allele at nucleotide position 46 of SEQ ID NO:240, a C allele at nucleotide position 101 of SEQ ID NO:149, a C allele at nucleotide position 101 of SEQ ID NO:264, a G allele at nucleotide position 101 of SEQ ID NO:176, and a T allele at nucleotide position 101 of SEQ ID NO:272;

(c) thereby identifying and/or selecting a *fusarium* head blight resistant wheat plant;

(d) crossing the wheat plant of (c) with a second wheat plant not having the haplotype;

(e) collecting seed from the cross in step (d); and (f) growing a progeny wheat plant from said seed which comprises said haplotype in its genome, thereby producing a wheat plant with improved *fusarium* head blight resistance relative to a wheat plant not comprising the haplotype.

* * * * *